US008772307B2

(12) United States Patent
Frank et al.

(10) Patent No.: US 8,772,307 B2
(45) Date of Patent: Jul. 8, 2014

(54) SUBSTITUTED SPIRO COMPOUNDS AND THEIR USE FOR PRODUCING PAIN-RELIEF MEDICAMENTS

(75) Inventors: Robert Frank, Aachen (DE); Melanie Reich, Aachen (DE); Ruth Jostock, Stolberg (DE); Gregor Bahrenberg, Aachen (DE); Hans Schick, Berlin (DE); Birgitta Henkel, Berlin (DE); Helmut Sonnenschein, Berlin (DE)

(73) Assignee: Gruenenthal GmbH, Aachen (DE)

( * ) Notice: Subject to any disclaimer, the term of this patent is extended or adjusted under 35 U.S.C. 154(b) by 1343 days.

(21) Appl. No.: 11/914,927

(22) PCT Filed: May 17, 2006

(86) PCT No.: PCT/EP2006/004652
§ 371 (c)(1),
(2), (4) Date: Jun. 19, 2008

(87) PCT Pub. No.: WO2006/122770
PCT Pub. Date: Nov. 23, 2006

(65) Prior Publication Data
US 2008/0269271 A1 Oct. 30, 2008

(30) Foreign Application Priority Data

May 19, 2005 (DE) .......................... 10 2005 023 783
Sep. 20, 2005 (DE) .......................... 10 2005 044 813

(51) Int. Cl.
*C07D 498/10* (2006.01)
*A61K 31/4747* (2006.01)
*A61P 1/00* (2006.01)
*A61P 3/00* (2006.01)
*A61P 11/00* (2006.01)
*A61P 17/00* (2006.01)
*A61P 25/00* (2006.01)
*A61P 25/28* (2006.01)
*A61P 25/30* (2006.01)
*A61P 29/00* (2006.01)

(52) U.S. Cl.
USPC .............. 514/278; 514/379; 546/16; 548/242

(58) Field of Classification Search
None
See application file for complete search history.

(56) References Cited

U.S. PATENT DOCUMENTS

| 6,774,132 B1 | 8/2004 | Claesson et al. |
| 2004/0192916 A1 | 9/2004 | Buschmann et al. |

FOREIGN PATENT DOCUMENTS

| CA | 2 608 385 A1 | 11/2006 | |
| WO | WO 96/38426 A1 | 12/1996 | |
| WO | WO 9638426 A1 * | 12/1996 | ........... C07D 261/04 |
| WO | WO 97/11940 A1 | 4/1997 | |
| WO | WO 9711940 A1 * | 4/1997 | ........... C07D 221/20 |
| WO | WO 97/33887 A1 | 9/1997 | |
| WO | WO 98/43962 A1 | 10/1998 | |
| WO | WO 03/000699 A1 | 1/2003 | |
| WO | WO 2004/043349 A2 | 5/2004 | |
| WO | WO 2005-021515 A2 | 3/2005 | |
| WO | WO 2005-021515 A3 | 3/2005 | |
| WO | WO 2005/110992 A1 | 11/2005 | |
| WO | WO 2005110992 A1 * | 11/2005 | ........... C07D 221/00 |

OTHER PUBLICATIONS

Lee et al., Analysis of Structure-Activity Relationships for the A-region of N-(4-t- butylbenzyl)-N'-[4-(methyl sulfonylamino)benzyl] thiourea Analogues as TRPV1 Antagonists, 15 Bioorg. & Med. Chem. Letts. 4136-4142 (2005).*
Hwang et al., OBOC Small-Molecule Combinatorial Library Encoded by Halogenated Mass-Tags, 6(21) Org. Letts. 3829-3832 (2004).*
Richard B. Silverman, The Organic Chemistry of Drug Design and Drug Action, Chapter 2: Drug Discovery, Design, and Development, Academic Press, p. 5-51 (1992).*
Gunthorpe & Chizh, Clinical Developments of TRPV1 Antagonists: Targeting a Pivotal Point in the Pain Pathway, 14(1/2) Drug Discovery Today, 56-67 (Jan. 2009).*
German Search Report dated Apr. 20, 2006 with English translation of relevant portion (Ten (10) Pages).
International Search Report date Aug. 16, 2006 with English translation of relevant portions (Six (6) Pages).
Form PCT/ISA/237 with English translation (Eleven (11) Pages).
Coderre, Terence J. et al., "Contribution of central neuroplasticity to pathological pain: review of clinical and experimental evidence", *Pain 52* (1993) pp. 259-285, Elsevier Science Publishers B.V.
Dubuisson David et al., "The Formalin Test: A Quantitative Study of the Analgesic Effects of Morphine, Meperidine, and Brain Stem Stimulation in Rats and Cats", *Pain*, 4 (1977) pp. 161-174, Elsevier/North-Holland Biomedical Press.
Hendershot L.C. et al., "Antagonism of the Frequency of Phenylquinone-Induced Writhing in the Mouse by Weak Analgesics and Nonanalgesics", vol. 125, pp. 237-240, *The Biochemical Research Laboratory, The Dow Chemical Company, Midland, Michigan*, (1958).
G. Ahern, Activation of TRPV1 by the Satiety Factor Oleoylethanolamide, The Journal of Biological Chemistry, vol. 278, No. 33, Aug. 15, 2003, pp. 30429-30434.
L.A. Birder et al., Altered urinary bladder function in mice lacking the vanilloid receptor TRPV1, Nature Neuroscience, vol. 5, No. 9, Sep. 2002, pp. 856-860.
E. Bodo et al., A Hot New Twist to Hair Biology: Involvement of Vanilloid Receptor-1 (VR1/TRPV1) Signaling in Human Hair Growth Control, American Journal of Pathology, vol. 166, No. 4, Apr. 2005, pp. 985-998.
D. Dawbarn et al., Intranigral Injection of Capsaicin Enhances Motor Activity and Depletes Nigral 5-Hydroxytryptamine But Not Substance P, Neuropharmacology, vol. 20, pp. 341-346, 1981.
P. Geppetti et al., Activation and sensitisation of the vanilloid receptor: role in gastrointestinal inflammation and function, British Journal of Pharmacology, 2004, vol. 141, No. 8, pp. 1313-1320.
J. Ghilardi et al., Selective Blockade of the Capsicin Receptor TRPV1 Attenuates Bone Cancer Pain, The Journal of Neuroscience, Mar. 23, 2005, vol. 25, No. 12, pp. 3126-3131.
P. Holzer, TRPV1 and the gut: from a tasty receptor for a painful vanilloid to a key player in hyperalgesia, European Journal of Pharmacology 500, 2004, pp. 231-241.

(Continued)

*Primary Examiner* — Janet L Andres
*Assistant Examiner* — Timothy R Rozof
(74) *Attorney, Agent, or Firm* — Crowell & Moring LLP

(57) ABSTRACT

The present invention relates to substituted spiro compounds, to processes for preparing them, to medicaments comprising these compounds and to the use of these compounds for producing medicaments.

22 Claims, No Drawings

(56) References Cited

OTHER PUBLICATIONS

H. Rami et al., The therapeutic potential of TRPV1 (VRI) antagonists: clinical answers await, Drug Discover Today: Therapeutic Strategies, vol. 1, No. 1, 2004, pp. 97-104.
C. Maggi, Therapeutic Potential of Capsaicin-like Molecules: Studies in Animals and Humans, Life Sciences, vol. 51, 1992, pp. 1777-1781.
S. Marinelli et al., Presynaptic Facilitation of Glutamatergic Synapses to Dopaminergic Neurons of the Rat Substantia Nigra by Endogenous Stimulation of Vanilloid Receptors, The Journal of Neuroscience, Apr. 15, 2003, vol. 23, No. 8, pp. 3136-3144.
H. Pan et al., Sensing Tissue Ischemia: Another New Function for Capsaicin Receptors?, Circulation Journal of the American Heart Association, Circulation 2004, vol. 110, Issue 13, pp. 1826-1831.
H. Schultz, The spice of life is at the root of cardiac pain, Journal of Physiology (2003), 551.2, p. 400.
Y. Yiangou et al., Vanilloid receptor 1 immunoreactivity in inflamed human bowel, The Lancet, vol. 357, p. 1338-1339, Apr. 28, 2001.
M. Zahner et al., Cardiac vanilloid receptor 1-expressing afferent nerves and their role in the cardiogenic sympathetic reflex in rats, Journal of Physiology (2003) 551.2, pp. 515-523.
T. Sprenger et al., Migraine pathogenesis and state of pharmacological treatment options, BMC Medicine 2009, 7:71.
G.A. Lambert et al., The effects of the TRPV1 receptor antagonist SB-705498 on trigeminovascular sensitisation and neurotransmission, Nauyn-Schmied Arch Pharmacol (2009) vol. 380, pp. 311-325.
R. Planells-Cases et al., Functional aspects and mechanisms of TRPV1 involvement in neurogenic inflammation that leads to thermal hyperalgesia, Pflugers Arch—Eur J. Physiol (2005) vol. 451, pp. 151-159.
V. Micale et al., Altered responses of dopamine D3 receptor null mice to excitotoxic or anxiogenic stimuli: Possible involvement of the endocannabinoid and endovanilloid systems, Neurobiology of Disease 36 (2009), pp. 70-80.
M. Fu et al., TRPV1: A potential target for antiepileptogenesis, Medical Hypotheses 73 (2009), pp. 100-102.
F. Leung, Capsaicin-sensitive intestinal mucosal afferent mechanism and body fat distribution, Life Sciences 83 (2008), pp. 1-5.
A. Suri et al., The emerging role of TRPV1 in diabetes and obesity, Trends in Pharmacological Sciences, vol. 29, No. 1, pp. 29-36 (2007).
J. Li et al., Increased GFR and renal excretory function by activation of TRPV in the isolated prefused kidney, Pharmacological Research vol. 57, Issue 3 (2008), pp. 239-246.
M. Ghasemi et al., Effect of anandamide on nonadrenergic noncholinergic-mediated relaxation of rat corpus cavernosum, European Journal of Pharmacology vol. 544, Issues 1-3 (2006), pp. 138-145.

S. Mandadi et al., Locomotor Networks Are Targets of Modulation by Sensory Transient Receptor Potential Vanilloid 1 and Transient Receptor Potential Melastatin 8 Channels, Neuroscience 162 (2009) pp. 1377-1397.
R. Marsch et al., Reduced Anxiety, Conditioned Fear, and Hippocampal Long-Term Potentiation in Transient Receptor Potential Vanilloid Type 1 Receptor-Deficient Mice, The Journal of Neuroscience, Jan. 24, 2007, vol. 27, No. 4, pp. 832-839.
H. Eilers, Anesthetic Activation of Nociceptors: Adding Insult to Injury?, Molecular Interventions, Oct. 2008, vol. 8, Issue 5, pp. 226-229.
Won-Sik Shim et al., TRPV1 Mediates Histamine-Induced Itching via the Activation of Phospolipase $A_2$ and 12-Lipoxygenase, The Journal of Neuroscience, Feb. 28, 2007, vol. 27, No. 9, pp. 2331-2337.
W. Huang, Enhanced postmyocardial infarction fibrosis via stimulation of the transforming growth factor-B-Smad2 signaling pathway: role of transient receptor potential vanilloid type 1 channels, Journal of Hypertension vol. 27 (2009).
I. J. You et al., Society for Neuroscience, Abstract, Vo. 912.22 (2007).
J. Donnerer et al., Pharmacology, Feb. 2005; vol. 73, Issue 2, pp. 97-101 (2005) E. pub Oct. 18, 2004.
Min Fu et al., TRPV1: A potential target for antielileptogenesis, Medical Hypothesis 73 (2009) 100-102.
John J. Adcock, TRPV1 receptors in sensitization of cough and pain reflexes, Pulmonary Pharmacology & Therapeutics 22 (2009) 65-70.
Teshamae S. Monteith et al., Acute Migraine Therapy: New Drugs and New Approaches, Current Treatment in Neurology (2011) 13: 1-14.
Magdalene M. Moran et al., Transient receptor potential channels as therapeutic targets, Nature Review, Drug Discovery, vol. 10, Aug. 2011, pp. 601-620.
Celia D. Cruz et al., Intrathecal delivery of resiniferatoxin (RTX) reduces detrusor overactivity and spinal expression of TRPV1 in spinal cord injured animals, Experimental Neurology 214 (2008) 301-308.
Naoki Yoshimura et al., Therapeutic receptor targets for lower urinary tract dysfunction, Nauyn-Schmiedeberg's Arch Pharmacol (2008) 377:437-448.
Carols Silva et al., Bladder sensory densitization decreases urinary urgency, BMC Urology 2007, 7-9.
Klaus Urbahns et al., Naphthol derivatives as TRPV1 inhibitors for the treatment of urinary incontinence, Bioorganic & Medicinal Chemistry Letters 21 (2011) 3354-3357.

\* cited by examiner

SUBSTITUTED SPIRO COMPOUNDS AND THEIR USE FOR PRODUCING PAIN-RELIEF MEDICAMENTS

The present invention relates to substituted spiro compounds, to processes for preparing them, to medicaments comprising these compounds and to the use of these compounds for producing medicaments.

The treatment of pain, in particular of neuropathic pain, is of great importance in medicine. Effective pain therapies are in demand across the globe. The urgent need for action to provide patient-friendly and targeted treatment of chronic and non-chronic states of pain, meaning the successful and satisfactory treatment of the patient's pain, is also reflected in the large number of scientific studies which have recently appeared in the field of applied analgesics or basic research in nociception.

A suitable starting point for the treatment of pain, in particular of neuropathic pain, is provided by the subtype 1 vanilloid receptor (VR1/TRPV1) which is often also referred to as a capsaicin receptor. This receptor is stimulated, inter alia, by vanilloids, such as for example capsaicin, heat and protons and plays a central role in the production of pain. In addition, it is important for a large number of further physiological and pathophysiological processes such as, for example, migraine; depression; neurodegenerative diseases; cognitive diseases; panic attacks; epilepsy; coughing; diarrhea; pruritus; disturbances of the cardiovascular system; eating disorders; medication dependency; medication abuse and in particular urinary incontinence.

An object of the present invention was therefore to provide new compounds which are suitable, in particular, as pharmacological active ingredients in medicaments, preferably in medicaments for the treatment of disturbances or diseases which are transmitted, at least in some cases, by vanilloid receptors 1 (VR1/TRPV1 receptors).

It has surprisingly been found that substituted spiro compounds of general formula I as indicated below are suitable for combating pain and display outstanding affinity to the subtype 1 vanilloid receptor (VR1/TRPV1 receptor) and are therefore suitable, in particular, for the prophylaxis and/or treatment of disturbances or diseases transmitted, at least in some cases, by vanilloid receptors 1 (VR1/TRPV1).

The present invention therefore relates to substituted spiro compounds of general formula I,

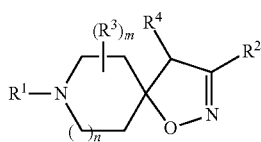

I wherein
m is equal to 0, 1, 2, 3 or 4,
n is equal to 0, 1 or 2,
$R^1$ represents an unsubstituted or at least singly substituted, unsaturated or saturated cycloaliphatic radical which optionally has at least one heteroatom as ring member and can be bound via a linear or branched, unsubstituted or at least singly substituted alkylene, alkenylene or alkinylene group and/or condensed with an unsubstituted or at least singly substituted mono- or polycyclic ring system,
an unsubstituted or at least singly substituted aryl or heteroaryl radical which can be bound via a linear or branched, unsubstituted or at least singly substituted alkylene, alkenylene or alkinylene group and/or condensed with an unsubstituted or at least singly substituted mono- or polycyclic ring system,
a —C(=O)—NR$^5$R$^6$ group,
a —C(=S)—NR$^7$R$^8$ group,
a —C(=O)—R$^9$ group
or an —S(=O)$_2$—R$^{10}$ group;
$R^2$ represents a linear or branched, saturated or unsaturated, unsubstituted or at least singly substituted aliphatic radical optionally having at least one heteroatom as chain member;
an unsubstituted or at least singly substituted, unsaturated or saturated cycloaliphatic radical which optionally has at least one heteroatom as ring member and can be bound via a linear or branched, unsubstituted or at least singly substituted alkylene, alkenylene or alkinylene group optionally having at least one heteroatom as chain member and/or condensed with an unsubstituted or at least singly substituted mono- or polycyclic ring system, an unsubstituted or at least singly substituted phenyl radical;
an unsubstituted or at least singly substituted phenyl radical which is condensed with an unsubstituted or at least singly substituted mono- or polycyclic ring system,
an unsubstituted or at least singly substituted naphthyl or heteroaryl radical which can be condensed with an unsubstituted or at least singly substituted mono- or polycyclic ring system,
or an unsubstituted or at least singly substituted aryl or heteroaryl radical which is bound via a linear or branched, unsubstituted or at least singly substituted alkylene, alkenylene or alkinylene group optionally having at least one heteroatom as chain member and can optionally be condensed with an unsubstituted or at least singly substituted mono- or polycyclic ring system;
$R^3$ represents a halogen radical, a nitro group, a hydroxy group, a thiol group; an —O—R$^{11}$ group, an —S—R$^{12}$ group, or a linear or branched, saturated or unsaturated, unsubstituted or at least singly substituted aliphatic radical;
$R^4$ represents a hydrogen radical, a halogen radical, a nitro group, a hydroxy group, a thiol group; an oxo group (=O), an —O—R$^{11}$ group, an —S—R$^{12}$ group, or a linear or branched, saturated or unsaturated, unsubstituted or at least singly substituted aliphatic radical;
$R^5$ and $R^7$, independently of one another, each
represent a linear or branched, saturated or unsaturated, unsubstituted or at least singly substituted aliphatic radical optionally having at least one heteroatom as chain member,
an unsubstituted or at least singly substituted, unsaturated or saturated cycloaliphatic radical which optionally has at least one heteroatom as ring member and can be bound via a linear or branched, unsubstituted or at least singly substituted alkylene, alkenylene or alkinylene group optionally having at least one heteroatom as chain member and/or condensed with an unsubstituted or at least singly substituted mono- or polycyclic ring system and/or bridged with at least one linear or branched, unsubstituted or at least singly substituted alkylene group,
an unsubstituted or at least singly substituted aryl or heteroaryl radical which can be bound via a linear or branched, unsubstituted or at least singly substituted alkylene, alkenylene or alkinylene group optionally having at least one heteroatom as chain member and/or condensed with an unsubstituted or at least singly substituted mono- or polycyclic ring system, $R^6$ and $R^8$, independently of one another, each
represent a hydrogen radical,
a linear or branched, saturated or unsaturated, unsubstituted or at least singly substituted aliphatic radical optionally having at least one heteroatom as chain member,
an unsubstituted or at least singly substituted, unsaturated or saturated cycloaliphatic radical which optionally has at least one heteroatom as ring member and can be bound via a linear or branched, unsubstituted or at least singly substituted alkylene, alkenylene or alkinylene group optionally having at least one heteroatom as chain member and/or condensed with an unsubstituted or at least singly substituted mono- or polycyclic ring system and/or bridged with at least one linear or branched, unsubstituted or at least singly substituted alkylene group,
an unsubstituted or at least singly substituted aryl or heteroaryl radical which can be bound via a linear or branched, unsubstituted or at least singly substituted alkylene, alkenylene or alkinylene group optionally having at least one heteroatom as chain member and/or condensed with an unsubstituted or at least singly substituted mono- or polycyclic ring system, $R^9$ and $R^{10}$, independently of one another, each
represent a linear or branched, saturated or unsaturated, unsubstituted or at least singly substituted aliphatic radical;
an unsubstituted or at least singly substituted, unsaturated or saturated cycloaliphatic radical which optionally has at least one heteroatom as ring member and can be bound via a linear or branched, unsubstituted or at least singly substituted alkylene, alkenylene or alkinylene group and/or condensed with an unsubstituted or at least singly substituted mono- or polycyclic ring system,
or an unsubstituted or at least singly substituted aryl or heteroaryl radical which can be bound via a linear or branched, unsubstituted or at least singly substituted alkylene, alkenylene or alkinylene group and/or condensed with an unsubstituted or at least singly substituted mono- or polycyclic ring system;
and
$R^{11}$ and $R^{12}$, independently of one another, each
represent a linear or branched, saturated or unsaturated, unsubstituted aliphatic radical;
an unsubstituted, unsaturated or saturated cycloaliphatic radical which optionally has at least one heteroatom as ring member and can be bound via a linear or branched, unsubstituted alkylene, alkenylene or alkinylene group and/or condensed with an unsubstituted mono- or polycyclic ring system,
or an unsubstituted aryl or heteroaryl radical which can be bound via a linear or branched, unsubstituted alkylene, alkenylene or alkinylene group and/or condensed with an unsubstituted mono- or polycyclic ring system;
wherein the substituents of the above-mentioned aliphatic radicals can be selected independently of one another from the group consisting of F, Cl, Br, I, —CN, —NO$_2$, —OH, —SH and —NH$_2$;
in each case optionally in the form of one of their pure stereoisomers, in particular enantiomers or diastereomers, their racemates or in the form of a mixture of stereoisomers, in particular of enantiomers and/or diastereomers, in any desired mixing ratio, or respectively in the form of corresponding salts, or respectively in the form of corresponding solvates.

Preferably, the radicals $R^1$, $R^4$ and $R^2$ have alkylene, alkenylene or alkinylene groups which can be respectively with substituents selected independently of one another from the group consisting of F, Cl, Br, —OH, —SH, —NH$_2$, —CN, —NO$_2$ and phenyl; wherein the phenyl radical can be substituted with 1, 2, 3, 4 or 5 substituents selected independently of one another from the group consisting of F, Cl, Br, I, —CN, —CF$_3$, —O—CH$_3$, —O—C$_2$H$_5$, —NO$_2$, —O—CF$_3$, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —C(=O)—CH$_3$, —C(=O)—C$_2$H$_5$, —C(=O)—C(CH$_3$)$_3$, cyclohexyl, cyclopentyl, —O-phenyl, —O-benzyl and phenyl.

Preferably, the radical $R^2$, in any of the definitions indicated in the present document, can represent an unsubstituted or at least singly substituted phenyl radical, on the condition that not one of the meta positions and the para position of this phenyl radical are substituted with substituents which are respectively bound via an identical atom selected from the group consisting of oxygen, sulphur and nitrogen. This condition rules out the substituents mentioned in a corresponding position in document WO 2005/21515 A1.

Preferably, the radical $R^2$ can comprise a phenyl radical as defined above, an unsubstituted or at least singly substituted phenyl radical which is condensed with an unsubstituted or at least singly substituted mono- or polycyclic ring system, or repesents an unsubstituted or at least singly substituted naphthyl or heteroaryl radical which can be condensed with an unsubstituted or at least singly substituted mono- or polycyclic ring system which is selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl; 2H-benzo[1.4]oxazin-3(4H)-onyl, (3,4)-dihydroquinolin-2(1H)-onyl, [3,4]-dihydro-2H-1,4-benzoxazinyl and benzothiazolyl, wherein the radicals can be respectively unsubstituted or at least singly substituted.

Aliphatic radicals include in the sense of the present invention acyclic saturated or unsaturated hydrocarbon radicals which can be branched or straight chained and unsubstituted or singly substituted or multiply substituted by the same or different substituents, containing preferably 1 to 20 (i.e. 1, 2, 3, 4, 5, 6, 7, 8, 9, 10, 11, 12, 13, 14, 15, 16, 17, 18, 19 or 20), particularly preferably 1 to 12 (i.e. 1, 2, 3, 4, 5, 6, 7, 8, 9, 10, 11 or 12), most particularly preferably 1 to 6 (i.e. 1, 2, 3, 4, 5 or 6) carbon atoms, i.e. $C_{1-20}$, $C_{1-12}$, $C_{1-6}$ alkyls, $C_{2-20}$, $C_{2-12}$, $C_{2-6}$ alkenyls and $C_{2-20}$, $C_{2-12}$, $C_{2-6}$ alkinyls. Alkenyls have at least one C—C double bond and alkinyls at least one C—C triple bond. Advantageously, aliphatic radicals can be selected from the group comprising methyl, ethyl, n-propyl, isopropyl, n-butyl, isobutyl, sec-butyl, tert-butyl, n-pentyl, isopentyl, neo-pentyl, n-hexyl, 2-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosanyl, —(CH$_2$)—(CH$_2$)—(C(CH$_3$)$_3$), —(CH$_2$)—(CH)(C$_2$H$_5$)—(CH$_2$)—(CH$_2$)—(CH$_2$)—(CH$_3$), ethenyl (vinyl), ethinyl, propenyl (—CH$_2$CH=CH$_2$, —CH=CH—CH$_3$, —C(=CH$_2$)—CH$_3$), 2-methylpropenyl, propinyl (—CH$_2$—C≡CH, —C≡C—CH$_3$), butenyl, butinyl, pentenyl, pentinyl, hexenyl, hexinyl, octenyl and octinyl.

The above-mentioned aliphatic radicals can preferably have 1, 2 or 3 heteroatoms selected from the group comprising oxygen, sulphur and nitrogen, i.e. —N(H)— and —N($C_{1-6}$ alkyl), as chain members.

Examples of aliphatic radicals having 1, 2 or 3 heteroatoms include —($CH_2$)—($CH_2$)—O—$CH_3$, —($CH_2$)—($CH_2$)—($CH_2$)—O—$CH_3$, —($CH_2$)—($CH_2$)—($CH_2$)—N($C_2H_5$)($C_2H_5$), —($CH_2$)—($CH_2$)—S—$CH_3$, —($CH_2$)—($CH_2$)—($CH_2$)—S—$CH_3$, —($CH_2$)—($CH_2$)—($CH_2$)—N($CH_3$)—($CH_3$) and —($CH_2$)—O—$CH_3$.

In relation to aliphatic radicals, the term "substituted"—unless otherwise defined—refers in the sense of the present invention to the single or multiple substitution, preferably the single, double, triple, quadruple, quintuple, sextuple, septuple, octuple or nonuple substitution, of one or more hydrogen atoms by, for example, F, Cl, Br, I, —CN, —$NO_2$, —OH, —SH and —$NH_2$, the multiple substitution being carried out either on different or on identical atoms several times, for example twice or three times, for example three times on the same carbon atom as in the case of —$CF_3$ or —$CH_2CF_3$ or at various locations as in the case of —CH(OH)—CH=CCl—$CH_2Cl$. The multiple substitution can be carried out with the same or with different substituents. Preferred substituted aliphatic radicals include —$CH_2$—Cl, —$CH_2$—Br, —$CH_2$—$CH_2$—Cl, —$CH_2$—$CH_2$—Br, —$CH_2$—$CH_2$—$CH_2$—Br and —$CH_2$—$CH_2$—$CH_2$—Cl.

Cycloaliphatic radicals in the sense of the present invention are cyclic saturated or unsaturated hydrocarbon radicals containing preferably 3, 4, 5, 6, 7, 8, 9, 10, 11, 12, 13, 14, 15 or 16, particularly preferably 3, 4, 5, 6, 7 or 8 carbon atoms, wherein each radical can be unsubstituted or singly substituted or multiply substituted by the same or different substituents. Cycloaliphatic radicals can preferably have 1, 2, 3, 4 or 5 heteroatoms selected independently of one another from the group consisting of oxygen, nitrogen (NH) and sulphur as ring members.

Examples of cycloaliphatic radicals, which can optionally be bridged with 1 or 2 linear or branched $C_{1-5}$ alkylene groups and condensed with a mono- or polycyclic ring system, include cyclopropyl, cyclobutyl, cyclopentyl, cyclohexyl, cyclooctyl, cyclononyl, cyclodecyl, cycloundecyl, cyclododecyl, cycloheptyl, cyclopentenyl, cyclohexenyl, cycloheptenyl, [6,6]-dimethyl-[3.1.1]-bicycloheptyl, adamantyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, indanyl, indenyl, (1,4)-benzodioxanyl, (1,2,3,4)-tetrahydronaphthyl, (1,2,3,4)-tetrahydroquinolinyl, (1,2,3,4)-tetrahydroquinazolinyl, (1,3,4,5)-tetrahydropyrido[4,3-b]indolyl, (3,4)-dihydro-1H-isoquinolinyl, (1,3,4,9)-tetrahydro-[b]-carbolinyl, imidazolidinyl, (1,3)-thiazolidinyl, 9H-fluorenyl and 9H-xanthenyl.

A mono- or polycyclic ring system refers in the sense of the present invention to mono- or polycyclic hydrocarbon radicals which are saturated or unsaturated and can optionally have 1, 2, 3, 4 or 5 heteroatom(s) as ring member(s) which are selected independently of one another from the group consisting of oxygen, nitrogen and sulphur. A mono- or polycyclic ring system of this type can, for example, be condensed (anellated) with an aryl radical or a heteroaryl radical.

If a polycyclic ring system such as, for example, a bicyclic ring system is present, the various rings can, each independently of one another, have a differing degree of saturation, i.e. be saturated or unsaturated. Preferably, a polycyclic ring system is a bicyclic ring system.

Examples of aryl radicals which are condensed with a mono- or polycyclic ring system include [1,3]-benzodioxolyl, [1,4]-benzodioxanyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, [3,4]-dihydro-2H-1,4-benzoxazinyl, 2H-benzo[1.4]oxazin-3(4H)-onyl and (3,4)-dihydroquinolin-2(1H)-onyl.

In relation to cycloaliphatic radicals and mono- or polycyclic ring systems, the term "substituted"—unless otherwise defined—refers in the sense of the present invention to the single or multiple substitution, preferably the single, double, triple, quadruple, quintuple, sextuple, septuple, octuple or nonuple substitution, of one or more hydrogen atoms by, for example, oxo (=O), thioxo (=S), F, Cl, Br, I, —CN, —$CF_3$, —$SF_5$, —OH, —O—$C_{1-5}$ alkyl, —$NH_2$, —$NO_2$, —O—$CF_3$, —S—$CF_3$, —SH, —S—$C_{1-5}$ alkyl, —$C_{1-5}$ alkyl, —C(=O)—OH, —C(=O)—O—$C_{1-5}$ alkyl, —O—C(=O)—$C_{1-5}$ alkyl, —NH—$C_{1-5}$ alkyl, —N($C_{1-5}$ alkyl)$_2$, —NH—C(=O)—O—$C_{1-5}$ alkyl, —C(=O)—H, —C(=O)—$C_{1-5}$ alkyl, —C(=O)—$NH_2$, —C(=O)—NH—$C_{1-5}$ alkyl, C(=O)—N—($C_{1-5}$ alkyl)$_2$, —S(=OC)$_2$—$C_{1-5}$ alkyl, —S(=O)$_2$ phenyl, —NH—S(=O)$_2$—$C_{1-5}$ alkyl, —S(=O)$_2$—NH—$C_{1-5}$ alkyl, cyclohexyl, cyclopentyl, morpholinyl, piperidinyl, pyrrolidinyl, piperazinyl, pyridinyl, pyridazinyl, —($CH_2$)-benzo[b]furanyl, —O-phenyl, —O-benzyl, phenyl and benzyl, wherein in each case the cyclic portion of the radicals pyridinyl, cyclopentyl, cyclohexyl, morpholinyl, piperidinyl, pyrrolidinyl, piperazinyl, pyridazinyl, —S(=O)$_2$ phenyl, —O-phenyl, —O-benzyl, phenyl, —($CH_2$)-benzo[b]furanyl and benzyl can be substituted with 1, 2, 3, 4 or 5 substituents selected independently of one another from the group consisting of F, Cl, Br, —OH, —$CF_3$, —$SF_5$, —CN, —$NO_2$, —$C_{1-5}$ alkyl, —O—$C_{1-5}$ alkyl, —O—$CF_3$, —S—$CF_3$, phenyl and —O-benzyl. The multiple substitution be carried out either on different or on identical atoms several times, for example twice or three times. The multiple substitution can be carried out with the same or with different substituents.

The expression aryl radical refers for the purposes of the present invention preferably to a radical which is selected from the group comprising phenyl, naphthyl, phenanthrenyl and anthracenyl and is unsubstituted or singly or multiply substituted by the same or different substituents. Preferably, the aryl is an unsubstituted or singly substituted phenyl, 1-naphthyl or 2-naphthyl or a phenyl, 1-naphthyl or 2-naphthyl substituted several times, for example twice, three, four or five times, by the same or different substituents.

Heteroaryl radicals in the sense of the present invention are heterocycles which are heteroaromatic. Heteroaryl radicals have preferably 5 to 14 members, i.e. 5, 6, 7, 8, 9, 10, 11, 12, 13 or 14 members, and have preferably 1, 2, 3, 4 or 5 heteroatoms selected independently of one another from the group comprising oxygen, nitrogen and sulphur. Each heteroaryl radical can be unsubstituted or singly substituted or substituted several times, for example twice, three, four or five times, by the same or different substituents.

Examples of heteroaryl radicals in the sense of the present invention include thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, benzothiazolyl, benzo[2,1,3]thiadiazolyl, [1,2,3]-benzothiadiazolyl, [2,1,3]-benzoxadiazolyl and [1,2,3]-benzoxadiazolyl.

In relation to aryl and heteroaryl radicals, in the sense of the present invention, "substituted" refers to the single or multiple, for example the single, double, triple, quadruple or quintuple, substitution of one or more hydrogen atoms of the ring system by suitable substituents. Insofar as these suitable substituents are not defined in relation to aryl or heteroaryl radicals elsewhere in the description or in the claims, suitable substituents include F, Cl, Br, I, —CN, —CF$_3$, —SF$_5$, —OH, —O—C$_{1-10}$ alkyl, —NH$_2$, —NO$_2$, —O—CF$_3$, —S—CF$_3$, —SH, —S—C$_{1-5}$ alkyl, —C$_{1-10}$ alkyl, —C(=O)—OH, —C(=O)—O—C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-5}$ alkyl, —NH—S(=O)$_2$—C$_{1-5}$ alkylenephenyl, —NH—S(=O)$_2$—C$_{1-5}$ alkylenenaphthyl, —NH—S(=O)$_2$ phenyl —NH—S(=O)$_2$ naphthyl, —S(=O)$_2$—NH—C$_{1-5}$ alkyl, cyclohexyl, cyclopentyl, morpholinyl, piperidinyl, pyrrolidinyl, piperazinyl, pyridinyl, pyridazinyl, —(CH$_2$)-benzo[b]furanyl, —O-phenyl, —O-benzyl, phenyl and benzyl, wherein in each case the cyclic portion of the radicals pyridinyl, cyclopentyl, cyclohexyl, morpholinyl, piperidinyl, pyrrolidinyl, piperazinyl, pyridazinyl, S(=O)$_2$ phenyl, —O-phenyl, —O-benzyl, phenyl, —(CH$_2$)-benzo[b]furanyl, —NH—S(=O)$_2$—C$_{1-5}$ alkylenephenyl, —NH—S(=O)$_2$—C$_{1-5}$ alkylenenaphthyl, —NH—S(=O)$_2$ phenyl, —NH—S(=O)$_2$ naphthyl and benzyl can be substituted with 1, 2, 3, 4 or 5 substituents selected independently of one another from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl. The multiple substitution is carried out with the same or with different substituents.

The radicals selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, 2H-benzo[1.4]oxazin-3(4H)-onyl, (3,4)-dihydroquinolin-2(1H)-onyl, [3,4]-dihydro-2H-1,4-benzoxazinyl and benzothiazolyl can be substituted like the above-mentioned aryl and heteroaryl radicals.

If R$^2$ represents a substituted phenyl radical, this substituted phenyl radical can particularly preferably be selected from the group consisting of biphenyl, 2-pentafluorosulphanylphenyl, 2-methanesulphonamidephenyl, 2-ethanesulphonamidephenyl, 2-trifluoromethylphenyl, 2-butoxyphenyl, 2-(1,1)-dimethylpropylphenyl, 2-nitrophenyl, 2-ethylbenzoate, 2-acetamidephenyl, 2-dimethylaminophenyl, 2-diethylaminophenyl, 2-aminophenyl, 2-benzenesulphonamide, 2-trifluoromethylsulphanylphenyl, 2-ethylphenyl, 2-tert-butylphenyl, 2-methylbenzoate, 2-methanesulphonylphenyl, 2-ethylaminosulphonylphenyl, 2-methylaminosulphonylphenyl, 2-bromophenyl, 2-chlorophenyl, 2-fluorophenyl, 2-methylphenyl, 2-trifluoromethoxyphenyl, 2-methoxyphenyl, 2-ethoxyphenyl, 2-propylphenyl, 2-cyanophenyl, 2-acetylphenyl, 2-isopropylphenyl, 2-iodophenyl, 3-pentafluorosulphanylphenyl, 3-chlorophenyl, 3-methylphenyl, 3-butoxyphenyl, 3-nitrophenyl, 3-tert-butylphenyl, 3-trifluoromethylsulphanylphenyl, 3-trifluoromethylphenyl, 3-methanesulphonylphenyl, 3-methanesulphonamidephenyl, 3-ethanesulphonamidephenyl, 3-benzenesulphonamide, 3-ethylbenzoate, 3-fluorophenyl, 3-propylphenyl, 3-isopropylphenyl, 3-bromophenyl, 3-dimethylaminophenyl, 3-(1,1)-dimethylpropylphenyl, 3-acetamidephenyl, 3-diethylaminophenyl, 3-aminophenyl, 3-methoxyphenyl, 3-ethylphenyl, 3-ethylaminosulphonylphenyl, 3-methylaminosulphonylphenyl, 3-ethoxyphenyl, 3-cyanophenyl, 3-iodophenyl, 3-trifluoromethoxyphenyl, 3-acetylphenyl, 4-methanesulphonylphenyl, 4-methylaminosulphonylphenyl, 4-ethylaminosulphonylphenyl, 4-methanesulphonamidephenyl, 4-ethanesulphonamidephenyl, 4-pentafluorosulphanylphenyl, 4-bromophenyl, 4-methoxyphenyl, 4-chlorophenyl, 4-benzenesulphonamide, 4-fluorophenyl, 4-tert-butylphenyl, 4-cyanophenyl, 4-butoxyphenyl, 4-nitrophenyl, 4-trifluoromethylsulphanylphenyl, 4-methylphenyl, 4-isopropylphenyl, 4-trifluoromethylphenyl, 4-dimethylaminophenyl, 4-propylphenyl, 4-diethylaminophenyl, 4-ethyl benzoate, 4-aminophenyl, 4-iodophenyl, 4-trifluoromethoxyphenyl, 4-(1,1)-dimethylpropylphenyl, 4-(3,5-dichlorophenylsulphamoyl)phenyl, 4-acetamidephenyl, 4-ethylphenyl, 4-ethoxyphenyl, 4-methylbenzoate, 4-acetylphenyl, 2-fluoro-3-trifluoromethylphenyl, (2,3)-difluorophenyl, (2,3)-dimethylphenyl, (2,3)-dichlorophenyl, 3-fluoro-2-trifluoromethylphenyl, (2,4)-dichlorophenyl, (2,4)-difluorophenyl, 4-fluoro-2-trifluoromethylphenyl, (2,4)-dimethoxyphenyl, 2-chloro-4-fluorophenyl, 2-chloro-4-nitrophenyl, (2,4)-d ibromophenyl, 2-fluoro-4-trifluoromethylphenyl, (2,5)-difluorophenyl, 2-fluoro-5-trifluoromethylphenyl, 5-fluoro-2-trifluoromethylphenyl, 5-chloro-2-trifluoromethyl phenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-methoxy-5-nitrophenyl, 2-fluoro-6-trifluoromethylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl, (2,6)-dibromophenyl, (2,6)-dichlorophenyl, 3-chloro-2-fluorophenyl, (3,4)-dichlorophenyl, 4-chloro-3-nitrophenyl, 4-fluoro-3-trifluoromethylphenyl, 3-fluoro-4-trifluoromethylphenyl, (3,4)-difluorophenyl, 4-chloro-3-trifluoromethyl, 4-bromo-3-methylphenyl, 4-bromo-5-methylphenyl, 3-chloro-4-fluorophenyl, 4-fluoro-3-nitrophenyl, 4-bromo-3-nitrophenyl, (3,4)-dibromophenyl, 4-chloro-3-methylphenyl, 4-bromo-3-methylphenyl, 4-fluoro-3-methylphenyl, 4-methyl-3-nitrophenyl, (3,5)-dimethoxyphenyl, (3,5)-bis-trifluoromethylphenyl, (3,5)-difluorophenyl, (3,5)-dinitrophenyl, (3,5)-dichlorophenyl, 3-fluoro-5-trifluoromethylphenyl, 5-fluoro-3-trifluoromethylphenyl, (3,5)-dibromophenyl, 5-chloro-4-flubrophenyl, 5-bromo-4-methylphenyl, (2,3,4)-trifluorophenyl, (2,3,4)-trichlorophenyl, (2,3,6)-trifluorophenyl, 5-chloro-2-methoxyphenyl, (2,3)-difluoro-4-methylphenyl, (2,4,5)-trifluorophenyl, (2,4,5)-trichlorophenyl, (2,4)-dichloro-5-fluorophenyl, (2,4,6)-trichlorophenyl, (2,4,6)-trimethylphenyl, (2,4,6)-trifluorophenyl, (2,4,6)-trimethoxyphenyl, (2,3,4,5)-tetrafluorophenyl, 4-methoxy-2,3,6-trimethylphenyl, 4-methoxy-2,3,6-trimethylphenyl, 4-chloro-2,5-dimethylphenyl, 2-chloro-6-fluoro-3-methylphenyl, 6-chloro-2-fluoro-3-methyl, (2,3,4,5,6)-pentafluorophenyl, 3-fluoro-4-methylsulphonamidophenyl, 3-chloro-4-methylsulphonamidophenyl, 3-bromo-4-methylsulphonamidophenyl, 3-methoxy-4-methylsulphonamidophenyl, 3-hydroxy-4-methylsulphonamidophenyl, 3-trifluoromethyl-4-methylsulphonamidophenyl, 3-trifluoromethoxy-4-methylsulphonamidophenyl, 3-methyl-4-methylsul phonamidophenyl, 3-ethyl-4-methylsulphonamidophenyl, 3-isopropyl-4-methylsulphonamidophenyl, 3-propyl-4-methylsulphonamidophenyl, 3-tert-butyl-4-methylsulphonamidophenyl, 3-fluoro-4-phenylsulphonamidophenyl, 3-chloro-4-phenylsulphonamidophenyl, 3-bromo-4-phenyl sulphonamidophenyl, 3-methoxy-4- phenylsulphonamidophenyl, 3-hydroxy-4-phenylsulphonamidophenyl, 3-trifluoromethyl-4-phenylsulphonamidophenyl, 3-trifluoromethoxy-4-phenylsulphonamidophenyl, 3-methyl-4-phenylsulphonamidophenyl, 3-ethyl-4-phenylsulphonamidophenyl, 3-isopropyl-4-phenylsulphonamidophenyl, 3-propyl-4-phenylsulphonamidophenyl, 3-tert-butyl-4-phenylsulphonamidophenyl, 4-fluoro-3-methylsulphonamidophenyl, 4-chloro-3-methylsulphonamidophenyl, 4-bromo-3-methylsulphonamidophenyl, 4-methoxy-3-methylsulphonamidophenyl, 4-hydroxy-3-methylsulphonamidophenyl, 4-trifluoromethyl-3-methylsulphonamidophenyl, 4-trifluoromethoxy-3-methylsulphonamidophenyl, 4-methyl-3-methylsulphonamidophenyl, 4-ethyl-3-methylsulphonamidophenyl, 4-isopropyl-3-methylsulphonamidophenyl, 4-propyl-3-methylsulphonamidophenyl, 4-tert-butyl-3-methylsulphonamidophenyl, 4-fluoro-3-phenylsulphonamidophenyl, 4-chloro-3-phenylsulphonamidophenyl, 4-bromo-3-phenylsulphonamidophenyl, 4-methoxy-3-phenylsulphonamidophenyl, 4-hydroxy-3-phenylsulphonamidophenyl, 4-trifluoromethyl-3-phenylsulphonamidophenyl, 4-trifluoromethoxy-3-phenylsulphonamidophenyl, 4-methyl-3-phenylsulphonamidophenyl, 4-ethyl-3-phenylsulphonamidophenyl, 4-isopropyl-3-phenylsulphonamidophenyl, 4-propyl-3-phenylsulphonamidophenyl, 4-tert-butyl-3-phenylsulphonamidophenyl, 2-cyclohexylphenyl, 3-cyclohexylphenyl and 4-cyclohexylphenyl.

The above-mentioned linear or branched alkylene, alkenylene or alkinylene groups preferably have 1 to 5 carbon atoms, i.e. the groups are $C_{1-5}$ alkylene, $C_{2-5}$ alkenylene or $C_{2-5}$ alkinylene groups which can be respectively unsubstituted or substituted with 1, 2, 3, 4 or 5 substituents selected independently of one another from the group consisting of F, Cl, Br, —OH, —SH, —NH$_2$, —CN, —NO$_2$ and phenyl, wherein the phenyl radical can be substituted with 1, 2, 3, 4 or 5 substituents selected independently of one another from the group consisting of methyl, ethyl, n-propyl, isopropyl, n-butyl, isobutyl, sec-butyl, tert-butyl, n-pentyl, isopentyl and neo-pentyl.

The above-mentioned alkylene, alkenylene or alkinylene groups optionally each have 1 or 2 heteroatom(s) selected from the group consisting of oxygen, nitrogen, i.e.—N(H)— and —N($C_{1-6}$ alkyl)-, and sulphur as chain member(s).

Preferably, alkylene groups can be selected from the group consisting of —(CH$_2$)—, —(CH$_2$)$_2$—, —C(H)(CH$_3$)—, —C(CH$_3$)$_2$—, —(CH$_2$)$_3$—, —(CH$_2$)$_4$—, —(CH$_2$)$_5$—, —C(H)(CH$_3$)—(CH$_2$)—, —C(H)(C$_2$H$_5$)—(CH$_2$)—, —C(phenyl)$_2$-, —C(H)(phenyl)-, —(CH$_2$)—O—, —(CH$_2$)—N(CH$_3$)—, —(CH$_2$)—S—, —(CH$_2$)—(CH$_2$)—N(CH$_3$)— and —(CH$_2$)—(CH$_2$)—N(C$_2$H$_5$)—.

Preferably, alkenylene groups can be selected from the group consisting of —CH═CH—, —C(CH$_3$)═CH—, —C(C$_2$H$_5$)═CH—, —CH═C(CH$_3$)—, —CH═C(C$_2$H$_5$)—, —CH═C(phenyl)-, —CH═C(p-tolyl), —C(phenyl)═CH— and —C(p-tolyl)═CH—.

The alkinylene group is preferably a —C≡C— group.

Preferred are substituted spiro compounds of the above-indicated general formula I, wherein
m is equal to 0, 1, 2, 3 or 4,
n is equal to 0, 1 or 2, $R^1$ represents an unsaturated or saturated, optionally substituted 3, 4, 5, 6, 7, 8 or 9-membered cycloaliphatic radical which can be condensed with a saturated, unsaturated or aromatic, optionally substituted mono- or polycyclic ring system;
an optionally substituted 5 to 14-membered aryl or heteroaryl radical which can be condensed with a saturated or unsaturated, optionally substituted mono- or polycyclic ring system,
a —C(═O)—NR$^5$R$^6$ group,
a —C(═S)—NR$^7$R$^8$ group,
a —C(═O)—R$^9$ group,
an —S(═O)$_2$—R$^{10}$ group,
or —(CHR$^{13}$)—(CHR$^{14}$)$_f$—(CHR$^{15}$)$_h$—R$^{16}$ wherein f=0 or 1 and h=0 or 1;
$R^2$ a linear or branched, saturated or unsaturated, optionally substituted $C_{1-10}$ aliphatic radical;
an unsaturated or saturated, optionally substituted 3, 4, 5, 6, 7, 8 or 9-membered cycloaliphatic radical which can be condensed with a saturated, unsaturated or aromatic, optionally substituted mono- or polycyclic ring system;
a phenyl radical which can be substituted with 1, 2, 3, 4 or 5 substituents selected independently of one another from the group consisting of F, Cl, Br, I, —CN, —CF$_3$, —SF$_5$, —OH, —O—$C_{1-5}$ alkyl, —NH$_2$, —NO$_2$, —O—CF$_3$, —S—CF$_3$, —SH, —S—$C_{1-5}$ alkyl, —$C_{1-10}$ alkyl, —C(═O)—OH, —C(═O)—O—$C_{1-5}$ alkyl, —O—C(═O)—$C_{1-5}$ alkyl, —NH—$C_{1-5}$ alkyl, —N($C_{1-5}$ alkyl)$_2$, —NH—C(═O)—O—$C_{1-5}$ alkyl, —C(═O)—H, —C(═O)—$C_{1-5}$ alkyl, —C(═O)—NH$_2$, —C(═O)—NH—$C_{1-5}$ alkyl, C(═O)—N—($C_{1-5}$ alkyl)$_2$, —S(═O)$_2$—$C_{1-5}$ alkyl, —S(═O)$_2$ phenyl, —NH—S(═O)$_2$—$C_{1-5}$ alkyl, —NH—S(═O)$_2$—$C_{1-5}$ alkylenephenyl, —NH—S(═O)$_2$—$C_{1-5}$ alkylenenaphthyl, —NH—S(═O)$_2$ phenyl, —NH—S(═O)$_2$ naphthyl, cyclohexyl, cyclopentyl, morpholinyl, piperidinyl, piperazinyl, pyrrolidinyl, pyridinyl, pyridazinyl, —(CH$_2$)-benzo[b]furanyl, —O-phenyl, —O-benzyl, phenyl and benzyl, wherein in each case the cyclic portion of the radicals pyridinyl, cyclopentyl, cyclohexyl, morpholinyl, piperidinyl, piperazinyl, pyrrolidinyl, pyridazinyl, —S(═O)$_2$ phenyl, —O-phenyl, —O-benzyl, phenyl, —(CH$_2$)— benzo[b]furanyl, —NH—S(═O)$_2$—$C_{1-5}$ alkylenephenyl, —NH—S(═O)$_2$—$C_{1-5}$ alkylenenaphthyl, —NH—S(═O)$_2$ phenyl, —NH—S(═O)$_2$ naphthyl and benzyl can be substituted with 1, 2, 3, 4 or 5 substituents selected independently of one another from the group consisting of F, Cl, Br, —OH, —CF$_3$, —SF$_5$, —CN, —NO$_2$, —$C_{1-5}$ alkyl, —O—$C_{1-5}$ alkyl, —O—CF$_3$, —S—CF$_3$, phenyl and —O-benzyl,
on the condition that not one of the meta positions and the para position of this phenyl radical are substituted with substituents which are respectively bound to the phenyl radical via an identical atom selected from the group consisting of oxygen, sulphur and nitrogen;
represents an optionally substituted radical selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, 2H-benzo[1.4]oxazin-3(4H)-onyl, (3,4)-dihydroquinolin-2(1H)-onyl, [3,4]-dihydro-2H-1,4-benzoxazinyl and benzothiazolyl, or represents —(CHR$^{17}$)—X$_q$—(CHR$^{18}$)$_r$—Y$_s$—CHR$^{19}$)$_t$—Z$_u$—R$^{20}$ wherein q=0 or 1, r=0 or 1, s=0 or 1, t=0 or 1, u=0 or 1, wherein X, Y and Z, independently of one another, each represent O, S, NH, N(CH$_3$), N(C$_2$H$_5$) or N[CH(CH$_3$)$_2$];

R$^3$ represents a halogen radical, a nitro group, a hydroxy group, a thiol group; an —O—R$^{11}$ group, an —S—R$^{12}$ group, or a linear or branched, saturated or unsaturated, optionally substituted C$_{1-10}$ aliphatic radical;

R$^4$ represents a hydrogen radical, a halogen radical, a nitro group, a hydroxy group, a thiol group; an oxo group (=O), an —O—R$^{11}$ group, an —S—R$^{12}$ group, or a linear or branched, saturated or unsaturated, optionally substituted C$_{1-10}$ aliphatic radical;

R$^5$ and R$^7$, independently of one another, each
  represent a linear or branched, saturated or unsaturated, optionally substituted C$_{1-20}$ aliphatic radical;
  an unsaturated or saturated, optionally substituted 3, 4, 5, 6, 7, 8, 9, 10, 11 or 12-membered cycloaliphatic radical which can be condensed with a saturated, unsaturated or aromatic, optionally substituted mono- or polycyclic ring system and/or bridged with one or two linear or branched, optionally substituted C$_{1-5}$ alkylene groups;
  an optionally substituted 5 to 14-membered aryl or heteroaryl radical which can be condensed with a saturated or unsaturated, optionally substituted mono- or polycyclic ring system;
  or —(CR$^{21}$R$^{22}$)—X$_v$—(CHR$^{23}$)$_w$—Y$_x$—(CHR$^{24}$)$_y$—Z$_z$—R$^{25}$ wherein v=0 or 1, w=0 or 1, x=0 or 1, y=0 or 1, z=0 or 1, wherein X, Y and Z, independently of one another, each represent O, S, NH, N(CH$_3$), N(C$_2$H$_5$) or N[CH(CH$_3$)$_2$];

R$^6$ and R$^8$, independently of one another, each
  represent a hydrogen radical;
  a linear or branched, saturated or unsaturated, optionally substituted C$_{1-20}$ aliphatic radical;
  an unsaturated or saturated, optionally substituted 3, 4, 5, 6, 7, 8, 9, 10, 11 or 12-membered cycloaliphatic radical which can be condensed with a saturated, unsaturated or aromatic, optionally substituted mono- or polycyclic ring system and/or bridged with one or two linear or branched, optionally substituted C$_{1-5}$ alkylene groups;
  an optionally substituted 5 to 14-membered aryl or heteroaryl radical which can be condensed with a saturated or unsaturated, optionally substituted mono- or polycyclic ring system;
  or —(CR$^{21}$R$^{22}$)—X$_v$—(CHR$^{23}$)$_w$—Y$_x$—(CHR$^{24}$)$_y$—Z$_z$—R$^{25}$ wherein v=0 or 1, w=0 or 1, x=0 or 1, y=0 or 1, z=0 or 1, wherein X, Y and Z, independently of one another, each represent O, S, NH, N(CH$_3$), N(C$_2$H$_5$) or N[CH(CH$_3$)$_2$];

R$^9$ and R$^{10}$, independently of one another, each
  represent a linear or branched, saturated or unsaturated, optionally substituted C$_{1-10}$ aliphatic radical;
  an unsaturated or saturated, optionally substituted 3, 4, 5, 6, 7, 8 or 9-membered cycloaliphatic radical which can be condensed with a saturated, unsaturated or aromatic, optionally substituted mono- or polycyclic ring system;
  an optionally substituted 5 to 14-membered aryl or heteroaryl radical which can be condensed with a saturated or unsaturated, optionally substituted mono- or polycyclic ring system,
  —(CR$^{26}$R$^{27}$)—(CHR$^{28}$)$_{aa}$—(CHR$^{29}$)$_{bb}$—R$^{30}$ wherein aa=0 or 1 and bb =0 or 1;
  —CR$^{31}$=CR$^{32}$—R$^{33}$
  or —C≡C—R$^{34}$;

R$^{11}$ and R$^{12}$, independently of one another, each
  represent a linear or branched, saturated or unsaturated C$_{1-10}$ aliphatic radical;
  an unsaturated or saturated 3, 4, 5, 6, 7, 8 or 9-membered cycloaliphatic radical which can be condensed with a saturated, unsaturated or aromatic mono- or polycyclic ring system;
  or a 5 to 14-membered aryl or heteroaryl radical which can be condensed with a saturated or unsaturated mono- or polycyclic ring system;

R$^{13}$, R$^{14}$, R$^{15}$, R$^{17}$, R$^{18}$, R$^{19}$, R$^{21}$, R$^{22}$, R$^{23}$, R$^{24}$, R$^{2}$, R$^{29}$ and R$^{31}$, independently of one another, each
  represent a hydrogen radical;
  a linear or branched, saturated or unsaturated, optionally substituted C$_{1-10}$ aliphatic radical,
  or an optionally substituted 5 to 14-membered aryl or heteroaryl radical which can be condensed with a saturated or unsaturated, optionally substituted mono- or polycyclic ring system;

R$^{26}$ and R$^{27}$, independently of one another, each
  represent a hydrogen radical;
  a linear or branched, saturated or unsaturated, optionally substituted C$_{1-10}$ aliphatic radical,
  an optionally substituted 5 to 14-membered aryl or heteroaryl radical which can be condensed with a saturated or unsaturated, optionally substituted mono- or polycyclic ring system;
  or —OH;

R$^{32}$ represents a hydrogen radical;
  a linear or branched, saturated or unsaturated, optionally substituted C$_{1-10}$ aliphatic radical,
  an optionally substituted 5 to 14-membered aryl or heteroaryl radical which can be condensed with a saturated or unsaturated, optionally substituted mono- or polycyclic ring system;
  or represents —(CH$_2$)$_{cc}$—R$^{35}$ wherein cc=1, 2, 3 or 4 or represents —CH=CH—R$^{36}$;

R$^{16}$, R$^{20}$, R$^{25}$, R$^{30}$, R$^{33}$ and R$^{34}$, independently of one another, each
  represent a linear or branched, saturated or unsaturated, optionally substituted C$_{1-10}$ aliphatic radical,
  an unsaturated or saturated, optionally substituted 3, 4, 5, 6, 7, 8 or 9-membered cycloaliphatic radical which can be bridged with 1, 2, 3, 4 or 5 linear or branched, optionally substituted C$_{1-5}$ alkylene groups and/or condensed with a saturated, unsaturated or aromatic, optionally substituted mono- or polycyclic ring system;
  or an optionally substituted 5 to 14-membered aryl or heteroaryl radical which can be condensed with a saturated or unsaturated, optionally substituted mono- or polycyclic ring system;

and

R$^{35}$ and R$^{36}$, independently of one another, each
  represent an optionally substituted 6 or 10-membered aryl radical which can be condensed with a saturated or unsaturated, optionally substituted mono- or polycyclic ring system;

wherein
the above-mentioned C$_{1-10}$ aliphatic radicals and C$_{1-20}$ aliphatic radicals can in each case optionally be substituted with 1, 2, 3, 4, 5, 6, 7, 8 or 9 substituents selected independently of one another from the group consisting of F, Cl, Br, I, —CN, —NO$_2$, —OH, —SH and —NH$_2$;

the above-mentioned cycloaliphatic radicals can in each case optionally be substituted with 1, 2, 3, 4 or 5 substituents selected independently of one another from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—OH, —C(=O)—O—C$_{1-5}$ alkyl, —O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-15}$ alkyl, —S(=O)$_2$—NH—C$_{1-5}$ alkyl, cyclohexyl, cyclopentyl, pyridinyl, pyridazinyl, —(CH$_2$)-benzo[b]furanyl, —O-phenyl, —O-benzyl, phenyl and benzyl, wherein in each case the cyclic portion of the radicals pyridinyl, cyclopentyl, cyclohexyl, pyridazinyl, —S(=O)$_2$ phenyl, —O-phenyl, —O-benzyl, phenyl, —(CH$_2$)-benzo[b]furanyl and benzyl can be substituted with 1, 2, 3, 4 or 5 substituents selected independently of one another from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl,
and the above-mentioned cycloaliphatic radicals can in each case optionally have 1, 2, 3, 4 or 5 heteroatom(s) selected independently of one another from the group consisting of oxygen, nitrogen and sulphur as ring member(s);
the rings of the above-mentioned mono- or polycyclic ring systems can in each case optionally be substituted with 1, 2, 3, 4 or 5 substituents selected independently of one another from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—OH, —C(=O)—O—C$_{1-5}$ alkyl, —O—C(=O)—C$_{1-5}$ alkyl, —NH—C$_{1-15}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-5}$ alkyl, —S(=O)$_2$—NH—C$_{1-5}$ alkyl, cyclohexyl, cyclopentyl, morpholinyl, piperidinyl, pyrrolidinyl, piperazinyl, pyridinyl, pyridazinyl, —(CH$_2$)-benzo[b]furanyl, —O-phenyl, —O-benzyl, phenyl and benzyl, wherein in each case the cyclic portion of the radicals pyridinyl, cyclopentyl, cyclohexyl, morpholinyl, piperidinyl, pyrrolidinyl, piperazinyl, pyridazinyl, —S(=O)$_2$ phenyl, —O-phenyl, —O-benzyl, phenyl, —(CH$_2$)-benzo[b]furanyl and benzyl can be substituted with 1, 2, 3, 4 or 5 substituents selected independently of one another from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl,
and the rings of the above-mentioned mono- or polycyclic ring systems each have 5, 6 or 7 members and can in each case optionally have 1, 2, 3, 4 or 5 heteroatom(s) as ring member(s) which are selected independently of one another from the group consisting of oxygen, nitrogen and sulphur;
and, unless otherwise indicated, the above-mentioned radicals selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, 2H-benzo[1.4]oxazin-3(4H)-onyl, (3,4)-dihydroquinolin-2(1H)-onyl, [3,4]-dihydro-2H-1,4-benzoxazinyl and benzothiazolyl and aryl or heteroaryl radicals can in each case optionally be substituted with 1, 2, 3, 4 or 5 substituents selected independently of one another from the group consisting of F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-10}$ alkyl, —C(=O)—OH, —C(=O)—O—C$_{1-5}$ alkyl, —O—C(=O)—C$_{1-15}$ alkyl, —NH—C$_{1-5}$ alkyl, —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-15}$ alkyl, C(=O)—N—(C$_{1-5}$ alkyl)$_2$, —S(=O)$_2$—C$_{1-5}$ alkyl, —S(=O)$_2$ phenyl, —NH—S(=O)$_2$—C$_{1-5}$ alkyl, —NH—S(=O)$_2$—C$_{1-5}$ alkylenephenyl, —NH—S(=O)$_2$—C$_{1-5}$ alkylenenaphthyl, —NH—S(=O)$_2$ phenyl, —NH—S(=O)$_2$ naphthyl, cyclohexyl, cyclopentyl, morpholinyl, piperidinyl, piperazinyl, pyrrolidinyl, pyridinyl, pyridazinyl, —(CH$_2$)-benzo[b]furanyl, —O-phenyl, —O-benzyl, phenyl and benzyl, wherein in each case the cyclic portion of the radicals pyridinyl, cyclopentyl, cyclohexyl, morpholinyl, piperidinyl, piperazinyl, pyrrolidinyl, pyridazinyl, —S(=O)$_2$ phenyl, —O-phenyl, —O-benzyl, phenyl, —(CH$_2$)— benzo[b]furanyl, —NH—S(=O)$_2$—C$_{1-5}$ alkylenephenyl, —NH—S(=O)$_2$—C$_{1-5}$ alkylenenaphthyl, —NH—S(=O)$_2$ phenyl, —NH—S(=O)$_2$ naphthyl and benzyl can be substituted with 1, 2, 3, 4 or 5 substituents selected independently of one another from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl,
the above-mentioned heteroaryl radicals can in each case optionally have 1, 2, 3, 4 or 5 heteroatom(s) selected independently of one another from the group consisting of oxygen, nitrogen and sulphur as ring member(s);
and
the above-mentioned C$_{1-5}$ alkylene groups can in each case optionally be substituted with 1, 2, 3, 4 or 5 substituents selected independently of one another from the group consisting of F, Cl, Br, —OH, —SH, —NH$_2$, —CN and NO$_2$;
in each case optionally in the form of one of their pure stereoisomers, in particular enantiomers or diastereomers, their racemates or in the form of a mixture of stereoisomers, in particular of enantiomers and/or diastereomers, in any desired mixing ratio, or respectively in the form of corresponding salts, or respectively in the form of corresponding solvates.

A person skilled in the art will understand that for m is equal to 0, the following general formula Ia is obtained:

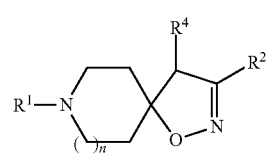

Ia

Also preferred are substituted spiro compounds of the above-indicated general formula I, wherein
n is equal to 0, 1 or 2;
and m and R$^1$ to R$^{36}$ are each as defined above, in each case optionally in the form of one of their pure stereoisomers, in particular enantiomers or diastereomers, their racemates or in the form of a mixture of stereoisomers, in particular of enantiomers and/or diastereomers, in any desired mixing ratio, or respectively in the form of corresponding salts, or respectively in the form of corresponding solvates.

A person skilled in the art will understand that for n is equal to 1, the following general formula Ib is obtained:

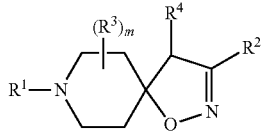

Ib

Particularly preferred are substituted spiro compounds of the above-indicated general formula I, wherein m is equal to 0, 1, 2, 3 or 4;

n is equal to 0, 1 or 2 ist;

$R^1$ represents a (hetero)cycloaliphatic radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;

represents a radical selected from the group consisting of indolyl, isoindolyl, benzo[b]furanyl, benzo[b]thiophenyl, indazolyl, quinazolinyl, quinoxalinyl, quinolinyl, isoquinolinyl, benzimidazolyl, benzoxazolyl, benzotriazolyl, benzisoxazolyl and benzothiazolyl, wherein the radical can in each case optionally be substituted with 1, 2, 3, 4 or 5 substituents selected independently of one another from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$;

represents a —C(=O)—NR$^5$R$^6$ group;

represents a —C(=S)—NR$^7$R$^8$ group;

a —C(=O)—R$^9$ group, an —S(=O)$_2$—R$^{10}$ group, or represents —(CHR$^{13}$)—R$^{16}$; —(CHR$^{13}$)—(CHR$^{14}$)—R$^{16}$ or —(CHR$^{13}$)—(CHR$^{14}$)—(CHR$^{15}$)—R$^{16}$;

$R^2$ represents a radical selected from the group consisting of methyl, ethyl, n-propyl, isopropyl, n-butyl, sec-butyl, isobutyl, tert-butyl, n-pentyl, sec-pentyl, n-hexyl and n-heptyl;

represents a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;

a phenyl radical which can be substituted with 1, 2, 3, 4 or 5 substituents selected independently of one another from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, cyclopentyl, cyclohexyl, —S(=O)$_2$—CH$_3$, —S(=O)$_2$—C$_2$H$_5$, —NH—S(=O)$_2$—CH$_3$, —NH—S(=O)$_2$—C$_2$H$_5$, —NH—S(=O)$_2$ phenyl, —S(=O)$_2$—NH—CH$_3$ and —S(=O)$_2$—NH—C$_2$H$_5$;

on the condition that not one of the meta positions and the para position of this phenyl radical are substituted with substituents which are respectively bound to the phenyl radical via an identical atom selected from the group consisting of oxygen, sulphur and nitrogen;

represents a radical selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, 2H-benzo[1.4]oxazin-3(4H)-onyl, (3,4)-dihydroquinolin-2(1H)-onyl, [1,2,3,4]-tetrahydroquinazolinyl, [3,4]-dihydro-2H-1,4-benzoxazinyl and benzothiazolyl, wherein the radical can in each case optionally be substituted with 1, 2, 3, 4 or 5 substituents selected independently of one another from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —S(=O)$_2$—CH$_3$, —S(=O)$_2$—C$_2$H$_5$, —NH—S(=O)$_2$—CH$_3$, —NH—S(=O)$_2$—C$_2$H$_5$, —S(=O)$_2$—NH—CH$_3$ and —S(=O)$_2$—NH—C$_2$H$_5$;

or represents —(CHR$^{17}$)—R$^{20}$, —(CHR$^{17}$)—(CHR$^{18}$)—R$^{20}$ or —(CHR$^{17}$)—(CHR$^{18}$)—(CHR$^{19}$)—R$^{20}$;

$R^3$ represents a radical selected from the group consisting of methyl, ethyl, n-propyl, isopropyl, n-butyl, sec-butyl, isobutyl, tert-butyl, n-pentyl, sec-pentyl, n-hexyl and n-heptyl;

$R^4$ represents a hydrogen radical or represents a radical selected from the group consisting of methyl, ethyl, n-propyl, isopropyl, n-butyl, sec-butyl, isobutyl, tert-butyl, n-pentyl, sec-pentyl, n-hexyl and n-heptyl;

$R^5$ and $R^7$, independently of one another, each represent a radical selected from the group consisting of methyl, ethyl, n-propyl, isopropyl, n-butyl, sec-butyl, isobutyl, tert-butyl, n-pentyl, sec-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosanyl, vinyl, 1-propenyl, 2-propenyl, 1-butenyl, 2-butenyl, 3-butenyl, 2-methyl-1-propenyl, ethinyl, 1-propinyl, 2-propinyl, 1-butinyl, 2-butinyl and 3-butinyl, wherein the radical can in each case optionally be substituted with 1, 2, 3, 4 or 5 substituents selected independently of one another from the group consisting of F, Cl and Br;

represent a radical selected from the group consisting of cyclopropyl, cyclobutyl, cyclopentyl, cyclohexyl, cycloheptyl, cyclooctyl, cyclononyl, cyclodecyl, cycloundecyl, cyclododecyl, cyclopentenyl, cyclohexenyl, cycloheptenyl, adamantyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, indanyl and indenyl; wherein the radical can in each case optionally be substituted with 1, 2 or 3 substituents selected independently of one another from the group consisting of methyl, ethyl, n-propyl, isopropyl, n-butyl, sec-butyl, isobutyl and tert-butyl;

represent a radical selected from the group consisting of phenyl, (1,3)-benzodioxolyl, (1,4)-benzodioxanyl, naphthyl, thiophenyl, furanyl, pyrrolyl, pyrazolyl, pyranyl, pyridinyl, imidazolyl, thiazolyl, oxazolyl, isoxazolyl, pyridazinyl, pyrazinyl and pyrimidinyl, wherein the radical can in each case optionally be substituted with 1, 2, 3, 4 or 5 substituents selected independently of one another from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—C($CH_3$)$_3$, —O—C(=O)—$CH_3$, —O—C(=O)—$C_2H_5$, —O—C(=O)—C($CH_3$)$_3$, —N($CH_3$)$_2$, —N($C_2H_5$)$_2$, —NH—$CH_3$, —NH—$C_2H_5$, —NH—C(=O)—O—$CH_3$, —NH—C(=O)—O—$C_2H_5$, —NH—C(=O)—O—C($CH_3$)$_3$, —C(=O)—H, —C(=O)—$CH_3$, —C(=O)—$C_2H_5$, —C(=O)—C($CH_3$)$_3$, —C(=O)—$NH_2$, —C(=O)—NH—$CH_3$, —C(=O)—NH—$C_2H_5$, —C(=O)—N($CH_3$)$_2$, —C(=O)—N—($C_2H_5$)$_2$, —S(=O)$_2$—$CH_3$, —S(=O)$_2$—$C_2H_5$, —S(=O)$_2$ phenyl, —NH—S(=O)$_2$—$CH_3$, —NH—S(=O)$_2$—$C_2H_5$, —S(=O)$_2$—NH—$CH_3$, —S(=O)$_2$—NH—$C_2H_5$, cyclohexyl, cyclopentyl, pyridinyl, pyridazinyl, —($CH_2$)-benzo[b]furanyl, —O-phenyl, —O-benzyl, phenyl and benzyl, wherein in each case the cyclic portion of the radicals pyridinyl, cyclopentyl, cyclohexyl, pyridazinyl, —S(=O)$_2$ phenyl, —O-phenyl, —O-benzyl, phenyl, —($CH_2$)— benzo[b]furanyl and benzyl can be substituted with 1, 2, 3, 4 or 5 substituents selected independently of one another from the group consisting of F, Cl, Br, —OH, —$CF_3$, —$SF_5$, —CN, —$NO_2$, methyl, ethyl, n-propyl, isopropyl, n-butyl, sec-butyl, isobutyl, tert-butyl, —O—$CH_3$, —O—$C_2H_5$, —O—$CF_3$, —S—$CF_3$, phenyl and —O-benzyl;

or represent —($CR^{21}R^{22}$)—$R^{25}$, —($CR^{21}R^{22}$)—($CHR^{23}$)—$R^{25}$, —($C^{21}R^{22}$)—($CHR^{23}$)—O—$R^{25}$, —($CR^{21}R^{22}$)—($CHR^{23}$)—($CHR^{24}$)—$R^{25}$, —($CR^{21}R^{22}$)—($CHR^{23}$)—($CHR^{24}$)—O—$R^{25}$, ($CR^{21}R^{22}$)—($CHR^{23}$)—($CHR^{24}$)—N($CH_3$)—$R^{25}$ or —($CR^{21}R^{22}$)—($CHR^{23}$)—($CHR^{24}$)—N($C_2H_5$)—$R^{25}$;

$R^6$ and $R^8$ each represent a hydrogen radical;

or a radical selected from the group consisting of methyl, ethyl, n-propyl, isopropyl, n-butyl, sec-butyl, isobutyl and tert-butyl;

$R^9$ and $R^{10}$, independently of one another, each represent a radical selected from the group consisting of 9H-fluorenyl, 9H-xanthenyl, phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl and benzothiazolyl, wherein the radical can in each case optionally be substituted with 1, 2, 3, 4 or 5 substituents selected independently of one another from the group consisting of F, Cl, Br, I, —CN, —$CF_3$, —O—$CF_3$, —S—$CF_3$, —$SF_5$, —OH, —O—$CH_3$, —O—$C_2H_5$, —NH—S(=O)$_2$—$CH_3$, morpholinyl, piperidinyl, pyrrolidinyl, piperazinyl, phenyl, methyl, ethyl, n-propyl, isopropyl, n-butyl, sec-butyl, isobutyl, tert-butyl, n-pentyl, n-hexyl, n-heptyl and n-octyl;

represent —($CR^{26}R^{27}$)—$R^{30}$, —($CR^{26}R^{27}$)—($CHR^{28}$)—$R^{30}$, —($CR^{26}R^{27}$)—($CHR^{28}$)—($CHR^2$)—$R^{30}$, —$CR^{31}$=$CR^{32}$—$R^{33}$ or —C=C—$R^{34}$;

$R^{13}$, $R^{14}$, $R^{15}$, $R^{17}$, $R^{18}$, $R^{19}$, $R^{21}$, $R^{22}$, $R^{23}$, $R^{24}$, $R^{28}$, $R^{29}$ and $R^{31}$, independently of one another, each represent a hydrogen radical;

represent a radical selected from the group consisting of methyl, ethyl, n-propyl, isopropyl, n-butyl, sec-butyl, isobutyl and tert-butyl;

or represent a phenyl radical which can be substituted with 1, 2, 3, 4 or 5 substituents selected independently of one another from the group consisting of F, Cl, Br, I, —CN, —$CF_3$, —O—$CH_3$, —O—$C_2H_5$, —$NO_2$, —O—$CF_3$, methyl, ethyl, n-propyl, isopropyl, n-butyl, sec-butyl, isobutyl and tert-butyl;

$R^{16}$ represents a radical selected from the group consisting of phenyl, naphthyl, thiophenyl, furanyl, pyrrolyl, pyrazolyl, pyrazinyl and pyridinyl, wherein the radical can in each case optionally be substituted with 1, 2, 3, 4 or 5 substituents selected independently of one another from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—C($CH_3$)$_3$, —O—C(=O)—$CH_3$, —O—C(=O)—$C_2H_5$, —O—C(=O)—C($CH_3$)$_3$, —S(=O)$_2$—$CH_3$, —S(=O)$_2$—$C_2H_5$, —NH—S(=O)$_2$—$CH_3$, —NH—S(=O)$_2$—$C_2H_5$, —S(=O)$_2$—NH—$CH_3$ and —S(=O)$_2$—NH—$C_2H_5$;

$R^{20}$ represents a radical selected from the group consisting of phenyl and naphthyl, wherein the radical can in each case optionally be substituted with 1, 2, 3, 4 or 5 substituents selected independently of one another from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, n-pentyl, n-hexyl, n-heptyl and n-octyl;

$R^{25}$ represents a radical selected from the group consisting of methyl, ethyl, n-propyl, isopropyl, n-butyl, sec-butyl, isobutyl and tert-butyl;

represents a radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl;

or represents a radical selected from the group consisting of phenyl, naphthyl, (1,3)-benzodioxolyl, (1,4)-benzodioxanyl, thiophenyl and furanyl, wherein the radical can in each case optionally be substituted with 1, 2, 3, 4 or 5 substituents selected independently of one another from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—C($CH_3$)$_3$, —O—C(=O)—$CH_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$ and —C(=O)—C(CH$_3$)$_3$;

R$^{26}$ and R$^{27}$, independently of one another, each
represent a hydrogen radical;
represent a radical selected from the group consisting of methyl, ethyl, n-propyl, isopropyl, n-butyl, sec-butyl, isobutyl and tert-butyl;
represent a phenyl radical which can be substituted with 1, 2, 3, 4 or 5 substituents selected independently of one another from the group consisting of F, Cl, Br, I, —CN, —CF$_3$, —O—CH$_3$, —O—C$_2$H$_5$, —NO$_2$, —O—CF$_3$, methyl, ethyl, n-propyl, isopropyl, n-butyl, sec-butyl, isobutyl and tert-butyl;
or represent —OH;

R$^{32}$ represents a hydrogen radical;
represents a radical selected from the group consisting of methyl, ethyl, n-propyl, isopropyl, n-butyl, sec-butyl, isobutyl and tert-butyl;
represents a radical selected from the group consisting of phenyl, naphthyl, furanyl and thiophenyl which can optionally be substituted with 1, 2, 3, 4 or 5 substituents selected independently of one another from the group consisting of —SF$_5$, F, Cl, Br, I, —CF$_3$, —O—CF$_3$, —S—CF$_3$, —O—CH$_3$, —O—C$_2$H$_5$, phenyl, —S—CH$_3$, —S—C$_2$H$_5$, cyclopentyl, cyclohexyl, methyl, ethyl, n-propyl, isopropyl, n-butyl, sec-butyl, isobutyl and tert-butyl;
represents —(CH$_2$)$_{cc}$—R$^{35}$ wherein cc 1, 2 or 3 or represents —CH=CH—R$^{36}$;

R$^{30}$, R$^{33}$ and R$^{34}$, independently of one another, each
represent a radical selected from the group consisting of methyl, ethyl, n-propyl, isopropyl, n-butyl, sec-butyl, isobutyl and tert-butyl;
or represent a radical selected from the group consisting of phenyl, pyridinyl and naphthyl, wherein the radical can in each case optionally be substituted with 1, 2, 3, 4 or 5 substituents selected independently of one another from the group consisting of —SF$_5$, F, Cl, Br, —CF$_3$, —O—CF$_3$, —S—CF$_3$, phenyl, morpholinyl, piperidinyl, pyrrolidinyl, piperazinyl, cyclopentyl, cyclohexyl, —OH, —O—CH$_3$, —O—C$_2$H$_5$, methyl, ethyl, n-propyl, isopropyl, n-butyl, sec-butyl, isobutyl, tert-butyl, n-pentyl, n-hexyl, n-heptyl and n-octyl;
and
R$^{35}$ and R$^{36}$, independently of one another, each
represent a phenyl radical which can be substituted with 1, 2, 3, 4 or 5 substituents selected independently of one another from the group consisting of F, Cl, Br, I, —CN, —CF$_3$, —O—CH$_3$, —O—C$_2$H$_5$, —NO$_2$, —O—CF$_3$, methyl, ethyl, n-propyl, isopropyl, n-butyl, sec-butyl, isobutyl and tert-butyl;

in each case optionally in the form of one of their pure stereoisomers, in particular enantiomers or diastereomers, their racemates or in the form of a mixture of stereoisomers, in particular of enantiomers and/or diastereomers, in any desired mixing ratio, or respectively in the form of corresponding salts, or respectively in the form of corresponding solvates.

Most particularly preferred are substituted spiro compounds of the above-indicated general formula I, wherein
m is equal to 0, 1 or 2;
n is equal to 0, 1 or 2;

R$^1$ represents a radical selected from the group consisting of benzimidazolyl, benzoxazolyl, benzotriazolyl, benzisoxazolyl and benzothiazolyl, wherein the radical can be respectively with 1, 2, 3, 4 or 5 substituents selected independently of one another from the group consisting of F, Cl, Br, —CF$_3$, —O—CF$_3$, —S—CF$_3$, methyl, ethyl, n-propyl, isopropyl, n-butyl, sec-butyl, isobutyl and tert-butyl;
represents a —C(=O)—NR$^5$R$^6$ group;
represents a —C(=S)—NR$^7$R$^8$ group;
represents a —C(=O)—R$^9$ group;
or represents an —S(=O)$_2$—R$^{10}$ group;

R$^2$ represents a radical selected from the group consisting of methyl, ethyl, n-propyl, isopropyl, n-butyl, sec-butyl, isobutyl, tert-butyl, n-pentyl, sec-pentyl, n-hexyl and n-heptyl;
represents a phenyl radical of general formula XX

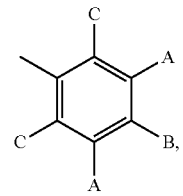

XX wherein the free line represents the bond of this phenyl radical to the spiro compound of general formula I;
A and B each represent a substituent selected independently of one another from the group consisting of H, F, Cl, Br, I, —CF$_3$, —SF$_5$, —OH, —O—CH$_3$, —O—C$_2$H$_5$, —O—CF$_3$, —S—CF$_3$, methyl, ethyl, n-propyl, isopropyl, n-butyl, sec-butyl, isobutyl, tert-butyl, cyclopentyl, cyclohexyl, —NH—S(=O)$_2$—CH$_3$ and —NH—S(=O)$_2$ phenyl;
on the condition that not one of positions A and position B of this phenyl radical are substituted with substituents which are respectively bound to the phenyl radical via an identical atom selected from the group consisting of oxygen, sulphur and nitrogen;
C represents in each case H;
represents a radical selected from the group consisting of naphthyl, quinolinyl, (1,4)-benzodioxanyl, (1,3)-benzodioxolyl, pyridinyl, thiazolyl and oxazolyl, wherein the radical can in each case optionally be substituted with 1, 2, 3, 4 or 5 substituents selected independently of one another from the group consisting of F, Cl, Br, I, —O—CH$_3$, —O—C$_2$H$_5$, methyl, ethyl, n-propyl, isopropyl, n-butyl, sec-butyl, isobutyl, tert-butyl, —S(=O)$_2$—CH$_3$, —S(=O)$_2$—C$_2$H$_5$, —NH—S(=O)$_2$—CH$_3$, —NH—S(=O)$_2$—C$_2$H$_5$, —S(=O)$_2$—NH—CH$_3$ and —S(=O)$_2$—NH—C$_2$H$_5$;
or represents —(CHR$^{17}$)—R$^{20}$, —(CHR$^{17}$)—(CHR$^{18}$)—R$^{20}$ or —(CHR$^{17}$)—(CHR$^{18}$)—(CHR$^{19}$)—R$^{20}$;

R$^3$ represents a radical selected from the group consisting of methyl, ethyl, n-propyl, isopropyl, n-butyl, sec-butyl, isobutyl, tert-butyl and n-pentyl;
R$^4$ represents a hydrogen radical;
R$^5$ and R$^7$, independently of one another, each represent a radical selected from the group consisting of methyl, ethyl, n-propyl, isopropyl, n-butyl, sec-butyl, isobutyl, tert-butyl, n-pentyl, sec-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosanyl, vinyl, 1-propenyl, 2-propenyl, 1-butenyl, 2-butenyl, 3-butenyl and 2-methyl-1-propenyl, wherein the radical can in each case optionally be substituted with 1, 2, 3, 4 or 5 substituents selected independently of one another from the group consisting of F, Cl and Br;

represent a radical selected from the group consisting of cyclopropyl, cyclobutyl, cyclopentyl, cyclohexyl, cycloheptyl, cyclooctyl, cyclononyl, cyclodecyl, cycloundecyl, cyclododecyl, cyclopentenyl, cyclohexenyl, cycloheptenyl and adamantyl; wherein the radical can in each case optionally be substituted with 1, 2 or 3 substituents selected independently of one another from the group consisting of methyl, ethyl, n-propyl, isopropyl, n-butyl, sec-butyl, isobutyl and tert-butyl;

represent a radical selected from the group consisting of phenyl, naphthyl, (1,4)-benzodioxanyl, and pyridinyl, wherein the radical can in each case optionally be substituted with 1, 2, 3, 4 or 5 substituents selected independently of one another from the group consisting of $-SF_5$, F, Cl, Br, I, $-CN$, $-CF_3$, $-O-CH_3$, $-O-C_2H_5$, $-NO_2$, $-O-CF_3$, $-S-CH_3$, $-S-C_2H_5$, methyl, ethyl, n-propyl, isopropyl, n-butyl, sec-butyl, isobutyl, tert-butyl, $-C(=O)-OH$, $-C(=O)-O-CH_3$, $-C(=O)-O-C_2H_5$, $-C(=O)-O-C(CH_3)_3$, $-O-C(=O)-CH_3$, $-O-C(=O)-C_2H_5$, $-O-C(=O)-C(CH_3)_3$, $-N(CH_3)_2$, $-N(C_2H_5)_2$, $-NH-CH_3$, $-NH-C_2H_5$, $-C(=O)-CH_3$, $-C(=O)-C_2H_5$, $-C(=O)-C(CH_3)_3$, cyclohexyl, cyclopentyl, $-O$-phenyl, $-O$-benzyl and phenyl, wherein in each case the cyclic portion of the radicals cyclopentyl, cyclohexyl, $-O$-phenyl, $-O$-benzyl and phenyl can be substituted with 1, 2, 3, 4 or 5 substituents selected independently of one another from the group consisting of F, Cl, Br, methyl, ethyl, n-propyl, isopropyl, n-butyl, sec-butyl, isobutyl and tert-butyl;

or represent $-(CR^{21}R^{22})-R^{25}$, $-(CR^{21}R^{22})-(CHR^{23})-R^{25}$, $-(CR^{21}R^{22})-(CHR^{21})-O-R^{25}$, $-(CR^{21}R^{22})-(CHR^{23})-(CHR^{24})-R^{25}$, $-(CR^{21}R^{22})-(CHR^{23})-(CHR^{24})-O-R^{25}$, $-(CR^{21}R^{22})-(CHR^{23})-(CHR^{24})-N(CH_3)-R^{25}$ or $-(CR^{21}R^{22})-(CHR^{23})-(CHR^{24})-N(C_2H_5)-R^{25}$;

$R^6$ and $R^8$ each represent a hydrogen radical;
or represent a methyl or ethyl radical;

$R^9$ represents a radical selected from the group consisting of 9H-fluorenyl, 9H-xanthenyl, phenyl, pyridinyl and naphthyl, wherein the radical can in each case optionally be substituted with 1, 2, 3, 4 or 5 substituents selected independently of one another from the group consisting of F, Cl, Br, I, $-CF_3$, $-O-CF_3$, $-S-CF_3$, $-OH$, $-O-CH_3$, $-O-C_2H_5$, $-NH-S(=O)_2-CH_3$, morpholinyl, piperidinyl, pyrrolidinyl, piperazinyl, phenyl, methyl, ethyl, n-propyl, isopropyl, n-butyl, sec-butyl, isobutyl, tert-butyl, n-pentyl, n-hexyl, n-heptyl and n-octyl;

represents $-(CR^{26}R^{27})-R^{30}$, $-(CR^{26}R^{27})-(CHR^{28})-R^{30}$, $-(CR^{26}R^{27})-(CHR^{28})-(CHR^{29})-R^{30}$, $-CR^{31}=CR^{32}-R^{33}$ or $-C\equiv C-R^{34}$;

$R^{10}$ represents a radical selected from the group consisting of phenyl and naphthyl, wherein the radical can in each case optionally be substituted with 1, 2, 3, 4 or 5 substituents selected independently of one another from the group consisting of F, Cl, Br, I, $-CF_3$, $-OH$, $-O-CH_3$, $-O-C_2H_5$, methyl, ethyl, n-propyl, isopropyl, n-butyl, sec-butyl, isobutyl and tert-butyl;

represents $-(CR^{26}R^{27})-R^{30}$, $-(CR^{26}R^{27})-(CHR^{28})-R^{30}$, $-(CR^{26}R^{27})-(CHR^{28})-(CHR^2)-R^{30}$, $-CR^{31}=CR^{32}-R^{33}$ or $-C\equiv C-R^{34}$;

$R^{17}$, $R^{18}$, $R^{19}$, $R^{23}$, $R^{24}$, $R^{23}$ and $R^{29}$, independently of one another, each
represent a hydrogen radical;
represent a radical selected from the group consisting of methyl, ethyl, n-propyl, isopropyl, n-butyl, sec-butyl, isobutyl and tert-butyl;
or represent a phenyl radical;

$R^{20}$ represents a phenyl radical;

$R^{21}$ and $R^{22}$, independently of one another, each represent a hydrogen radical;
represent a radical selected from the group consisting of methyl, ethyl, n-propyl, isopropyl, n-butyl, sec-butyl, isobutyl and tert-butyl;
or represent a phenyl radical;

$R^{25}$ represents a radical selected from the group consisting of methyl, ethyl, n-propyl, isopropyl, n-butyl, sec-butyl, isobutyl and tert-butyl;
represents a radical selected from the group consisting of cyclopentyl, cyclohexyl, tetrahydrofuranyl, tetrahydrothiophenyl, pyrrolidinyl, morpholinyl, piperidinyl and piperazinyl;
or represents a radical selected from the group consisting of phenyl, naphthyl, (1,3)-benzodioxolyl, (1,4)-benzodioxanyl, thiophenyl and furanyl, wherein the radical can in each case optionally be substituted with 1, 2, 3, 4 or 5 substituents selected independently of one another from the group consisting of F, Cl, Br, $-OH$, $-O-CH_3$, $-O-C_2H_5$, methyl, ethyl, n-propyl, isopropyl, n-butyl, sec-butyl, isobutyl and tert-butyl;

$R^{25}$ and $R^{27}$, independently of one another, each represent a hydrogen radical;
represent a radical selected from the group consisting of methyl, ethyl, n-propyl, isopropyl, n-butyl, sec-butyl, isobutyl and tert-butyl;
represent a phenyl radical or $-OH$;

$R^{30}$ represents a phenyl radical which can be substituted with 1, 2, 3, 4 or 5 substituents selected independently of one another from the group consisting of F, Cl, Br, $-NH-S(=O)_2-CH_3$, methyl, ethyl, n-propyl, isopropyl, n-butyl, sec-butyl, isobutyl and tert-butyl;

$R^{31}$ represents a hydrogen radical;
or represents a radical selected from the group consisting of methyl, ethyl, n-propyl, isopropyl, n-butyl, sec-butyl, isobutyl and tert-butyl;

$R^{32}$ represents a hydrogen radical;
represents a radical selected from the group consisting of methyl, ethyl, n-propyl, isopropyl, n-butyl, sec-butyl, isobutyl and tert-butyl;
represents a radical selected from the group consisting of phenyl, naphthyl, furanyl and thiophenyl which can optionally be substituted with 1, 2, 3, 4 or 5 substituents selected independently of one another from the group consisting of $-SF_5$, F, Cl, Br, I, $-CF_3$, $-O-CF_3$, $-S-CF_3$, $-O-CH_3$, $-O-C_2H_5$, phenyl, $-S-CH_3$, $-S-C_2H_5$, cyclopentyl, cyclohexyl, methyl, ethyl, n-propyl, isopropyl, n-butyl, sec-butyl, isobutyl and tert-butyl;
represents $-CH_2-R^{35}$ or $-CH=CH-R^{36}$;

$R^{33}$ and $R^{34}$, independently of one another, each
represent a radical selected from the group consisting of methyl, ethyl, n-propyl, isopropyl, n-butyl, sec-butyl, isobutyl and tert-butyl; or represent a radical selected from the group consisting of phenyl, pyridinyl and naphthyl, wherein the radical can in each case optionally be substituted with 1, 2, 3, 4 or 5 substituents selected independently of one another from the group consisting of —SF$_5$, F, Cl, Br, —CF$_3$, —O—CF$_3$, —S—CF$_3$, phenyl, morpholinyl, piperidinyl, pyrrolidinyl, piperazinyl, cyclopentyl, cyclohexyl, —OH, —O—CH$_3$, —O—C$_2$H$_5$, methyl, ethyl, n-propyl, isopropyl, n-butyl, sec-butyl, isobutyl, tert-butyl, n-pentyl, n-hexyl, n-heptyl and n-octyl;
and
R$^{35}$ and R$^{36}$ each represent a phenyl radical;
in each case optionally in the form of one of their pure stereoisomers, in particular enantiomers or diastereomers, their racemates or in the form of a mixture of stereoisomers, in particular of enantiomers and/or diastereomers, in any desired mixing ratio, or respectively in the form of corresponding salts, or respectively in the form of corresponding solvates.

Also most particularly preferred are substituted spiro compounds of the above-indicated general formula I, wherein
m is equal to 0, 1 or 2;
n is equal to 0, 1 or 2;
R$^1$ represents a radical selected from the group consisting of benzimidazolyl, benzoxazolyl, benzotriazolyl, benzisoxazolyl and benzothiazolyl, wherein the radical can in each case be substituted with 1, 2, 3, 4 or 5 substituents selected independently of one another from the group consisting of F, Cl, Br, —CF$_3$, —O—CF$_3$, —S—CF$_3$, methyl, ethyl, n-propyl, isopropyl, n-butyl, sec-butyl, isobutyl and tert-butyl;
represents a —C(=O)—NR$^5$R$^6$ group;
represents a —C(=S)—NR$^7$R$^8$ group;
represents a —C(=O)—R$^9$ group;
or represents an —S(=O)$_2$—R$^{10}$ group;
R$^2$ represents a tert-butyl radical;
represents a radical selected from the group consisting of phenyl, 2-methanesulphonamidephenyl, 2-ethanesulphonamidephenyl, 2-trifluoromethylphenyl, 2-trifluoromethylsulphanylphenyl, 2-ethylphenyl, 2-tert-butylphenyl, 2-ethylaminosulphonylphenyl, 2-methylaminosulphonylphenyl, 2-bromophenyl, 2-chlorophenyl, 2-fluorophenyl, 2-methylphenyl, 2-trifluoromethoxyphenyl, 2-methoxyphenyl, 2-ethoxyphenyl, 2-propylphenyl, 2-iodophenyl, 3-chlorophenyl, 3-methylphenyl, 3-tert-butylphenyl, 3-trifluoromethylsulphanylphenyl, 3-trifluoromethylphenyl, 3-methanesulphonamidephenyl, 3-ethanesulphonamidephenyl, 3-fluorophenyl, 3-propylphenyl, 3-isopropylphenyl, 3-bromophenyl, 3-methoxyphenyl, 3-ethylphenyl, 3-ethylaminosulphonylphenyl, 3-methylaminosulphonylphenyl, 3-ethoxyphenyl, 3-trifluoromethoxyphenyl, 3-iodophenyl, 4-methylaminosulphonylphenyl, 4-ethylaminosulphonylphenyl, 4-methanesulphonamidephenyl, 4-ethanesulphonamidephenyl, 4-bromophenyl, 4-methoxyphenyl, 4-chlorophenyl, 4-fluorophenyl, 4-tert-butylphenyl, 4-trifluoromethylsulphanylphenyl, 4-methylphenyl, 4-isopropylphenyl, 4-trifluoromethylphenyl, 4-propylphenyl, 4-iodophenyl, 4-trifluoromethoxyphenyl, 4-ethylphenyl, 4-ethoxyphenyl, 2-fluoro-3-trifluoromethylphenyl, (2,3)-difluorophenyl, (2,3)-dimethylphenyl, (2,3)-dichlorophenyl, 3-fluoro-2-trifluoromethylphenyl, (2,4)-dichlorophenyl, (2,4)-difluorophenyl, 4-fluoro-2-trifluoromethylphenyl, (2,4)-dimethoxyphenyl, 2-chloro-4-fluorophenyl, (2,4)-dibromophenyl, 2-fluoro-4-trifluoromethylphenyl, (2,5)-difluorophenyl, 2-fluoro-5-trifluoromethylphenyl, 5-fluoro-2-trifluoromethylphenyl, 5-chloro-2-trifluoromethylphenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-fluoro-6-trifluoromethylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl, (2,6)-dibromophenyl, (2,6)-dichlorophenyl, 3-chloro-2-fluorophenyl, (3,4)-dichlorophenyl, 4-fluoro-3-trifluoromethylphenyl, 3-fluoro-4-trifluoromethyl phenyl, (3,4)-difluorophenyl, 4-chloro-3-trifluoromethyl, 4-bromo-3-methylphenyl, 4-bromo-5-methylphenyl, 3-chloro-4-fluorophenyl, (3,4)-dibromophenyl, 4-chloro-3-methylphenyl, 4-bromo-3-methylphenyl, 4-fluoro-3-methylphenyl, (3,5)-dimethoxyphenyl, (3,5)-bis-trifluoromethylphenyl, (3,5)-difluorophenyl, (3,5)-dichlorophenyl, 3-fluoro-5-trifluoromethylphenyl, 5-fluoro-3-trifluoromethylphenyl, (3,5)-dibromophenyl, 5-chloro-4-fluorophenyl, 5-bromo-4-methylphenyl, (2,3,4)-trifluorophenyl, (2,3,4)-trichlorophenyl, (2,3,6)-trifluorophenyl, 5-chloro-2-methoxyphenyl, (2,3)-difluoro-4-methylphenyl, (2,4,5)-trifluorophenyl, (2,4,5)-trichlorophenyl, (2,4)-dichloro-5-fluorophenyl, (2,4,6)-trichlorophenyl, (2,4,6)-trimethylphenyl, (2,4,6)-trifluorophenyl, (2,4,6)-trimethoxyphenyl, (2,3,4,5)-tetrafluorophenyl, 4-methoxy-2,3,6-trimethylphenyl, 4-methoxy-2,3,6-trimethylphenyl, 4-chloro-2,5-dimethylphenyl, 2-chloro-6-fluoro-3-methylphenyl, 6-chloro-2-fluoro-3-methyl, (2,3,4,5,6)-pentafluorophenyl, 3-fluoro-4-methylsulphonamidophenyl, 3-chloro-4-methylsulphonamidophenyl, 3-bromo-4-methylsulphonamidophenyl, 3-methoxy-4-methylsulphonamidophenyl, 3-hydroxy-4-methylsulphonamidophenyl, 3-trifluoromethyl-4-methylsulphonamidophenyl, 3-trifluoromethoxy-4-methylsulphonamidophenyl, 3-methyl-4-methylsulphonamidophenyl, 3-ethyl-4-methylsulphonamidophenyl, 3-isopropyl-4-methylsulphonamidophenyl, 3-propyl-4-methylsulphonamidophenyl, 3-tert-butyl-4-methylsulphonamidophenyl, 3-fluoro-4-phenylsulphonamidophenyl, 3-chloro-4-phenylsulphonamidophenyl, 3-bromo-4-phenylsulphonamidophenyl, 3-methoxy-4-phenylsulphonamidophenyl, 3-hydroxy-4-phenylsulphonamidophenyl, 3-trifluoromethyl-4-phenylsulphonamidophenyl, 3-trifluoromethoxy-4-phenylsulphonamidophenyl, 3-methyl-4-phenylsulphonamidophenyl, 3-ethyl-4-phenylsulphonamidophenyl, 3-isopropyl-4-phenylsulphonamidophenyl, 3-propyl-4-phenylsulphonamidophenyl, 3-tert-butyl-4-phenylsulphonamidophenyl, 4-fluoro-3-methylsulphonamidophenyl, 4-chloro-3-methylsulphonamidophenyl, 4-bromo-3-methylsulphonamidophenyl, 4-methoxy-3-methylsulphonamidophenyl, 4-hydroxy-3-methylsulphonamidophenyl, 4-trifluoromethyl-3-methylsulphonamidophenyl, 4-trifluoromethoxy-3-methylsulphonamidophenyl, 4-methyl-3-methylsulphonamidophenyl, 4-ethyl-3-methylsulphonamidophenyl, 4-isopropyl-3-methylsulphonamidophenyl, 4-propyl-3-methylsulphonamidophenyl, 4-tert-butyl-3-methylsulphonamidophenyl, 4-fluoro-3-phenylsulphonamidophenyl, 4-chloro-3-phenylsulphonamidophenyl, 4-bromo-3-phenylsulphonamidophenyl, 4-methoxy-3- phenylsulphonamidophenyl, 4-hydroxy-3-phenylsulphonamidophenyl, 4-trifluoromethyl-3-phenylsulphonamidophenyl, 4-trifluoromethoxy-3-phenylsulphonamidophenyl, 4-methyl-3-phenylsulphonamidophenyl, 4-ethyl-3-phenylsulphonamidophenyl, 4-isopropyl-3-phenylsulphonamidophenyl, 4-propyl-3-phenylsulphonamidophenyl, 4-tert-butyl-3-phenylsulphonamidophenyl, 2-cyclohexylphenyl, 3-cyclohexylphenyl and 4-cyclohexylphenyl;

represents a radical selected from the group consisting of quinolinyl, (1,4)-benzodioxanyl, (1,3)-benzodioxolyl, naphthyl and thiazolyl;

represents a pyridinyl radical, wherein the radical can be respectively substituted with 1 or 2 substituents selected independently of one another from the group consisting of F, Cl and Br;

represents —(CHR$^{17}$)—R$^{20}$ or —(CHR$^{17}$)—(CHR$^{18}$)—R$^{20}$;

R$^3$ represents a methyl or ethyl radical;

R$^4$ represents a hydrogen radical;

R$^5$ and R$^7$, independently of one another, each represent a radical selected from the group consisting of methyl, ethyl, n-propyl, isopropyl, n-butyl, sec-butyl, isobutyl, tert-butyl, n-pentyl, sec-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosanyl, vinyl, 1-propenyl, 2-propenyl, 1-butenyl, 2-butenyl, 3-butenyl and 2-methyl-1-propenyl, wherein the radical can in each case optionally be substituted with 1, 2, 3, 4 or 5 substituents selected independently of one another from the group consisting of F, Cl and Br;

represent a radical selected from the group consisting of cyclopropyl, cyclobutyl, cyclopentyl, cyclohexyl, cycloheptyl, cyclooctyl, cyclononyl, cyclodecyl, cycloundecyl, cyclododecyl, cyclopentenyl, cyclohexenyl, cycloheptenyl and adamantyl; wherein the radical can in each case optionally be substituted with 1, 2 or 3 substituents selected independently of one another from the group consisting of methyl, ethyl, n-propyl, isopropyl, n-butyl, sec-butyl, isobutyl and tert-butyl;

represent a radical selected from the group consisting of phenyl, naphthyl, (1,4)-benzodioxanyl and pyridinyl, wherein the radical can in each case optionally be substituted with 1, 2, 3, 4 or 5 substituents selected independently of one another from the group consisting of —SF$_5$, F, Cl, Br, I, —CN, —CF$_3$, —O—CH$_3$, —O—C$_2$H$_5$, —NO$_2$, —O—CF$_3$, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —C(=O)—CH$_3$, —C(=O)—C$_2$H$_5$, —C(=O)—C(CH$_3$)$_3$, cyclohexyl, cyclopentyl, —O-phenyl, —O-benzyl and phenyl, wherein in each case the cyclic portion of the radicals cyclopentyl, cyclohexyl, —O-phenyl, —O-benzyl and phenyl can be substituted with 1, 2, 3, 4 or 5 substituents selected independently of one another from the group consisting of F, Cl, Br, methyl, ethyl, n-propyl, isopropyl, n-butyl, sec-butyl, isobutyl and tert-butyl;

or represent —(CR$^{21}$R$^{22}$)—R$^{25}$, —(CR$^{21}$R$^{22}$)—(CHR$^{23}$)—R$^{25}$, —(CR$^{21}$R$^{22}$)—(CHR$^{23}$)—O—R$^{25}$, —(CR$^{21}$R$^{22}$)—(CHR$^{23}$)—(CHR$^{24}$)—R$^{25}$, —(CR$^{21}$R$^{22}$)—(CHR$^{23}$)—(CHR$^{24}$)—O—R$^{25}$, —(CR$^{21}$R$^{22}$)—(CHR$^{23}$)—(CHR$^{24}$)—N(CH$_3$)—R$^{25}$ or —(CR$^{21}$R$^{22}$)—(CHR$^{23}$)—(CHR$^{24}$)—N(C$_2$H$_5$)—R$^{25}$;

R$^6$ and R$^8$ each represent a hydrogen radical;

or represent a methyl or ethyl radical;

R$^9$ represents a radical selected from the group consisting of 9H-fluorenyl, 9H-xanthenyl, phenyl, pyridinyl and naphthyl, wherein the radical can in each case optionally be substituted with 1, 2, 3, 4 or 5 substituents selected independently of one another from the group consisting of F, Cl, Br, I, —CF$_3$, —O—CF$_3$, —S—CF$_3$, —OH, —O—CH$_3$, —O—C$_2$H$_5$, —NH—S(=O)$_2$—CH$_3$, morpholinyl, piperidinyl, pyrrolidinyl, piperazinyl, phenyl, methyl, ethyl, n-propyl, isopropyl, n-butyl, sec-butyl, isobutyl, tert-butyl, n-pentyl, n-hexyl, n-heptyl and n-octyl;

represents —(CR$^{26}$R$^{27}$)—R$^{30}$, —(CR$^{26}$R$^{27}$)—(CHR$^{28}$)—R$^{30}$, —(CR$^{26}$R$^{27}$)—(CHR$^{28}$)—(CHR$^{21}$)—R$^{30}$, —CR$^{31}$=CR$^{32}$—R$^{33}$ or —C≡C—R$^{34}$;

R$^{10}$ represents a radical selected from the group consisting of phenyl and naphthyl, wherein the radical can in each case optionally be substituted with 1, 2, 3, 4 or 5 substituents selected independently of one another from the group consisting of F, Cl, Br, I, —CF$_3$, —OH, —O—CH$_3$, —O—C$_2$H$_5$, methyl, ethyl, n-propyl, isopropyl, n-butyl, sec-butyl, isobutyl and tert-butyl;

represents —(CR$^{26}$R$^{27}$)—R$^{30}$, —(CR$^{26}$R$^{27}$)—(CHR$^{28}$)—R$^{30}$, —(CR$^{26}$R$^{27}$)—(CHR$^{28}$)—(CHR$^{29}$)—R$^3$, —CR$^{31}$=CR$^{32}$—R$^{33}$ or —C≡C—R$^{34}$;

R$^{17}$, R$^{18}$, R$^{19}$, R$^{23}$, R$^{24}$, R$^{28}$ and R$^{29}$, independently of one another, each represent a hydrogen radical;

represent a radical selected from the group consisting of methyl, ethyl, n-propyl, isopropyl, n-butyl, sec-butyl, isobutyl and tert-butyl;

or represent a phenyl radical;

R$^{20}$ represents a phenyl radical;

R$^{21}$ and R$^{22}$, independently of one another, each represent a hydrogen radical;

represent a radical selected from the group consisting of methyl, ethyl, n-propyl, isopropyl, n-butyl, sec-butyl, isobutyl and tert-butyl;

or represent a phenyl radical;

R$^{25}$ represents a radical selected from the group consisting of methyl, ethyl, n-propyl, isopropyl, n-butyl, sec-butyl, isobutyl and tert-butyl;

represents a radical selected from the group consisting of cyclopentyl, cyclohexyl, tetrahydrofuranyl, tetrahydrothiophenyl, pyrrolidinyl, morpholinyl, piperidinyl and piperazinyl;

or represents a radical selected from the group consisting of phenyl, naphthyl, (1,3)-benzodioxolyl, (1,4)-benzodioxanyl, thiophenyl and furanyl, wherein the radical can in each case optionally be substituted with 1, 2, 3, 4 or 5 substituents selected independently of one another from the group consisting of F, Cl, Br, —OH, —O—CH$_3$, —O—C$_2$H$_5$, methyl, ethyl, n-propyl, isopropyl, n-butyl, sec-butyl, isobutyl and tert-butyl;

R$^{26}$ and R$^{27}$, independently of one another, each represent a hydrogen radical a radical selected from the group consisting of methyl, ethyl, n-propyl, isopropyl, n-butyl, sec-butyl, isobutyl and tert-butyl;

represent a phenyl radical or represent —OH;

R$^{30}$ represents a phenyl radical which can be substituted with 1, 2, 3, 4 or 5 substituents selected independently of one another from the group consisting of F, Cl, Br, —NH—S $(=O)_2$—$CH_3$, methyl, ethyl, n-propyl, isopropyl, n-butyl, sec-butyl, isobutyl and tert-butyl;

$R^{31}$ represents a hydrogen radical;

or represents a radical selected from the group consisting of methyl, ethyl, n-propyl, isopropyl, n-butyl, sec-butyl, isobutyl and tert-butyl;

$R^{32}$ represents a hydrogen radical;

represents a radical selected from the group consisting of methyl, ethyl, n-propyl, isopropyl, n-butyl, sec-butyl, isobutyl and tert-butyl;

represents a radical selected from the group consisting of phenyl, naphthyl, furanyl and thiophenyl which can optionally be substituted with 1, 2, 3, 4 or 5 substituents selected independently of one another from the group consisting of —$SF_5$, F, Cl, Br, I, —$CF_3$, —O—$CF_3$, —S—$CF_3$, —O—$CH_3$, —O—$C_2H_5$, phenyl, —S—$CH_3$, —S—$C_2H_5$, cyclopentyl, cyclohexyl, methyl, ethyl, n-propyl, isopropyl, n-butyl, sec-butyl, isobutyl and tert-butyl;

represents —$CH_2$—$R^{35}$ or —CH=CH—$R^{36}$;

$R^{33}$ and $R^{34}$, independently of one another, each represent a radical selected from the group consisting of methyl, ethyl, n-propyl, isopropyl, n-butyl, sec-butyl, isobutyl and tert-butyl;

or represent a radical selected from the group consisting of phenyl, pyridinyl and naphthyl, wherein the radical can in each case optionally be substituted with 1, 2, 3, 4 or 5 substituents selected independently of one another from the group consisting of —$SF_5$, F, Cl, Br, —$CF_3$, —O—$CF_3$, —S—$CF_3$, phenyl, morpholinyl, piperidinyl, pyrrolidinyl, piperazinyl, cyclopentyl, cyclohexyl, —OH, —O—$CH_3$, —O—$C_2H_5$, methyl, ethyl, n-propyl, isopropyl, n-butyl, sec-butyl, isobutyl, tert-butyl, n-pentyl, n-hexyl, n-heptyl and n-octyl;

and $R^{35}$ and $R^{36}$ each represent a phenyl radical;

in each case optionally in the form of one of their pure stereoisomers, in particular enantiomers or diastereomers, their racemates or in the form of a mixture of stereoisomers, in particular of enantiomers and/or diastereomers, in any desired mixing ratio, or respectively in the form of corresponding salts, or respectively in the form of corresponding solvates.

Preference may also be given to substituted spiro compounds according to the invention of general formula I which in a FLIPR assay in a concentration of 10 μM display inhibition of the $Ca^{2+}$ ion inflow in dorsal root ganglia of rats of at least 30%, preferably of at least 40%, particularly preferably of at least 50%, most particularly preferably of at least 70%, even more preferably of at least 90%, compared to the maximum achievable inhibition of the $Ca^{2+}$ ion inflow with capsaicin in a concentration of 10 μM.

In the FLIPR assay, the $Ca^{2+}$ inflow is quantified using a $Ca^{2+}$-sensitive dye (type Fluo-4, Molecular Probes Europe BV, Leiden, Netherlands) in a fluorescent imaging plate reader (FLIPR, Molecular Devices, Sunnyvale, USA), as described hereinafter.

The present invention further relates to a process for preparing compounds according to the invention of the above-indicated general formula I in which at least one compound of general formula II,

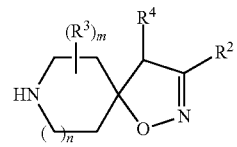

II wherein $R^2$, $R^3$, $R^4$, m and n are as defined above, is reacted in a reaction medium with at least one isocyanate of general formula $R^5$—N=C=O, wherein $R^5$ is as defined above, optionally in the presence of at least one base, preferably in the presence of at least one base selected from the group consisting of triethylamine, 4,4-dimethylaminopyridine, diisopropylethylamine, pyridine and N-methylmorpholine, to form at least one compound of general formula I, wherein $R^2$, $R^3$, $R^4$, m and n are as defined above and $R^1$ represents —C(=O)—$NR^5R^6$, wherein $R^5$ is as defined above and $R^6$ represents a hydrogen radical, and the at least one compound of general formula I is optionally purified and/or isolated or at least one compound of general formula II is reacted in a reaction medium with at least one isothiocyanate of general formula S=C=N—$R^7$, wherein $R^7$ is as defined above, optionally in the presence of at least one base, preferably in the presence of at least one base selected from the group consisting of triethylamine, 4,4-dimethylaminopyridine, diisopropylethylamine, pyridine and N-methylmorpholine, to form at least one compound of general formula I, wherein $R^2$, $R^3$, $R^4$, m and n are as defined above and $R^1$ represents —C(=S)—N—$R^7R^8$, wherein $R^7$ is as defined above and $R^8$ represents a hydrogen radical, and the at least one compound of general formula I is optionally purified and/or isolated and optionally at least one compound of general formula I, wherein $R^2$, $R^3$, $R^4$, m and n are as defined above and $R^1$ represents —C(=O)—$NR^5R^6$ or —C(=S)—N—$R^7R^8$, wherein $R^6$ and $R^8$ each represent a hydrogen radical, is reacted in a reaction medium, in the presence of at least one base, preferably in the presence of at least one metal hydride salt or a metal alcoholate salt, particularly preferably in the presence of a metal hydride salt or a metal alcoholate salt selected from the group consisting of sodium hydride, potassium hydride, potassium tert-butanolate, sodium tert-butanolate, potassium methanolate, sodium methanolate, sodium ethanolate and potassium ethanolate, with at least one compound of general formula LG-$R^6$ or of general formula LG-$R^8$, wherein LG represents a leaving group, preferably a halogen atom, particularly preferably a chlorine atom, and $R^6$ and $R^8$ are as defined above except for hydrogen, to form at least one compound of general formula I, wherein $R^2$ to $R^4$, m and n are as defined above and $R^1$ represents —C(=O)—$NR^5R^6$ or —C(=S)—N—$R^7R^8$, and the at least one compound of general formula I is optionally purified and/or isolated, or at least one compound of general formula II is reacted in a reaction medium, in the presence of at least one base, preferably in the presence of at least one metal hydride salt, particularly preferably in the presence of sodium and/or potassium hydride, with at least one compound of general formula LG-$R^1$, wherein $R^1$ is as defined above, except for —C(=O)—$NR^5R^6$, —C(=S)—$NR^7R^8$, —C(=O)—$R^9$ and —S(=O)—$R^{10}$, and LG represents a leaving group, preferably a halogen atom, particularly preferably a chlorine atom, to form at least one compound of general formula I, wherein $R^1$ to $R^4$, m and n are as defined above, and the at least one compound of general formula I is optionally purified and/or isolated or at least one compound of general formula II is reacted in a reaction medium in the presence of at least one reducing agent with at least one compound of general formula $R^1$—C(=O)—H, wherein $R^1$ is as defined above, except for —C(=O)—$NR^5R^6$, —C(=S)—$NR^7R^8$, —C(=O)—$R^9$ and —S(=O)—$R^{10}$, to form at least one compound of general formula I, wherein $R^1$ to $R^4$, m and n are as defined above, and the at least one compound of general formula I is optionally purified and/or isolated or at least one compound of general formula II is reacted in a reaction medium, optionally in the presence of at least one base, with at least one compound of general formula $R^9$—C(=O)-LG, wherein $R^9$ is as defined above and LG represents a leaving group, preferably a halogen radical, or in a reaction medium in the presence of at least one coupling reagent, optionally in the presence of at least one base, with a compound of general formula $R^9$—C(=O)—OH, wherein $R^9$ is as defined above, to form at least one compound of general formula I, wherein $R^2$ to $R^4$, m and n are as defined above and $R^1$ represents —C(=O)—$R^9$, and the at least one compound of general formula I is optionally purified and/or isolated or at least one compound of general formula II is reacted in a reaction medium, optionally in the presence of at least one base, with at least one compound of general formula $R^{10}$—S(=O)$_2$-LG, wherein $R^{10}$ is as defined above and LG represents a leaving group, preferably a halogen radical, to form at least one compound of general formula I, wherein $R^2$ to $R^4$, m and n are as defined above and $R^1$ represents —S(=O)$_2$—$R^{10}$, and the at least one compound of general formula I is optionally purified and/or isolated.

Preferably, compounds of general formula II are reacted with an isocyanate of general formula $R^5$—N=C=O, wherein $R^5$ is as defined above, or with an isothiocyanate of general formula $R^7$—N=C=S, wherein $R^7$ is as defined above, in a reaction medium, preferably selected from the group consisting of acetonitrile, toluene, dimethylformamide, benzene, ethanol, methanol, water and corresponding mixtures, optionally in the presence of at least one base, preferably in the presence of at least one base selected from the group consisting of triethylamine, N-methylmorpholine, pyridine, 4,4-dimethylaminopyridine and diisopropylethylamine, to form compounds of general formula I, wherein $R^1$ represents —C(=O)—$NR^5R^6$ or —C(=S)—$NR^7R^8$, and $R^6$ and $R^8$ each represent a hydrogen radical.

Also preferably, compounds of general formula II are reacted with compounds of general formula LG-$R^1$, wherein $R^1$ is as defined above except for —C(=O)—$NR^5R^6$, —C(=S)—$NR^7R^8$, —C(=O)—$R^9$ and —S(=O)—$R^{10}$, and LG represents a leaving group, preferably a halogen atom, particularly preferably a chlorine atom, in a reaction medium, preferably selected from the group consisting of dichloromethane, toluene, tetrahydrofuran, acetonitrile, diethyl ether, dioxane and corresponding mixtures, optionally in the presence of at least one base, preferably in the presence of at least one metal hydride salt, particularly preferably in the presence of sodium and/or potassium hydride, to form compounds of general formula I, wherein $R^1$ is as defined above except for —C(=O)—$NR^5R^6$, —C(=S)—$NR^7R^8$, —C(=O)—$R^9$ and —S(=O)—$R^{10}$.

Also preferably, compounds of general formula II are reacted with compounds of general formula $R^1$—C(=O)—H, wherein $R^1$ is as defined above except for —C(=O)—$NR^5R^6$, —C(=S)—$NR^7R^8$, —C(=O)—$R^9$ and —S(=O)—$R^{10}$, in a reaction medium, preferably selected from the group consisting of diethyl ether, tetrahydrofuran, methanol, ethanol, dichloromethane, toluene and corresponding mixtures, with the addition of at least one reducing agent, preferably with the addition of at least one reducing agent selected from the group consisting of sodium borohydride, sodium acetoxyborohydride, sodium cyanoborohydride and borane-pyridine complex (pyridine borane, $BH_3.C_5H_5N$), particularly preferably in the presence of borane-pyridine complex, to form compounds of general formula I, wherein $R^1$ is as defined above except for —C(=O)—$NR^5R^6$, —C(=S)—$NR^7R^8$, —C(=O)—$R^9$ and —S(=O)—$R^{10}$.

Also preferably, compounds of the above-indicated general formula II are reacted with carboxylic acids of general formula $R^9$—C(=O)—OH, wherein $R^9$ is as defined above, in a reaction medium, preferably selected from the group consisting of diethyl ether, tetrahydrofuran, acetonitrile, methanol, ethanol, dimethylformamide, dichloromethane and corresponding mixtures, optionally in the presence of at least one coupling reagent, preferably selected from the group consisting of N,N'-carbonyldiimidazole, 1-benzotriazolyloxy-tris-(dimethylamino)phosphonium hexafluorophosphate (BOP), dicyclohexylcarbodiimide (DCC), N'-(3-dimethylaminopropyl)-N-ethylcarbodiimide (EDCI), N-[(dimethyamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-hydroxybenzotriazole (HOBt) and 1-hydroxy-7-azabenzotriazole (HOAt), optionally in the presence of at least one inorganic base, preferably selected from the group consisting of potassium carbonate and caesium carbonate, or at least one organic base, preferably selected from the group consisting of triethylamine, pyridine, dimethylaminopyridine, N-methylmorpholine and diisopropylethylamine, preferably at temperatures of −70° C. to 100° C. to form compounds of general formula I, wherein $R^1$ represents —C(=O)—$R^9$.

Also preferably, compounds of general formula II are reacted with carboxylic acid derivates or carbonic acid derivates of general formula $R^9$—C(=O)-LG, wherein $R^4$ is as defined above and LG represents a halogen radical, preferably chlorine or bromine, in a reaction medium, preferably selected from the group consisting of diethyl ether, tetrahydrofuran, acetonitrile, methanol, ethanol, dimethylformamide, dichloromethane and corresponding mixtures, optionally in the presence of at least one organic base, preferably selected from the group consisting of triethylamine, dimethylaminopyridine, N-methylmorpholine, pyridine and diisopropylamine, or at least one inorganic base at temperatures of preferably −70° C. to 100° C. to form compounds of general formula I.

Also preferably, compounds of general formula II are reacted with sulphonic acid derivatives of general formula LG—S(=O)$_2$—$R^{10}$, wherein $R^{10}$ is as defined above and LG represents a leaving group, preferably a halogen atom, particularly preferably a chlorine atom, in a reaction medium, preferably selected from the group consisting of diethyl ether, tetrahydrofuran, acetonitrile, methanol, ethanol, dimethylformamide, dichloromethane and corresponding mixtures, optionally in the presence of an organic base, preferably selected from the group consisting of triethylamine, 4,4-dimethylaminopyridine, N-methylmorpholine, pyridine and diisopropylethylamine, or an inorganic base, at temperatures of preferably −70° C. to 100° C. to form compounds of general formula I, wherein $R^1$ represents —S(=O)$_2$—$R^{11}$.

The compounds of general formula II may be obtained as illustrated in Diagram 1.

Diagram 1.

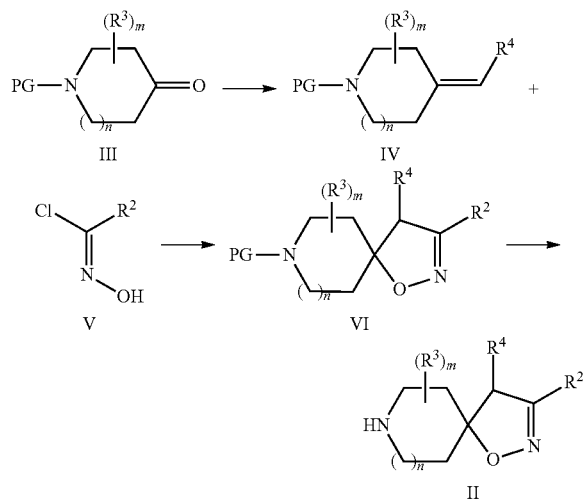

In step 1, compounds of general formula III, wherein m, n and $R^3$ are as defined above and PG represents a protective group, preferably a tert-butyloxycarbonyl group, are reacted in a reaction medium, preferably in a reaction medium selected from the group consisting of tetrahydrofuran, toluene, diethyl ether and corresponding mixtures, with a reagent for converting carbonyl groups into double bonds, preferably with a Wittig reagent of general formula $R_3P(CH_2)R^4X$; wherein R represents an aryl radical, X represents a halogen atom and $R^4$ is as defined above; or a Wittig-Horner reagent of general formula (RO)$_2$—P(=O)—(CH$_2$)—$R^4$, wherein R represents an aryl radical and $R^4$ is as defined above, particularly preferably with methyltriphenylphosphonium bromide, at temperatures between 0° C. and 30° C. in the presence of a base, preferably in the presence of an alkali metal alcoholate salt, particularly preferably in the presence of potassium tert-butylate, to form compounds of general formula IV, wherein m, n, $R^3$, $R^4$ and PG are as defined above.

In step 2, compounds of general formula IV are reacted in a reaction medium, preferably in a reaction medium selected from the group consisting of methanol, tetrahydrofuran, dichloromethane and corresponding mixtures, in the presence of at least one base, preferably in the presence of sodium hydrogen carbonate, lithium hydroxide, triethylamine or N-diisopropylethylamine, with compounds of general formula V, wherein $R^2$ is as defined above, at temperatures between 0° C. and 100° C. to form compounds of general formula VI, wherein m, n, PG, $R^2$, $R^3$ and $R^4$ are as defined above.

In step 3, compounds of general formula VI, wherein PG represents a tert-butyloxycarbonyl group, are reacted in a reaction medium preferably selected from the group consisting of methanol, ethanol, isopropanol, water, diethyl ether, tetrahydrofuran and corresponding mixtures in the presence of at least one acid preferably selected from the group consisting of hydrochloric acid, sulphuric acid, trifluoroacetic acid and acetic acid at temperatures of preferably 20 to 30° C. to form compounds of general formula II. Particularly preferably, the compound of general formula VI is reacted in a 5 M hydrochloric acid solution in isopropanol at a temperature of preferably 20 to 30° C. to form a compound of general formula II in the form of a corresponding hydrochloride.

The compounds of the above-indicated formulae $R_3P$(CH$_2$)R$^4$X, (RO)$_2$—P(=O)—(CH$_2$)—R$^4$, $R^1$—C(=O)—H, LG-$R^1$, LG-$R^6$, LG-$R^1$, $R^5$—N=C=O, $R^7$—N=C=S, III, V, $R^{10}$—S(=O)$_2$-LG, $R^9$—C(=O)-LG and $R^9$—C(=O)—OH are each commercially available and can also be prepared using conventional processes known to a person skilled in the art.

The above-described reactions can each be carried out under the conventional conditions with which a person skilled in the art is familiar, for example with regard to pressure or the order in which the components are added. If appropriate, a person skilled in the art can determine by simple preliminary tests the procedure which is optimal under the respective conditions. The intermediate and end products obtained as a result of the above-described reactions can each, if it is desirable and/or necessary, be purified and/or isolated using conventional methods known to a person skilled in the art. Suitable purification processes include, for example, extraction processes and chromatographic processes such as column chromatography or preparative chromatography. All of the above-described process steps and in each case also the purification and/or isolation of intermediate or end products can be carried out partly or completely under an inert gas atmosphere, preferably under a nitrogen atmosphere.

The substituted spiro compounds according to the invention of the above-mentioned general formulae I, Ia and Ib, referred to hereinafter simply as spiro compounds of general formula I, and corresponding stereoisomers can be isolated both in the form of their free bases, their free acids and also in the form of corresponding salts, in particular physiologically compatible salts. The free bases of the respective substituted spiro compounds according to the invention of the above-mentioned general formula I and of corresponding stereoisomers can, for example, be converted by reaction with an inorganic or organic acid, preferably with hydrochloric acid, hydrobromic acid, sulphuric acid, phosphoric acid, methanesulphonic acid, p-toluenesulphonic acid, carbonic acid, formic acid, acetic acid, oxalic acid, succinic acid, tartaric acid, mandelic acid, fumaric acid, lactic acid, citric acid, glutamic acid or aspartic acid, into the corresponding salts, preferably physiologically compatible salts. The free bases of the respective substituted spiro compounds of the above-mentioned general formula I and of corresponding stereoisomers can also be converted with the free acid or a salt of a sugar substitute, such as, for example, saccharin, cyclamate or acesulfame, into the corresponding physiologically compatible salts. Accordingly, the free acids of the substituted spiro compounds of the above-mentioned general formula I and of corresponding stereoisomers can be converted by reaction with a suitable base into the corresponding physiologically compatible salts. Examples include the alkali metal salts, alkaline-earth metal salts or ammonium salts [NH$_x$R$_{4-x}$]$^+$, wherein x=0, 1, 2, 3 or 4 and R represents a linear or branched $C_{1-4}$ alkyl radical.

The substituted spiro compounds according to the invention of the above-mentioned general formula I and of corresponding stereoisomers can optionally also be obtained, like the corresponding acids, the corresponding bases or salts of these compounds, using conventional methods known to a person skilled in the art in the form of their solvates, preferably in the form of their hydrates.

If the substituted spiro compounds according to the invention of the above-mentioned general formula I are obtained after preparation thereof in the form of a mixture of their stereoisomers, preferably in the form of their racemates or other mixtures of their various enantiomers and/or diastereomers, they can be separated and optionally isolated using conventional methods known to a person skilled in the art.

Examples include chromatographic separation processes, in particular liquid chromatography processes under normal pressure or under elevated pressure, preferably MPLC and HPLC processes, and fractionated crystallisation processes. These allow, in particular, the separation from one another of individual enantiomers of diastereomeric salts formed, for example, by means of HPLC on a chiral stationary phase or by means of crystallisation with chiral acids, for example (+)-tartaric acid, (−)-tartaric acid or (+)-10-camphorsulphonic acid.

The substituted spiro compounds according to the invention of the above-mentioned general formula I and corresponding stereoisomers and in each case the corresponding acids, bases, salts and solvates are toxicologically safe and are therefore suitable as pharmaceutical active ingredients in medicaments.

The present invention therefore further relates to a medicament comprising at least one spiro compound according to the invention of the above-indicated general formula I, in each case optionally in the form of one of its pure stereoisomers, in particular enantiomers or diastereomers, its racemates or in the form of a mixture of stereoisomers, in particular of enantiomers and/or diastereomers, in any desired mixing ratio, or respectively in the form of a corresponding salt, or respectively in the form of a corresponding solvate, and optionally one or more pharmaceutically compatible adjuvants.

These medicaments according to the invention are suitable, in particular, for vanilloid receptor 1 (VR1/TRPV1) regulation, preferably for vanilloid receptor 1 (VR1/TRPV1) inhibition and/or for vanilloid receptor 1 (VR1/TRPV1) stimulation.

Also preferably, the medicaments according to the invention are suitable for the prophylaxis and/or treatment of disturbances or diseases transmitted, at least in some cases, by vanilloid receptors 1.

Preferably, the medicament according to the invention is suitable for the treatment and/or prophylaxis of one or more diseases selected from the group consisting of pain, preferably of pain selected from the group consisting of acute pain, chronic pain, neuropathic pain and visceral pain; arthralgia; migraine; depression; neuropathy; nerve injuries; neurodegenerative diseases, preferably selected from the group consisting of multiple sclerosis, Alzheimer's disease, Parkinson's disease and Huntington's disease; cognitive dysfunctions, preferably cognitive deficiencies, particularly preferably paramnesia; epilepsy; respiratory diseases, preferably selected from the group consisting of asthma and pneumonia; coughing; urinary incontinence; OAB (overactive bladder); stomach ulcers; irritable bowel syndrome; strokes; irritations of the eyes; irritations of the skin; neurotic skin diseases; inflammatory diseases, preferably intestinal inflammations; diarrhoea; pruritus; eating disorders, preferably selected from the group consisting of bulimia, cachexia, anorexia and obesity; medication dependency; medication abuse; withdrawal symptoms in medication dependency; development of tolerance to medication, preferably to natural or synthetic opioids; drug addiction; drug abuse; withdrawal symptoms in drug addiction; alcohol addiction; alcohol abuse and withdrawal symptoms in alcohol addiction; for diuresis; for antinatriuresis; for influencing the cardiovascular system; for increasing vigilance; for increasing libido; for modulating motor activity; for anxiolysis; for local anaesthetics and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Particularly preferably, the medicament according to the invention is suitable for the treatment and/or prophylaxis of one or more diseases selected from the group consisting of pain, preferably of pain selected from the group consisting of acute pain, chronic pain, neuropathic pain and visceral pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiencies, particularly preferably paramnesia; urinary incontinence; OAB (overactive bladder); medication dependency; medication abuse; withdrawal symptoms in medication dependency; development of tolerance to medication, preferably development of tolerance to natural or synthetic opioids; drug addiction; drug abuse; withdrawal symptoms in drug addiction; alcohol addiction; alcohol abuse and withdrawal symptoms in alcohol addiction.

Most particularly preferably, the medicament according to the invention is suitable for the treatment and/or prophylaxis of pain, preferably of pain selected from the group consisting of acute pain, chronic pain, neuropathic pain and visceral pain, and/or urinary incontinence.

The present invention further relates to the use of at least one spiro compound according to the invention, including the compounds excluded hereinbefore, and optionally of one or more pharmaceutically compatible adjuvants for producing a medicament for vanilloid receptor 1 (VR1/TRPV1) regulation, preferably for vanilloid receptor 1 (VR1/TRPV1) inhibition and/or for vanilloid receptor 1 (VR1/TRPV1) stimulation.

Preferred is the use of at least one substituted spiro compound according to the invention, including the compounds excluded hereinbefore, and optionally of one or more pharmaceutically compatible adjuvants for producing a medicament for the prophylaxis and/or treatment of disturbances or diseases transmitted, at least in some cases, by vanilloid receptors 1.

Particularly preferred is the use of at least one spiro compound according to the invention, including the compounds excluded hereinbefore, and optionally of one or more pharmaceutically compatible adjuvants for producing a medicament for the treatment and/or prophylaxis of one or more diseases selected from the group consisting of pain, preferably of pain selected from the group consisting of acute pain, chronic pain, neuropathic pain and visceral pain and arthralgia.

Particularly preferred is the use of at least one spiro compound according to the invention, including the compounds excluded hereinbefore, and optionally of one or more pharmaceutically compatible adjuvants for producing a medicament for the treatment and/or prophylaxis of one or more diseases selected from the group consisting of migraine; depression; neuropathy; nerve injuries; neurodegenerative diseases, preferably selected from the group consisting of multiple sclerosis, Alzheimer's disease, Parkinson's disease and Huntington's disease; cognitive dysfunctions, preferably cognitive deficiencies, particularly preferably paramnesia; epilepsy; urinary incontinence; OAB (overactive bladder); stomach ulcers; irritable bowel syndrome; strokes; diarrhoea;

pruritus; eating disorders, preferably selected from the group consisting of bulimia, cachexia, anorexia and obesity; medication dependency; medication abuse; withdrawal symptoms in medication dependency; development of tolerance to medication, preferably to natural or synthetic opioids; drug addiction; drug abuse; withdrawal symptoms in drug addiction; alcohol addiction; alcohol abuse and withdrawal symptoms in alcohol addiction; for diuresis; for antinatriuresis; for influencing the cardiovascular system; for increasing vigilance; for increasing libido; for modulating motor activity; for anxiolysis; for local anaesthetics and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Particularly preferred is the use of at least one spiro compound according to the invention and optionally of one or more pharmaceutically compatible adjuvants for producing a medicament for the treatment and/or prophylaxis of one or more diseases selected from the group consisting of respiratory diseases, preferably selected from the group consisting of asthma and pneumonia; coughing; irritations of the eyes; irritations of the skin; neurotic skin diseases and inflammatory diseases, preferably intestinal inflammations.

Most particularly preferred is the use of at least one substituted spiro compound according to the invention, including the compounds excluded hereinbefore, and optionally of one or more pharmaceutically compatible adjuvants for producing a medicament for the treatment and/or prophylaxis of one or more diseases selected from the group consisting of pain, preferably of pain selected from the group consisting of acute pain, chronic pain, neuropathic pain and visceral pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiencies, particularly preferably paramnesia; urinary incontinence; OAB (overactive bladder); medication dependency; medication abuse; withdrawal symptoms in medication dependency; development of tolerance to medication, preferably development of tolerance to natural or synthetic opioids; drug addiction; drug abuse; withdrawal symptoms in drug addiction; alcohol addiction; alcohol abuse and withdrawal symptoms in alcohol addiction.

Still more preferred is the use of at least one substituted spiro compound according to the invention, including the compounds excluded hereinbefore, and optionally of one or more pharmaceutically compatible adjuvants for producing a medicament for the treatment and/or prophylaxis of pain, preferably selected from the group consisting of acute pain, chronic pain, neuropathic pain and visceral pain, and/or urinary incontinence.

The medicament according to the invention is suitable for administration to adults and children, including toddlers and babies.

The medicament according to the invention can be provided as a liquid, semisolid or solid pharmaceutical dosage form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, optionally compressed to form tablets, introduced into capsules or suspended in a liquid, and also be administered as such.

In addition to at least one substituted spiro compound of the above-indicated general formula I, optionally in the form of one of its pure stereoisomers, in particular enantiomers or diastereomers, its racemate or in the form of mixtures of stereoisomers, in particular of enantiomers or diastereomers, in any desired mixing ratio, or optionally in the form of a corresponding salt or respectively in the form of a corresponding solvate, the medicament according to the invention conventionally comprises further physiologically compatible pharmaceutical adjuvants which can be selected, for example, from the group consisting of excipients, fillers, solvents, diluting agents, surface-active substances, dyes, preservatives, disintegrants, slip additives, lubricants, aroma substances and binding agents.

The selection of the physiologically compatible adjuvants and the amounts thereof to be used are dependent on whether the medicament is to be administered orally, subcutaneously, parenterally, intravenously, intraperitoneally, intradermally, intramuscularly, intranasally, buccally, rectally or locally, for example to infections on the skin, the mucous membranes and on the eyes. Preferably suitable for oral administration are preparations in the form of tablets, dragées, capsules, granules, pellets, drops, juices and syrups, for parenteral, solutions to be administered topically and by inhalation, suspensions, easily reconstitutable dry preparations and sprays. The substituted spiro compounds according to the invention used in the medicament according to the invention in a repository in dissolved form or in a plaster, optionally with the addition of means promoting skin penetration, are suitable percutaneous administration preparations. Preparation forms to be administered orally or percutaneously can also release the respective substituted spiro compound according to the invention in a delayed manner.

The medicaments according to the invention are prepared using conventional means, devices, methods and processes known in the art such as are described, for example, in "Remington's Pharmaceutical Sciences", A. R. Gennaro (Editor), 17th edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted spiro compounds according to the invention of the above-indicated general formula I may vary and is, for example, dependent on the patient's weight or age and on the type of administration, the indication and the severity of the disease. Conventionally, 0.001 to 100 mg/kg, preferably 0.05 to 75 mg/kg, particularly preferably 0.05 to 50 mg/kg of the patient's body weight of at least one compound of this type according to the invention are administered.

Pharmacological Methods:

I. Functional Testing Carried Out on the Vanilloid Receptor 1 (VR1/TRPV1 Receptor)

The agonistic or antagonistic effect of the substances to be tested can be determined on the rat-species vanilloid receptor 1 (VR1/TRPV1) using the following assay. According to this assay, the $Ca^{2+}$ inflow is quantified through the receptor channel using a $Ca^{2+}$-sensitive dye (type Fluo-4, Molecular Probes Europe BV, Leiden, Netherlands) in a fluorescent imaging plate reader (FLIPR, Molecular Devices, Sunnyvale, USA).

Method:
Complete medium: 50 mL HAMS F12 nutrient mixture (Gibco Invitrogen GmbH, Karlsruhe, Germany) with 10% by volume of FCS (foetal calf serum, Gibco Invitrogen GmbH, Karlsruhe, Germany, heat-activated);
2 mM L-glutamine (Sigma, Munich, Germany);
1% by weight of AA solution (antibiotic/antimyotic solution, PAA, Pasching, Austria)
and 25 ng/ml NGF medium (2.5 S, Gibco Invitrogen GmbH, Karlsruhe, Germany)

Cell culture plate: Poly-D-lysine-coated, black 96 well plates having a clear base (96 well black/clear plate, BD Biosciences, Heidelberg, Germany) were additionally coated with laminin (Gibco Invitrogen GmbH, Karlsruhe, Germany), the laminin being diluted with PBS (Ca—Mg-free PBS, Gibco Invitrogen GmbH, Karlsruhe, Germany) to a concentration of 100 µg/mL. Aliquots having a laminin concentration of 100 µg/mL were removed and stored at −20° C. The aliquots were diluted with PBS in a ratio of 1:10 to 10 µg/mL laminin and in each case 50 µL of the solution were pipetted into a recess in the cell culture plate. The cell culture plates were incubated for at least two hours at 37° C., the excess solution was removed by suction-filtration and the recesses were each washed twice with PBS. The coated cell culture plates were stored with excess PBS which was not removed until just before the feeding of the cells.

Preparation of the Cells:

The vertebral column was removed from decapitated rats and placed immediately into cold HBSS buffer (Hank's buffered saline solution, Gibco Invitrogen GmbH, Karlsruhe, Germany), i.e. buffer located in an ice bath, mixed with 1% by volume (percent by volume) of an AA solution (antibiotic/antimyotic solution, PAA, Pasching, Austria). The vertebral column was cut longitudinally and removed together with fasciae from the vertebral canal. Subsequently, the dorsal root ganglia (DRG) were removed and again stored in cold HBSS buffer mixed with 1% by volume of an AA solution. The DRG, from which all blood remnants and spinal nerves had been removed, were transferred in each case to 500 µL of cold type 2 collagenase (PAA, Pasching, Austria) and incubated for 35 minutes at 37° C. After the addition of 2.5% by volume of trypsin (PAA, Pasching, Austria), incubation was continued for 10 minutes at 37° C. After complete incubation, the enzyme solution was carefully pipetted off and 500 µL of complete medium were added to each of the remaining DRG. The DRG were in each case suspended several times, drawn through cannulae No. 1, No. 12 and No. 16 using a syringe and transferred to a 50 mL Falcon tube which was filled up to 15 mL with complete medium. The contents of each Falcon tube was in each case filtered through a 70 µm Falcon filter element and centrifuged for 10 minutes at 1,200 rpm and room temperature. The resulting pellet was in each case taken up in 250 µL of complete medium and the number of cells determined.

The number of cells in the suspension was set to $3 \times 10^5$ per mL and 150 µL of this suspension were in each case introduced into a recess in the cell culture plates coated as described hereinbefore. In the incubator the plates were left for two to three days at 37° C., 5% by volume of $CO_2$ and 95% relative humidity.

Subsequently, the cells were loaded with 2 µM of Fluo-4 and 0.01% by volume of Pluronic F127 (Molecular Probes Europe BV, Leiden, Netherlands) in HBSS buffer (Hank's buffered saline solution, Gibco Invitrogen GmbH, Karlsruhe, Germany) for 30 min at 37° C., washed 3 times with HBSS buffer and after further incubation for 15 minutes at room temperature used for $Ca^{2+}$ measurement in a FLIPR assay. The $Ca^{2+}$-dependent fluorescence was measured before and after the addition of substances ($\lambda ex=488$ nm, $\lambda em=540$ nm). Quantification was carried out by measuring the highest fluorescence intensity (FC, Fluorescence Counts) over time.

FLIPR Assay:

The FLIPR protocol consists of 2 substance additions. First the compounds to be tested (10 µM) were pipetted onto the cells and the $Ca^{2+}$ inflow was compared with the control (capsaicin 10 µM). This provides the result in % activation based on the $Ca^{2+}$ signal after the addition of 10 µM capsaicin (CP). After 5 minutes' incubation, 100 nM of capsaicin were administered and the $Ca^{2+}$ inflow was also determined.

Desensitising agonists and antagonists led to suppression of the $Ca^{2+}$ inflow. The % inhibition was calculated compared to the maximum achievable inhibition with 10 µM of capsaicin.

Triple analyses (n=3) were carried out and repeated in at least 3 independent experiments (N=4).

II. Functional Testing Carried Out on the Vanilloid Receptor (VR1)

The agonistic or antagonistic effect of the substances to be tested can also be determined on the vanilloid receptor (VR1) using the following assay. According to this assay, the $Ca^{2+}$ inflow is quantified through the channel using a $Ca^{2+}$-sensitive dye (type Fluo-4, Molecular Probes Europe BV, Leiden, Netherlands) in a fluorescent imaging plate reader (FLIPR, Molecular Devices, Sunnyvale, USA).

Method:

Chinese hamster ovary cells (CHO K1 cells, European Collection of Cell Cultures (ECACC) United Kingdom) were stably transfected with the VR1 gene. For functional testing, these cells were plated out on poly-D-lysine-coated black 96 well plates having a clear base (BD Biosciences, Heidelberg, Germany) at a density of 25,000 cells/well. The cells were incubated overnight at 37° C. and 5% $CO_2$ in a culture medium (Ham's F12 nutrient mixture, 10% by volume of FCS (foetal calf serum), 18 µg/ml L-proline). The next day the cells were incubated with Fluo-4 (Fluo-4 2 µM, 0.01% by volume of Pluronic F127, Molecular Probes in HBSS (Hank's buffered saline solution), Gibco Invitrogen GmbH, Karlsruhe, Germany) for 30 minutes at 37° C. Subsequently, the plates were washed 3 times with HBSS buffer and after further incubation for 15 minutes at room temperature used for $Ca^{2+}$ measurement in a FLIPR assay. The $Ca^{2+}$-dependent fluorescence was measured before and after the addition of the substances to be tested ($\lambda ex$ wavelength=488 nm, $\lambda em=540$ nm). Quantification was carried out by measuring the highest fluorescence intensity (FC, Fluorescence Counts) over time.

FLIPR Assay:

The FLIPR protocol consists of 2 substance additions. First the compounds to be tested (10 µM) were pipetted onto the cells and the $Ca^{2+}$ inflow was compared with the control (capsaicin 10 µM) (% activation based on the $Ca^{2+}$ signal after the addition of 10 µM capsaicin). After 5 minutes' incubation, 100 nM of capsaicin were administered and the $Ca^{2+}$ inflow was also determined.

Desensitising agonists and antagonists led to suppression of the $Ca^{2+}$ inflow. The % inhibition was calculated compared to the maximum achievable inhibition with 10 μM of capsaicin.

III. Formalin Test Carried Out on Mice

In the formalin test, the testing to determine the antinociceptive effect of the compounds according to the invention was carried out on male mice (NMRI, 20 to 30 g body weight, Iffa, Credo, Belgium).

In the formalin test as described by D. Dubuisson et al., Pain 1977, 4, 161-174, a distinction is drawn between the first (early) phase (0 to 15 minutes after the injection of formalin) and the second (late) phase (15 to 60 minutes after the injection of formalin). The early phase, as an immediate reaction to the injection of formalin, is a model of acute pain, whereas the late phase is regarded as a model of persistent (chronic) pain (T. J. Coderre et al., Pain 1993, 52, 259-285). The corresponding descriptions in the literature are introduced herewith by way of reference and form part of the disclosure.

The compounds according to the invention were tested in the second phase of the formalin test to obtain information about the effects of substances on chronic/inflammatory pain.

The moment at which the compounds according to the invention were administered before the injection of formalin was selected as a function of the type of administration. 10 mg of the test substances/kg of body weight were administered intravenously 5 minutes before the injection of formalin which was carried out by a single subcutaneous injection of formalin (20 μL, 1% aqueous solution) into the dorsal side of the right hind paw, thus inducing in free moving test animals a nociceptive reaction which manifests itself in marked licking and biting of the respective paw.

Subsequently, the nociceptive behaviour was continuously detected by observing the animals over a test period of three minutes in the second (late) phase of the formalin test (21 to 24 minutes after the injection of formalin). The pain behaviour was quantified by adding up the seconds over which the animals displayed licking and biting of the respective paw during the test period.

The comparison was carried out in each case with control animals which were given vehicles (0.9% aqueous sodium chloride solution) instead of the compounds according to the invention before the administration of formalin. Based on the quantification of the pain behaviour, the effect of the substance was determined in the formalin test as a percentage change relative to the corresponding control.

After the injection of substances having an antinociceptive effect in the formalin test, the described behaviour of the animals, i.e. licking and biting, was reduced or eliminated.

IV. Testing of Analgesic Efficacy in the Writhing Test

The testing of analgesic efficacy in the compounds according to the invention of general formula I was carried out by phenylquinone-induced writhing in mice (modified in accordance with I. C. Hendershot and J. Forsaith (1959), J. Pharmacol. Exp. Ther. 125, 237-240). The corresponding description in the literature is introduced herewith by way of reference and forms part of the disclosure.

Male NMRI mice weighing from 25 to 30 g were used for this purpose. 10 minutes after intravenous administration of the compounds to be tested, groups of 10 animals per compound dose received 0.3 ml/mouse of a 0.02% aqueous solution of phenylquinone (phenylbenzoquinone, Sigma, Deisenhofen, Germany; solution prepared by adding 5% by weight of ethanol and stored in a water bath at 45° C.) administered intraperitoneally. The animals were placed individually into observation cages. A pushbutton counter was used to record the number of pain-induced stretching movements (what are known as writhing reactions=straightening of the torso with stretching of the rear extremities) for 5 to 20 minutes after phenylquinone administration. The control was provided by animals which had received only physiological saline solution. All of the compounds were tested at the standard dosage of 10 mg/kg.

The invention will be described hereinafter with reference to a few examples. This description is intended merely by way of example and does not limit the general idea of the invention.

EXAMPLES

The yields of the compounds prepared are not optimised.

All temperatures are uncorrected.

Abbreviations abs. absolute aq. aqueous eq. equivalent amount of substance

Boc tert-butoxycarbonyl

D days

DCM dichloromethane

DMF dimethylformamide

EtOAc ethyl acetate

EtOH ethanol sat. saturated

MeOH methanol

NMR nuclear magentic resonance spectroscopy

RT room temperature

THF tetrahydrofuran

The chemicals and solvents used were purchased from the conventional suppliers (Acros, Avocado, Aldrich, Bachem, Fluka, Lancaster, Maybridge, Merck, Sigma, TCI, etc.) or synthesised using the methods known to a person skilled in the art.

The stationary phase used for the column chromatography was silica gel 60 (0.040-0.063 mm) from E. Merck, Darmstadt.

The thin-layer chromatographic tests were carried out using HPTLC precoated plates, silica gel 60 F 254, from E. Merck, Darmstadt.

The mixing ratios of solvents, mobile solvents or for chromatographic tests are in each case specified in volume/volume.

The analysis was carried out by mass spectroscopy and NMR.

Preparation of substituted
1-oxa-2,8-diazaspiro[4.5]dec-2-ene derivatives
according to the invention 1. Synthesis of
3-phenyl-1-oxa-2,8-diazaspiro[4.5]dec-2-ene The synthesis of 3-phenyl-1-oxa-2,8-diazaspiro[4.5]dec-2-ene (E) is illustrated in Diagram 2.

Diagram 2.

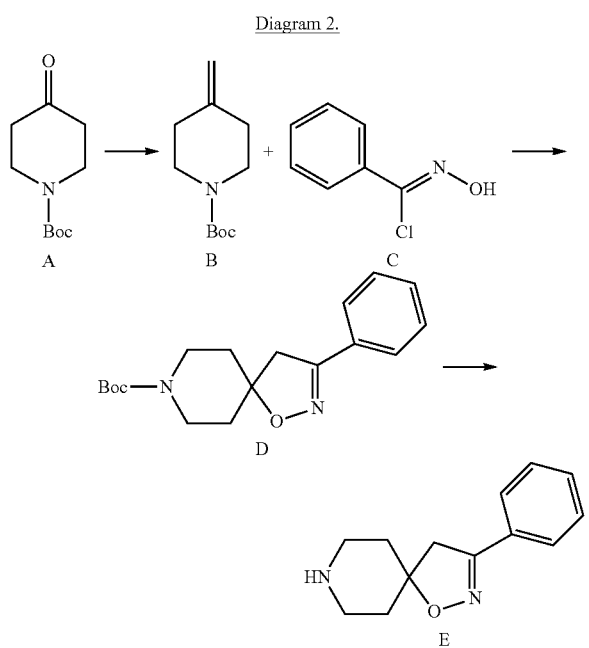

Synthesis of 4-methylene piperidine-1-carboxylic acid tert-butyl ester (B)

1.6 g (14 mmol) potassium tert-butylate were added to a suspension of 5.34 g (15 mmol) methyltriphenylphosphonium bromide in 50 ml diethyl ether while stirring at 0° C. (ice bath). After stirring for 15 min, a solution of 2.00 g (10 mmol) 1-Boc-4-piperidone (A) in 15 ml diethyl ether was added slowly. The suspension was stirred for a further 30 min at 0° C. After the addition of 60 ml 10% aq. NH$_4$Cl solution, the organic phase was separated off, dried over magnesium sulphate and desolventised under vacuum. After chromatography on silica gel (hexane:EtOAc=5:1), 1.71 g (89%) 4-methylene piperidine-1-carboxylic acid tert-butyl ester (B) were obtained as a colourless liquid.

$^1$H-NMR spectrum (d$_6$-DMSO): δ=1.47 ppm (s, 9H, C(CH$_3$)$_3$); 2.16-2.19 ppm (m, 4H, CH$_2$); 3.40-3.44 ppm (m, 4H, CH$_2$); 4.74 (s, 2H, C=CH$_2$).

Synthesis of 1-chloro-1-hydroxyiminomethylbenzene (C)

N-chlorosuccinimide (4.63 g, 34.7 mmol) was added to a solution of benzaldehyde oxime (3.5 g, 28.9 mmol) in DMF (30 ml) at RT, causing the temperature to rise briefly to 50° C. The reaction mixture was cooled in an ice bath, stirred for 3 h at RT, mixed with water (100 ml) while being cooled with ice and extracted with ether (3×100 ml). The combined organic phases were washed with water (150 ml) and sat. aq. NaCl solution (150 ml), dried and the solvent was removed under vacuum. The desired product 1-chloro-1-hydroxyiminomethylbenzene (C) was obtained as a yellowish solid (4.28 g).

Synthesis of 3-phenyl-1-oxa-2,8-diazaspiro[4.5]dec-2-ene-8-carboxylic acid tert-butyl ester (D)

A solution of 1-chloro-1-hydroxyiminomethylbenzene (C) (93.6 g, 601 mmol) in DCM (400 ml) was slowly added dropwise to a solution of 4-methylene piperidine-1-carboxylic acid tert-butyl ester (B) (39.5 g, 200 mmol) in DCM (400 ml) at 0° C. A solution of triethylamine (6.7 ml) in DCM (400 ml) was then slowly added dropwise and the resulting mixture was stirred for 48 hours at RT.

The reaction mixture was diluted with DCM and washed with water, 10% aq. citric acid solution and sat. aq. NaCl solution. The organic phase was dried and the solvent removed under vacuum. The residue was taken up in ether (40 ml), wherein the desired product formed as a white precipitate which was removed by suction-filtration and then dried. 36.4 g (57% of the theoretical amount) of the desired product were obtained.

Synthesis of 3-phenyl-1-oxa-2,8-diazaspiro[4.5]dec-2-ene (E) as a hydrochloride salt A solution of 3-phenyl-1-oxa-2,8-diazaspiro[4.5]dec-2-ene-8-carboxylic acid tert-butyl ester (D) (3.08 g, 9.73 mmol) in MeOH (90 ml) was mixed at 0° C. with conc. HCl (16.5 ml). The reaction mixture was stirred overnight, the solvent removed under vacuum and the residue was added slowly to cooled ether (500 ml). After 48 hours there had formed a fine precipitate which was removed by suction-filtration and dried. The desired product (1.87 g, 76% of the theoretical amount) was obtained as a white solid.

2. Synthesis of 3-(3-chloropyridin-2-yl)-1-oxa-2,8-diazaspiro[4.5]dec-2-ene (K)

The synthesis of 3-(3-chloropyridin-2-yl)-1-oxa-2,8-diazaspiro[4.5]dec-2-ene (K) is illustrated in Diagram 3.

Diagram 3.

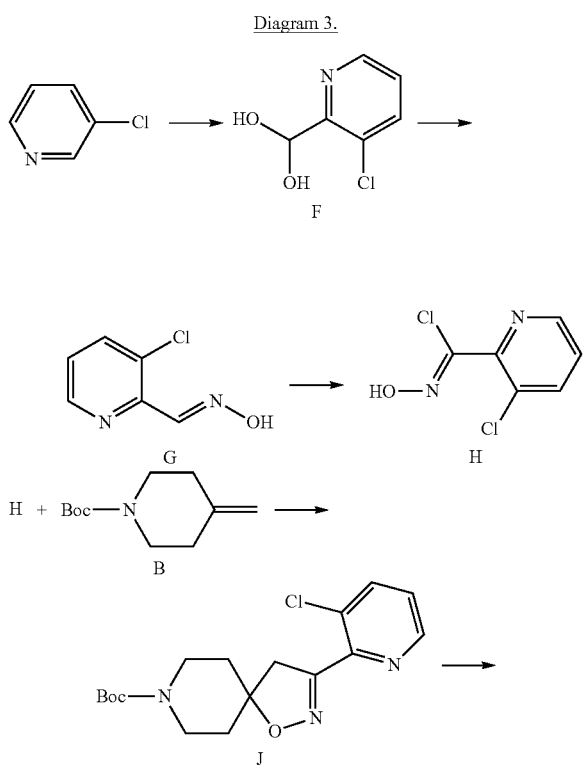

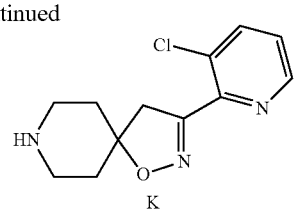

K

Synthesis of 3-chloropyridine-2-carbaldehyde (F)

A 2.5 M solution of n-butyllithium (96 ml, 240 ml) in n-hexane was added to a solution of N,N dimethylaminoethanol (10.65 g, 120 mmol) in abs. THF (70 ml) at −5° C. under argon within 25 min. The reaction mixture was stirred for 30 min at 0° C. and cooled down to −70° C. At a temperature of −70 to −65° C., a solution of 3-chloropyridine (3.8 ml, 4.5 g, 40 mmol) in abs. THF (60 ml) was added within 10 min and stirred for a further hour at this temperature. Abs. DMF (12.3 ml, 11.7 g, 160 mmol) in THF (100 ml) was then added within 15 min at −65 to −60° C. The dark brown solution was heated within 1 h to 10° C. At a temperature of −20 to −10° C., the reaction mixture was hydrolysed with sat. ammonium chloride solution (120 ml). The mixture was then stirred for 30 min at 0° C. The phases were not separated. The organic solvents were removed under vacuum. The residue was extracted with DCM (120 ml). The phases were separated. The aqueous phase was extracted with DCM (3×120 ml). The organic phases were combined and concentrated without drying. The residue was a brown oil which was further purified by adding water (4×50 ml) and decanting. After the addition of DCM (250 ml) and sodium sulphate, the mixture was dried overnight and then concentrated. The crude product of the 3-chloropyridine-2-carbaldehyde (F) was obtained as a hydrate (brown oil 8.73 g, theoretical yield 6.3 g). Chromatographic purification of the crude product was not possible. The crude product was used without further purification.

Synthesis of chloropyridine-2-carbaldehyde oxime (G)

The aldehyde hydrate F (6.3 g, 40 mmol) was dissolved in EtOH (170 ml) and mixed successively with hydroxylamine hydrochloride (4.16 g, 60 mmol) and Amberlyst A 21 (25.5 g, basic ion exchanger). The reaction mixture was stirred for 20 h at RT and the ion exchanger then separated off by filtration. The filtrate was concentrated, the solid brown residue washed with water (3×50 ml) and separated off by filtration. The crude product was taken up in DCM (30 ml) and stirred for 30 min. A solid was then separated off by filtration and washed with DCM (2×8 ml). The solid was obtained as a beige-coloured solid in a yield of 45% (2.79 g).

Synthesis of 4-(3-chloropyridin-2-yl)hydroxymoyl chloride (H)

A solution of N-chlorosuccinimide (8.94 g, 66.0 mmol) in abs. DMF (50 ml) was added to a solution of compound G (8.61 g, 55.0 mmol) in abs. DMF (70 ml) at a temperature of 30-40° C. within 20 min. Cooling in an ice bath was carried out if necessary. The clear reaction mixture was stirred for 3 h at RT and then mixed with diethyl ether (600 ml) and water (400 ml). The phases were separated. The aqueous phase was extracted with diethyl ether (200 ml). The combined organic phases were washed successively with water (300 ml) and sat. NaCl solution (200 ml). The organic phase was dried and concentrated. The crude product of compound H was obtained as a brown solid (8.1 g, 77%) and immediately reacted further.

Synthesis of 3-(3-chloropyridin-2-yl)-1-oxa-2,8-diazaspiro[4.5]dec-2-ene-8-carboxylic acid tert-butyl ester (J)

Compound H (8.1 g, 42.4 mmol), dissolved in abs. THF (80 ml), was added dropwise at 0° C. within 10 min to a solution of compound B (5.97 g, 30.3 mmol) in abs. THF (80 ml). A solution of triethylamine (23.7 ml, 17.1 g, 170 mmol) in abs. THF (30 ml) was added to this mixture at 0° C. within 15 min. As the reaction was highly exothermic, cooling was carried out in an ice/sodium chloride mixture. A solid formed during the addition. The reaction mixture was stirred for 16 h at RT. For working up the mixture, water (120 ml) was added and THF removed under vacuum. The remaining aqueous phase was extracted with DCM (130 ml). The organic phase was washed successively with 10% citric acid solution (2×150 ml) and sat. NaCl solution (150 ml). The organic phase was dried and concentrated (11.4 g, brown oil). The residue was separated by chromatography [silica gel 60 (400 g); EtOAc/cyclohexane 1:3 (1.7 l), EtOAc/cyclohexane 1:2 (2.4 l), EtOAc/cyclohexane 1:1 (0.6 l)]. Compound J was obtained as a colourless solid in a yield of 20% (2.1 g) having a melting point of 97-102° C.

Synthesis of 3-(3-chloropyridin-2-yl)-1-oxa-2,8-diazaspiro[4.5]dec-2-ene (K) as hydrochloride Compound J (2.1 g, 5.97 mmol) was dissolved in DCM (35 ml) and mixed with a 5N hydrochloric acid solution in propan-2-ol (23.8 ml, 119 mmol). After a reaction time of 2 h, the hydrochloride of compound K formed as a colourless solid and was isolated in a yield of 99% (1.7 g) having a melting point of 241-245° C.

3. Synthesis of 3-(thiazol-2-yl)-1-oxa-2,8-diazaspiro[4.5]dec-2-ene (O)

The synthesis of 3-(thiazol-2-yl)-1-oxa-2,8-diazaspiro[4.5]dec-2-ene is illustrated in Diagram 4.

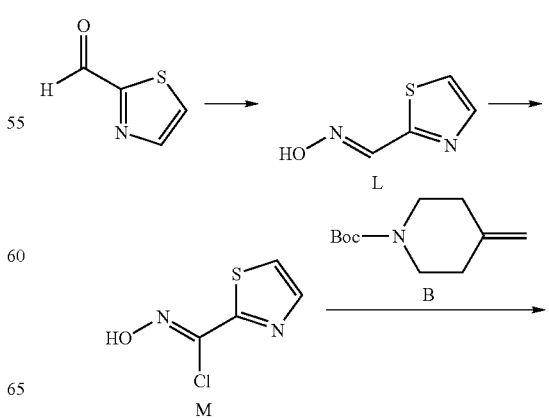

Diagram 4.

-continued

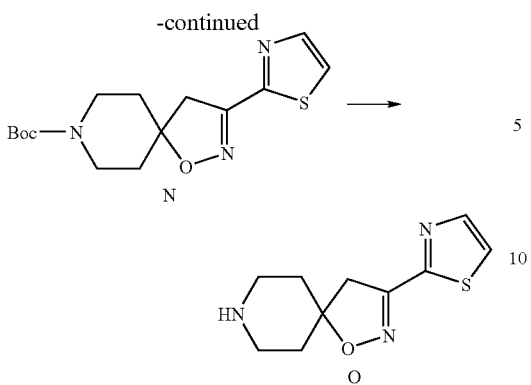

Synthesis of thiazole-2-carbaldehyde oxime (L)

Thiazole-2-carbaldehyde (14.0 g, 124 mmol) was dissolved in EtOH (450 ml) and mixed successively with hydroxylamine hydrochloride (12.9 g, 186 mmol) and Amberlyst A 21 (79 g, basic ion exchanger). The reaction mixture was stirred for 24 h at RT and the ion exchanger then separated off by filtration. The filtrate was concentrated, the solid residue taken up in EtOAc (350 ml) and washed with water (3×90 ml). The organic phase was dried and concentrated. Compound L was obtained as a yellow solid in a yield of 94% (14.92 g).

Synthesis of thiazol-2-ylhydroxymoyl chloride (M)

A solution of N-chlorosuccinimide (18.9 g, 139 mmol) in abs. DMF (65 ml) was added to a solution of compound L (14.9 g, 116 mmol) in abs. DMF (40 ml) at a temperature of 30-40° C. within 20 min. Cooling in an ice bath was carried out if necessary. The reaction mixture was stirred for 3 h at RT and then mixed with diethyl ether (650 ml) and water (440 ml). As a solid precipitated between the phases, the mixture was filtered before the separation of the phases. The aqueous phase was extracted with diethyl ether (2×200 ml). The combined organic phases were washed successively with water (300 ml) and sat. NaCl solution (200 ml). The organic phase was dried and concentrated. The crude product of compound M was obtained as a yellow solid (13.6 g) and immediately reacted further.

Synthesis of 3-(thiazol-2-yl)-1-oxa-2,8-diazaspiro [4.5]dec-2-ene-8-carboxylic acid tert-butyl ester (N)

Compound M (13.6 g, 116 mmol), dissolved in abs. THF (180 ml) and abs. diethyl ether (80 ml), was added dropwise at 0° C. within 10 min to a solution of compound B (13.2 g, 66.7 mmol) in abs. THF (100 ml). A solution of triethylamine (65.1 ml, 23.3 g, 464 mmol) in abs. THF (60 ml) was added to this mixture at 0° C. within 30 min. As the reaction was highly exothermic, cooling was carried out in an ice/sodium chloride mixture. A solid formed during the addition. The reaction mixture was stirred for 16 h at RT. The solid was removed by suction-filtration, the filtrate concentrated and the dark brown oily residue was stirred with diethyl ether (300 ml) and water (120 ml) for 10 min. After separation of the phases, the aqueous phase was extracted with diethyl ether (2×100 ml). The combined organic extracts were washed successively with 10% citric acid solution (2×150 ml) and sat. NaCl solution (100 ml). The organic phase was dried and concentrated to approx. 50 ml. This solution was mixed with n-hexane until the mixture turned cloudy and then stored for 24 h at −18° C. The desired product N formed, contaminated by a secondary product, as a light brown solid (3.81 g) and was removed by suction-filtration. The filtrate was concentrated and the dark brown oily residue was separated by chromatography [silica gel 60 (200 g); cyclohexane/EtOAc 5:1 (1,900 ml); 3:1 (1,100 ml)]. There could be obtained 1.0 g of the desired product N which still contained impurities.

Synthesis of 3-(thiazol-2-yl)-1-oxa-2,8-diazaspiro [4.5]dec-2-ene (O)

Compound N (3.8 g, 11.75 mmol) was dissolved in DCM (55 ml) and mixed with a 5.5 N hydrochloric acid solution in propan-2-ol (43 ml, 235 mmol). A solid formed immediately. After a reaction time of 1 h, the solid was removed by suction-filtration and the mixture concentrated. The light brown oil obtained was mixed with diethyl ether (20 ml) and EtOH (2 ml) and stirred for 7 h at RT. The solid obtained (1.0 g) was removed by suction-filtration and the filtrate stirred for 16 h. Further solid (618 mg) could be obtained. Both fractions were combined. The desired product O was isolated as a yellow compound in a yield of 53% having a melting point of 244-251° C.

4. Synthesis of 3-phenyl-1-oxa-2,7-diazaspiro[4.4]non-2-ene (R)

The synthesis of 3-phenyl-1-oxa-2,7-diazaspiro[4.4]non-2-ene is illustrated in Diagram 5.

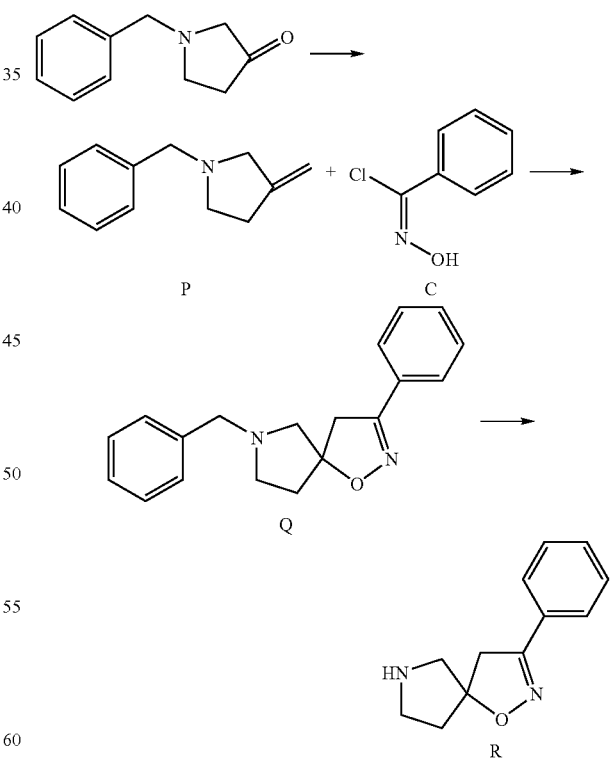

Synthesis of 1-benzyl-3-methylenepyrrolidine (P)

Potassium tert-butylate (2.1 g, 18.8 mmol, dissolved in 20 ml abs. THF) was added to a suspension of methyltriphenylphosphonium bromide (7.5 g, 21 mmol) in dry THF (20 ml) under argon at 0° C. within 30 min. The yellow reaction mixture was stirred for 30 min at 0° C. before 1-benzyl-pyrrolidin-3-one (2.46 g, 15 mmol) dissolved in abs. THF (20 ml) was added dropwise within 30 min at 0° C. The mixture obtained was left for 30 min at 0° C., brought to RT within 1 h and stirred for a further 15 h. For working up, the mixture was added to sat. NH$_4$Cl solution (50 ml) and then extracted with EtOAc (3×20 ml). The desired product P was converted into the corresponding hydrochloride by extraction with 2 N HCl (20 ml). The organic phase was washed with water (3×20 ml) and the combined aqueous phases were basified with K$_2$CO$_3$. The desired product P was obtained in the form of a layer of oil and was separated off by reextraction with EtOAc (3×20 ml). After drying of the combined organic phases over Na$_2$SO$_4$ and removal of the solvent, the desired product P was present in a sufficiently pure form (2.17 g, 83%).

Synthesis of 7-benzyl-3-phenyl-1-oxa-2,7-diazaspiro [4.4]non-2-ene (Q)

Compound C (3.9 g, 25.2 mmol, dissolved in abs. DCM (25 ml)) was added dropwise to a solution of 1-benzyl-3-methylenepyrrolidine (P) (2.18 g, 12.6 mmol) in abs. DCM (25 ml) at 0° C. within 10 min. A solution of triethylamine (14 ml, 10.2 g, 100.1 mmol) in abs. DCM (25 ml) was added to this mixture at 0° C. within 10 min. As the reaction was highly exothermic, cooling was carried out in an ice/sodium chloride mixture. The reaction mixture was stirred for 16 h at RT. For working up the mixture, DCM (50 ml) and water (70 ml) were added. The phases were separated. The aqueous solution was extracted with DCM (2×20 ml). The combined organic phases were washed successively with water (50 ml) and sat. NaCl solution (50 ml) and then dried and concentrated (5.3 g, yellow oil). The residue was purified by column chromatography [silica gel 60 (500 g); EtOAc/cyclohexane 1:2 (3 l)]. The desired compound Q was obtained as a solid in a yield of (2.4 g, 65%) having a melting point of 31-40° C.

Synthesis of 3-phenyl-1-oxa-2,7-diazaspiro[4.4]non-2-ene (R)

Compound Q (700 mg, 2.1 mmol) was dissolved in a mixture of THF (80 ml) and MeOH (10 ml) and mixed with palladium catalyst (Pd/C, 5%, 555 mg) and subjected to hydrogen pressure of 3 bar over a total of 2.5 h at RT. The catalyst was removed using a frit. After removal of the solvent there were obtained 420 mg of an oily residue (theoretical yield 424 mg) which consisted largely of the desired product R and was used without further purification.

5. Synthesis of 6-methyl-3-phenyl-1-oxa-2,8-diaza-spiro[4.5]dec-2-ene (U)

The synthesis of 6-methyl-3-phenyl-1-oxa-2,8-diazaspiro [4.5]dec-2-ene is illustrated in Diagram 6.

Diagram 6.

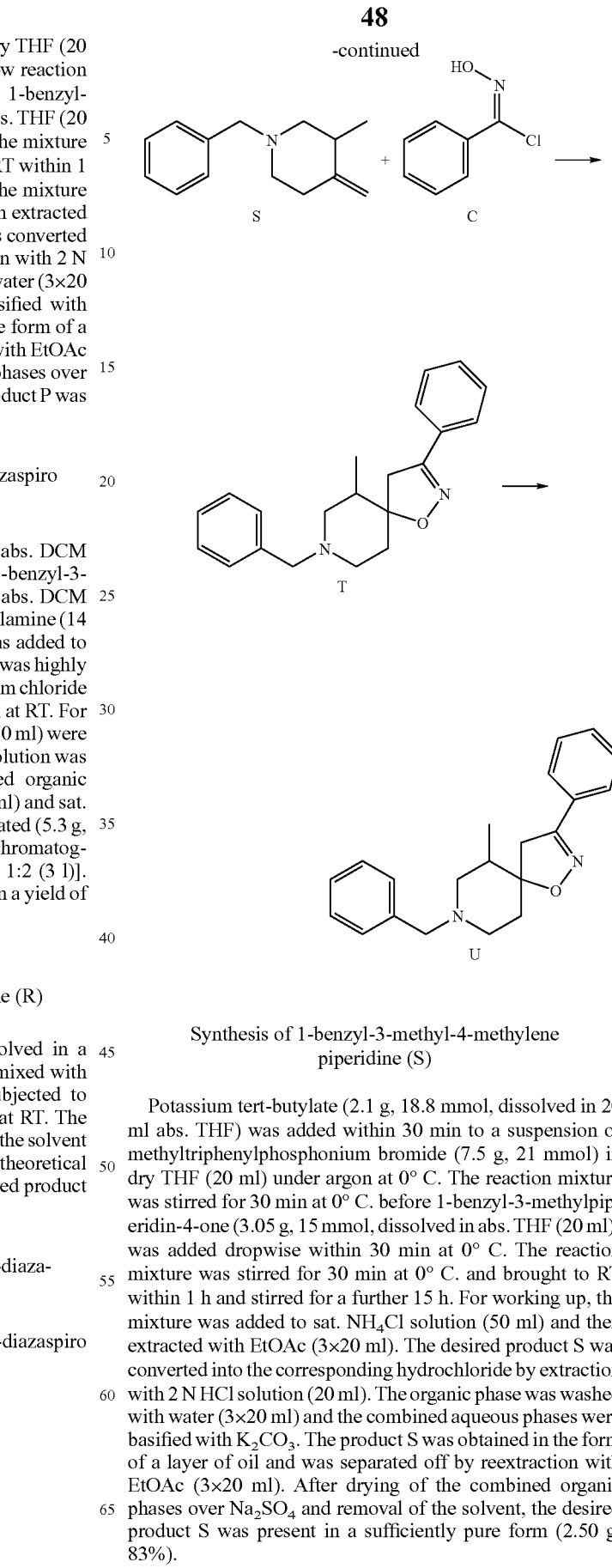

Synthesis of 1-benzyl-3-methyl-4-methylene piperidine (S)

Potassium tert-butylate (2.1 g, 18.8 mmol, dissolved in 20 ml abs. THF) was added within 30 min to a suspension of methyltriphenylphosphonium bromide (7.5 g, 21 mmol) in dry THF (20 ml) under argon at 0° C. The reaction mixture was stirred for 30 min at 0° C. before 1-benzyl-3-methylpiperidin-4-one (3.05 g, 15 mmol, dissolved in abs. THF (20 ml)) was added dropwise within 30 min at 0° C. The reaction mixture was stirred for 30 min at 0° C. and brought to RT within 1 h and stirred for a further 15 h. For working up, the mixture was added to sat. NH$_4$Cl solution (50 ml) and then extracted with EtOAc (3×20 ml). The desired product S was converted into the corresponding hydrochloride by extraction with 2 N HCl solution (20 ml). The organic phase was washed with water (3×20 ml) and the combined aqueous phases were basified with K$_2$CO$_3$. The product S was obtained in the form of a layer of oil and was separated off by reextraction with EtOAc (3×20 ml). After drying of the combined organic phases over Na$_2$SO$_4$ and removal of the solvent, the desired product S was present in a sufficiently pure form (2.50 g, 83%).

Synthesis of 8-benzyl-6-methyl-3-phenyl-1-oxa-2,8-diazaspiro[4.5]dec-2-ene (T)

Compound C (4.49 g, 28.9 mmol, dissolved in abs. DCM (25 ml)) was added dropwise to a solution of compound S (2.5 g, 14.45 mmol) in abs. DCM (25 ml) at 0° C. within 10 min. A solution of triethylamine (16 ml, 11.7 g, 115.6 mmol) in abs. DCM (25 ml) was added to this mixture within 10 min at 0° C. As the reaction was highly exothermic, cooling was carried out in a mixture of ice/sodium chloride. The reaction mixture was stirred for 16 h at RT. For working up the mixture, DCM (50 ml) and water (70 ml) were added. The phases were separated. The aqueous solution was extracted with DCM (2×20 ml). The combined organic phases were washed successively with water (50 ml) and sat. NaCl solution (50 ml) and then dried and concentrated (4.9 g, yellow oil). The residue was purified by column chromatography [silica gel 60 (500 g); EtOAc/cyclohexane 1:2 (3 l)]. The desired product was obtained as a diastereomer mixture in a yield of (2.28 g, 50%) having a melting point of 101-108° C.

Synthesis of 6-methyl-3-phenyl-1-oxa-2,8-diazaspiro[4.5]dec-2-ene (U)

Compound T (600 mg, 1.65 mmol) was mixed in MeOH (50 ml) with palladium catalyst (Pd/C, 5%, 500 mg) and subjected to hydrogen pressure of 3 bar for 30 min at RT. The catalyst was removed using a frit. After removal of the solvent there were obtained 340 mg (~90% yield) of an oily residue which consisted largely of the desired product U and was used without further purification.

6. Synthesis of 3-benzyl-1-oxa-2,8-diazaspiro[4.5]dec-2-ene (Y)

The synthesis of 3-benzyl-1-oxa-2,8-diazaspiro[4.5]dec-2-ene is represented in the following Diagram 7.

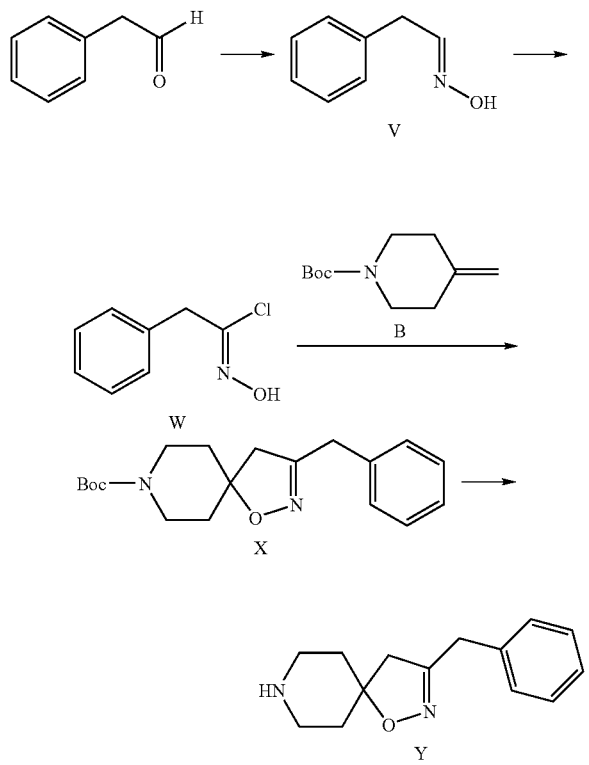

Diagram 7.

Synthesis of phenylacetaldehyde oxime (V)

Phenylacetaldehyde (12.0 g, 7.8 ml, 0.1 mol) was dissolved in EtOH (360 ml) and mixed while stirring successively with hydroxylamine hydrochloride (10.4 g, 0.15 mol) and abs. pyridine (9.7 ml, 0.12 mol). After stirring for 1.5 h at RT, the reaction mixture was concentrated, the residue taken up in toluene (1×100 ml) and the solvent removed again under vacuum. The oily residue was stirred with EtOAc (350 ml) and water (90 ml) for 15 min. Subsequently, the phases were separated. The organic phase was washed with water (2×80 ml), dried and concentrated. The oil obtained crystallised after a short time. The oil was recrystallised from n-hexane (20 ml). Compound V was obtained as a white solid in a yield of 31% (4.13 g) having a melting point of 90-94° C.

Synthesis of phenylacetohydroximoyl chloride (W)

A solution of N-chlorosuccinimide (3.25 g, 24 mmol) in abs. DMF (18 ml) was added to a solution of compound V (2.7 g, 20 mmol) in abs. DMF (12 ml) at a temperature of 30-40° C. within 20 min. Cooling in an ice bath was carried out if necessary. The reaction mixture was stirred for 3 h at RT and then mixed with diethyl ether (175 ml) and water (115 ml). The phases were separated and the aqueous phase was extracted with diethyl ether (2×75 ml). The combined organic extracts were washed successively with water (100 ml) and sat. NaCl solution (100 ml). The organic phase was dried and concentrated. Compound W was obtained as a yellowish-green oil (3.33 g) and immediately reacted further.

Synthesis of 3-benzyl-1 oxa-2,8-diazaspiro[4.5]dec-2-ene-8-carboxylic acid tert-butyl ester (X)

Compound W (3.33 g, 20 mmol), dissolved in abs. DCM (15 ml), was added dropwise at 0° C. within 10 min to a solution of compound B (2.81 g, 14.3 mmol in abs. DCM (22 ml)). A solution of triethylamine (11.2 ml, 80 mmol) in abs. DCM (10 ml) was added to this mixture at 0° C. within 10 min. As the reaction was highly exothermic, cooling was carried out with a mixture of ice and sodium chloride. The reaction mixture was stirred for 16 h at RT. For working up the mixture, DCM (15 ml) and water (45 ml) were added and the mixture was stirred for 15 min. After separation of the phases, the aqueous phase was extracted with DCM (2×45 ml). The phases were separated. The organic phase was washed successively with 10% citric acid solution (2×30 ml) and sat. NaCl solution (30 ml). The organic phase was dried and concentrated (5.3 g, brown oil). The residue was separated by chromatography [silica gel 60 (180 g); cyclohexane/EtOAc 7:1 (1,200 ml); 5:1 (900 ml)]. The desired product X was obtained in a yield of 681 mg (11%).

Synthesis of 3-benzyl-1-oxa-2,8-diazaspiro[4.5]dec-2-ene (Y)

Compound X (670 mg, 2.0 mmol) was dissolved in DCM (20 ml) and mixed with a 5.5 N hydrochloric acid solution in propan-2-ol (7.3 ml, 40 mmol). After a reaction time of 4 h, the mixture was concentrated to approx. 10 ml and then stirred in an ice bath. The precipitated solid was removed by suction-filtration and washed with diethyl ether. 395 mg (74%, mp 198-204° C.) of the hydrochloride of 3-benzyl-1-oxa-2,8-diazaspiro[4.5]dec-2-ene were obtained.

The hydrochloride (340 mg, 1.27 mmol) was stirred with DCM (20 ml) and sat. NaHCO₃ solution (10 ml) for 1 h. After separation of the phases, the aqueous phase was extracted with DCM (2×10 ml). The organic extracts were dried and concentrated. 3-benzyl-1-oxa-2,8-diazaspiro[4.5]dec-2-ene was obtained in a yield of 98% (286.5 mg) having a melting point of 51-54° C.

7. Synthesis of 3-phenethyl-1-oxa-2,8-diazaspiro[4.5]dec-2-ene (CC)

The synthesis of 3-phenethyl-1-oxa-2,8-diazaspiro[4.5] dec-2-ene is represented in the following Diagram 8.

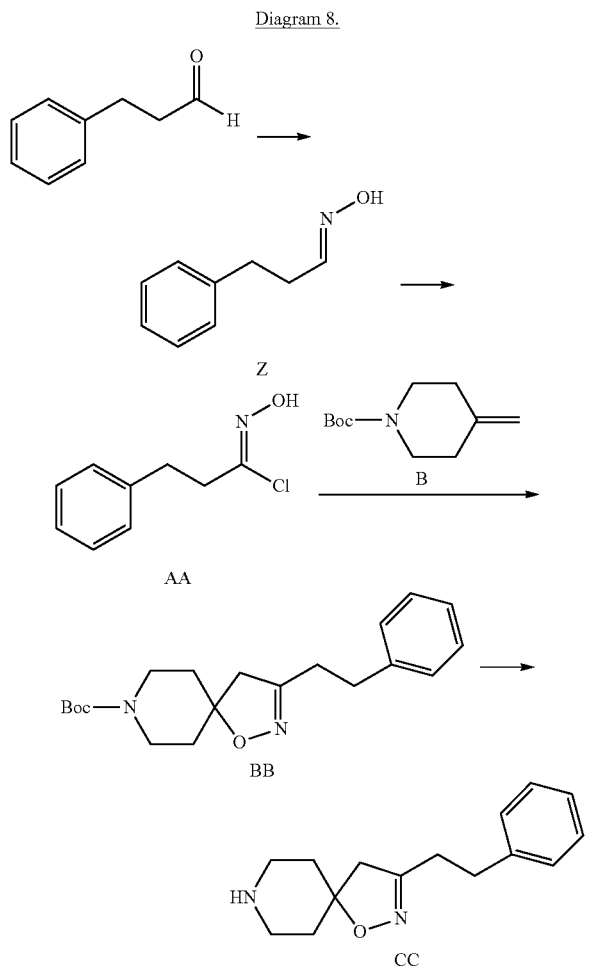

Diagram 8.

Synthesis of 3-phenylpropionaldehyde oxime (Z)

Phenylpropionaldehyde (3.35 g, 3.3 ml, 25 mmol) was dissolved in EtOH (90 ml) and mixed successively with hydroxylamine hydrochloride (2.6 g, 37.5 mmol) and abs. pyridine (2.42 ml, 30 mmol) while stirring. After stirring for 4 h, the solvent was removed under vacuum, the residue taken up in toluene (1×50 ml) and the solvent removed again under vacuum. The oily residue was stirred with EtOAc (50 ml) and water (30 ml) for 15 min. Subsequently, the phases were separated. The organic phase was washed with water (2×20 ml), dried and concentrated. The oil obtained (4.71 g) was highly contaminated and crystallised only in part. The oil was dissolved in n-hexane (20 ml) and stored for 18 h at 5° C. The precipitated plates were removed by suction-filtration. Compound Z was obtained as a white solid in a yield of 24% (892 mg) having a melting point of 85-93° C.

Synthesis of 3-phenyl propanehydroximoyl chloride (AA)

A solution of N-chlorosuccinimide (2.24 g, 16.6 mmol) in abs. DMF (11 ml) was added to a solution of compound Z (2.06 g, 13.8 mmol) in abs. DMF (10 ml) at a temperature of 30-40° C. within 20 min. Cooling in an ice bath was carried out if necessary. The reaction mixture was stirred for 3 h at RT and then mixed with diethyl ether (120 ml) and water (80 ml). The phases were separated. The aqueous phase was extracted with diethyl ether (2×50 ml). The combined organic extracts were washed successively with water (80 ml) and sat. NaCl solution (100 ml). The organic phase was dried and concentrated. 3-phenyl propanehydroximoyl chloride was obtained as a light green oil (2.47 g) and immediately reacted further.

Synthesis of 3-phenethyl-1-oxa-2,8-diazaspiro[4.5] dec-2-ene-8-carboxylic acid tert-butyl ester (BB)

Compound BB (2.47 g, 13.8 mmol), dissolved in abs. DCM (10 ml), was added dropwise at 0° C. within 10 min to a solution of compound B (1.94 g, 9.85 mmol) in abs. DCM (15 ml). A solution of triethylamine (7.75 ml, 55.2 mmol) in abs. DCM (10 ml) was added to this mixture at 0° C. within 10 min. As the reaction was highly exothermic, cooling was carried out in an ice/sodium chloride mixture. The reaction mixture was stirred for 16 h at RT. For working up the mixture, DCM (10 ml) and water (30 ml) were added and the mixture was stirred for 15 min. After separation of the phases, the aqueous phase was extracted with DCM (2×45 ml). The phases were separated. The organic phase was washed successively with 10% citric acid solution (2×20 ml) and sat. NaCl solution (20 ml). The organic phase was dried and concentrated. There were obtained 3.88 g of a light brown oil which crystallised slowly. The crude product was heated with cyclohexane (20 ml) and EtOAc (3 ml) until the mixture had completely dissolved and then cooled down in an ice bath. The precipitated solid was removed by suction-filtration and washed with cyclohexane (10 ml). The desired product BB was obtained as a white solid in a yield of 26% (1.22 g) having a melting point of 121-124° C.

Synthesis of 3-phenethyl-1-oxa-2,8-diazaspiro[4.5]dec-2-ene (CC)

Compound BB (1.1 g, 3.2 mmol) was dissolved in DCM (20 ml) and mixed with a 5.5 N solution of hydrogen chloride in propan-2-ol (11.6 ml, 64 mmol). After a reaction time of 2 h, the mixture was concentrated to approx. 10 ml and then stirred in an ice bath. The precipitated solid was removed by suction-filtration and washed with diethyl ether. 799 mg (89%, mp 252-254° C.) of the hydrochloride of 3-phenethyl-1-oxa-2,8-diazaspiro[4.5]dec-2-ene were obtained.

The hydrochloride (733 mg, 2.6 mmol) was stirred with DCM (30 ml) and sat. NaHCO$_3$ solution (10 ml) for 1.5 h. After separation of the phases, the aqueous phase was extracted with DCM (2×10 ml). The combined organic extracts were dried and concentrated. 3-Phenethyl-1-oxa-2, 8-diazaspiro[4.5]dec-2-ene was obtained in a yield of 97% (617 mg) having a melting point of 106-109° C.

Synthesis of 3-(4-chlorophenyl)-1-oxa-2,8-diazaspiro[4.5]dec-2-ene-8-carboxylic acid tert-butyl ester The chloride 4-chlorophenylhydroxymoyl chloride (14.7 g, 77.3 mmol), dissolved in abs. DCM (120 ml), was added dropwise at 0° C. within 10 min to a solution of the olefin tert-butyl 4-methylene piperidine-1-carboxylate (11.5 g, 58.5 mmol) in abs. DCM (80 ml). A solution of triethylamine (47 ml, 33.8 g, 334 mmol) in abs. DCM (50 ml) was added to this mixture at 0° C. within 15 min. As the reaction was highly exothermic, cooling was carried out with ice/sodium chloride. Triethylamine hydrochloride formed during the addition. The reaction mixture was stirred for 16 h at RT. For working up the mixture, DCM (30 ml) and water (130 ml) were added. The phases were separated. The organic phase was extracted successively with 10% aq. citric acid solution (2×150 ml) and sat. aq. NaCl solution (100 ml). The organic phase was dried and concentrated (22.8 g, yellow solid). The residue was mixed with diethyl ether (100 ml) and stirred for 1 h at RT. There remained a solid which was separated off by filtration and washed with diethyl ether (2×40 ml) (10.49 g). The filtrate was concentrated to 25 ml and the solid thereby precipitated separated off (1.96 g). Both fractions were combined. The spiro compound 3-(4-chlorophenyl)-1-oxa-2,8-diazaspiro[4.5]dec-2-ene-8-carboxylic acid tert-butyl ester was obtained as a colourless solid in a yield of 61% having a melting point of 138-141° C.

Synthesis of 3-(4-chlorophenyl)-1-oxa-2,8-diazaspiro[4.5]dec-2-ene hydrochloride The spiro compound 3-(4-chlorophenyl)-1-oxa-2,8-diazaspiro[4.5]dec-2-ene-8-carboxylic acid tert-butyl ester (9.48 g, 27.0 mmol) was dissolved in DCM (150 ml) and mixed with a 5 N aq. hydrochloric acid solution in propan-2-ol (130 ml, 651 mmol). After a reaction time of 1.5 h, the mixture was concentrated. The solid residue was mixed with DCM (50 ml), stirred for 15 min at RT, removed by suction-filtration and washed with DCM (2×50 ml). The hydrochloride 3-(4-chlorophenyl)-1-oxa-2,8-diazaspiro[4.5]dec-2-ene hydrochloride was obtained as a colourless compound in a yield of 95% (7.33 g) having a melting point of 284-287° C.

Synthesis of 3-(4-tert-butylphenyl)-1-oxa-2,8-diazaspiro[4.5]dec-2-ene-8-carboxylic acid tert-butyl ester The chloride (4-tert-butylphenyl)hydroxymoyl chloride (16.9 g, 83.1 mmol), dissolved in abs. DCM (60 ml), was added dropwise at 0° C. within 10 min to a solution of the olefin tert-butyl 4-methylene piperidine-1-carboxylate (11.5 g, 58.5 mmol) in abs. DCM (80 ml). A solution of triethylamine (47 ml, 33.8 g, 334 mmol) in abs. DCM (50 ml) was added to this mixture within 15 min at 0° C. As the reaction was highly exothermic, cooling was carried out with ice/sodium chloride. Triethylamine hydrochloride formed during the addition. The reaction mixture was stirred for 16 h at RT. For working up the mixture, DCM (30 ml) and water (130 ml) were added. The phases were separated. The organic phase was extracted successively with 10% aq. citric acid solution (2×150 ml) and sat. aq. NaCl solution (150 ml). The organic phase was dried and concentrated (24.0 g, light brown solid). The residue was mixed with n-hexane (50 ml) and stirred for 20 min at RT. There remained a solid which was separated off by filtration and washed with n-hexane (3×30 ml). The spiro compound 3-(4-tert-butylphenyl)-1-oxa-2,8-diazaspiro[4.5]dec-2-ene-8-carboxylic acid tert-butyl ester was obtained as a colourless solid in a yield of 61% having a melting point of 172-173° C.

Synthesis of 3-(3-fluoro-4-methanesulphonylaminomethylphenyl)-1-oxa-2,8-diazaspiro-[4.5]dec-2-ene-8-carboxylic acid tert-butyl ester The chloride 3-fluoro-4-methanesulphonylaminophenylhydroxymoyl chloride (6.16 g, 23.09 mmol), dissolved in abs. THF (50 ml), was added dropwise at 0° C. within 15 min to a solution of the olefin tert-butyl 4-methylene piperidine-1-carboxylate (3.24 g, 16.5 mmol) in abs. THF (30 ml). A solution of triethylamine (13 ml, 9.4 g, 92.3 mmol) in abs. THF (15 ml) was added to this mixture at 0° C. within 10 min. As the reaction was highly exothermic, cooling was carried out with ice/sodium chloride.

Triethylamine hydrochloride formed during the addition. The reaction mixture was stirred for 3 d at RT. For working up the mixture, water (60 ml) was added and THF removed under vacuum. After the addition of DCM (100 ml) and water (20 ml) there formed a brown solid which was separated off before the separation of the phases. The organic phase was mixed with 10% citric acid solution (100 ml), wherein there again formed a brown solid which could be separated by filtration only after stirring for 4 hours. The phases of the filtrate were separated. The organic phase was extracted successively with 10% citric acid solution (100 ml) and sat. aq. NaCl solution (100 ml). The organic phase was dried and concentrated (6.1 g, light brown oil). The residue was separated by chromatography [silica gel 60 (300 g); EtOAc/cyclohexane 1:2 (3.2 l), 1:1 (2 l)]. The spiro compound 3-(3-fluoro-4-methanesulphonylaminomethylphenyl)-1-oxa-2,8-diazaspiro-[4.5]dec-2-ene-8-carboxylic acid tert-butyl ester was obtained as a beige-coloured solid in a yield of 1.4 g, (20%) having a melting point of 178-182° C.

Synthesis of N-[2-fluoro-4-(1-oxa-2,8-diazaspiro[4.5]dec-2-ene-3-yl)phenyl]methanesulphonamide hydrochloride The spiro compound 3-(3-fluoro-4-methanesulphonylaminomethylphenyl)-1-oxa-2,8-diazaspiro-[4.5]dec-2-ene-8-carboxylic acid tert-butyl ester (1.38 g, 3.23 mmol) was dissolved in DCM (30 ml) and mixed with a 5 N aq. hydrochloric acid solution in propan-2-ol (12.9 ml, 64.7 mmol). After a reaction time of 2 h, the hydrochloride N-[2-fluoro-4-(1-oxa-2,8-diazaspiro[4.5]dec-2-ene-3-yl)phenyl]methanesulphonamide hydrochloride was separated off by filtration and washed with DCM (2×10 ml) (0.878 g). The filtrate was mixed with diethyl ether (50 ml) and stirred for 30 min. Still further hydrochloride formed. The hydrochloride N-[2-fluoro-4-(1-oxa-2,8-diazaspiro[4.5]dec-2-ene-3-yl)phenyl]methanesulphonamide hydrochloride was obtained as a colourless compound in a total yield of 87% (1.02 g) having a melting point of 269-274° C. (AS 4492).

Synthesis of 8-benzyl-3-phenyl-1-oxa-2,8-diazaspiro[4.6]undec-2-ene

The chloride 1-chloro-1-hydroxyiminomethylbenzene (1.4 g, 9.4 mmol), dissolved in abs. DCM (25 ml), was added dropwise to a solution of 1-benzyl-4-methylene azepane (0.94 g, 4.7 mmol) in abs. DCM (25 ml) at 0° C. within 10 min. A solution of triethylamine (5.2 ml, 3.8 g, 54.4 mmol) in abs. DCM (25 ml) was added to this mixture at 0° C. within 10 min. As the reaction was highly exothermic, cooling was carried out with ice/sodium chloride. Triethylamine hydrochloride formed during the addition. The reaction mixture was stirred for 24 h at RT. For working up the mixture, DCM (30 ml) and water (40 ml) were added. The phases were separated. The aqueous solution was extracted with DCM (2×20 ml). The combined organic phases were washed successively with water (50 ml) and sat. aq. NaCl solution (50 ml), then dried and concentrated (2.1 g, yellow oil). The residue was purified by column chromatography [silica gel 60 (120 g); EtOAc/cyclohexane 1:1 (1,51)]. The spiro compound 8-benzyl-3-phenyl-1-oxa-2,8-diazaspiro[4.6]undec-2-ene was obtained as a beige solid in a yield of 0.9 g (60%) having a melting point of 42-57° C.

Synthesis of 3-phenyl-1-oxa-2,8-diazaspiro[4.6]undec-2-ene-8-carboxylic acid benzyl ester Chloroformic acid benzyl ester (0.7 ml, 5 mmol) was added to a solution of the benzyl compound 8-benzyl-3-phenyl-1-oxa-2,8-diazaspiro[4.6]undec-2-ene (830 mg, 2.6 mmol) in abs. toluene (30 ml) at RT within 10 min while stirring and with the exclusion of moisture. Although there was hardly any starting material left in the DC after just 2 h, the mixture was left for a further 15 h at RT. For working up, the reaction mixture was first mixed with $Et_3N$ (2 ml, 14.5 mmol) and stirred for 1 h at RT. Subsequently, 1 N HCl (30 ml) was added to the reaction mixture. The organic phase was separated off and the aqueous solution extracted with EtOAc (3×20 ml). The combined organic phases were washed with $H_2O$ (10 ml) and sat. aq. $NaHCO_3$ solution (10 ml), dried over $Na_2SO_4$ and then concentrated. 3-Phenyl-1-oxa-2,8-diazaspiro[4.6]undec-2-ene-8-carboxylic acid benzyl ester was obtained as a colourless oil in a yield of 823 mg (97%) by chromatographic purification (mobile solvent:cyclohexane/EtOAc 4:1) of the crude product.

Synthesis of 3-phenyl-1-oxa-2,8-diazaspiro[4.6]undec-2-ene

The amine 3-phenyl-1-oxa-2,8-diazaspiro[4.6]undec-2-ene-8-carboxylic acid benzyl ester (770 mg, 2.11 mmol) was mixed in MeOH (50 ml) with the palladium catalyst (Pd/C, 5%, 500 mg) and hydrogenated for 45 min at RT (hydrogen pressure: 2 bar). The catalyst was removed using a frit provided with a 1 cm thick layer of Celite. The solvent was removed by distillation under vacuum. The amine 3-phenyl-1-oxa-2,8-diazaspiro[4.6]undec-2-ene was thus obtained in a yield of 434 mg (89%) as a light yellow oil.

8. General Directions for Reacting Amines of General Formula Ii with Isocyanates or Thioisocyanates of General Formula $R^5$—N=C=O or $R^7$—N=C=S a. Manual Synthesis
General Directions:

The isocyanate (2 mmol) was added to a solution of the amine (2 mmol) in abs. THF (20 mL) under argon at RT within 10 min. The mixture was stirred for 3 h and then mixed with 2 N aq. HCl (10 ml). The acidic reaction mixture was stirred for 10 min and then extracted with EtOAc (3×20 mL). The combined organic phases were washed with sat. aq. $NaHCO_3$ solution (10 mL), dried over $Na_2SO_4$ and concentrated to dryness under vacuum. The residue was recrystallised from a suitable solvent (15 mL, hexane, toluene or DCM) or purified by column chromatography ($SiO_2$, hexane/EtOAc in various mixtures).

Synthesis of compound 390: 3-(3-chloropyridin-2-yl)-1-oxa-2,8-diazaspiro[4.5]dec-2-ene-8-carboxylic acid-(4-tert-butylphenyl)amide Compound K (0.130 g, 0.451 mmol) was dissolved in toluene (15 ml) and triethylamine (0.12 ml, 0.867 mmol) and 4-tert-butylphenyl isocyanate (0.08 ml, 0.451 mmol) were successively added. The reaction mixture was heated to boiling point and boiled under reflux for 3 h. After cooling of the reaction mixture to RT, the mixture was stirred for 36 h. The reaction mixture was extracted with EtOAc (3×20 ml). The combined organic phases were washed with sat. $Na_2HCO_3$ solution (10 ml), dried over $Na_2SO_4$ and concentrated to dryness under vacuum. After purification of the residue by column chromatography (hexane:EtOAc 1:1), the product was obtained in a yield of 83% (0.160 g).

Synthesis of exemplary compound 438: 3-thiazol-2-yl-1-oxa-2,8-diazaspiro[4.5]dec-2-ene-8-carboxylic acid-(4-tert-butylphenyl)amide Compound O (0.150 g, 0.578 mmol) was dissolved in toluene (15 ml) and mixed successively with triethylamine (0.12 ml, 0.867 mmol) and 4-tert-butylphenyl isocyanate (0.102 ml, 0.578 mmol). The reaction mixture was heated to boiling point and boiled under reflux for 3 h. After cooling to RT, the mixture was stirred for 36 h. The reaction mixture was extracted with EtOAc (3×20 ml). The combined organic phases were washed with sat. $Na_2HCO_3$ solution (10 ml), dried over $Na_2SO_4$ and concentrated to dryness under vacuum. After purification of the residue by column chromatography (hexane:EtOAc 1:1), the desired product was obtained in a yield of 52% (0.120 g).

Synthesis of exemplary compound 370: 2-(4-tert-butyl phenyl)-1-(3-phenyl-1-oxa-2,8-diazaspiro[4.5]dec-2-en-8-yl)propan-1-one The hydrochloride of the amine 3-phenyl-1-oxa-2,8-diazaspiro[4.5]dec-2-ene (1.5 g, 5.9 mmol) was dissolved in water (20 ml), mixed with sat. aq. $NaHCO_3$ solution (20 ml) and stirred for 1 h at RT. There formed the amine 3-phenyl-1-oxa-2,8-diazaspiro[4.5]dec-2-ene which was separated off by filtration and obtained as a colourless solid in a yield of 92% (1.17 g) having a melting point of 115° C.

A solution of the acid 2-(4-tert-butylphenyl)propionic acid (300 mg, 1.45 mmol) in abs. dimethylformamide (25 ml) was mixed with N,N'-carbonyldiimidazole (235 mg, 1.45 mmol) and stirred for 1.5 h at room temperature. Subsequently, the amine 3-phenyl-1-oxa-2,8-diazaspiro[4.5]dec-2-ene (346 mg, 1.6 mmol) was added. After a reaction time of 4 d at room temperature, the clear reaction mixture was concentrated. The residue was taken up in DCM (30 ml) and 0.5 N aq. hydrochloric acid (20 ml). The phases were separated. The organic phase was washed successively with 0.5 N aq. hydrochloric acid (20 ml), sat. aq. $NaHCO_3$ solution (2×15 ml) and sat. aq. NaCl solution (15 ml). The organic phase was dried and concentrated. The solid colourless residue was taken up in a mixture of diethyl ether (10 ml) and n-hexane (10 ml) and stirred for 15 min at RT. The amide 2-(4-tert-butylphenyl)-1-(3-phenyl-1-oxa-2,8-diazaspiro[4.5]dec-2-en-8-yl)propan-1-one was obtained as a colourless solid in a yield of 62% (364 mg) having a melting point of 143-145° C.

Synthesis of exemplary compound 371: N-(4-tert-butylphenyl)-3-phenyl-1-oxa-2,7-diazaspiro[4.4]non-2-ene-7-carboxamide 4-Tert-butylphenyl isocyanate (350 mg, 2 mmol) was added to a solution of compound R (420 mg crude product, approx. 2 mmol) in abs. THF (20 ml) under argon at RT within 10 min. After 1 h the cloudy solution was mixed with triethylamine (0.3 ml, 2.22 mmol). The reaction mixture was stirred for a further 2 h and then mixed with 2 N HCl solution (10 ml). The acidic reaction mixture was stirred for 10 min and then extracted with EtOAc (3×20 ml). The combined organic phases were washed with sat. Na$_2$HCO$_3$ solution (10 ml), dried over Na$_2$SO$_4$ and concentrated to dryness under vacuum. The residue was recrystallised from toluene (15 ml). The desired product N-(4-tert-butylphenyl)-3-phenyl-1-oxa-2,7-diazaspiro[4.4]non-2-ene-7-carboxamide was thus obtained in a yield of 415 mg (55%) having a melting point of 207-208° C. (from EtOH, crystal transformation between 183 and 188° C.).

Synthesis of exemplary compound 373: 3-phenyl-1-oxa-2,8-diazaspiro[4.6]undec-2-ene-8-carboxylic acid-(4-tert-butylphenyl)amide The isocyanate 4-tert-butylphenyl isocyanate [350 mg, 2 mmol, dissolved in abs. THF (1 ml)], was added to a solution of the amine 3-phenyl-1-oxa-2,8-diazaspiro[4.6]undec-2-ene (430 mg, 1.87 mmol) in abs. THF (20 ml) under argon at RT within 10 min. The mixture was stirred for 30 min at RT, mixed with triethylamine (0.4 ml, 2.8 mmol) and then stirred for a further 2 h. For working up, 1 N aq. HCl (30 ml) was added to the reaction mixture. The acidic reaction mixture was stirred for 10 min and then extracted with EtOAc (3×20 ml). The combined organic phases were washed with saturated NaCl and NaHCO$_3$ solutions (10 ml each), dried over Na$_2$SO$_4$ and concentrated to dryness under vacuum. The residue obtained was purified by flash chromatography (mobile solvent:a:cyclohexane/EtOAc=3:1; b:cyclohexane/EtOAc=1:1). The compound 3-phenyl-1-oxa-2,8-diazaspiro[4.6]undec-2-ene-8-carboxylic acid-(4-tert-butyl phenyl)amide (270 mg, melting point: 137-142° C.) was obtained in a yield of 34%.

Synthesis of exemplary compound 379: 8-(5-tert-butyl-1H-benzimidazol-2-yl)-3-phenyl-1-oxa-2,8-diazaspiro[4.5]dec-2-ene The chlorine compound 5-tert-butyl-2-chloro-1H-benzimidazole (104.3 mg, 0.5 mmol) and the amine 3-phenyl-1-oxa-2,8-diazaspiro[4.5]dec-2-ene (108.2 mg, 0.5 mmol) were dissolved in dimethylformamide (5 ml). As the stability of the reactants was not known, first the mixture was stirred for 2 d at RT, then the temperature was increased to 80° C. for 6 h and afterwards the mixture was heated at 140° C. 15 h while stirring. A reaction was observed in the DC only at elevated temperature. For working up, the clear dark brown reaction mixture was mixed with water (30 ml) and diethyl ether (20 ml). The phases were separated. The aqueous phase was extracted with diethyl ether (3×15 ml). The extracts were combined, washed with sat. aq. NaCl solution (5 ml) and then dried with anhydrous Na$_2$SO$_4$. The solvent was removed by distillation. The residue was purified by flash chromatography [silica gel 60 (20 g); eluent: cyclohexane/EtOAc 1:1 (400 ml), 1:3 (400 ml)]. There were isolated two new products: a less polar product 8-(5-tert-butyl-1H-benzimidazol-2-yl)-3-phenyl-1-oxa-2,8-diazaspiro[4.5]dec-2-ene (60.0 mg, mp 230-236° C., 31%) and a more polar product 8-(5-tert-butyl-1H-benzimidazol-2-yl)-3-phenyl-1-oxa-2,8-diazaspiro[4.5]dec-2-ene (57.8 mg, mp 112° C., 30%). The desired structure was confirmed analytically only for the less polar component 8-(5-tert-butyl-1H-benzimidazol-2-yl)-3-phenyl-1-oxa-2,8-diazaspiro[4.5]dec-2-ene.

Synthesis of exemplary compound 369: 6-methyl-3-phenyl-1-oxa-2,8-diazaspiro[4.5]dec-2-ene-8-carboxylic acid-(4-tert-butylphenyl)amide 4-Tert-butylphenyl isocyanate [260 mg, 1.48 mmol, dissolved in abs. THF (1 ml)] was added to a solution of compound U (320 mg crude product, approx. 1.39 mmol) in abs. THF (20 ml) under argon at RT within 10 min. The mixture was stirred for two hours and then mixed with 2N HCl solution (10 ml). The acidic reaction mixture was stirred for 10 min and then extracted with EtOAc (3×20 ml). The combined organic phases were washed with sat. NaHCO$_3$ solution (10 ml), dried over Na$_2$SO$_4$ and concentrated to dryness under vacuum. The residue obtained was purified by flash chromatography (mobile solvent:cyclohexane/EtOAc=7:3). 6-Methyl-3-phenyl-1-oxa-2,8-diazaspiro[4.5]dec-2-ene-8-carboxylic acid-(4-tert-butylphenyl)amide was thus obtained as a diastereoisomer mixture (melting point from 65° C.) in a yield of 170 mg (30%).

Synthesis of exemplary compound 386: 3-benzyl-1-oxa-2,8-diazaspiro[4.5]dec-2-ene-8-carboxylic acid-(4-tert-butylphenyl)amide 4-Tert-butylphenyl isocyanate (0.218 ml, 1.24 mmol), dissolved in abs. DCM (5 ml), was added dropwise to a solution of compound Y (286 mg, 1.24 mmol) in abs. DCM (10 ml) at RT within 20 min. After stirring for 3.5 h at RT, the solution was washed with 10% citric acid solution (1×10 ml) and water (1×10 ml), dried and concentrated. The colourless oil obtained (742 mg) contained few impurities. The oil was mixed with diethyl ether (10 ml) and stored at 5° C. The precipitated solid was removed by suction-filtration and washed with diethyl ether (5 ml). The desired product 3-benzyl-1-oxa-2,8-diazaspiro[4.5]dec-2-ene-8-carboxylic acid-(4-tert-butylphenyl)amide was obtained in a yield of 73% (369 mg) having a melting point of 137-139° C.

Synthesis of exemplary compound 387: N-(4-tert-butylphenyl)-3-phenethyl-1-oxa-2,8-diazaspiro[4.5]dec-2-ene-8-carboxamide 4-Tert-butylphenyl isocyanate (0.44 ml, 2.5 mmol), dissolved in abs. DCM (5 ml), was added dropwise to a solution of compound CC (610 mg, 2.5 mmol) in abs. DCM (15 ml) at RT within 20 min. After stirring for 3 h at RT, the solution was washed with 10% citric acid solution (1×10 ml) and water (1×10 ml), dried and concentrated. The residue (683 mg) was stirred with diethyl ether (10 ml) for 18 h. The precipitated solid was removed by suction-filtration and washed with diethyl ether (5 ml). The target product N-(4-tert-butylphenyl)-3-phenethyl-1-oxa-2,8-diazaspiro[4.5]dec-2-ene-8-carboxamide was obtained in a yield of 55% (575 mg) having a melting point of 153-154° C.

b. Automated Synthesis

There were first produced the following parent solutions:
Solution I: 0.05 M solution of the amine of general formula II in toluene
Solution II: 0.1 M solution of the isocyanate of general formula R$^5$—N=C=O or the isothiocyanate of general formula R$^7$—N=C=S in toluene Solution I (2 mL) was placed in a dry threaded glass container with a septum cap at RT and mixed with solution II (1 mL). The reaction mixture was stirred under reflux for 6 h in a strike reactor. The reaction mixture was transferred to vials and the solvent removed using GeneVac equipment.

The following isocyanates of general formula R$^5$—N=C=O were used for synthesis: phenyl isocyanate, 2-methylphenyl isocyanate, m-tolyl isocyanate, p-tolyl isocyanate, 2-ethylphenyl isocyanate, 3-ethylphenyl isocyanate, 4-ethylphenyl isocyanate, 2-propylphenyl isocyanate, 2-fluorophenyl isocyanate, 3-fluorophenyl isocyanate, 4-fluorophenyl isocyanate, 2-chlorophenyl isocyanate, 3-chlorophenyl isocyanate, 4-chlorophenyl isocyanate, 2-bromophenyl isocyanate, 3-bromophenyl isocyanate, 4-bromophenyl isocyanate, 3-iodophenyl isocyanate, 4-iodophenyl isocyanate, 2-methoxyphenyl isocyanate, 3-methoxyphenyl isocyanate, 4-methoxyphenyl isocyanate, 2-ethoxyphenyl isocyanate, 4-ethoxyphenyl isocyanate, 2-(methylthio)phenyl isocyanate, 3-(methylthio)phenyl isocyanate, 4-(methylthio)phenyl isocyanate, 2-isopropylphenyl isocyanate, 4-isopropylphenyl isocyanate, 4-butylphenyl isocyanate, 3-cyanophenyl isocyanate, 2-methoxycarbonylphenyl isocyanate, 3-methoxycarbonylphenyl isocyanate, ethyl-2-isocyanatebenzoate, 3-ethoxycarbonylphenyl isocyanate, 4-ethoxycarbonylphenyl isocyanate, 2-(trifluoromethyl)phenyl isocyanate, 3-(trifluoromethyl)phenyl isocyanate, 4-(trifluoromethyl)phenyl isocyanate, 1-naphthyl isocyanate, 2-biphenyl isocyanate, 4-biphenyl isocyanate, 4-pentafluorosulphanyl isocyanate, 2-phenoxyphenyl isocyanate, 4-phenoxyphenyl isocyanate, 4-benzyloxyphenyl isocyanate, 4-(dimethylamino)phenyl isocyanate, 2,6-difluorophenyl isocyanate, 2,5-difluorophenyl isocyanate, 2,4-difluorophenyl isocyanate, 3,4-difluorophenyl isocyanate, 2,6-dichlorophenyl isocyanate, 2,3-dichlorophenyl isocyanate, 2,5-dichlorophenyl isocyanate, 3,5-dichlorophenyl isocyanate, 2,4-dichlorophenyl isocyanate, 3,4-dichlorophenyl isocyanate, 2,4-dibromophenyl isocyanate, 2-chloro-5-(trifluoromethyl)phenyl isocyanate, 4-chloro-2-(trifluoromethyl)phenyl isocyanate, 4-chloro-3-(trifluoromethyl)phenyl isocyanate, 4-bromo-2-(trifluoromethyl)phenyl isocyanate, 3,5-bis-(trifluoromethyl)phenyl isocyanate, 2-(trifluoromethoxy)phenyl isocyanate, 2,4-dimethoxyphenyl isocyanate, 2,5-dimethoxyphenyl isocyanate, 3,5-dimethoxyphenyl isocyanate, 2-fluoro-5-methylphenyl isocyanate, 3-fluoro-4-methylphenyl isocyanate, 3-chloro-2-methylphenyl isocyanate, 4-chloro-2-methylphenyl isocyanate, 5-chloro-2-methylphenyl isocyanate, 3-chloro-4-methylphenyl isocyanate, 4-bromo-2-methylphenyl isocyanate, 3-chloro-4-fluorophenyl isocyanate, 4-bromo-2-fluorophenyl isocyanate, 3,5-dimethyl phenyl isocyanate, 2,6-dimethylphenyl isocyanate, 3,4-dimethylphenyl isocyanate, 2,5-dimethylphenyl isocyanate, 2,4-dimethylphenyl isocyanate, 2-ethyl-6-methylphenyl isocyanate, 2-isopropyl-6-methylphenyl isocyanate, 2-tert-butyl-6-methylphenyl isocyanate, 2,6-diethylphenyl isocyanate, 2-ethyl-6-isopropylphenyl isocyanate, 2,6-diisopropylphenyl isocyanate, 4-methoxy-2-methylphenyl isocyanate, 2-methoxy-5-methylphenyl isocyanate, 5-chloro-2-methoxyphenyl isocyanate, 4-bromo-2,6-dimethylphenyl isocyanate, 2,4,5-trichlorophenyl isocyanate, 2,4-dibromo-6-fluorophenyl isocyanate, 2-bromo-4,6-difluorophenyl isocyanate, 5-chloro-2,4-dimethoxyphenyl isocyanate, 3,4,5-trimethoxyphenyl isocyanate, 2,4,5-trimethylphenyl isocyanate, 2,4,6-trimethylphenyl isocyanate, 4-trifluoromethoxyphenyl isocyanate, n-propyl isocyanate, n-butyl isocyanate, cyclohexyl isocyanate, 2-chloroethyl isocyanate, 3-chloropropyl isocyanate, 2-bromoethyl isocyanate, benzyl isocyanate, phenylethyl isocyanate, 3-methylbenzyl isocyanate, 4-methylbenzyl isocyanate, 2-ethylbenzyl isocyanate, 3-ethylbenzyl isocyanate, 4-ethylbenzyl isocyanate, 4-fluorobenzyl isocyanate, 2-chlorobenzyl isocyanate, 1-(4-bromophenyl)ethyl isocyanate, 2,4-dichlorobenzyl isocyanate, 3,4-dichlorobenzyl isocyanate, 4-methoxybenzyl isocyanate, 1-(1-naphthyl)ethyl isocyanate, 2-methylbenzyl isocyanate, n-pentyl isocyanate, 4-tert-butylphenyl isocyanate.

The following isothiocyanates of general formula $R^7$—N=C=S were used for synthesis: methyl isothiocyanate, ethyl isothiocyanate, n-propyl isothiocyanate, n-butyl isothiocyanate, n-pentyl isothiocyanate, n-hexyl isothiocyanate, n-heptyl isothiocyanate, n-octyl isothiocyanate, n-nonyl isothiocyanate, n-decyl isothiocyanate, n-dodecyl isothiocyanate, n-tetradecyl isothiocyanate, n-octadecyl isothiocyanate, isopropyl isothiocyanate, isobutyl isothiocyanate, tert-butyl isothiocyanate, tert-amyl isothiocyanate, allyl isothiocyanate, methallyl isothiocyanate, chloromethyl isothiocyanate, 2-chloroethyl isothiocyanate, 2-methoxyethyl isothiocyanate, 3-ethoxypropyl isothiocyanate, 3-(diethylamino)propyl isothiocyanate, cyclopropyl isothiocyanate, cyclopentyl isothiocyanate, cyclohexyl isothiocyanate, cyclohexylmethyll isothiocyanate, cyclooctyl isothiocyanate, cyclododecyl isothiocyanate, 1-adamantyl isothiocyanate, 2-(isothiocyanatomethyl)tetrahydrofuran, 2-(4-morpholino)ethyl isothiocyanate, 3-(4-morpholino)propyl isothiocyanate, 2-furylmethyl isothiocyanate, phenyl isothiocyanate, 2-methylphenyl isothiocyanate, 3-methylphenyl isothiocyanate, p-tolyl isothiocyanate, 2-ethylphenyl isothiocyanate, benzyl isothiocyanate, 2-phenylethyl isothiocyanate, alpha-methylbenzyl isothiocyanate, 3-phenylpropyl isothiocyanate, 2-isopropylphenyl isothiocyanate, 4-isopropylphenyl isothiocyanate, 4-butylphenyl isothiocyanate, 2-fluorophenyl isothiocyanate, 3-fluorophenyl isothiocyanate, 4-fluorophenyl isothiocyanate, 2-chlorophenyl isothiocyanate, 3-chlorophenyl isothiocyanate, 4-chlorophenyl isothiocyanate, 2-bromophenyl isothiocyanate, 3-bromophenyl isothiocyanate, 4-bromophenyl isothiocyanate, 2-iodophenyl isothiocyanate, 4-iodophenyl isothiocyanate, 4-fluorobenzyl isothiocyanate, 1-(4-fluorophenyl)ethyl isothiocyanate, 2-chlorobenzyl isothiocyanate, 4-chlorobenzyl isothiocyanate, 2-(4-chlorophenyl)ethyl isothiocyanate, 2-(trifluoromethyl)phenyl isothiocyanate, 3-(trifluoromethyl)phenyl isothiocyanate, 4-(trifluoromethyl)phenyl isothiocyanate, 2-(methylthio)phenyl isothiocyanate, 3-(methylthio)phenyl isothiocyanate, 4-(methylthio)phenyl isothiocyanate, 2-methoxyphenyl isothiocyanate, 3-methoxyphenyl isothiocyanate, 4-methoxyphenyl isothiocyanate, 4-methoxybenzyl isothiocyanate, 2-nitrophenyl isothiocyanate, 3-nitrophenyl isothiocyanate, 4-nitrophenyl isothiocyanate, 3-pyridyl isothiocyanate, 4-cyanophenyl isothiocyanate, 3-cyanophenyl isothiocyanate, (4-isothiocyanatophenyl)dimethylamine, 4-diethylaminophenyl isothiocyanate, 4-acetylphenyl isothiocyanate, 3-carbonylphenyl isothiocyanate, 4-ethoxyphenyl isothiocyanate, 4-isothiocyanatophenylacetate, 4-benzyloxyphenyl isothiocyanate, 2-methoxycarbonylphenyl isothiocyanate, 3-methoxycarbonylphenyl isothiocyanate, 4-methoxycarbonylphenyl isothiocyanate, ethyl-2-isothiocyanatobenzoate, 4-ethoxycarbonylphenyl isothiocyanate, 2,4-dimethylphenyl isothiocyanate, 2,6-dimethylphenyl isothiocyanate, 3,5-dimethylphenyl isothiocyanate, 2-ethyl-6-methylphenyl isothiocyanate, 4-pentafluorosulphanyl isothiocyanate, 2-ethyl-6-isopropylphenyl isothiocyanate, 2,6-diethylphenyl isothiocyanate, 2,6-diisopropylphenyl isothiocyanate, 2-chloro-6-methylphenyl isothiocyanate, 5-chloro-2-methylphenyl isothiocyanate, 3-chloro-4-methylphenyl isothiocyanate, 4-chloro-2-methylphenyl isothiocyanate, 4-bromo-2-methylphenyl isothiocyanate, 2-bromo-4-methylphenyl isothiocyanate, 2,4-difluorophenyl isothiocyanate, 2,6-difluorophenyl isothiocyanate, 2,5-difluorophenyl isothiocyanate, 2,3-dichlorophenyl isothiocyanate, 2,6-dichlorophenyl isothiocyanate, 2,5-dichlorophenyl isothiocyanate, 3,4-dichlorophenyl isothiocyanate, 2,4-dichlorophenyl isothiocyanate, 3,5-dichlorophenyl isothiocyanate, 3,4-dichlorobenzyl isothiocyanate, 4-bromo-2-chlorophenyl isothiocyanate, 4-chloro-3-nitrophenyl isothiocyanate, 2-chloro-4-nitrophenyl isothiocyanate, 5-chloro-2-methoxyphenyl isothiocyanate, 2-chloro-5-(trifluoromethyl)phenyl isothiocyanate, 4-chloro-3-(trifluoromethyl)phenyl isothiocyanate, 4-bromo-2-(trifluoromethyl)isothiocyanate, 3,5-bis-(trifluoromethyl)phenyl isothiocyanate, 2-methoxy-5-methylphenyl isothiocyanate, 2,5-dimethoxyphenyl isothiocyanate, 2,4-dimethoxyphenyl isothiocyanate, 3,5-dimethoxyphenyl isothiocyanate, 3,4-dimethoxyphenyl isothiocyanate, 4-methoxy-2-nitrophenyl isothiocyanate, 2-methoxy-4-nitrophenyl isothiocyanate, 4-methyl-2-nitrophenyl isothiocyanate, (2-methoxy-5-phenyl)phenyl isothiocyanate, 2,4,6-trifluorophenyl isothiocyanate, 2,4,5-trichlorophenyl isothiocyanate, 2,4,6-trichlorophenyl isothiocyanate, 2,3,4-trichlorophenyl isothiocyanate, 2,4,6-tribromophenyl isothiocyanate, 2,4,6-trimethylphenyl isothiocyanate, 4-bromo-2,6-dimethylphenyl isothiocyanate, 3,4,5-trimethoxyphenyl isothiocyanate, 2,3,5,6-tetrafluorophenyl isothiocyanate, 2,3,4,5-tetrachlorophenyl isothiocyanate, pentafluorophenyl isothiocyanate, 1-naphthyl isothiocyanate, 3,4-methylenedioxobenzyl isothiocyanate, triphenylmethyl isothiocyanate, 4-(trans-4-propylcyclohexyl)phenyl isothiocyanate, 4-tert-butylphenyl isothiocyanate.

The following substituted spiro compounds according to the invention were prepared as described under 1a.

| Name | [M + H] |
|---|---|
| [1] 3-(3-methoxyphenyl)-1-oxa-2,8-diazaspiro[4.5]dec-2-ene-8-carboxylic acid phenylamide | 366.4 |
| [2] 3-phenyl-1-oxa-2,8-diazaspiro[4.5]dec-2-ene-8-carboxylic acid phenylamide | 336.4 |
| [3] 3-(4-chlorophenyl)-1-oxa-2,8-diazaspiro[4.5]dec-2-ene-8-carboxylic acid phenylamide | 370.9 |
| [4] 3-(4-tert-butylphenyl)-1-oxa-2,8-diazaspiro[4.5]dec-2-ene-8-carboxylic acid phenylamide | 392.5 |
| [5] 3-p-tolyl-1-oxa-2,8-diazaspiro[4.5]dec-2-ene-8-carboxylic acid phenylamide | 350.4 |
| [6] 3-(4-trifluoromethylphenyl)-1-oxa-2,8-diazaspiro[4.5]dec-2-ene-8-carboxylic acid phenylamide | 404.4 |
| [7] 3-(3-methoxyphenyl)-1-oxa-2,8-diazaspiro[4.5]dec-2-ene-8-carboxylic acid-m-tolylamide | 380.5 |
| [8] 3-(3-methoxyphenyl)-1-oxa-2,8-diazaspiro[4.5]dec-2-ene-8-carboxylic acid-m-tolylamide | 380.5 |
| [9] 3-phenyl-1-oxa-2,8-diazaspiro[4.5]dec-2-ene-8-carboxylic acid-m-tolylamide | 350.4 |
| [10] 3-(4-chlorophenyl)-1-oxa-2,8-diazaspiro[4.5]dec-2-ene-8-carboxylic acid-m-tolylamide | 384.9 |
| [11] 3-(4-tert-butylphenyl)-1-oxa-2,8-diazaspiro[4.5]dec-2-ene-8-carboxylic acid-m-tolylamide | 406.5 |
| [12] 3-p-tolyl-1-oxa-2,8-diazaspiro[4.5]dec-2-ene-8-carboxylic acid-m-tolylamide | 364.5 |
| [13] 3-(4-trifluoromethylphenyl)-1-oxa-2,8-diazaspiro[4.5]dec-2-ene-8-carboxylic acid-m-tolylamide | 418.4 |
| [14] 3-(3-methoxyphenyl)-1-oxa-2,8-diazaspiro[4.5]dec-2-ene-8-carboxylic acid-(3-ethylphenyl)amide | 394.5 |
| [15] 3-(3-methoxyphenyl)-1-oxa-2,8-diazaspiro[4.5]dec-2-ene-8-carboxylic acid-(3-ethylphenyl)amide | 394.5 |
| [16] 3-phenyl-1-oxa-2,8-diazaspiro[4.5]dec-2-ene-8-carboxylic acid-(3-ethylphenyl)amide | 364.5 |
| [17] 3-(4-chlorophenyl)-1-oxa-2,8-diazaspiro[4.5]dec-2-ene-8-carboxylic acid-(3-ethylphenyl)amide | 398.9 |
| [18] 3-(4-tert-butylphenyl)-1-oxa-2,8-diazaspiro[4.5]dec-2-ene-8-carboxylic acid-(3-ethylphenyl)amide | 420.6 |
| [19] 3-p-tolyl-1-oxa-2,8-diazaspiro[4.5]dec-2-ene-8-carboxylic acid-(3-ethylphenyl)amide | 378.5 |
| [20] 3-(4-trifluoromethylphenyl)-1-oxa-2,8-diazaspiro[4.5]dec-2-ene-8-carboxylic acid-(3-ethylphenyl)amide | 432.5 |
| [21] 3-(3-methoxyphenyl)-1-oxa-2,8-diazaspiro[4.5]dec-2-ene-8-carboxylic acid-(2-propylphenyl)amide | 408.5 |
| [22] 3-phenyl-1-oxa-2,8-diazaspiro[4.5]dec-2-ene-8-carboxylic acid-(2-propylphenyl)amide | 378.5 |
| [23] 3-(4-chlorophenyl)-1-oxa-2,8-diazaspiro[4.5]dec-2-ene-8-carboxylic acid-(2-propylphenyl)amide | 412.9 |
| [24] 3-(4-tert-butylphenyl)-1-oxa-2,8-diazaspiro[4.5]dec-2-ene-8-carboxylic acid-(2-propylphenyl)amide | 434.6 |
| [25] 3-p-tolyl-1-oxa-2,8-diazaspiro[4.5]dec-2-ene-8-carboxylic acid-(2-propylphenyl)amide | 392.5 |
| [26] 3-(4-trifluoromethylphenyl)-1-oxa-2,8-diazaspiro[4.5]dec-2-ene-8-carboxylic acid-(2-propylphenyl)amide | 446.5 |
| [27] 3-(3-methoxyphenyl)-1-oxa-2,8-diazaspiro[4.5]dec-2-ene-8-carboxylic acid-(4-fluorophenyl)amide | 384.4 |
| [28] 3-phenyl-1-oxa-2,8-diazaspiro[4.5]dec-2-ene-8-carboxylic acid-(4-fluorophenyl)amide | 354.4 |
| [29] 3-(4-chlorophenyl)-1-oxa-2,8-diazaspiro[4.5]dec-2-ene-8-carboxylic acid-(4-fluorophenyl)amide | 388.8 |
| [30] 3-(4-tert-butylphenyl)-1-oxa-2,8-diazaspiro[4.5]dec-2-ene-8-carboxylic acid-(4-fluorophenyl)amide | 410.5 |
| [31] 3-p-tolyl-1-oxa-2,8-diazaspiro[4.5]dec-2-ene-8-carboxylic acid-(4-fluorophenyl)amide | 368.4 |
| [32] 3-(4-trifluoromethylphenyl)-1-oxa-2,8-diazaspiro[4.5]dec-2-ene-8-carboxylic acid-(4-fluorophenyl)amide | 422.4 |
| [33] 3-(3-methoxyphenyl)-1-oxa-2,8-diazaspiro[4.5]dec-2-ene-8-carboxylic acid-(3-chlorophenyl)amide | 400.9 |
| [34] 3-phenyl-1-oxa-2,8-diazaspiro[4.5]dec-2-ene-8-carboxylic acid-(3-chlorophenyl)amide | 370.9 |
| [35] 3-(4-chlorophenyl)-1-oxa-2,8-diazaspiro[4.5]dec-2-ene-8-carboxylic acid-(3-chlorophenyl)amide | 405.3 |
| [36] 3-(4-tert-butylphenyl)-1-oxa-2,8-diazaspiro[4.5]dec-2-ene-8-carboxylic acid-(3-chlorophenyl)amide | 427.0 |
| [37] 3-p-tolyl-1-oxa-2,8-diazaspiro[4.5]dec-2-ene-8-carboxylic acid-(3-chlorophenyl)amide | 384.9 |
| [38] 3-(4-trifluoromethylphenyl)-1-oxa-2,8-diazaspiro[4.5]dec-2-ene-8-carboxylic acid-(3-chlorophenyl)amide | 438.8 |
| [39] 3-(3-methoxyphenyl)-1-oxa-2,8-diazaspiro[4.5]dec-2-ene-8-carboxylic acid-(4-chlorophenyl)amide | 400.9 |
| [40] 3-phenyl-1-oxa-2,8-diazaspiro[4.5]dec-2-ene-8-carboxylic acid-(4-chlorophenyl)amide | 370.9 |
| [41] 3-(4-chlorophenyl)-1-oxa-2,8-diazaspiro[4.5]dec-2-ene-8-carboxylic acid-(4-chlorophenyl)amide | 405.3 |
| [42] 3-(4-tert-butylphenyl)-1-oxa-2,8-diazaspiro[4.5]dec-2-ene-8-carboxylic acid-(4-chlorophenyl)amide | 427.0 |
| [43] 3-p-tolyl-1-oxa-2,8-diazaspiro[4.5]dec-2-ene-8-carboxylic acid-(4-chlorophenyl)amide | 384.9 |
| [44] 3-phenyl-1-oxa-2,8-diazaspiro[4.5]dec-2-ene-8-carboxylic acid-(4-iodophenyl)amide | 462.3 |
| [45] 3-(4-tert-butylphenyl)-1-oxa-2,8-diazaspiro[4.5]dec-2-ene-8-carboxylic acid-(4-iodophenyl)amide | 518.4 |
| [46] 3-(4-trifluoromethylphenyl)-1-oxa-2,8-diazaspiro[4.5]dec-2-ene-8-carboxylic acid-(4-iodophenyl)amide | 530.3 |
| [47] 3-(3-methoxyphenyl)-1-oxa-2,8-diazaspiro[4.5]dec-2-ene-8-carboxylic acid-(4-methoxyphenyl)amide | 396.5 |
| [48] 3-phenyl-1-oxa-2,8-diazaspiro[4.5]dec-2-ene-8-carboxylic acid-(4-methoxyphenyl)amide | 366.4 |
| [49] 3-(4-chlorophenyl)-1-oxa-2,8-diazaspiro[4.5]dec-2-ene-8-carboxylic acid-(4-methoxyphenyl)amide | 400.9 |
| [50] 3-(4-tert-butylphenyl)-1-oxa-2,8-diazaspiro[4.5]dec-2-ene-8-carboxylic acid-(4-methoxyphenyl)amide | 422.5 |
| [51] 3-p-tolyl-1-oxa-2,8-diazaspiro[4.5]dec-2-ene-8-carboxylic acid-(4-methoxyphenyl)amide | 380.5 |
| [52] 3-(4-trifluoromethylphenyl)-1-oxa-2,8-diazaspiro[4.5]dec-2-ene-8-carboxylic acid-(4-methoxyphenyl)amide | 434.4 |
| [53] 3-(3-methoxyphenyl)-1-oxa-2,8-diazaspiro[4.5]dec-2-ene-8-carboxylic acid-(2-methylsulphanylphenyl)amide | 412.5 |
| [54] 3-phenyl-1-oxa-2,8-diazaspiro[4.5]dec-2-ene-8-carboxylic acid-(2-methylsulphanylphenyl)amide | 382.5 |
| [55] 3-(4-chlorophenyl)-1-oxa-2,8-diazaspiro[4.5]dec-2-ene-8-carboxylic acid-(2-methylsulphanylphenyl)amide | 416.9 |
| [56] 3-(4-tert-butylphenyl)-1-oxa-2,8-diazaspiro[4.5]dec-2-ene-8-carboxylic acid-(2-methylsulphanylphenyl)amide | 438.6 |
| [57] 3-p-tolyl-1-oxa-2,8-diazaspiro[4.5]dec-2-ene-8-carboxylic acid-(2-methylsulphanylphenyl)amide | 396.5 |
| [58] 3-(4-trifluoromethylphenyl)-1-oxa-2,8-diazaspiro[4.5]dec-2-ene-8-carboxylic acid-(2-methylsulphanylphenyl)amide | 450.5 |
| [59] 3-(3-methoxyphenyl)-1-oxa-2,8-diazaspiro[4.5]dec-2-ene-8-carboxylic acid-(3-methylsulphanylphenyl)amide | 412.5 |
| [60] 3-phenyl-1-oxa-2,8-diazaspiro[4.5]dec-2-ene-8-carboxylic acid-(3-methylsulphanylphenyl)amide | 382.5 |
| [61] 3-(4-chlorophenyl)-1-oxa-2,8-diazaspiro[4.5]dec-2-ene-8-carboxylic acid-(3-methylsulphanylphenyl)amide | 416.9 |
| [62] 3-(4-tert-butylphenyl)-1-oxa-2,8-diazaspiro[4.5]dec-2-ene-8-carboxylic acid-(3-methylsulphanylphenyl)amide | 438.6 |
| [63] 3-p-tolyl-1-oxa-2,8-diazaspiro[4.5]dec-2-ene-8-carboxylic acid-(3-methylsulphanylphenyl)amide | 396.5 |

| Name | [M + H] |
|---|---|
| [64] 3-(4-trifluoromethylphenyl)-1-oxa-2,8-diazaspiro[4.5]dec-2-ene-8-carboxylic acid-(3-methylsulphanylphenyl)amide | 450.5 |
| [65] 3-(3-methoxyphenyl)-1-oxa-2,8-diazaspiro[4.5]dec-2-ene-8-carboxylic acid-(4-methylsulphanylphenyl)amide | 412.5 |
| [66] 3-phenyl-1-oxa-2,8-diazaspiro[4.5]dec-2-ene-8-carboxylic acid-(4-methylsulphanylphenyl)amide | 382.5 |
| [67] 3-(4-chlorophenyl)-1-oxa-2,8-diazaspiro[4.5]dec-2-ene-8-carboxylic acid-(4-methylsulphanylphenyl)amide | 416.9 |
| [68] 3-(4-tert-butylphenyl)-1-oxa-2,8-diazaspiro[4.5]dec-2-ene-8-carboxylic acid-(4-methylsulphanylphenyl)amide | 438.6 |
| [69] 3-p-tolyl-1-oxa-2,8-diazaspiro[4.5]dec-2-ene-8-carboxylic acid-(4-methylsulphanylphenyl)amide | 396.5 |
| [70] 3-(4-trifluoromethylphenyl)-1-oxa-2,8-diazaspiro[4.5]dec-2-ene-8-carboxylic acid-(4-methylsulphanylphenyl)amide | 450.5 |
| [71] 3-(3-methoxyphenyl)-1-oxa-2,8-diazaspiro[4.5]dec-2-ene-8-carboxylic acid-(2-isopropylphenyl)amide | 408.5 |
| [72] 3-phenyl-1-oxa-2,8-diazaspiro[4.5]dec-2-ene-8-carboxylic acid-(2-isopropylphenyl)amide | 378.5 |
| [73] 3-(4-chlorophenyl)-1-oxa-2,8-diazaspiro[4.5]dec-2-ene-8-carboxylic acid-(2-isopropylphenyl)amide | 412.9 |
| [74] 3-(4-tert-butylphenyl)-1-oxa-2,8-diazaspiro[4.5]dec-2-ene-8-carboxylic acid-(2-isopropylphenyl)amide | 434.6 |
| [75] 3-p-tolyl-1-oxa-2,8-diazaspiro[4.5]dec-2-ene-8-carboxylic acid-(2-isopropylphenyl)amide | 392.5 |
| [76] 3-(4-trifluoromethylphenyl)-1-oxa-2,8-diazaspiro[4.5]dec-2-ene-8-carboxylic acid-(2-isopropylphenyl)amide | 446.5 |
| [77] 3-(3-methoxyphenyl)-1-oxa-2,8-diazaspiro[4.5]dec-2-ene-8-carboxylic acid-(4-isopropylphenyl)amide | 408.5 |
| [78] 3-phenyl-1-oxa-2,8-diazaspiro[4.5]dec-2-ene-8-carboxylic acid-(4-isopropylphenyl)amide | 378.5 |
| [79] 3-(4-chlorophenyl)-1-oxa-2,8-diazaspiro[4.5]dec-2-ene-8-carboxylic acid-(4-isopropylphenyl)amide | 412.9 |
| [80] 3-(4-tert-butylphenyl)-1-oxa-2,8-diazaspiro[4.5]dec-2-ene-8-carboxylic acid-(4-isopropylphenyl)amide | 434.6 |
| [81] 3-p-tolyl-1-oxa-2,8-diazaspiro[4.5]dec-2-ene-8-carboxylic acid-(4-isopropylphenyl)amide | 392.5 |
| [82] 3-(4-trifluoromethylphenyl)-1-oxa-2,8-diazaspiro[4.5]dec-2-ene-8-carboxylic acid-(4-isopropylphenyl)amide | 446.5 |
| [83] 3-(3-methoxyphenyl)-1-oxa-2,8-diazaspiro[4.5]dec-2-ene-8-carboxylic acid-(2-trifluoromethylphenyl)amide | 434.4 |
| [84] 3-phenyl-1-oxa-2,8-diazaspiro[4.5]dec-2-ene-8-carboxylic acid-(2-trifluoromethylphenyl)amide | 404.4 |
| [85] 3-(4-chlorophenyl)-1-oxa-2,8-diazaspiro[4.5]dec-2-ene-8-carboxylic acid-(2-trifluoromethylphenyl)amide | 438.8 |
| [86] 3-(4-tert-butylphenyl)-1-oxa-2,8-diazaspiro[4.5]dec-2-ene-8-carboxylic acid-(2-trifluoromethylphenyl)amide | 460.5 |
| [87] 3-p-tolyl-1-oxa-2,8-diazaspiro[4.5]dec-2-ene-8-carboxylic acid-(2-trifluoromethylphenyl)amide | 418.4 |
| [88] 3-(4-trifluoromethylphenyl)-1-oxa-2,8-diazaspiro[4.5]dec-2-ene-8-carboxylic acid-(2-trifluoromethylphenyl)amide | 472.4 |
| [89] 3-(3-methoxyphenyl)-1-oxa-2,8-diazaspiro[4.5]dec-2-ene-8-carboxylic acid-(3-trifluoromethylphenyl)amide | 434.4 |
| [90] 3-phenyl-1-oxa-2,8-diazaspiro[4.5]dec-2-ene-8-carboxylic acid-(3-trifluoromethylphenyl)amide | 404.4 |
| [91] 3-(4-chlorophenyl)-1-oxa-2,8-diazaspiro[4.5]dec-2-ene-8-carboxylic acid-(3-trifluoromethylphenyl)amide | 438.8 |
| [92] 3-(4-tert-butylphenyl)-1-oxa-2,8-diazaspiro[4.5]dec-2-ene-8-carboxylic acid-(3-trifluoromethylphenyl)amide | 460.5 |
| [93] 3-p-tolyl-1-oxa-2,8-diazaspiro[4.5]dec-2-ene-8-carboxylic acid-(3-trifluoromethylphenyl)amide | 418.4 |
| [94] 3-(4-trifluoromethylphenyl)-1-oxa-2,8-diazaspiro[4.5]dec-2-ene-8-carboxylic acid-(3-trifluoromethylphenyl)amide | 472.4 |
| [95] 3-phenyl-1-oxa-2,8-diazaspiro[4.5]dec-2-ene-8-carboxylic acid biphenyl-4-amide | 412.5 |
| [96] 3-(4-tert-butylphenyl)-1-oxa-2,8-diazaspiro[4.5]dec-2-ene-8-carboxylic acid biphenyl-4-amide | 468.6 |
| [97] 3-p-tolyl-1-oxa-2,8-diazaspiro[4.5]dec-2-ene-8-carboxylic acid biphenyl-4-amide | 426.5 |
| [98] 3-(3-methoxyphenyl)-1-oxa-2,8-diazaspiro[4.5]dec-2-ene-8-carboxylic acid-(2-phenoxyphenyl)amide | 458.5 |
| [99] 3-phenyl-1-oxa-2,8-diazaspiro[4.5]dec-2-ene-8-carboxylic acid-(2-phenoxyphenyl)amide | 428.5 |
| [100] 3-(4-chlorophenyl)-1-oxa-2,8-diazaspiro[4.5]dec-2-ene-8-carboxylic acid-(2-phenoxyphenyl)amide | 462.9 |
| [101] 3-(4-tert-butylphenyl)-1-oxa-2,8-diazaspiro[4.5]dec-2-ene-8-carboxylic acid-(2-phenoxyphenyl)amide | 484.6 |
| [102] 3-p-tolyl-1-oxa-2,8-diazaspiro[4.5]dec-2-ene-8-carboxylic acid-(2-phenoxyphenyl)amide | 442.5 |
| [103] 3-(4-trifluoromethylphenyl)-1-oxa-2,8-diazaspiro[4.5]dec-2-ene-8-carboxylic acid-(2-phenoxyphenyl)amide | 496.5 |
| [104] 3-(3-methoxyphenyl)-1-oxa-2,8-diazaspiro[4.5]dec-2-ene-8-carboxylic acid-(4-benzyloxyphenyl)amide | 472.6 |
| [105] 3-phenyl-1-oxa-2,8-diazaspiro[4.5]dec-2-ene-8-carboxylic acid-(4-benzyloxyphenyl)amide | 442.5 |
| [106] 3-(4-chlorophenyl)-1-oxa-2,8-diazaspiro[4.5]dec-2-ene-8-carboxylic acid-(4-benzyloxyphenyl)amide | 477.0 |
| [107] 3-(4-tert-butylphenyl)-1-oxa-2,8-diazaspiro[4.5]dec-2-ene-8-carboxylic acid-(4-benzyloxyphenyl)amide | 498.6 |
| [108] 3-p-tolyl-1-oxa-2,8-diazaspiro[4.5]dec-2-ene-8-carboxylic acid-(4-benzyloxyphenyl)amide | 456.6 |
| [109] 3-(4-trifluoromethylphenyl)-1-oxa-2,8-diazaspiro[4.5]dec-2-ene-8-carboxylic acid-(4-benzyloxyphenyl)amide | 510.5 |
| [110] 3-(3-methoxyphenyl)-1-oxa-2,8-diazaspiro[4.5]dec-2-ene-8-carboxylic acid cyclohexylamide | 372.5 |
| [111] 3-phenyl-1-oxa-2,8-diazaspiro[4.5]dec-2-ene-8-carboxylic acid cyclohexylamide | 342.5 |
| [112] 3-(4-chlorophenyl)-1-oxa-2,8-diazaspiro[4.5]dec-2-ene-8-carboxylic acid cyclohexylamide | 376.9 |
| [113] 3-(4-tert-butylphenyl)-1-oxa-2,8-diazaspiro[4.5]dec-2-ene-8-carboxylic acid cyclohexylamide | 398.6 |
| [114] 3-p-tolyl-1-oxa-2,8-diazaspiro[4.5]dec-2-ene-8-carboxylic acid cyclohexylamide | 356.5 |
| [115] 3-(4-trifluoromethylphenyl)-1-oxa-2,8-diazaspiro[4.5]dec-2-ene-8-carboxylic acid cyclohexylamide | 410.5 |
| [116] 3-(3-methoxyphenyl)-1-oxa-2,8-diazaspiro[4.5]dec-2-ene-8-carboxylic acid benzylamide | 380.5 |
| [117] 3-phenyl-1-oxa-2,8-diazaspiro[4.5]dec-2-ene-8-carboxylic acid benzylamide | 350.4 |
| [118] 3-(4-chlorophenyl)-1-oxa-2,8-diazaspiro[4.5]dec-2-ene-8-carboxylic acid benzylamide | 384.9 |
| [119] 3-(4-tert-butylphenyl)-1-oxa-2,8-diazaspiro[4.5]dec-2-ene-8-carboxylic acid benzylamide | 406.5 |
| [120] 3-p-tolyl-1-oxa-2,8-diazaspiro[4.5]dec-2-ene-8-carboxylic acid benzylamide | 364.5 |
| [121] 3-(4-trifluoromethylphenyl)-1-oxa-2,8-diazaspiro[4.5]dec-2-ene-8-carboxylic acid benzylamide | 418.4 |
| [122] 3-(3-methoxyphenyl)-1-oxa-2,8-diazaspiro[4.5]dec-2-ene-8-carboxylic acid phenethylamide | 394.5 |
| [123] 3-phenyl-1-oxa-2,8-diazaspiro[4.5]dec-2-ene-8-carboxylic acid phenethylamide | 364.5 |
| [124] 3-(4-chlorophenyl)-1-oxa-2,8-diazaspiro[4.5]dec-2-ene-8-carboxylic acid phenethylamide | 398.9 |
| [125] 3-(4-tert-butylphenyl)-1-oxa-2,8-diazaspiro[4.5]dec-2-ene-8-carboxylic acid phenethylamide | 420.6 |
| [126] 3-p-tolyl-1-oxa-2,8-diazaspiro[4.5]dec-2-ene-8-carboxylic acid phenethylamide | 378.5 |
| [127] 3-(4-trifluoromethylphenyl)-1-oxa-2,8-diazaspiro[4.5]dec-2-ene-8-carboxylic acid phenethylamide | 432.5 |
| [128] 3-(3-methoxyphenyl)-1-oxa-2,8-diazaspiro[4.5]dec-2-ene-8-carboxylic acid-4-methylbenzylamide | 394.5 |
| [129] 3-phenyl-1-oxa-2,8-diazaspiro[4.5]dec-2-ene-8-carboxylic acid-4-methylbenzylamide | 364.5 |
| [130] 3-(4-chlorophenyl)-1-oxa-2,8-diazaspiro[4.5]dec-2-ene-8-carboxylic acid-4-methylbenzylamide | 398.9 |
| [131] 3-(4-tert-butylphenyl)-1-oxa-2,8-diazaspiro[4.5]dec-2-ene-8-carboxylic acid-4-methylbenzylamide | 420.6 |
| [132] 3-p-tolyl-1-oxa-2,8-diazaspiro[4.5]dec-2-ene-8-carboxylic acid-4-methylbenzylamide | 378.5 |
| [133] 3-(4-trifluoromethylphenyl)-1-oxa-2,8-diazaspiro[4.5]dec-2-ene-8-carboxylic acid-4-methylbenzylamide | 432.5 |
| [134] 3-(3-methoxyphenyl)-1-oxa-2,8-diazaspiro[4.5]dec-2-ene-8-carboxylic acid-4-methoxybenzylamide | 410.5 |
| [135] 3-phenyl-1-oxa-2,8-diazaspiro[4.5]dec-2-ene-8-carboxylic acid-4-methoxybenzylamide | 380.5 |
| [136] 3-(4-chlorophenyl)-1-oxa-2,8-diazaspiro[4.5]dec-2-ene-8-carboxylic acid-4-methoxybenzylamide | 414.9 |
| [137] 3-(4-tert-butylphenyl)-1-oxa-2,8-diazaspiro[4.5]dec-2-ene-8-carboxylic acid-4-methoxybenzylamide | 436.6 |

| Name | [M + H] |
|---|---|
| [138] 3-p-tolyl-1-oxa-2,8-diazaspiro[4.5]dec-2-ene-8-carboxylic acid-4-methoxybenzylamide | 394.5 |
| [139] 3-(4-trifluoromethylphenyl)-1-oxa-2,8-diazaspiro[4.5]dec-2-ene-8-carboxylic acid-4-methoxybenzylamide | 448.5 |
| [140] 3-(3-methoxyphenyl)-1-oxa-2,8-diazaspiro[4.5]dec-2-ene-8-carboxylic acid-(4-tert-butylphenyl)amide | 422.5 |
| [141] 3-phenyl-1-oxa-2,8-diazaspiro[4.5]dec-2-ene-8-carboxylic acid-(4-tert-butylphenyl)amide | 392.5 |
| [142] 3-(4-chlorophenyl)-1-oxa-2,8-diazaspiro[4.5]dec-2-ene-8-carboxylic acid-(4-tert-butylphenyl)amide | 427.0 |
| [143] 3-(4-tert-butylphenyl)-1-oxa-2,8-diazaspiro[4.5]dec-2-ene-8-carboxylic acid-(4-tert-butylphenyl)amide | 448.6 |
| [144] 3-p-tolyl-1-oxa-2,8-diazaspiro[4.5]dec-2-ene-8-carboxylic acid-(4-tert-butylphenyl)amide | 406.5 |
| [145] 3-(4-trifluoromethylphenyl)-1-oxa-2,8-diazaspiro[4.5]dec-2-ene-8-carboxylic acid-(4-tert-butylphenyl)amide | 460.5 |
| [146] 3-(3-methoxyphenyl)-1-oxa-2,8-diazaspiro[4.5]dec-2-ene-8-carboxylic acid p-tolylamide | 380.5 |
| [147] 3-phenyl-1-oxa-2,8-diazaspiro[4.5]dec-2-ene-8-carboxylic acid p-tolylamide | 350.4 |
| [148] 3-(4-chlorophenyl)-1-oxa-2,8-diazaspiro[4.5]dec-2-ene-8-carboxylic acid p-tolylamide | 384.9 |
| [149] 3-(4-tert-butylphenyl)-1-oxa-2,8-diazaspiro[4.5]dec-2-ene-8-carboxylic acid p-tolylamide | 406.5 |
| [150] 3-(3-methoxyphenyl)-1-oxa-2,8-diazaspiro[4.5]dec-2-ene-8-carboxylic acid o-tolylamide | 380.5 |
| [151] 3-phenyl-1-oxa-2,8-diazaspiro[4.5]dec-2-ene-8-carboxylic acid o-tolylamide | 350.4 |
| [152] 3-(4-chlorophenyl)-1-oxa-2,8-diazaspiro[4.5]dec-2-ene-8-carboxylic acid o-tolylamide | 384.9 |
| [153] 3-(4-tert-butylphenyl)-1-oxa-2,8-diazaspiro[4.5]dec-2-ene-8-carboxylic acid o-tolylamide | 406.5 |
| [154] 3-p-tolyl-1-oxa-2,8-diazaspiro[4.5]dec-2-ene-8-carboxylic acid o-tolylamide | 364.5 |
| [155] 3-(4-trifluoromethylphenyl)-1-oxa-2,8-diazaspiro[4.5]dec-2-ene-8-carboxylic acid o-tolylamide | 418.4 |
| [156] 3-(3-methoxyphenyl)-1-oxa-2,8-diazaspiro[4.5]dec-2-ene-8-carboxylic acid-(2-ethylphenyl)amide | 394.5 |
| [157] 3-phenyl-1-oxa-2,8-diazaspiro[4.5]dec-2-ene-8-carboxylic acid-(2-ethylphenyl)amide | 364.5 |
| [158] 3-(4-chlorophenyl)-1-oxa-2,8-diazaspiro[4.5]dec-2-ene-8-carboxylic acid-(2-ethylphenyl)amide | 398.9 |
| [159] 3-(4-tert-butylphenyl)-1-oxa-2,8-diazaspiro[4.5]dec-2-ene-8-carboxylic acid-(2-ethylphenyl)amide | 420.6 |
| [160] 3-p-tolyl-1-oxa-2,8-diazaspiro[4.5]dec-2-ene-8-carboxylic acid-(2-ethylphenyl)amide | 378.5 |
| [161] 3-(4-trifluoromethylphenyl)-1-oxa-2,8-diazaspiro[4.5]dec-2-ene-8-carboxylic acid-(2-ethylphenyl)amide | 432.5 |
| [162] 3-(3-methoxyphenyl)-1-oxa-2,8-diazaspiro[4.5]dec-2-ene-8-carboxylic acid-(4-ethylphenyl)amide | 394.5 |
| [163] 3-phenyl-1-oxa-2,8-diazaspiro[4.5]dec-2-ene-8-carboxylic acid-(4-ethylphenyl)amide | 364.5 |
| [164] 3-(4-chlorophenyl)-1-oxa-2,8-diazaspiro[4.5]dec-2-ene-8-carboxylic acid-(4-ethylphenyl)amide | 398.9 |
| [165] 3-(4-tert-butylphenyl)-1-oxa-2,8-diazaspiro[4.5]dec-2-ene-8-carboxylic acid-(4-ethylphenyl)amide | 420.6 |
| [166] 3-p-tolyl-1-oxa-2,8-diazaspiro[4.5]dec-2-ene-8-carboxylic acid-(4-ethylphenyl)amide | 378.5 |
| [167] 3-(4-trifluoromethylphenyl)-1-oxa-2,8-diazaspiro[4.5]dec-2-ene-8-carboxylic acid-(4-ethylphenyl)amide | 432.5 |
| [168] 3-(3-methoxyphenyl)-1-oxa-2,8-diazaspiro[4.5]dec-2-ene-8-carboxylic acid-(2-fluorophenyl)amide | 384.4 |
| [169] 3-phenyl-1-oxa-2,8-diazaspiro[4.5]dec-2-ene-8-carboxylic acid-(2-fluorophenyl)amide | 354.4 |
| [170] 3-(4-chlorophenyl)-1-oxa-2,8-diazaspiro[4.5]dec-2-ene-8-carboxylic acid-(2-fluorophenyl)amide | 388.8 |
| [171] 3-(4-tert-butylphenyl)-1-oxa-2,8-diazaspiro[4.5]dec-2-ene-8-carboxylic acid-(2-fluorophenyl)amide | 410.5 |
| [172] 3-p-tolyl-1-oxa-2,8-diazaspiro[4.5]dec-2-ene-8-carboxylic acid-(2-fluorophenyl)amide | 368.4 |
| [173] 3-(4-trifluoromethylphenyl)-1-oxa-2,8-diazaspiro[4.5]dec-2-ene-8-carboxylic acid-(2-fluorophenyl)amide | 422.4 |
| [174] 3-(3-methoxyphenyl)-1-oxa-2,8-diazaspiro[4.5]dec-2-ene-8-carboxylic acid-(3-fluorophenyl)amide | 384.4 |
| [175] 3-phenyl-1-oxa-2,8-diazaspiro[4.5]dec-2-ene-8-carboxylic acid-(3-fluorophenyl)amide | 354.4 |
| [176] 3-(4-chlorophenyl)-1-oxa-2,8-diazaspiro[4.5]dec-2-ene-8-carboxylic acid-(3-fluorophenyl)amide | 388.8 |
| [177] 3-(4-tert-butylphenyl)-1-oxa-2,8-diazaspiro[4.5]dec-2-ene-8-carboxylic acid-(3-fluorophenyl)amide | 410.5 |
| [178] 3-p-tolyl-1-oxa-2,8-diazaspiro[4.5]dec-2-ene-8-carboxylic acid-(3-fluorophenyl)amide | 368.4 |
| [179] 3-(4-trifluoromethylphenyl)-1-oxa-2,8-diazaspiro[4.5]dec-2-ene-8-carboxylic acid-(3-fluorophenyl)amide | 422.4 |
| [180] 3-(3-methoxyphenyl)-1-oxa-2,8-diazaspiro[4.5]dec-2-ene-8-carboxylic acid-(2-chlorophenyl)amide | 400.9 |
| [181] 3-phenyl-1-oxa-2,8-diazaspiro[4.5]dec-2-ene-8-carboxylic acid-(2-chlorophenyl)amide | 370.9 |
| [182] 3-(4-chlorophenyl)-1-oxa-2,8-diazaspiro[4.5]dec-2-ene-8-carboxylic acid-(2-chlorophenyl)amide | 405.3 |
| [183] 3-(4-tert-butylphenyl)-1-oxa-2,8-diazaspiro[4.5]dec-2-ene-8-carboxylic acid-(2-chlorophenyl)amide | 427.0 |
| [184] 3-p-tolyl-1-oxa-2,8-diazaspiro[4.5]dec-2-ene-8-carboxylic acid-(2-chlorophenyl)amide | 384.9 |
| [185] 3-(4-trifluoromethylphenyl)-1-oxa-2,8-diazaspiro[4.5]dec-2-ene-8-carboxylic acid-(2-chlorophenyl)amide | 438.8 |
| [186] 3-(3-methoxyphenyl)-1-oxa-2,8-diazaspiro[4.5]dec-2-ene-8-carboxylic acid-(2-bromophenyl)amide | 445.3 |
| [187] 3-phenyl-1-oxa-2,8-diazaspiro[4.5]dec-2-ene-8-carboxylic acid-(2-bromophenyl)amide | 415.3 |
| [188] 3-(4-chlorophenyl)-1-oxa-2,8-diazaspiro[4.5]dec-2-ene-8-carboxylic acid-(2-bromophenyl)amide | 449.8 |
| [189] 3-(4-tert-butylphenyl)-1-oxa-2,8-diazaspiro[4.5]dec-2-ene-8-carboxylic acid-(2-bromophenyl)amide | 471.4 |
| [190] 3-p-tolyl-1-oxa-2,8-diazaspiro[4.5]dec-2-ene-8-carboxylic acid-(2-bromophenyl)amide | 429.3 |
| [191] 3-(4-trifluoromethylphenyl)-1-oxa-2,8-diazaspiro[4.5]dec-2-ene-8-carboxylic acid-(2-bromophenyl)amide | 483.3 |
| [192] 3-(3-methoxyphenyl)-1-oxa-2,8-diazaspiro[4.5]dec-2-ene-8-carboxylic acid-(3-bromophenyl)amide | 445.3 |
| [193] 3-phenyl-1-oxa-2,8-diazaspiro[4.5]dec-2-ene-8-carboxylic acid-(3-bromophenyl)amide | 415.3 |
| [194] 3-(4-tert-butylphenyl)-1-oxa-2,8-diazaspiro[4.5]dec-2-ene-8-carboxylic acid-(3-bromophenyl)amide | 471.4 |
| [195] 3-(4-trifluoromethylphenyl)-1-oxa-2,8-diazaspiro[4.5]dec-2-ene-8-carboxylic acid-(3-bromophenyl)amide | 483.3 |
| [196] 3-(3-methoxyphenyl)-1-oxa-2,8-diazaspiro[4.5]dec-2-ene-8-carboxylic acid-(4-bromophenyl)amide | 445.3 |
| [197] 3-phenyl-1-oxa-2,8-diazaspiro[4.5]dec-2-ene-8-carboxylic acid-(4-bromophenyl)amide | 415.3 |
| [198] 3-(3-methoxyphenyl)-1-oxa-2,8-diazaspiro[4.5]dec-2-ene-8-carboxylic acid-(2-methoxyphenyl)amide | 396.5 |
| [199] 3-phenyl-1-oxa-2,8-diazaspiro[4.5]dec-2-ene-8-carboxylic acid-(2-methoxyphenyl)amide | 366.4 |
| [200] 3-(4-chlorophenyl)-1-oxa-2,8-diazaspiro[4.5]dec-2-ene-8-carboxylic acid-(2-methoxyphenyl)amide | 400.9 |
| [201] 3-(4-tert-butylphenyl)-1-oxa-2,8-diazaspiro[4.5]dec-2-ene-8-carboxylic acid-(2-methoxyphenyl)amide | 422.5 |
| [202] 3-p-tolyl-1-oxa-2,8-diazaspiro[4.5]dec-2-ene-8-carboxylic acid-(2-methoxyphenyl)amide | 380.5 |
| [203] 3-(4-trifluoromethylphenyl)-1-oxa-2,8-diazaspiro[4.5]dec-2-ene-8-carboxylic acid-(2-methoxyphenyl)amide | 434.4 |
| [204] 3-(3-methoxyphenyl)-1-oxa-2,8-diazaspiro[4.5]dec-2-ene-8-carboxylic acid-(3-methoxyphenyl)amide | 396.5 |
| [205] 3-phenyl-1-oxa-2,8-diazaspiro[4.5]dec-2-ene-8-carboxylic acid-(3-methoxyphenyl)amide | 366.4 |
| [206] 3-(4-chlorophenyl)-1-oxa-2,8-diazaspiro[4.5]dec-2-ene-8-carboxylic acid-(3-methoxyphenyl)amide | 400.9 |
| [207] 3-(4-tert-butylphenyl)-1-oxa-2,8-diazaspiro[4.5]dec-2-ene-8-carboxylic acid-(3-methoxyphenyl)amide | 422.5 |
| [208] 3-p-tolyl-1-oxa-2,8-diazaspiro[4.5]dec-2-ene-8-carboxylic acid-(3-methoxyphenyl)amide | 380.5 |
| [209] 3-(4-trifluoromethylphenyl)-1-oxa-2,8-diazaspiro[4.5]dec-2-ene-8-carboxylic acid-(3-methoxyphenyl)amide | 434.4 |
| [210] 3-(3-methoxyphenyl)-1-oxa-2,8-diazaspiro[4.5]dec-2-ene-8-carboxylic acid-(4-trifluoromethylphenyl)amide | 434.4 |
| [211] 3-phenyl-1-oxa-2,8-diazaspiro[4.5]dec-2-ene-8-carboxylic acid-(4-trifluoromethylphenyl)amide | 404.4 |
| [212] 3-(4-chlorophenyl)-1-oxa-2,8-diazaspiro[4.5]dec-2-ene-8-carboxylic acid-(4-trifluoromethylphenyl)amide | 438.8 |
| [213] 3-(4-tert-butylphenyl)-1-oxa-2,8-diazaspiro[4.5]dec-2-ene-8-carboxylic acid-(4-trifluoromethylphenyl)amide | 460.5 |

| Name | [M + H] |
|---|---|
| [214] 3-p-tolyl-1-oxa-2,8-diazaspiro[4.5]dec-2-ene-8-carboxylic acid-(4-trifluoromethylphenyl)amide | 418.4 |
| [215] 3-(4-trifluoromethylphenyl)-1-oxa-2,8-diazaspiro[4.5]dec-2-ene-8-carboxylic acid-(4-trifluoromethylphenyl)amide | 472.4 |
| [216] 3-(3-methoxyphenyl)-1-oxa-2,8-diazaspiro[4.5]dec-2-ene-8-carboxylic acid-(4-phenoxyphenyl)amide | 458.5 |
| [217] 3-(4-chlorophenyl)-1-oxa-2,8-diazaspiro[4.5]dec-2-ene-8-carboxylic acid-(4-phenoxyphenyl)amide | 462.9 |
| [218] 3-(4-tert-butylphenyl)-1-oxa-2,8-diazaspiro[4.5]dec-2-ene-8-carboxylic acid-(4-phenoxyphenyl)amide | 484.6 |
| [219] 3-p-tolyl-1-oxa-2,8-diazaspiro[4.5]dec-2-ene-8-carboxylic acid-(4-phenoxyphenyl)amide | 442.5 |
| [220] 3-(4-trifluoromethylphenyl)-1-oxa-2,8-diazaspiro[4.5]dec-2-ene-8-carboxylic acid-(4-phenoxyphenyl)amide | 496.5 |
| [221] 3-(3-methoxyphenyl)-1-oxa-2,8-diazaspiro[4.5]dec-2-ene-8-carboxylic acid-(2-chloro-5-trifluoromethylphenyl)amide | 468.9 |
| [222] 3-phenyl-1-oxa-2,8-diazaspiro[4.5]dec-2-ene-8-carboxylic acid-(2-chloro-5-trifluoromethylphenyl)amide | 438.8 |
| [223] 3-(4-chlorophenyl)-1-oxa-2,8-diazaspiro[4.5]dec-2-ene-8-carboxylic acid-(2-chloro-5-trifluoromethylphenyl)amide | 473.3 |
| [224] 3-(4-tert-butylphenyl)-1-oxa-2,8-diazaspiro[4.5]dec-2-ene-8-carboxylic acid-(2-chloro-5-trifluoromethylphenyl)amide | 495.0 |
| [225] 3-p-tolyl-1-oxa-2,8-diazaspiro[4.5]dec-2-ene-8-carboxylic acid-(2-chloro-5-trifluoromethylphenyl)amide | 452.9 |
| [226] 3-(4-trifluoromethylphenyl)-1-oxa-2,8-diazaspiro[4.5]dec-2-ene-8-carboxylic acid-(2-chloro-5-trifluoromethylphenyl)amide | 506.8 |
| [227] 3-(3-methoxyphenyl)-1-oxa-2,8-diazaspiro[4.5]dec-2-ene-8-carboxylic acid-(4-chloro-2-trifluoromethylphenyl)amide | 468.9 |
| [228] 3-phenyl-1-oxa-2,8-diazaspiro[4.5]dec-2-ene-8-carboxylic acid-(4-chloro-2-trifluoromethylphenyl)amide | 438.8 |
| [229] 3-(4-chlorophenyl)-1-oxa-2,8-diazaspiro[4.5]dec-2-ene-8-carboxylic acid-(4-chloro-2-trifluoromethylphenyl)amide | 473.3 |
| [230] 3-(4-tert-butylphenyl)-1-oxa-2,8-diazaspiro[4.5]dec-2-ene-8-carboxylic acid-(4-chloro-2-trifluoromethylphenyl)amide | 495.0 |
| [231] 3-p-tolyl-1-oxa-2,8-diazaspiro[4.5]dec-2-ene-8-carboxylic acid-(4-chloro-2-trifluoromethylphenyl)amide | 452.9 |
| [232] 3-(3-methoxyphenyl)-1-oxa-2,8-diazaspiro[4.5]dec-2-ene-8-carboxylic acid-(4-chloro-3-trifluoromethylphenyl)amide | 468.9 |
| [233] 3-phenyl-1-oxa-2,8-diazaspiro[4.5]dec-2-ene-8-carboxylic acid-(4-chloro-3-trifluoromethylphenyl)amide | 438.8 |
| [234] 3-(4-chlorophenyl)-1-oxa-2,8-diazaspiro[4.5]dec-2-ene-8-carboxylic acid-(4-chloro-3-trifluoromethylphenyl)amide | 473.3 |
| [235] 3-(4-tert-butylphenyl)-1-oxa-2,8-diazaspiro[4.5]dec-2-ene-8-carboxylic acid-(4-chloro-3-trifluoromethylphenyl)amide | 495.0 |
| [236] 3-p-tolyl-1-oxa-2,8-diazaspiro[4.5]dec-2-ene-8-carboxylic acid-(4-chloro-3-trifluoromethylphenyl)amide | 452.9 |
| [237] 3-(4-trifluoromethylphenyl)-1-oxa-2,8-diazaspiro[4.5]dec-2-ene-8-carboxylic acid-(4-chloro-3-trifluoromethylphenyl)amide | 506.8 |
| [238] 3-(3-methoxyphenyl)-1-oxa-2,8-diazaspiro[4.5]dec-2-ene-8-carboxylic acid-(2-tert-butyl-6-methylphenyl)amide | 436.6 |
| [239] 3-phenyl-1-oxa-2,8-diazaspiro[4.5]dec-2-ene-8-carboxylic acid-(2-tert-butyl-6-methylphenyl)amide | 406.5 |
| [240] 3-(4-chlorophenyl)-1-oxa-2,8-diazaspiro[4.5]dec-2-ene-8-carboxylic acid-(2-tert-butyl-6-methylphenyl)amide | 441.0 |
| [241] 3-(4-tert-butylphenyl)-1-oxa-2,8-diazaspiro[4.5]dec-2-ene-8-carboxylic acid-(2-tert-butyl-6-methylphenyl)amide | 462.6 |
| [242] 3-p-tolyl-1-oxa-2,8-diazaspiro[4.5]dec-2-ene-8-carboxylic acid-(2-tert-butyl-6-methylphenyl)amide | 420.6 |
| [243] 3-(4-trifluoromethylphenyl)-1-oxa-2,8-diazaspiro[4.5]dec-2-ene-8-carboxylic acid-(2-tert-butyl-6-methylphenyl)amide | 474.5 |
| [244] 3-(3-methoxyphenyl)-1-oxa-2,8-diazaspiro[4.5]dec-2-ene-8-carboxylic acid-(4-trifluoromethoxyphenyl)amide | 450.4 |
| [245] 3-phenyl-1-oxa-2,8-diazaspiro[4.5]dec-2-ene-8-carboxylic acid-(4-trifluoromethoxyphenyl)amide | 420.4 |
| [246] 3-(4-chlorophenyl)-1-oxa-2,8-diazaspiro[4.5]dec-2-ene-8-carboxylic acid-(4-trifluoromethoxyphenyl)amide | 454.8 |
| [247] 3-(4-tert-butylphenyl)-1-oxa-2,8-diazaspiro[4.5]dec-2-ene-8-carboxylic acid-(4-trifluoromethoxyphenyl)amide | 476.5 |
| [248] 3-p-tolyl-1-oxa-2,8-diazaspiro[4.5]dec-2-ene-8-carboxylic acid-(4-trifluoromethoxyphenyl)amide | 434.4 |
| [249] 3-(3-methoxyphenyl)-1-oxa-2,8-diazaspiro[4.5]dec-2-ene-8-thiocarboxylic acid cyclohexylamide | 388.5 |
| [250] 3-phenyl-1-oxa-2,8-diazaspiro[4.5]dec-2-ene-8-thiocarboxylic acid cyclohexylamide | 358.5 |
| [251] 3-(4-chlorophenyl)-1-oxa-2,8-diazaspiro[4.5]dec-2-ene-8-thiocarboxylic acid cyclohexylamide | 393.0 |
| [252] 3-(4-tert-butylphenyl)-1-oxa-2,8-diazaspiro[4.5]dec-2-ene-8-thiocarboxylic acid cyclohexylamide | 414.6 |
| [253] 3-p-tolyl-1-oxa-2,8-diazaspiro[4.5]dec-2-ene-8-thiocarboxylic acid cyclohexylamide | 372.5 |
| [254] 3-(4-trifluoromethylphenyl)-1-oxa-2,8-diazaspiro[4.5]dec-2-ene-8-thiocarboxylic acid cyclohexylamide | 426.5 |
| [255] 3-(3-methoxyphenyl)-1-oxa-2,8-diazaspiro[4.5]dec-2-ene-8-thiocarboxylic acid phenylamide | 382.5 |
| [256] 3-phenyl-1-oxa-2,8-diazaspiro[4.5]dec-2-ene-8-thiocarboxylic acid phenylamide | 352.5 |
| [257] 3-(4-chlorophenyl)-1-oxa-2,8-diazaspiro[4.5]dec-2-ene-8-thiocarboxylic acid phenylamide | 386.9 |
| [258] 3-(4-tert-butylphenyl)-1-oxa-2,8-diazaspiro[4.5]dec-2-ene-8-thiocarboxylic acid phenylamide | 408.6 |
| [259] 3-p-tolyl-1-oxa-2,8-diazaspiro[4.5]dec-2-ene-8-thiocarboxylic acid phenylamide | 366.5 |
| [260] 3-(4-trifluoromethylphenyl)-1-oxa-2,8-diazaspiro[4.5]dec-2-ene-8-thiocarboxylic acid phenylamide | 420.5 |
| [261] 3-(3-methoxyphenyl)-1-oxa-2,8-diazaspiro[4.5]dec-2-ene-8-thiocarboxylic acid-(3-trifluoromethylphenyl)amide | 450.5 |
| [262] 3-phenyl-1-oxa-2,8-diazaspiro[4.5]dec-2-ene-8-thiocarboxylic acid-(3-trifluoromethylphenyl)amide | 420.5 |
| [263] 3-(4-chlorophenyl)-1-oxa-2,8-diazaspiro[4.5]dec-2-ene-8-thiocarboxylic acid-(3-trifluoromethylphenyl)amide | 454.9 |
| [264] 3-(4-tert-butylphenyl)-1-oxa-2,8-diazaspiro[4.5]dec-2-ene-8-thiocarboxylic acid-(3-trifluoromethylphenyl)amide | 476.6 |
| [265] 3-p-tolyl-1-oxa-2,8-diazaspiro[4.5]dec-2-ene-8-thiocarboxylic acid-(3-trifluoromethylphenyl)amide | 434.5 |
| [266] 3-(4-trifluoromethylphenyl)-1-oxa-2,8-diazaspiro[4.5]dec-2-ene-8-thiocarboxylic acid-(3-trifluoromethylphenyl)amide | 488.5 |
| [267] 3-(3-methoxyphenyl)-1-oxa-2,8-diazaspiro[4.5]dec-2-ene-8-thiocarboxylic acid-(2-methoxyphenyl)amide | 412.5 |
| [268] 3-phenyl-1-oxa-2,8-diazaspiro[4.5]dec-2-ene-8-thiocarboxylic acid-(2-methoxyphenyl)amide | 382.5 |
| [269] 3-(4-chlorophenyl)-1-oxa-2,8-diazaspiro[4.5]dec-2-ene-8-thiocarboxylic acid-(2-methoxyphenyl)amide | 416.9 |
| [270] 3-(4-tert-butylphenyl)-1-oxa-2,8-diazaspiro[4.5]dec-2-ene-8-thiocarboxylic acid-(2-methoxyphenyl)amide | 438.6 |
| [271] 3-p-tolyl-1-oxa-2,8-diazaspiro[4.5]dec-2-ene-8-thiocarboxylic acid-(2-methoxyphenyl)amide | 396.5 |
| [272] 3-(4-trifluoromethylphenyl)-1-oxa-2,8-diazaspiro[4.5]dec-2-ene-8-thiocarboxylic acid-(2-methoxyphenyl)amide | 450.5 |
| [273] 3-(3-methoxyphenyl)-1-oxa-2,8-diazaspiro[4.5]dec-2-ene-8-thiocarboxylic acid-(3-methoxyphenyl)amide | 412.5 |
| [274] 3-phenyl-1-oxa-2,8-diazaspiro[4.5]dec-2-ene-8-thiocarboxylic acid-(3-methoxyphenyl)amide | 382.5 |
| [275] 3-(4-chlorophenyl)-1-oxa-2,8-diazaspiro[4.5]dec-2-ene-8-thiocarboxylic acid-(3-methoxyphenyl)amide | 416.9 |
| [276] 3-p-tolyl-1-oxa-2,8-diazaspiro[4.5]dec-2-ene-8-thiocarboxylic acid-(3-methoxyphenyl)amide | 396.5 |
| [277] 3-(4-trifluoromethylphenyl)-1-oxa-2,8-diazaspiro[4.5]dec-2-ene-8-thiocarboxylic acid-(3-methoxyphenyl)amide | 450.5 |
| [278] 3-(3-methoxyphenyl)-1-oxa-2,8-diazaspiro[4.5]dec-2-ene-8-thiocarboxylic acid-(4-tert-butylphenyl)amide | 438.6 |
| [279] 3-phenyl-1-oxa-2,8-diazaspiro[4.5]dec-2-ene-8-thiocarboxylic acid-(4-tert-butylphenyl)amide | 408.6 |
| [280] 3-(4-chlorophenyl)-1-oxa-2,8-diazaspiro[4.5]dec-2-ene-8-thiocarboxylic acid-(4-tert-butylphenyl)amide | 443.0 |

| Name | [M + H] |
|---|---|
| [281] 3-(4-tert-butylphenyl)-1-oxa-2,8-diazaspiro[4.5]dec-2-ene-8-thiocarboxylic acid-(4-tert-butylphenyl)amide | 464.7 |
| [282] 3-p-tolyl-1-oxa-2,8-diazaspiro[4.5]dec-2-ene-8-thiocarboxylic acid-(4-tert-butylphenyl)amide | 422.6 |
| [283] 3-(4-trifluoromethylphenyl)-1-oxa-2,8-diazaspiro[4.5]dec-2-ene-8-thiocarboxylic acid-(4-tert-butylphenyl)amide | 476.6 |
| [284] 3-(3-methoxyphenyl)-1-oxa-2,8-diazaspiro[4.5]dec-2-ene-8-carboxylic acid-2-methylbenzylamide | 394.5 |
| [285] 3-phenyl-1-oxa-2,8-diazaspiro[4.5]dec-2-ene-8-carboxylic acid-2-methylbenzylamide | 364.5 |
| [286] 3-(4-chlorophenyl)-1-oxa-2,8-diazaspiro[4.5]dec-2-ene-8-carboxylic acid-2-methylbenzylamide | 398.9 |
| [287] 3-(4-tert-butylphenyl)-1-oxa-2,8-diazaspiro[4.5]dec-2-ene-8-carboxylic acid-2-methylbenzylamide | 420.6 |
| [288] 3-(4-chlorophenyl)-1-oxa-2,8-diazaspiro[4.5]dec-2-ene-8-thiocarboxylic acid cyclopentylamide | 378.9 |
| [289] 3-(4-tert-butylphenyl)-1-oxa-2,8-diazaspiro[4.5]dec-2-ene-8-thiocarboxylic acid cyclopentylamide | 400.6 |
| [290] 3-p-tolyl-1-oxa-2,8-diazaspiro[4.5]dec-2-ene-8-thiocarboxylic acid cyclopentylamide | 358.5 |
| [291] 3-(4-trifluoromethylphenyl)-1-oxa-2,8-diazaspiro[4.5]dec-2-ene-8-thiocarboxylic acid cyclopentylamide | 412.5 |
| [292] 3-p-tolyl-1-oxa-2,8-diazaspiro[4.5]dec-2-ene-8-thiocarboxylic acid cyclohexylmethylamide | 372.5 |
| [293] 3-(4-chlorophenyl)-1-oxa-2,8-diazaspiro[4.5]dec-2-ene-8-thiocarboxylic acid cyclohexylmethylamide | 407.0 |
| [294] 3-(4-tert-butylphenyl)-1-oxa-2,8-diazaspiro[4.5]dec-2-ene-8-thiocarboxylic acid cyclohexylmethylamide | 428.7 |
| [295] 3-p-tolyl-1-oxa-2,8-diazaspiro[4.5]dec-2-ene-8-thiocarboxylic acid cyclohexylmethylamide | 386.6 |
| [296] 3-(4-trifluoromethylphenyl)-1-oxa-2,8-diazaspiro[4.5]dec-2-ene-8-thiocarboxylic acid cyclohexylmethylamide | 440.5 |
| [297] 3-(3-methoxyphenyl)-1-oxa-2,8-diazaspiro[4.5]dec-2-ene-8-thiocarboxylic acid cyclooctylamide | 416.6 |
| [298] 3-phenyl-1-oxa-2,8-diazaspiro[4.5]dec-2-ene-8-thiocarboxylic acid cyclooctylamide | 386.6 |
| [299] 3-(4-chlorophenyl)-1-oxa-2,8-diazaspiro[4.5]dec-2-ene-8-thiocarboxylic acid cyclooctylamide | 421.0 |
| [300] 3-p-tolyl-1-oxa-2,8-diazaspiro[4.5]dec-2-ene-8-thiocarboxylic acid cyclooctylamide | 400.6 |
| [301] 3-(4-trifluoromethylphenyl)-1-oxa-2,8-diazaspiro[4.5]dec-2-ene-8-thiocarboxylic acid cyclooctylamide | 454.6 |
| [302] 3-(3-methoxyphenyl)-1-oxa-2,8-diazaspiro[4.5]dec-2-ene-8-thiocarboxylic acid-(2-morpholin-4-ylethyl)amide | 419.6 |
| [303] 3-tert-butyl-1-oxa-2,8-diazaspiro[4.5]dec-2-ene-8-carboxylic acid-(4-tert-butylphenyl)amide | 372.4 |
| [306] 3-phenyl-1-oxa-2,8-diazaspiro[4.5]dec-2-ene-8-carboxylic acid-(4-tert-butylphenyl)methylamide | 406.5 |
| 310] 3-tert-butyl-1-oxa-2,8-diazaspiro[4.5]dec-2-ene-8-carboxylic acid p-tolylamide | 330.4 |
| [311] 3-(4-trifluoromethoxyphenyl)-1-oxa-2,8-diazaspiro[4.5]dec-2-ene-8-carboxylic acid p-tolylamide | 434.4 |
| [312] 3-(3-methoxyphenyl)-1-oxa-2,8-diazaspiro[4.5]dec-2-ene-8-carboxylic acid-(4-tert-butylphenyl)amide | 422.6 |
| 319] 3-naphthalen-2-yl-1-oxa-2,8-diazaspiro[4.5]dec-2-ene-8-carboxylic acid-(4-ethylphenyl)amide | 442.4 |
| 322] 3-phenyl-1-oxa-2,8-diazaspiro[4.5]dec-2-ene-8-carboxylic acid benzhydrylamide | 426.4 |
| [329] 3-(3-chloropyridin-2-yl)-1-oxa-2,8-diazaspiro[4.5]dec-2-ene-8-carboxylic acid-(4-tert-butylphenyl)amide | 427.9 |
| [330] 3-phenyl-1-oxa-2,8-diazaspiro[4.5]dec-2-ene-8-thiocarboxylic acid-(4-pentafluorosulphanylphenyl)amide. | |
| 402 3-(3-methoxyphenyl)-1-oxa-2,8-diazaspiro[4.5]dec-2-ene-8-carboxylic acid-(2,3)-dihydrobenzo[1.4]dioxin-6-yl)amide | |
| 407 3-(4-isopropylphenyl)-1-oxa-2,8-diazaspiro[4.5]dec-2-ene-8-carboxylic acid-(4-tert-butylphenyl)amide | |
| 408 3-(2,3-dihydrobenzo[1,4]dioxin-6-yl)-1-oxa-2,8-diazaspiro[4.5]dec-2-ene-8-carboxylic acid-(4-tert-butylphenyl)amide | |
| 424 3-(2,3-dihydrobenzo[1.4]dioxin-6-yl)-1-oxa-2,8-diazaspiro[4.5]dec-2-ene-8-carboxylic acid-(4-trifluoromethylphenyl)amide | |
| 425 3-(3-chlorophenyl)-1-oxa-2,8-diazaspiro[4.5]dec-2-ene-8-carboxylic acid-(4-trilfuormethylphenyl)amide | |
| 427 3-(4-cyclohexylphenyl)-1-oxa-2,8-diaza-sprio[4.5]dec-2-ene-8-carboxylic acid-(4-trifluoromethylphenyl)amide | |
| [364] N-(4-tert-butylphenyl)-3-(2-fluorophenyl)-6-methyl-1-oxa-2,8-diazaspiro[4.5]dec-2-ene-8-carboxamide | 424.53 |
| [369] N-(4-tert-butylphenyl)-6-methyl-3-phenyl-1-oxa-2,8-diazaspiro[4.5]dec-2-ene-8-carboxamide | 406.54 |
| [371] N-(4-tert-butylphenyl)-3-phenyl-1-oxa-2,7-diazaspiro[4.4]non-2-ene-7-carboxamide | 378.49 |
| [372] N-(4-tert-butylbenzyl)-3-phenyl-1-oxa-2,8-diazaspiro[4.5]dec-2-ene-8-carboxamide | 406.54 |
| [373] N-(4-tert-butylphenyl)-3-phenyl-1-oxa-2,8-diazaspiro[4.6]undec-2-ene-8-carboxamide | 406.54 |
| [374] N-(4-tert-butylbenzyl)-3-(3-methoxyphenyl)-1-oxa-2,8-diazaspiro[4.5]dec-2-ene-8-carboxamide | 436.57 |
| [375] N-(1-(4-tert-butylphenyl)ethyl)-3-(3-methoxyphenyl)-1-oxa-2,8-diazaspiro[4.5]dec-2-ene-8-carboxamide | 450.59 |
| [376] N-(4-tert-butylcyclohexyl)-3-phenyl-1-oxa-2,8-diazaspiro[4.5]dec-2-ene-8-carboxamide | 398.56 |
| [377] N-(4-tert-butylphenethyl)-3-phenyl-1-oxa-2,8-diazaspiro[4.5]dec-2-ene-8-carboxamide | 420.57 |
| [378] N-(4-tert-butylphenyl)-3-(4-chloro-3-methoxyphenyl)-1-oxa-2,8-diazaspiro[4.5]dec-2-ene-8-carboxamide | 456.99 |
| [385] 6-methyl-3-phenyl-N-(4-(trifluoromethyl)phenyl)-1-oxa-2,8-diazaspiro[4.5]dec-2-ene-8-carboxamide | 418.43 |
| [386] 3-benzyl-N-(4-tert-butylphenyl)-1-oxa-2,8-diazaspiro[4.5]dec-2-ene-8-carboxamide | 406.54 |
| [387] N-(4-tert-butylphenyl)-3-phenethyl-1-oxa-2,8-diazaspiro[4.5]dec-2-ene-8-carboxamide | 420.57 |

9. Reaction of Amines of General Formula Ii with Carboxylic Acids of General Formula
$R^9$—C(=O)—OH a. Manual synthesis Synthesis of Exemplary Compound 307: (4-tert-butylphenyl)-(3-phenyl-1-oxa-2,8-diazaspiro[4.5]dec-2-en-8-yl)methanone

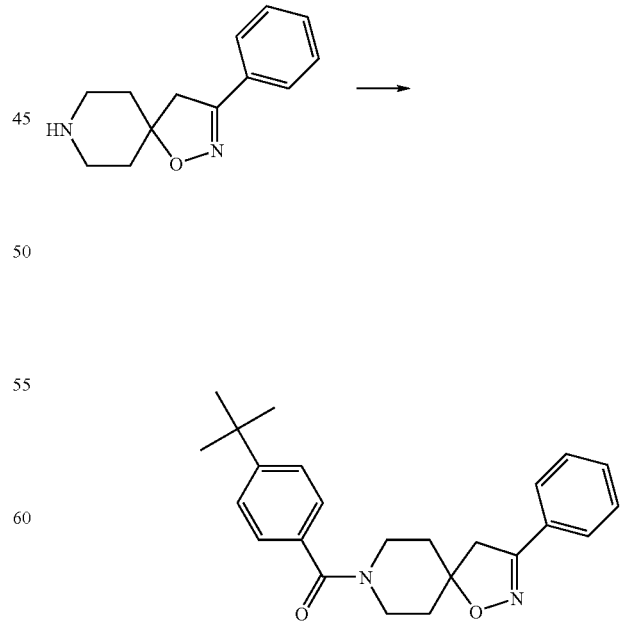

3-Phenyl-1-oxa-2,8-diazaspiro[4.5]dec-2-ene (E) was slowly added as a hydrochloride salt (250 mg) to a solution of N-ethyldiisopropylamine (560 µl, 3 mmol), 1-hydroxybenzotriazole hydrate (133 mg, 1 mmol), O-(benzotriazol-1-yl)-N,N,N',N'-tetramethyluronium tetrafluoroborate (318 mg, 1 mmol) and 4-tert-butylbenzoic acid (176 mg, µmol) in abs. THF (8 ml). The reaction mixture was stirred overnight and diluted with EtOAc. The organic phase was washed successively with sat. aq. NaCl solution, sat. aq. NaHCO₃ solution, sat. aq. NaCl solution and sat. aq. NH₄Cl solution and the solvent removed under vacuum. The desired product (4-tert-butylphenyl)-(3-phenyl-1-oxa-2,8-diazaspiro[4.5]dec-2-en-8-yl)methanone was obtained in a yield of 0.42 g.

Synthesis of exemplary compound 325: 3-(4-isopropyl phenyl)-1-(3-phenyl-1-oxa-2,8-diazaspiro[4.5]dec-2-en-8-yl)propenone

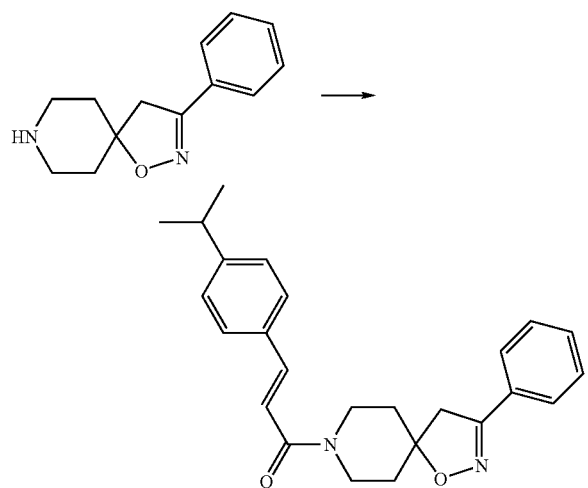

3-Phenyl-1-oxa-2,8-diazaspiro[4.5]dec-2-ene (E) was slowly added as a hydrochloride salt (250 mg) to a solution of N-ethyldiisopropylamine (560 µl, 3 mmol), 1-hydroxybenzotriazole hydrate (133 mg, 1 mmol), O-(benzotriazol-1-yl)-N,N,N',N'-tetramethyluronium tetrafluoroborate (318 mg, 1 mmol) and 4-isopropylcinnamic acid (188 mg, 1 mmol) in abs. THF (8 ml). The reaction mixture was stirred overnight and diluted with EtOAc. The organic phase was washed successively with sat. aq. NaCl solution, sat. aq. NaHCO₃ solution, sat. aq. NaCl solution and sat. aq. NH₄Cl solution and the solvent removed under vacuum. The desired product 3-(4-isopropylphenyl)-1-(3-phenyl-1-oxa-2,8-diazaspiro[4.5]dec-2-en-8-yl)propenone was obtained in a yield of 0.45 g.

Synthesis of Exemplary Compound 370: 2-(4-tert-butyl phenyl)-1-(3-phenyl-1-oxa-2,8-diazaspiro[4.5]dec-2-en-8-yl)propan-1-one Synthesis of 2-(4-tert-butylphenyl)propionic acid methyl ester

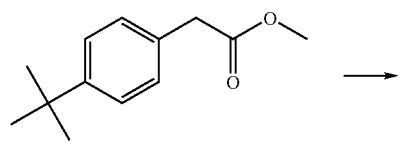

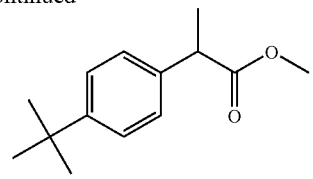

A solution of methyl-2-(4-tert-butylphenyl)acetate (1 g, 4.85 mmol) in abs. THF (30 ml) was mixed with a 1 M solution of bis-(trimethylsilyl)lithium amide in THF (5.33 ml, 5.33 mmol) at a temperature of −70° C. within 15 min. The reaction was highly exothermic. The mixture was kept for 20 min at −70° C. and at this temperature methyliodide (0.452 ml, 1.03 g, 7.26 mmol) was added within 5 min. Within 16 h the mixture was heated to RT. For working up, the reaction mixture was mixed with sat. NH₄Cl solution (30 ml). There were formed two phases and, as a solid, ammonium chloride which was separated off by filtration and washing with THF (2×8 ml). The filtrate was mixed with DCM (70 ml) and the phases were separated. The aqueous phase was extracted with DCM (2×20 ml). The organic phases were combined, dried and concentrated. There remained a colourless oil (1.08 g) which was purified by chromatography [silica gel 60 (50 g); cyclohexane (800 ml), EtOAc/cyclohexane 1:30 (600 ml)]. 2-(4-Tert-butylphenyl)propionic acid methyl ester was obtained as a colourless oil in a yield of 89% (946 mg).

Synthesis of 2-(4-tert-butylphenyl)propionic acid

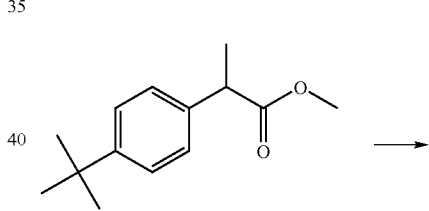

2-(4-Tert-butylphenyl)propionic acid methyl ester (946 mg, 4.29 mmol) was dissolved in MeOH (10 ml) and mixed with a solution of lithium hydroxide (154 mg, 6.44 mmol) in water (5 ml). The reaction mixture was stirred for 18 h at RT. The solvent was removed under vacuum and the aqueous residue mixed with diethyl ether (30 ml). The phases were separated. The aqueous phase was reextracted with diethyl ether (20 ml). The aqueous phase was adjusted to a pH of 3 using 1 N hydrochloric acid solution. There formed a clouding or precipitation which was extracted from the aqueous phase by the addition of EtOAc (2×20 ml). The organic phase was washed with sat. NaCl solution (20 ml), dried and concentrated. 2-(4-Tert-butylphenyl)propionic acid was obtained as a colourless solid in a yield of 83% (735 mg).

Synthesis of 2-(4-tert-butylphenyl)-1-(3-phenyl-1-oxa-2,8-diazaspiro[4.5]dec-2-en-8-yl)propan-1-one

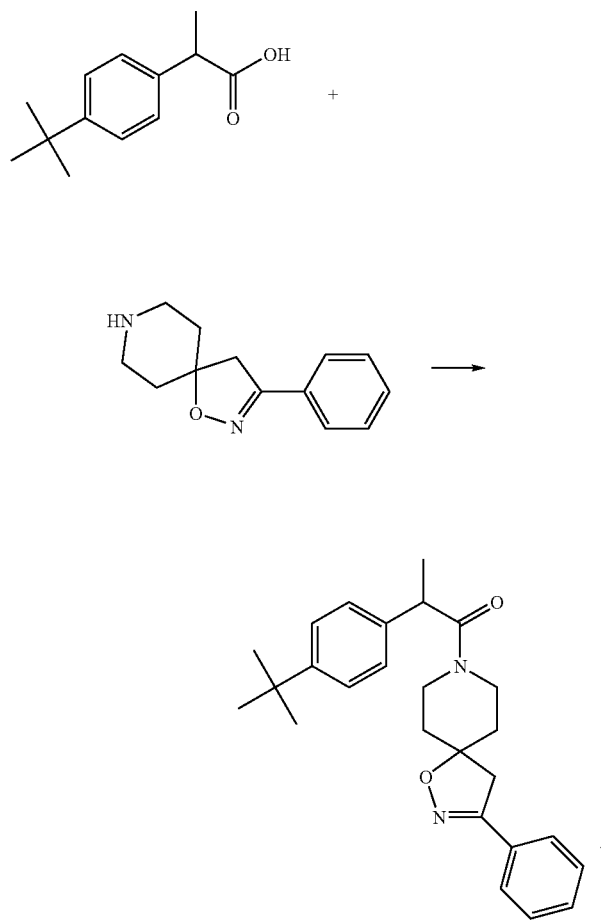

The hydrochloride of compound E (1.5 g, 5.9 mmol) was dissolved in water (20 ml), mixed with sat. NaHCO$_3$ solution (20 ml) and stirred for 1 h at RT. There formed compound E which was separated off by filtration. Compound E was obtained as a colourless solid in a yield of 92% (1.17 g) having a melting point of 115° C.

A solution of 2-(4-tert-butylphenyl)propionic acid (300 mg, 1.45 mmol) in abs. DMF (25 ml) was mixed with N,N'-carbonyldiimidazole (235 mg, 1.45 mmol) and stirred for 1.5 h at RT. Subsequently, compound E (346 mg, 1.6 mmol) was added. After a reaction time of 4 d at RT, the clear reaction mixture was concentrated. The residue was taken up in DCM (30 ml) and 0.5 N hydrochloric acid solution (20 ml). The phases were separated. The organic phase was washed successively with 0.5 N hydrochloric acid solution (20 ml), sat. NaHCO$_3$ solution (2×15 ml) and sat. NaCl solution (15 ml). The organic phase was dried and concentrated. The solid colourless residue was taken up in a mixture of diethyl ether (10 ml) and n-hexane (10 ml) and stirred for 15 min at RT. 22-(4-Tert-butylphenyl)-1-(3-phenyl-1-oxa-2,8-diazaspiro[4.5]dec-2-en-8-yl)propan-1-one was obtained as a colourless solid in a yield of 62% (364 mg) having a melting point of 143-145° C.

The following carboxylic acids of general formula HO—C(=O)—R$^9$ can preferably be used:

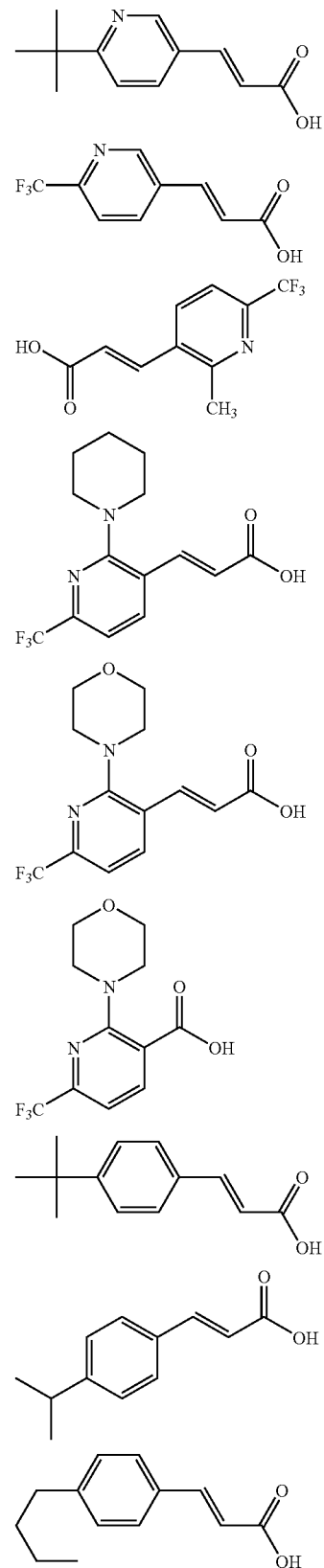

-continued
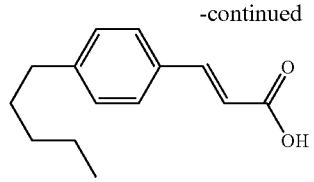
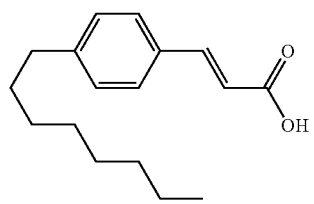
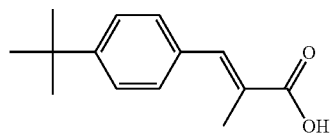
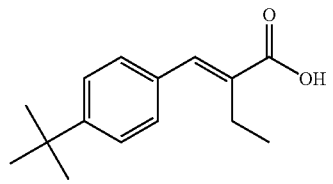
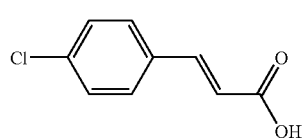
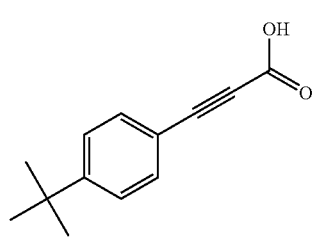
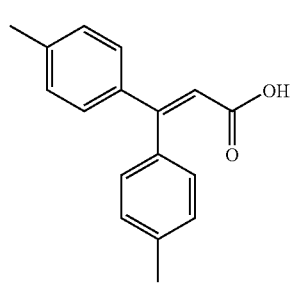
-continued
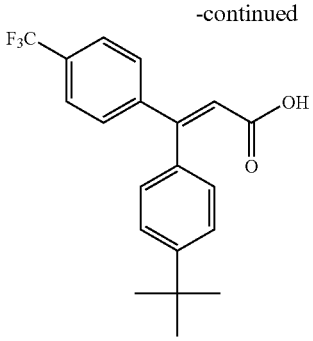
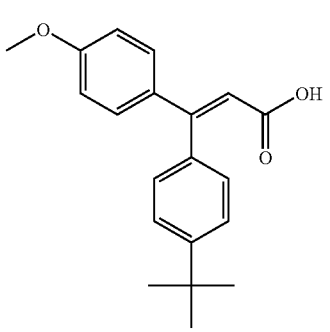
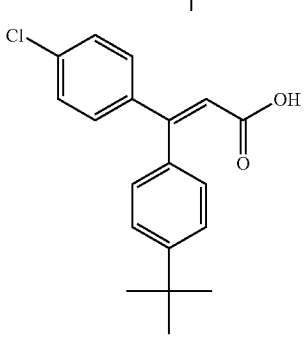
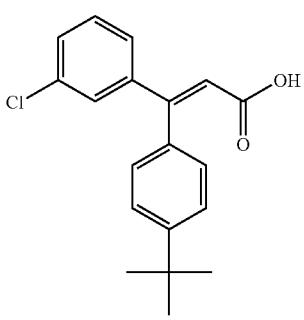
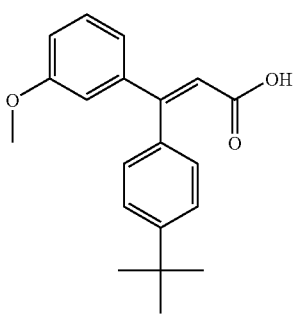

77
-continued
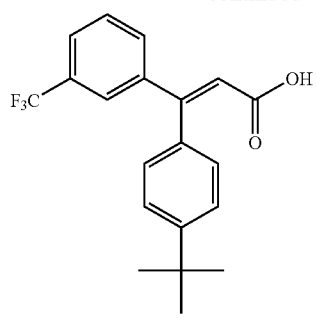
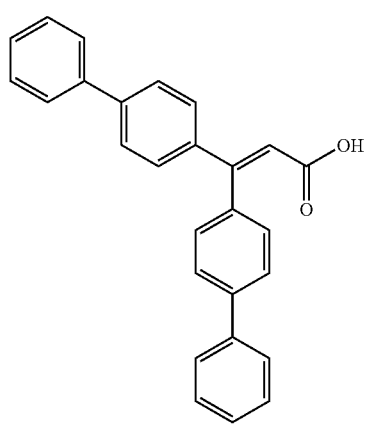
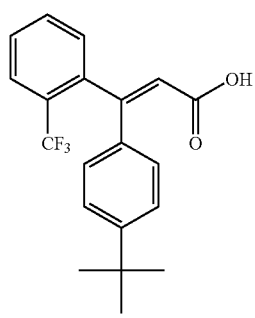
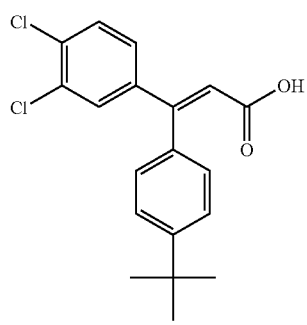
78
-continued
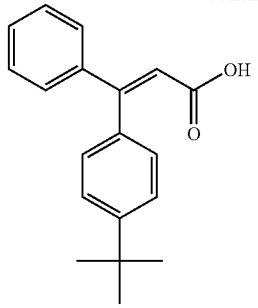
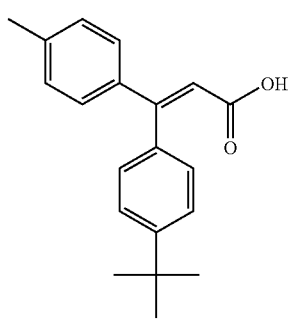
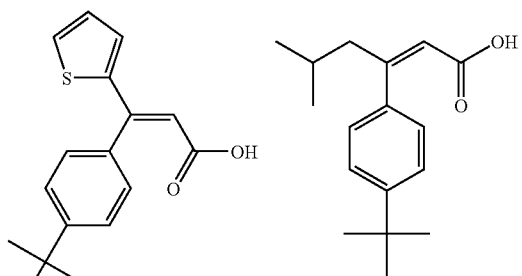
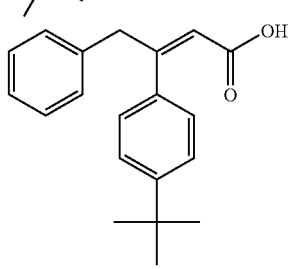
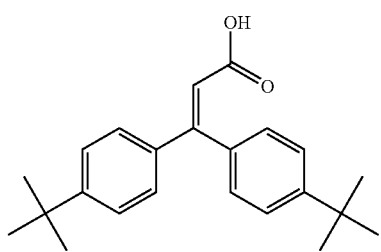

79
-continued
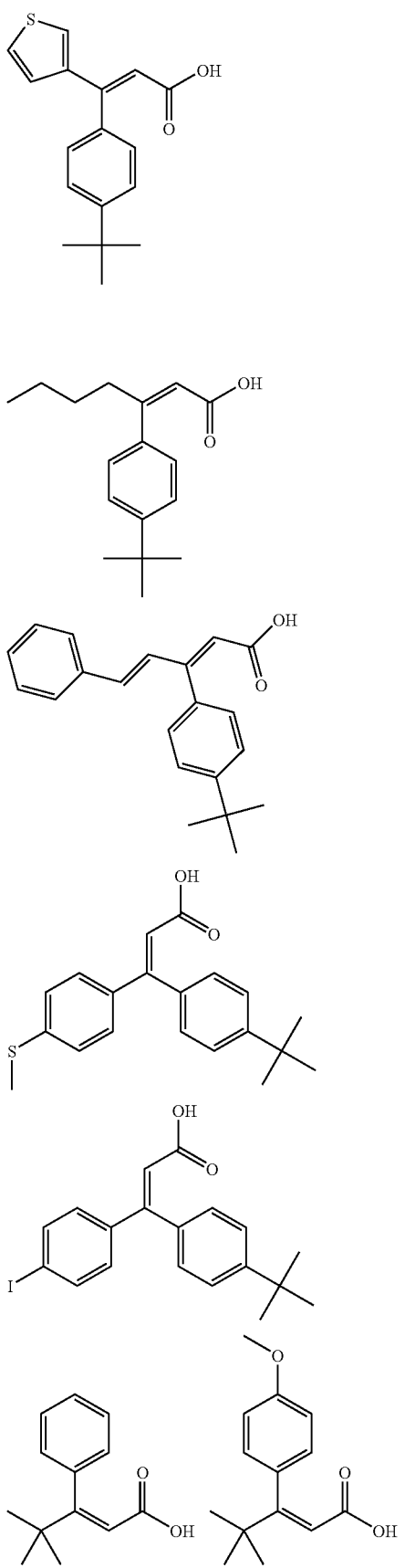
80
-continued
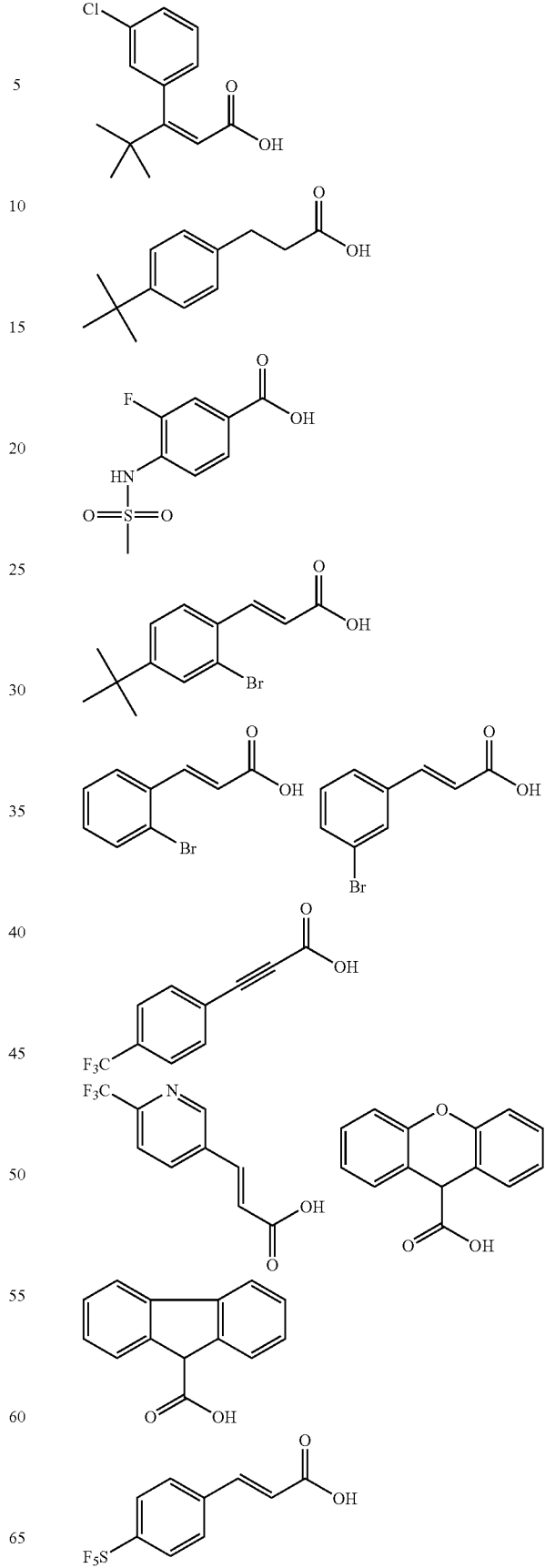

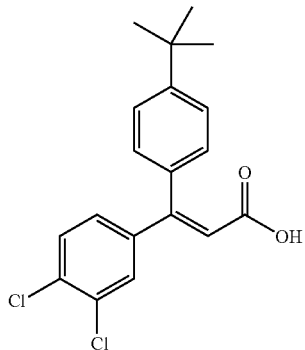 [SMILES: CC(C)(C)c1ccc(/C(=C\C(=O)O)c2ccc(Cl)c(Cl)c2)cc1]

The following substituted spiro compounds according to the invention were prepared as described under 2a.

| | Name | [M + H] |
|---|---|---|
| 304 | 3-phenyl-1-(3-phenyl-1-oxa-2,8-diazaspiro[4.5]dec-2-en-8-yl)propinone | 345.5 |
| 305 | 1-(3-tert-butyl-1-oxa-2,8-diazaspiro[4.5]dec-2-en-8-yl)-3-phenylpropinone | 325.5 |
| 308 | (4-hydroxy-3-methoxyphenyl)-(3-phenyl-1-oxa-2,8-diazaspiro[4.5]dec-2-en-8-yl)methanone | 367.4 |
| 309 | (4-iodophenyl)-(3-phenyl-1-oxa-2,8-diazaspiro[4.5]dec-2-en-8-yl)methanone | 447.2 |
| 313 | 2-(4-tert-butylphenyl)-1-(3-phenyl-1-oxa-2,8-diazaspiro[4.5]dec-2-en-8-yl)ethanone | 391.4 |
| 314 | 1-(3-phenyl-1-oxa-2,8-diazaspiro[4.5]dec-2-en-8-yl)-3-(4-trifluoromethylphenyl)propenone | 415.5 |
| 315 | 3-(4-hydroxy-3-methoxyphenyl)-1-(3-phenyl-1-oxa-2,8-diazaspiro[4.5]dec-2-en-8-yl)propenone | 393.6 |
| 316 | (4-tert-butylphenyl)-[3-(4-tert-butylphenyl)-1-oxa-2,8-diazaspiro[4.5]dec-2-en-8-yl]methanone | 384.2 |
| 317 | 3-(4-tert-butylphenyl)-1-[3-(4-tert-butylphenyl)-1-oxa-2,8-diazaspiro[4.5]dec-2-en-8-yl]propenone | 459.7 |
| 318 | 3-(4-tert-butylphenyl)-1-[3-(4-trifluoromethoxyphenyl)-1-oxa-2,8-diazaspiro[4.5]dec-2-en-8-yl]propenone | 487.5 |
| 320 | 1-(3-phenyl-1-oxa-2,8-diazaspiro[4.5]dec-2-en-8-yl)-3,3-di-p-tolylpropenone | 451.3 |
| 321 | 3-(4-tert-butylphenyl)-2-methyl-1-(3-phenyl-1-oxa-2,8-diazaspiro[4.5]dec-2-en-8-yl)propenone | 417.8 |
| 323 | 3-(4-tert-butylphenyl)-1-(3-phenyl-1-oxa-2,8-diazaspiro[4.5]dec-2-en-8-yl)propenone | 403.5 |
| 324 | 2-(4-tert-butylbenzylidene)-1-(3-phenyl-1-oxa-2,8-diazaspiro[4.5]dec-2-en-8-yl)butan-1-one | 431.5 |
| 326 | 3-(4-octylphenyl)-1-(3-phenyl-1-oxa-2,8-diazaspiro[4.5]dec-2-en-8-yl)propenone | 459.6 |
| 327 | 3-(4-butylphenyl)-1-(3-phenyl-1-oxa-2,8-diazaspiro[4.5]dec-2-en-8-yl)propenone | 403.4 |
| 328 | 3-(4-pentylphenyl)-1-(3-phenyl-1-oxa-2,8-diazaspiro[4.5]dec-2-en-8-yl)propenone | 417.7 |
| 388 | 3-(4-hydroxy-3-methoxyphenyl)-1-(3-phenyl-1-oxa-2,8-diazaspiro[4.5]decen-8-yl)propenone | |
| 389 | 3-(4-tert-butylphenyl)-1-(3-phenyl-1-oxa-2,8-diazaspiro[4.5]decen-8-yl)propenone | |
| 391 | 3,3-di-p-tolyl-1-(3-p-tolyl-1-oxa-2,8-diazaspiro[4.5]dec-2-en-8-yl)propenone | |
| 392 | [3-(4-tert-butylphenyl)-1-[3-(4-chlorophenyl)1-oxa-2,8-diazaspiro[4.5]dec-2-en-8-yl]propenone | |
| 393 | 3-(4-tert-butylphenyl)-2-ethyl-1-(3-p-tolyl-1-oxa-2,8-diazaspiro[4.5]dec-2-en-8-yl)propenone | |
| 394 | (4-tert-butylphenyl)-(3-p-tolyl-1-oxa-2,8-diazaspiro[4.5]dec-2-en-8-yl)methanone | |

| | Name | [M + H] |
|---|---|---|
| 395 | 3-(4-tert-butylphenyl)-1-(3-p-tolyl-1-oxa-2,8-diazaspiro[4.5]dec-2-en-8-yl)propenone | |
| 396 | 3-(4-tert-butylphenyl)-2-methyl-1-(3-p-tolyl-1-oxa-2,8-diazaspiro[4.5]dec-2-en-8-yl)propenone | |
| 397 | 2-(4-tert-butylphenyl)-1-[3-(3-methoxyphenyl)-1-oxa-2,8-diazaspiro[4.5]dec-2-en-8-yl]-but-2-en-1-one | |
| 398 | 3-(4-tert-butylphenyl)-1-[3-(3-methoxyphenyl)-1-oxa-2,8-diazaspiro[4.5]dec-2-en-8-yl]propinone | |
| 399 | 3-(4-tert-butylphenyl)-1-[3-(3-methoxyphenyl)-1-oxa-2,8-diazaspiro[4.5]dec-2-en-8-yl]propenone | |
| 400 | 1-[3-(3-methoxyphenyl)-1-oxa-2,8-diazaspiro[4.5]dec-2-en-8-yl]-2,2-diphenyl-propan-1-one | |
| 401 | 1-[3-(3-methoxyphenyl)-1-oxa-2,8-diazaspiro[4.5]dec-2-en-8-yl]-2,2-diphenylethanone | |
| 403 | 3-(6-tert-butylpyridin-3-yl)-1-[3-(3-methoxyphenyl)-1-oxa-2,8-diazaspiro[4.5]dec-2-en-8-yl]propenone | |
| 404 | 3-(6-tert-butylpyridin-3-yl)-1-[3-(4-chloro-3-methoxyphenyl)-1-oxa-2,8-diazaspiro[4.5]dec-2-en-8-yl]propenone | |
| 405 | 2,2-diphenyl-1-(3-phenyl-1-oxa-2,8-diazaspiro[4.5]dec-2-en-8-yl)-propan-1-one | |
| 406 | 3-(6-tert-butylpyridin-3-yl)-1-(3-phenyl-1-oxa-2,8-diazaspiro[4.5]dec-2-en-8-yl)propenone | |
| 409 | N-[2-fluoro-4-[3-(3-methoxyphenyl)-1-oxa-2,8-diazaspiro[4.5][dec-2-ene-8-carbonyl]phenyl]methanesulphonamide | |
| 410 | N-[2-fluoro-4-(3-phenyl-1-oxa-2,8-diazaspiro[4.5][dec-2-ene-8-carbonyl]phenyl]methanesulphonamide | |
| 411 | 3-(4-cyclohexylphenyl)-1-(3-phenyl-1-oxa-2,8-diazaspiro[4.5]dec-2-en-8-yl)propenone | |
| 412 | 1-[3-(3-methoxyphenyl)-1-oxa-2,8-diazaspiro[4.5]dec-2-en-8-yl]-2,2,2-triphenylethanone | |
| 413 | [3-(3-methoxyphenyl)-1-oxa-2,8-diazaspiro[4.5]dec-2-en-8-yl]-(9H-xanthen-9-yl)methanone | |
| 414 | [3-(4-chloro-3-methoxyphenyl)-1-oxa-2,8-diazaspiro[4.5]dec-2-en-8-yl]-(9H-fluoren-9-yl)methanone | |
| 415 | [3-(4-chloro-3-methoxyphenyl)-1-oxa-2,8-diazaspiro[4.5]dec-2-en-8-yl]-(2-chloro-6-trifluoromethylpyridin-3-yl)methanone | |
| 416 | [3-(3-methoxyphenyl)-1-oxa-2,8-diazaspiro[4.5]dec-2-en-8-yl]-(2-morpholin-4-yl-6-trifluoromethylpyridin-3-yl)methanone | |
| 417 | 3-(4-tert-butylphenyl)-1-[3-(3-chlorophenyl)-1-oxa-2,8-diazaspiro[4.5]dec-2-en-8-yl]propenone | |
| 418 | 3-(4-tert-butylphenyl)-1-[3-(2,3-dihydrobenzo[1.4]dioxin-6-yl)-1-oxa-2,8-diazaspiro[4.5]dec-2-en-8-ylpropenone | |
| 419 | 3-(4-tert-butylphenyl)-1-[3-(4-cyclohexylphenyl)-1-oxa-2,8-diazaspiro[4.5]dec-2-en-8-yl]propenone | |
| 420 | N-[4-[3-(4-cyclohexylphenyl)-1-oxa-2,8-diazaspiro[4.5]dec-2-ene-8-carbonyl]-2-fluorophenyl]methanesulphonamide | |
| 421 | 2-hydroxy-2,2-diphenyl-1-(3-phenyl-1-oxa-2,8-diazaspiro[4.5]dec-2-8-yl)ethanone | |
| 422 | (3-phenyl-1-oxa-2,8-diazaspiro[4.5]dec-2-en-8-yl)-(9H-xanthen-9-yl)methanone | |
| 423 | 3-(4-tert-butylphenyl)-1-(3-quinolin-3-yl-1-oxa-2,8-diazaspiro[4.5]dec-2-en-8-yl)propenone | |
| 426 | (4-tert-butylphenyl)-[3-(3-methoxyphenyl)-1-oxa-2,8-diazaspiro[4.5]dec-2-en-8-yl]methanone | |
| 428 | 3-(4-tert-butylphenyl)-3-(4-chlorophenyl)-1-[3-(3-chlorophenyl)-1-oxa-2,8-diazaspiro[4.5]dec-2-en-8-yl]propenone | |
| 429 | 3-(4-tert-butylphenyl)-1-[3-(3-chlorophenyl)-1-oxa-2,8-diazaspiro[4.5]dec-2-en-8-yl]-3-(3-methoxyphenyl)propenone | |
| 430 | 3-(4-tert-butylphenyl)-1-[3-(4-chloro-3-methoxyphenyl)-1-oxa-2,8-diazaspiro[4.5]dec-2-en-8-yl]-3-(4-trifluoromethylphenyl)propenone | |
| 431 | 3-(4-pentafluorosulphanylphenyl)-1-[3-(3-methoxyphenyl)-1-oxa-2,8-diazaspiro[4.5]dec-2-en-8-yl]propenone | |
| 432 | 3-(4-tert-butylphenyl)-1-[3-(4-chloro-3-methoxyphenyl)-1-oxa-2,8-diazaspiro[4.5]dec-2-en-8-yl]propenone | |

| Name | [M + H] |
|---|---|
| 433 [3-(4-tert-butylphenyl)-1-[3-(4-chloro-3-methoxyphenyl)-1-oxa-2,8-diazaspiro[4.5]dec-2-en-8-yl]propinone | |
| 434 3-(4-tert-butylphenyl)-1-[3-(3-methoxyphenyl)-1-oxa-2,8-diazaspiro[4.5]dec-2-en-8-yl]-3-(2-trifluoromethylphenyl)propenone | |
| 437 3,3-bis-(4-tert-butylphenyl)-1-(3-phenyl-1-oxa-2,8-diazaspiro[4.5]dec-2-en-8-yl)propenone | |
| [331] (3-(4-chloro-3-methoxyphenyl)-1-oxa-2,8-diazaspiro[4.5]dec-2-en-8-yl)(9H-xanthen-9-yl)methanone | 489.97 |
| [332] (9H-fluoren-9-yl)(3-(3-methoxyphenyl)-1-oxa-2,8-diazaspiro[4.5]dec-2-en-8-yl)methanone | 439.53 |
| [333] N-(4-tert-butylphenyl)-3-(3-chlorophenyl)-1-oxa-2,8-diazaspiro[4.5]dec-2-ene-8-carboxamide | 426.96 |
| [334] (E)-3-(4-cyclohexylphenyl)-1-(3-(3-methoxyphenyl)-1-oxa-2,8-diazaspiro[4.5]dec-2-en-8-yl)prop-2-en-1-one | 459.60 |
| [335] N-(4-tert-butylphenyl)-3-(4-cyclohexylphenyl)-1-oxa-2,8-diazaspiro[4.5]dec-2-ene-8-carboxamide | 474.66 |
| [336] (E)-3-(4-tert-butylphenyl)-1-(3-phenyl-1-oxa-2,8-diazaspiro[4.5]dec-2-en-8-yl)prop-2-en-1-one | 479.64 |
| [337] (2E,4E)-3-(4-tert-butylphenyl)-5-phenyl-1-(3-phenyl-1-oxa-2,8-diazaspiro[4.5]dec-2-en-8-yl)penta-2,4-dien-1-one | 505.67 |
| [338] (Z)-3-(4-tert-butylphenyl)-1-(3-phenyl-1-oxa-2,8-diazaspiro[4.5]dec-2-en-8-yl)-3-(thiophen-3-yl)prop-2-en-1-one | 485.66 |
| [339] (E)-3-(4-tert-butylphenyl)-1-(3-(3-methoxyphenyl)-1-oxa-2,8-diazaspiro[4.5]dec-2-en-8-yl)-3-(4-(trifluoromethyl)phenyl)prop-2-en-1-one | 577.66 |
| [340] (E)—N-(5-(8-(3-(4-tert-butylphenyl)acryloyl)-1-oxa-2,8-diazaspiro[4.5]dec-2-ene-3-yl)-2-fluorophenyl)methanesulphonamide | 514.63 |
| [341] (E)-3-(4-pentafluorosulphanyl)-1-(3-(3-methoxyphenyl)-1-oxa-2,8-diazaspiro[4.5]dec-2-en-8-yl)prop-2-en-1-one | 503.50 |
| [342] (E)-1-(3-(3-methoxyphenyl)-1-oxa-2,8-diazaspiro[4.5]dec-2-en-8-yl)-3-(2-morpholino-6-(trifluoromethyl)pyridin-3-yl)prop-2-en-1-one | 531.55 |
| [343] N-(2-fluoro-4-(1-oxo-1-(3-phenyl-1-oxa-2,8-diazaspiro[4.5]dec-2-en-8-yl)propan-2-yl)phenyl)methanesulphonamide | 460.54 |
| [344] N-(2-fluoro-4-(1-(3-(3-methoxyphenyl)-1-oxa-2,8-diazaspiro[4.5]dec-2-en-8-yl)-1-oxopropan-2-yl)phenyl)methanesulphonamide | 490.57 |
| [345] (Z)-3-(4-tert-butylphenyl)-1-(3-(3-methoxyphenyl)-1-oxa-2,8-diazaspiro[4.5]dec-2-en-8-yl)-3-(thiophen-3-yl)prop-2-en-1-one | 515.69 |
| [346] (E)-3-(3-bromophenyl)-1-(3-phenyl-1-oxa-2,8-diazaspiro[4.5]dec-2-en-8-yl)prop-2-en-1-one | 426.33 |
| [347] (E)-3-(2-bromophenyl)-1-(3-phenyl-1-oxa-2,8-diazaspiro[4.5]dec-2-en-8-yl)prop-2-en-1-one | 426.33 |
| [348] 3-(3-fluorophenyl)-N-(4-(trifluoromethyl)phenyl)-1-oxa-2,8-diazaspiro[4.5]dec-2-ene-8-carboxamide | 422.39 |
| [349] N-(4-tert-butylphenyl)-3-(4-fluorophenyl)-1-oxa-2,8-diazaspiro[4.5]dec-2-ene-8-carboxamide | 410.50 |
| [350] 3-(4-tert-butylphenyl)-1-(3-phenyl-1-oxa-2,8-diazaspiro[4.5]dec-2-en-8-yl)propan-1-one | 405.55 |
| [351] N-(4-tert-butylphenyl)-3-(3-fluorophenyl)-1-oxa-2,8-diazaspiro[4.5]dec-2-ene-8-carboxamide | 410.50 |
| [352] N-(4-tert-butylphenyl)-3-(2-fluorophenyl)-1-oxa-2,8-diazaspiro[4.5]dec-2-ene-8-carboxamide | 410.50 |
| [353] (E)-3-(4-tert-butylphenyl)-1-(3-(3-fluorophenyl)-1-oxa-2,8-diazaspiro[4.5]dec-2-en-8-yl)prop-2-en-1-one | 421.53 |
| [354] (Z)-1-(3-(3-methoxyphenyl)-1-oxa-2,8-diazaspiro[4.5]dec-2-en-8-yl)-4,4-dimethyl-3-phenylpent-2-en-1-one | 433.56 |
| [355] (E)-1-(3-phenyl-1-oxa-2,8-diazaspiro[4.5]dec-2-en-8-yl)-3-(2-(piperidin-1-yl)-6-(trifluoromethyl)pyridin-3-yl)prop-2-en-1-one | 499.55 |
| [356] (E)-1-(3-(3-chlorophenyl)-1-oxa-2,8-diazaspiro[4.5]dec-2-en-8-yl)-3-(2-(piperidin-1-yl)-6-(trifluoromethyl)pyridin-3-yl)prop-2-en-1-one | 533.99 |
| [357] (2E,4E)-3-tert-butyl-1-(3-(3-methoxyphenyl)-1-oxa-2,8-diazaspiro[4.5]dec-2-en-8-yl)-5-phenylpenta-2,4-dien-1-one | 459.60 |
| [358] (2E,4E)-3-(4-tert-butylphenyl)-1-(3-(3-fluorophenyl)-1-oxa-2,8-diazaspiro[4.5]dec-2-en-8-yl)-5-phenylpenta-2,4-dien-1-one | 523.66 |
| [359] (Z)-3-(4-tert-butylphenyl)-3-(3,4-dichlorophenyl)-1-(3-(2-fluorophenyl)-1-oxa-2,8-diazaspiro[4.5]dec-2-en-8-yl)prop-2-en-1-one | 566.52 |
| [360] (Z)-3-(4-tert-butylphenyl)-3-(3,4-dichlorophenyl)-1-(3-(3-fluorophenyl)-1-oxa-2,8-diazaspiro[4.5]dec-2-en-8-yl)prop-2-en-1-one | 566.52 |
| [361] 1-(3-(3-methoxyphenyl)-1-oxa-2,8-diazaspiro[4.5]dec-2-en-8-yl)-3-(4-(trifluoromethyl)phenyl)prop-2-yn-1-one | 443.44 |
| [362] (E)-1-(3-(3-methoxyphenyl)-1-oxa-2,8-diazaspiro[4.5]dec-2-en-8-yl)-3-(6-(trifluoromethyl)pyridin-3-yl)prop-2-en-1-one | 446.44 |
| [363] 1-(3-phenyl-1-oxa-2,8-diazaspiro[4.5]dec-2-en-8-yl)-3-(4-(trifluoromethyl)phenyl)prop-2-yn-1-one | 413.41 |
| [365] (E)-1-(3-(3-fluorophenyl)-1-oxa-2,8-diazaspiro[4.5]dec-2-en-8-yl)-3-(2-(piperidin-1-yl)-6-(trifluoromethyl)pyridin-3-yl)prop-2-en-1-one | 517.54 |
| [366] N-(2-fluoro-4-(1-(3-(3-fluorophenyl)-1-oxa-2,8-diazaspiro[4.5]dec-2-en-8-yl)-1-oxopropan-2-yl)phenyl)methanesulphonamide | 478.53 |
| [367] (E)-1-(6-methyl-3-phenyl-1-oxa-2,8-diazaspiro[4.5]dec-2-en-8-yl)-3-(2-(piperidin-1-yl)-6-(trifluoromethyl)pyridin-3-yl)prop-2-en-1-one | 513.58 |
| [368] (E)-3-(2-bromo-4-tert-butylphenyl)-1-(3-phenyl-1-oxa-2,8-diazaspiro[4.5]dec-2-en-8-yl)prop-2-en-1-one | 482.44 |
| [370] 2-(4-tert-butylphenyl)-1-(3-phenyl-1-oxa-2,8-diazaspiro[4.5]dec-2-en-8-yl)propan-1-one | 405.55 |
| [381] (E)-N-(2-fluoro-4-(3-oxo-3-(3-phenyl-1-oxa-2,8-diazaspiro[4.5]dec-2-en-8-yl)prop-1-enyl)phenyl)methanesulphonamide | 458.52 |
| [382] (E)-N-(2-fluoro-4-(3-(3-(3-methoxyphenyl)-1-oxa-2,8-diazaspiro[4.5]dec-2-en-8-yl)-3-oxoprop-1-enyl)phenyl)methanesulphonamide | 488.55 |

10. General Directions for Reacting Amines of General Formula Ii with Aldehydes of general formula $R^1$—C(=O)—H The respective aldehyde of general formula $R^1$—C(=O)—H (120 μmol in 0.5 mL MeOH) and then borane-pyridine complex ($BH_3.C_5H_5N$, 100 μmol in 0.5 mL MeOH) were added to a solution of the compound of general formula II (120 μmol in 0.5 mL MeOH) while stirring at RT. The reaction mixture was stirred for at least 16 hours at 64° C. and then mixed with 5% (percent by weight) hydrochloric acid solution in water (0.5 mL) while stirring. 10% (percent by weight) sodium hydroxide solution in water (1 mL) was added to the reaction mixture and the mixture was extracted three times with DCM (2 mL in each case). The combined organic phases were dried over $MgSO_4$ cartridges, the solvent was removed under vacuum and the residue purified by preparative HPLC in order to obtain the desired product of general formula II.

11. General Directions for Reacting Amines of General Formula Ii with Carboxylic Acid Halogenides of General Formula $R^9$—C(=O)-LG or with Sulphonic Acid Halogenides of General Formula $R^1$—S(=O)$_2$-LG The compound of general formula II (1.0 equivalent) was added at 0° C. to a solution consisting of the respective acid halogenide (1.5 equivalent), triethylamine (2.0 equivalent) and a catalytic amount of DMAP in DCM. The reaction solution was heated to RT and stirred overnight. After the addition of 10% (percent by weight) aq. NH$_4$Cl solution, the organic phase was separated off and dried over MgSO$_4$. The solvent was removed under vacuum and the residue purified by column chromatography on silica gel with EtOAc/hexane mixtures as the eluent in order to obtain the desired product of general formula I.

Pharmacological Data

The affinity of the spiro compounds according to the invention for the vanilloid receptor 1 (VR1/TRPV1 receptor) was determined as described hereinbefore.

| Compound according to the example | VR1 (human) (% stimulation compared to 10 μM CP) | VR1 (human) (% inhibition compared to 10 μM CP) | VR1 (rat) (% stimulation compared to 10 μM CP) | VR1 (rat) (% inhibition compared to 10 μM CP) |
|---|---|---|---|---|
| 3 | 0.01 | 13.41 | −0.73 | 43.84 |
| 22 | −0.14 | 10.14 | −0.73 | 40.30 |
| 39 | −0.14 | 24.96 | 0.11 | 73.96 |
| 42 | −0.22 | 2.57 | −0.73 | 39.91 |
| 44 | −0.15 | −4.40 | −0.73 | 85.64 |
| 45 | −0.04 | 0.17 | −0.73 | 55.49 |
| 47 | 0.01 | 11.44 | 0.92 | 48.33 |
| 56 | −0.22 | 16.36 | −0.04 | 47.31 |
| 59 | 0.01 | 2.09 | 0.51 | 48.58 |
| 65 | −0.07 | −10.79 | 0.08 | 80.47 |
| 69 | −0.32 | 7.01 | −0.47 | 87.20 |
| 77 | 0.10 | 5.49 | 3.81 | 95.44 |
| 78 | 0.11 | 11.82 | 0.02 | 95.02 |
| 79 | −0.35 | −17.55 | 0.38 | 46.46 |
| 80 | 0.89 | 3.60 | −0.47 | 62.09 |
| 81 | −0.35 | −2.79 | −0.47 | 58.80 |
| 90 | −0.15 | −7.62 | −0.47 | 55.87 |
| 103 | −0.35 | 8.28 | −0.47 | 50.85 |
| 122 | 0.07 | −13.10 | −0.47 | 49.19 |
| 140 | 9.37 | 9.67 | 1.40 | 99.22 |
| 141 | −0.30 | 20.36 | 0.42 | 98.48 |
| 142 | −0.07 | −18.80 | −0.20 | 63.02 |
| 143 | 4.12 | −7.17 | −0.33 | 45.73 |
| 144 | −0.18 | −16.58 | −0.43 | 94.47 |
| 145 | 2.49 | 4.26 | −0.20 | 59.87 |
| 146 | 0.29 | 9.95 | −0.13 | 58.05 |
| 156 | 0.69 | −7.89 | 0.20 | 48.20 |
| 163 | 0.12 | −3.15 | −0.43 | 84.27 |
| 164 | −0.04 | −2.13 | −0.43 | 72.93 |
| 165 | 1.92 | 1.69 | −0.43 | 56.21 |
| 167 | 0.06 | 17.47 | −0.43 | 47.40 |
| 174 | 5.90 | −25.03 | −0.28 | 47.79 |
| 192 | −0.04 | −6.74 | −0.07 | 52.07 |
| 193 | 0.11 | −2.64 | −0.17 | 43.59 |
| 197 | 0.06 | −17.17 | −0.35 | 59.91 |
| 201 | 8.56 | −0.70 | −0.43 | 54.17 |
| 205 | 0.33 | −23.85 | 0.15 | 39.94 |
| 210 | −0.21 | 7.12 | 0.22 | 98.00 |
| 211 | −0.18 | 9.23 | 0.33 | 97.52 |
| 212 | −0.21 | −16.07 | −0.43 | 61.93 |
| 221 | −0.04 | −11.55 | 0.95 | 72.82 |
| 225 | 0.31 | −4.50 | −0.47 | 47.78 |
| 236 | −0.28 | −10.27 | −0.47 | 45.15 |
| 244 | −0.28 | 3.09 | 9.79 | 89.14 |
| 245 | 0.28 | 10.98 | 2.55 | 99.05 |
| 262 | −0.28 | 7.81 | −0.54 | 52.53 |
| 278 | 0.66 | 28.06 | 0.73 | 88.07 |
| 290 | −0.28 | −7.84 | −0.47 | 48.38 |
| 314 | 0 | 6 | −6 | 82 |
| 323 | 0 | 36 | 0 | 98 |
| 325 | 0 | 6 | −6 | 63 |
| 329 | 38 | 37 | 71 | 96 |
| 330 | | | 1 | 103 |
| 333 | 8 | 29 | 9 | 101 |
| 337 | −1 | 16 | 1 | 95 |
| 342 | 0 | 53 | 0 | 60 |
| 346 | 0 | 3 | 0 | 62 |
| 348 | 0 | 60 | 3 | 101 |
| 349 | 1 | −12 | 5 | 100 |
| 350 | 0 | −4 | 1 | 81 |
| 351 | 3 | 83 | 6 | 101 |
| 352 | 2 | −3 | 7 | 95 |
| 353 | 0 | 23 | 0 | 84 |
| 355 | 0 | 63 | 0 | 98 |
| 356 | 0 | 52 | 0 | 88 |
| 358 | 0 | 41 | 0 | 95 |
| 359 | 0 | 26 | 3 | 57 |
| 360 | 0 | 12 | 3 | 80 |
| 361 | 0 | 12 | 0 | 58 |
| 362 | 0 | 19 | −1 | 44 |
| 363 | 0 | 30 | 0 | 81 |
| 364 | −1 | 50 | 4 | 106 |
| 365 | −1 | 74 | 0 | 94 |
| 366 | −1 | −20 | 0 | 29 |
| 367 | 0 | 93 | −1 | 96 |
| 368 | 0 | 66 | 0 | 83 |
| 369 | −1 | 19 | 0 | 110 |
| 371 | 1 | 12 | 35 | 99 |
| 378 | 42 | 81 | 33 | 99 |
| 385 | −2 | 18 | 1 | 77 |

| Compound according to the example | IC$_{50}$ CAP rat average [μM] | IC$_{50}$ CAP human average [μM] |
|---|---|---|
| 141 | 0.0780 | |
| 314 | 0.1500 | 0.8250 |
| 323 | 0.1810 | 1.4427 |
| 325 | 0.2700 | 0.8750 |
| 342 | 0.4785 | 1.5488 |
| 346 | 1.3580 | 4.3760 |
| 358 | 0.1485 | 1.1110 |
| 369 | 0.1752 | 1.0674 |
| 385 | 0.0598 | |

The invention claimed is:

1. A substituted spiro compound corresponding to formula I

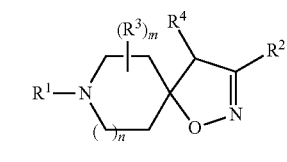

wherein m is 0, 1, 2, 3 or 4, n is 1, $R^1$ represents a —C(=O)—$R^9$ group;

$R^2$ represents a linear or branched, saturated or unsaturated, unsubstituted or mono- or polysubstituted aliphatic group optionally having at least one heteroatom as chain member;

an unsubstituted or mono- or polysubstituted, unsaturated or saturated cycloaliphatic group which optionally has at least one heteroatom as ring member and can be bound via a linear or branched, unsubstituted or mono- or polysubstituted alkylene, alkenylene or alkinylene group optionally having at least one heteroatom as chain member and/or condensed with an unsubstituted or mono- or polysubstituted mono- or polycyclic ring system, a phenyl group, unsubstituted or mono- or polysubstituted with one or more substituents independently selected from the group consisting of F, Cl, Br, I, —CN, —$CF_3$, —$SF_5$, —OH, —O—$C_{1-10}$ alkyl, —$NH_2$, —$NO_2$, —O—$CF_3$, —S—$CF_3$, —SH, —S—$C_{1-5}$ alkyl, —$C_{1-10}$ alkyl, —C(=O)—OH, —C(=O)—O—$C_{1-5}$ alkyl, —O—C(=O)—$C_{1-5}$ alkyl, —NH—$C_{1-5}$ alkyl, —N($C_{1-5}$ alkyl)$_2$, —NH—C(=O)—O—$C_{1-5}$ alkyl, —C(=O)—H, —C(=O)—$C_{1-5}$ alkyl, —C(=O)—$NH_2$, —C(=O)—NH—$C_{1-5}$ alkyl, C(=O)—N—($C_{1-5}$ alkyl)$_2$, —S(=O)$_2$—$C_{1-5}$ alkyl, —S(=O)$_2$ phenyl, —NH—S(=O)$_2$—$C_{1-5}$ alkyl, —NH—S(=O)$_2$—$C_{1-5}$ alkylenephenyl, —NH—S(=O)$_2$—$C_{1-5}$ alkylenenaphthyl, —NH—S(=O)$_2$ phenyl, —NH—S(=O)$_2$ naphthyl, —S(=O)$_2$—NH—$C_{1-5}$ alkyl, cyclohexyl, cyclopentyl, morpholinyl, piperidinyl, pyrrolidinyl, piperazinyl, pyridinyl, pyridazinyl, —($CH_2$)-benzo[b]furanyl, —O-phenyl, —O-benzyl, phenyl and benzyl, wherein in each case the cyclic portion of the radicals pyridinyl, cyclopentyl, cyclohexyl, morpholinyl, piperidinyl, pyrrolidinyl, piperazinyl, pyridazinyl, —S(=O)$_2$ phenyl, —O-phenyl, —O-benzyl, phenyl, —($CH_2$)-benzo[b]furanyl, —NH—S(=O)$_2$—$C_{1-5}$ alkylenephenyl, —NH—S(=O)$_2$—$C_{1-5}$ alkylenenaphthyl, —NH—S(=O)$_2$ phenyl, —NH—S(=O)$_2$ naphthyl and benzyl can be substituted with 1, 2, 3, 4 or 5 substituents selected independently of one another from the group consisting of F, Cl, Br, —OH, —$CF_3$, —$SF_5$, —CN, —$NO_2$, —$C_{1-5}$ alkyl, —O—$C_{1-5}$ alkyl, —O—$CF_3$, —S—$CF_3$, phenyl and —O-benzyl, with the proviso that either of the two meta positions and the para position of said phenyl group are not both substituted with substituents which are respectively bound to the phenyl group via an identical atom selected from the group consisting of oxygen, sulfur and nitrogen;

an unsubstituted or mono- or polysubstituted group selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl; 2H-benzo[1.4]oxazin-3(4H)-onyl, (3,4)-dihydroquinolin-2(1H)-onyl, [3,4]-dihydro-2H-1,4-benzoxazinyl and benzothiazolyl, or an unsubstituted or mono- or polysubstituted aryl or heteroaryl group which is bound via a linear or branched, unsubstituted or mono- or polysubstituted alkylene, alkenylene or alkinylene group optionally having at least one heteroatom as chain member and optionally can be condensed with an unsubstituted or mono- or polysubstituted mono- or polycyclic ring system;

$R^3$ represents a halogen group, a nitro group, a hydroxy group, a thiol group; an —O—$R^{11}$ group, an —S—$R^{12}$ group, or a linear or branched, saturated or unsaturated, unsubstituted or mono- or polysubstituted aliphatic group;

$R^4$ represents hydrogen;

$R^9$ represents a linear or branched, saturated or unsaturated, aliphatic group, unsubstituted or mono- or polysubstituted with one or more substituents independently selected from the group consisting of F, Cl, Br, I, —CN, —$NO_2$, —OH, —SH and —$NH_2$, wherein said aliphatic group is selected from the group consisting of methyl, ethyl, n-propyl, isopropyl, n-butyl, isobutyl, sec-butyl, tert-butyl, n-pentyl, isopentyl, neo-pentyl, n-hexyl, 2-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosanyl, —($CH_2$)—($CH_2$)—(C($CH_3$)$_3$), —($CH_2$)—(CH)($C_2H_5$)—($CH_2$)—($CH_2$)—($CH_2$)—($CH_3$), ethenyl (vinyl), ethinyl, propenyl (—$CH_2$CH=$CH_2$, —CH=CH—$CH_3$, —C(=$CH_2$)—$CH_3$), 2-methylpropenyl, propinyl (—$CH_2$—C≡CH, —C≡C—$CH_3$), butenyl, butinyl, pentenyl, pentinyl, hexenyl, hexinyl, octenyl and octinyl;

or an unsubstituted or mono- or polysubstituted aryl or heteroaryl group which can be bound via a linear or branched, alkylene, alkenylene, or alkinylene group, unsubstituted or mono- or polysubstituted with 1, 2, 3, 4 or 5 substituents independently selected from the group consisting of F, Cl, Br, —OH, —SH, —$NH_2$, —CN, —$NO_2$ and phenyl, wherein the phenyl radical can be substituted with 1, 2, 3, 4 or 5 substituents selected independently of one another from the group consisting of methyl, ethyl, n-propyl, isopropyl, n-butyl, isobutyl, sec-butyl, tert-butyl, n-pentyl, isopentyl and neo-pentyl, and/or condensed with an unsubstituted or mono- or polysubstituted mono- or polycyclic ring system, wherein said alkylene group is selected from the group consisting of —($CH_2$)—, —($CH_2$)$_2$—, —C(H)($CH_3$)—, —C($CH_3$)$_2$—, —($CH_2$)$_3$—, —($CH_2$)$_4$—, —($CH_2$)$_5$—, —C(H)($CH_3$)—($CH_2$)—, and —C(H)($C_2H_5$)—($CH_2$)—; and $R^{11}$ and $R^{12}$ each independently represent a linear or branched, saturated or unsaturated, unsubstituted aliphatic group;

an unsubstituted, unsaturated or saturated cycloaliphatic group which optionally has at least one heteroatom as ring member and can be bound via a linear or branched, unsubstituted alkylene, alkenylene or alkinylene group and/or condensed with an unsubstituted mono- or polycyclic ring system, or an unsubstituted aryl or heteroaryl group which can be bound via a linear or branched, unsubstituted alkylene, alkenylene or alkinylene group and/or condensed with an unsubstituted mono- or polycyclic ring system;
wherein the substituents of the above-mentioned aliphatic groups can be independently selected from the group consisting of F, Cl, Br, I, —CN, —NO$_2$, —OH, —SH and —NH$_2$;
or a salt thereof.

2. A compound according to claim 1, wherein said compound is present in the form of an isolated or purified stereoisomer.

3. A compound according to claim 1, wherein said compound is present in the form of a mixture of stereoisomers in any mixing ratio.

4. A compound according to claim 1, wherein said compound is present in the form of a racemic mixture.

5. A compound according to claim 1, wherein
m is 0, 1, 2, 3 or 4,
n is 1,
R$^1$ represents a —C(═O)—R$^9$ group, R$^2$ represents
a linear or branched, saturated or unsaturated, optionally substituted C$_{1-10}$ aliphatic group;
an unsaturated or saturated, optionally substituted 3, 4, 5, 6, 7, 8 or 9-membered cycloaliphatic group which optionally may be condensed with a saturated, unsaturated or aromatic, optionally substituted mono- or polycyclic ring system;
a phenyl group which can be substituted with 1, 2, 3, 4 or 5 substituents independently selected from the group consisting of F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-10}$ alkyl, —C(═O)—OH, —C(═O)—O—C$_{1-5}$ alkyl, —O—C(═O)—C$_{1-5}$ alkyl, —NH—C$_{1-5}$ alkyl, —N(C$_{1-5}$ alkyl)$_2$, —NH—C(═O)—O—C$_{1-5}$ alkyl, —C(═O)—H, —C(═O)—C$_{1-5}$ alkyl, —C(═O)—NH$_2$, —C(═O)—NH—C$_{1-5}$ alkyl, C(═O)—N—(C$_{1-5}$ alkyl)$_2$, —S(═O)$_2$—C$_{1-5}$ alkyl, —S(═O)$_2$ phenyl, —NH—S(═O)$_2$—C$_{1-5}$ alkyl, —NH—S(═O)$_2$—C$_{1-5}$ alkylenephenyl, —NH—S(═O)$_2$—C$_{1-5}$ alkylenenaphthyl, —NH—S(═O)$_2$ phenyl, —NH—S(═O)$_2$ naphthyl, cyclohexyl, cyclopentyl, morpholinyl, piperidinyl, piperazinyl, pyrrolidinyl, pyridinyl, pyridazinyl, —(CH$_2$)-benzo[b]furanyl, —O-phenyl, —O-benzyl, phenyl and benzyl, wherein in each case the cyclic portion of the groups pyridinyl, cyclopentyl, cyclohexyl, morpholinyl, piperidinyl, piperazinyl, pyrrolidinyl, pyridazinyl, —S(═O)$_2$ phenyl, —O-phenyl, —O-benzyl, phenyl, —(CH$_2$)— benzo[b]furanyl, —NH—S(═O)$_2$—C$_{1-5}$ alkylenephenyl, —NH—S(═O)$_2$—C$_{1-5}$ alkylenenaphthyl, —NH—S(═O)$_2$ phenyl, —NH—S(═O)$_2$ naphthyl and benzyl can be substituted with 1, 2, 3, 4 or 5 substituents independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl,
with the proviso that either of the two meta positions and the para position of said phenyl group are not both substituted with substituents which are respectively bound to the phenyl group via an identical atom selected from the group consisting of oxygen, sulfur and nitrogen;
an optionally substituted group selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, 2H-benzo[1.4]oxazin-3(4H)-onyl, (3,4)-dihydroquinolin-2(1H)-onyl, [3,4]-dihydro-2H-1,4-benzoxazinyl and benzothiazolyl, or —(CHR$^{17}$)—X$_q$—(CHR$^{18}$)$_r$—Y$_s$—(CHR$^{19}$)$_t$—Z$_u$—R$^{20}$
wherein q=0 or 1, r=0 or 1, s=0 or 1, t=0 or 1, u=0 or 1, and X, Y and Z each
independently represent O, S, NH, N(CH$_3$), N(C$_2$H$_5$) or N[CH(CH$_3$)$_2$];
R$^3$ represents a halogen group, a nitro group, a hydroxy group, a thiol group; an —O—R$^{11}$ group, an —S—R$^{12}$ group, or a linear or branched, saturated or unsaturated, optionally substituted C$_{1-10}$ aliphatic group;
R$^4$ represents hydrogen;
R$^9$ represents a linear or branched, saturated or unsaturated, optionally substituted C$_{1-10}$ aliphatic group; or
an optionally substituted 5 to 14-membered aryl or heteroaryl group which optionally may be condensed with a saturated, unsaturated, optionally substituted mono- or polycyclic ring system,
R$^{11}$ and R$^{12}$ each independently represent
a linear or branched, saturated or unsaturated C$_{1-10}$ aliphatic group;
an unsaturated or saturated 3, 4, 5, 6, 7, 8 or 9-membered cycloaliphatic group which optionally may be condensed with a saturated, unsaturated or aromatic mono- or polycyclic ring system; or
a 5 to 14-membered aryl or heteroaryl group which optionally may be condensed with a saturated or unsaturated mono- or polycyclic ring system;
R$^{17}$, R$^{18}$, and R$^{19}$ each independently represent hydrogen;
a linear or branched, saturated or unsaturated, optionally substituted C$_{1-10}$ aliphatic group, or an optionally substituted 5 to 14-membered aryl or heteroaryl group which optionally may be condensed with a saturated or unsaturated, optionally substituted mono- or polycyclic ring system; and
R$^{20}$ represents represents
a linear or branched, saturated or unsaturated, optionally substituted C$_{1-10}$ aliphatic group, an unsaturated or saturated, optionally substituted 3, 4, 5, 6, 7, 8 or 9-membered cycloaliphatic group which can be bridged with 1, 2, 3, 4 or 5 linear or branched, optionally substituted C$_{1-5}$ alkylene groups and/or condensed with a saturated, unsaturated or aromatic, optionally substituted mono- or polycyclic ring system; or
an optionally substituted 5 to 14-membered aryl or heteroaryl group which optionally may be condensed with a saturated or unsaturated, optionally substituted mono- or polycyclic ring system;
wherein
the above-mentioned C$_{1-10}$ aliphatic groups and C$_{1-20}$ aliphatic groups can in each case optionally be substituted with 1, 2, 3, 4, 5, 6, 7, 8 or 9 substituents independently selected from the group consisting of F, Cl, Br, I, —CN, —NO$_2$, —OH, —SH and —NH$_2$;
the above-mentioned cycloaliphatic groups can in each case optionally be substituted with 1, 2, 3, 4 or 5 substituents independently selected from the group consisting of oxo (═O), thioxo (═S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—$C_{1-5}$ alkyl, —$C_{1-5}$ alkyl, —C(=O)—OH, —C(=O)—O—$C_{1-5}$ alkyl, —O—C(=O)—$C_{1-5}$ alkyl, —NH—$C_{1-5}$ alkyl, —N($C_{1-5}$ alkyl)$_2$, —NH—C(=O)—O—$C_{1-5}$ alkyl, —C(=O)—H, —C(=O)—$C_{1-5}$ alkyl, —C(=O)—NH$_2$, —C(=O)—NH—$C_{1-5}$ alkyl, C(=O)—N—($C_{1-5}$ alkyl)$_2$, —S(=O)$_2$—$C_{1-5}$ alkyl, —S(=O)$_2$ phenyl, —NH—S(=O)$_2$—$C_{1-5}$ alkyl, —S(=O)$_2$—NH—$C_{1-5}$ alkyl, cyclohexyl, cyclopentyl, pyridinyl, pyridazinyl, —(CH$_2$)-benzo[b]furanyl, —O-phenyl, —O-benzyl, phenyl and benzyl, wherein in each case the cyclic portion of the groups pyridinyl, cyclopentyl, cyclohexyl, pyridazinyl, —S(=O)$_2$ phenyl, —O-phenyl, —O-benzyl, phenyl, —(CH$_2$)-benzo[b]furanyl and benzyl can be substituted with 1, 2, 3, 4 or 5 substituents independently selected from the group consisting of F, Cl, Br, —OH, —CF$_3$, —SF$_5$, —CN, —NO$_2$, —$C_{1-5}$ alkyl, —O—$C_{1-5}$ alkyl, —O—CF$_3$, —S—CF$_3$, phenyl and —O-benzyl, the above-mentioned cycloaliphatic groups can in each case optionally have 1, 2, 3, 4 or 5 heteroatom(s) independently selected from the group consisting of oxygen, nitrogen and sulfur as ring member(s);

the rings of the above-mentioned mono- or polycyclic ring systems can optionally be substituted in each case with 1, 2, 3, 4 or 5 substituents independently selected from the group consisting of oxo (=O), thioxo (=S), F, Cl, Br, I, —CN, —CF$_3$, —SF$_5$, —OH, —O—$C_{1-5}$ alkyl, —NH$_2$, —NO$_2$, —O—CF$_3$, —S—CF$_3$, —SH, —S—$C_{1-5}$ alkyl, —$C_{1-5}$ alkyl, —C(=O)—OH, —C(=O)—O—$C_{1-5}$ alkyl, —O—C(=O)—$C_{1-5}$ alkyl, —NH—$C_{1-5}$ alkyl, —N($C_{1-5}$ alkyl)$_2$, —NH—C(=O)—O—$C_{1-5}$ alkyl, —C(=O)—H, —C(=O)—$C_{1-5}$ alkyl, —C(=O)—NH$_2$, —C(=O)—NH—$C_{1-5}$ alkyl, C(=O)—N—($C_{1-5}$ alkyl)$_2$, —S(=O)$_2$—$C_{1-5}$ alkyl, —S(=O)$_2$ phenyl, —NH—S(=O)$_2$—$C_{1-5}$ alkyl, —S(=O)$_2$—NH—$C_{1-5}$ alkyl, cyclohexyl, cyclopentyl, morpholinyl, piperidinyl, pyrrolidinyl, piperazinyl, pyridinyl, pyridazinyl, —(CH$_2$)-benzo[b]furanyl, —O-phenyl, —O-benzyl, phenyl and benzyl, wherein in each case the cyclic portion of the groups pyridinyl, cyclopentyl, cyclohexyl, morpholinyl, piperidinyl, pyrrolidinyl, piperazinyl, pyridazinyl, —S(=O)$_2$ phenyl, —O-phenyl, —O-benzyl, phenyl, —(CH$_2$)— benzo[b]furanyl and benzyl can be substituted with 1, 2, 3, 4 or 5 substituents independently selected from the group consisting of F, Cl, Br, —OH, —CF$_3$, —SF$_5$, —CN, —NO$_2$, —$C_{1-5}$ alkyl, —O—$C_{1-5}$ alkyl, —O—CF$_3$, —S—CF$_3$, phenyl and —O-benzyl, the rings of the above-mentioned mono- or polycyclic ring systems each have 5, 6 or 7 members and can in each case optionally have 1, 2, 3, 4 or 5 heteroatom(s) as ring member(s) independently selected from the group consisting of oxygen, nitrogen and sulfur;

unless otherwise indicated, the above-mentioned groups selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, 2H-benzo[1.4]oxazin-3(4H)-onyl, (3,4)-dihydroquinolin-2(1H)-onyl, [3,4]-dihydro-2H-1,4-benzoxazinyl and benzothiazolyl and also aryl or heteroaryl groups can in each case optionally be substituted with 1, 2, 3, 4 or 5 substituents independently selected from the group consisting of F, Cl, Br, I, —CN, —CF$_3$, —SF$_5$, —OH, —O—$C_{1-5}$ alkyl, —NH$_2$, —NO$_2$, —O—CF$_3$, —S—CF$_3$, —SH, —S—$C_{1-5}$ alkyl, —$C_{1-10}$ alkyl, —C(=O)—OH, —C(=O)—O—$C_{1-5}$ alkyl, —O—C(=O)—$C_{1-5}$ alkyl, —NH—$C_{1-5}$ alkyl, —N($C_{1-5}$ alkyl)$_2$, —NH—C(=O)—O—$C_{1-5}$ alkyl, —C(=O)—H, —C(=O)—$C_{1-5}$ alkyl, —C(=O)—NH$_2$, —C(=O)—NH—$C_{1-5}$ alkyl, C(=O)—N—($C_{1-5}$ alkyl)$_2$, —S(=O)$_2$—$C_{1-5}$ alkyl, —S(=O)$_2$ phenyl, —NH—S(=O)$_2$—$C_{1-5}$ alkyl, —NH—S(=O)$_2$—$C_{1-5}$ alkylenephenyl, —NH—S(=O)$_2$—$C_{1-5}$ alkylenenaphthyl, —NH—S(=O)$_2$ phenyl, —NH—S(=O)$_2$ naphthyl, cyclohexyl, cyclopentyl, morpholinyl, piperidinyl, piperazinyl, pyrrolidinyl, pyridinyl, pyridazinyl, —(CH$_2$)-benzo[b]furanyl, —O-phenyl, —O-benzyl, phenyl and benzyl, wherein in each case the cyclic portion of the groups pyridinyl, cyclopentyl, cyclohexyl, morpholinyl, piperidinyl, piperazinyl, pyrrolidinyl, pyridazinyl, —S(=O)$_2$ phenyl, —O-phenyl, —O-benzyl, phenyl, —(CH$_2$)—benzo[b]furanyl, —NH—S(=O)$_2$—$C_{1-5}$ alkylenephenyl, —NH—S(=O)$_2$—$C_{1-5}$ alkylenenaphthyl, —NH—S(=O)$_2$ phenyl, —NH—S(=O)$_2$ naphthyl and benzyl can be substituted with 1, 2, 3, 4 or 5 substituents independently selected from the group consisting of F, Cl, Br, —OH, —CF$_3$, —SF$_5$, —CN, —NO$_2$, —$C_{1-5}$ alkyl, —O—$C_{1-5}$ alkyl, —O—CF$_3$, —S—CF$_3$, phenyl and —O-benzyl, the above-mentioned heteroaryl groups can in each case optionally have 1, 2, 3, 4 or 5 heteroatom(s) independently selected from the group consisting of oxygen, nitrogen and sulfur as ring member(s); and the above-mentioned $C_{1-5}$ alkylene groups can in each case optionally be substituted with 1, 2, 3, 4 or 5 substituents independently selected from the group consisting of F, Cl, Br, —OH, —SH, —NH$_2$, —CN and NO$_2$.

6. A compound according to claim 5, wherein $R^2$ represents a group selected from the group consisting of methyl, ethyl, n-propyl, isopropyl, n-butyl, sec-butyl, isobutyl, tert-butyl, n-pentyl, sec-pentyl, n-hexyl and n-heptyl, wherein the group can in each case optionally be substituted with 1, 2, 3, 4 or 5 substituents independently selected from the group consisting of F, Cl, Br, I, —CN, —NO$_2$, —OH, —SH and —NH$_2$;

a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, indanyl and indenyl, wherein the group can in each case optionally be substituted with 1, 2, 3, 4 or 5 substituents independently selected from the group consisting of oxo (=O), thioxo (=S), F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—

$CH_3$, $-NH-C(=O)-O-C_2H_5$, $-NH-C(=O)-O-C(CH_3)_3$, $-C(=O)-H_5$, $-C(=O)-CH_3$, $-C(=O)-C_2H_5$, $-C(=O)-C(CH_3)_3$, $-C(=O)-NH_2$, $-C(=O)-NH-CH_3$, $-C(=O)-NH-C_2H_5$, $-C(=O)-N-(CH_3)_2$, $-C(=O)-N-(C_2H_5)_2$, $-S(=O)_2-CH_3$, $-S(=O)_2-C_2H_5$, $-S(=O)_2$ phenyl, $-NH-S(=O)_2-CH_3$, $-NH-S(=O)_2-C_2H_5$, $-S(=O)_2-NH-CH_3$, $-S(=O)_2-NH-C_2H_5$, cyclohexyl, cyclopentyl, pyridinyl, pyridazinyl, $-(CH_2)-$ benzo[b]furanyl, $-O$-phenyl, $-O$-benzyl, phenyl and benzyl, wherein in each case the cyclic portion of the groups pyridinyl, cyclopentyl, cyclohexyl, pyridazinyl, $-S(=O)_2$ phenyl, $-O$-phenyl, $-O$-benzyl, phenyl, $-(CH_2)$-benzo[b]furanyl and benzyl can be substituted with 1, 2, 3, 4 or 5 substituents independently selected from the group consisting of F, Cl, Br, $-OH$, $-CF_3$, $-SF_5$, $-CN$, $-NO_2$, methyl, ethyl, n-propyl, isopropyl, n-butyl, sec-butyl, isobutyl, tert-butyl, $-O-CH_3$, $-O-C_2H_5$, $-O-CF_3$, $-S-CF_3$, phenyl and $-O$-benzyl;

a group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, [3,4]-dihydro-2H-1,4-benzoxazinyl and benzothiazolyl, wherein the group can in each case optionally be substituted with 1, 2, 3, 4 or 5 substituents independently selected from the group consisting of F, Cl, Br, I, $-CN$, $-CF_3$, $-SF_5$, $-OH$, $-O-CH_3$, $-O-C_2H_5$, $-NH_2$, $-NO_2$, $-O-CF_3$, $-S-CF_3$, $-SH$, $-S-CH_3$, $-S-C_2H_5$, methyl, ethyl, n-propyl, isopropyl, n-butyl, sec-butyl, isobutyl, tert-butyl, $-C(=O)-OH$, $-C(=O)-O-CH_3$, $-C(=O)-O-C_2H_5$, $-C(=O)-O-C(CH_3)_3$, $-O-C(=O)-CH_3$, $-O-C(=O)-C_2H_5$, $-O-C(=O)-C(CH_3)_3$, $-N(CH_3)_2$, $-N(C_2H_5)_2$, $-NH-CH_3$, $-NH-C_2H_5$, $-NH-C(=O)-O-CH_3$, $-NH-C(=O)-O-C_2H_5$, $-NH-C(=O)-O-C(CH_3)_3$, $-C(=O)-H$, $-C(=O)-CH_3$, $-C(=O)-C_2H_5$, $-C(=O)-C(CH_3)_3$, $-C(=O)-NH_2$, $-C(=O)-NH-CH_3$, $-C(=O)-NH-C_2H_5$, $-C(=O)-N-(CH_3)_2$, $-C(=O)-N-(C_2H_5)_2$, $-S(=O)_2-CH_3$, $-S(=O)_2-C_2H_5$, $-S(=O)_2$ phenyl, $-NH-S(=O)_2-CH_3$, $-NH-S(=O)_2-C_2H_5$, $-NH-S(=O)_2$ phenyl, $-S(=O)_2-NH-CH_3$, $-S(=O)_2-NH-C_2H_5$, cyclohexyl, cyclopentyl, pyridinyl, pyridazinyl, $-(CH_2)$-benzo[b]furanyl, $-O$-phenyl, $-O$-benzyl, phenyl and benzyl, wherein in each case the cyclic portion of the groups pyridinyl, cyclopentyl, cyclohexyl, pyridazinyl, $-S(=O)_2$ phenyl, $-NH-S(=O)_2$ phenyl, $-O$-phenyl, $-O$-benzyl, phenyl, $-(CH_2)$-benzo[b]furanyl and benzyl can be substituted with 1, 2, 3, 4 or 5 substituents independently selected from the group consisting of F, Cl, Br, $-OH$, $-CF_3$, $-SF_5$, $-CN$, $-NO_2$, methyl, ethyl, n-propyl, isopropyl, n-butyl, sec-butyl, isobutyl, tert-butyl, $-O-CH_3$, $-O-C_2H_5$, $-O-CF_3$, $-S-CF_3$, phenyl and $-O$-benzyl;

with the proviso that either of the two meta positions and the para position of said phenyl group are not both substituted with substituents which are respectively bound to the phenyl group via an identical atom selected from the group consisting of oxygen, sulfur and nitrogen; or $-(CHR^{17})-R^{20}$, $-(CHR^{17})-(CHR^{18})-R^{20}$ or $-(CHR^{17})-(CHR^{18})-(CHR^{19})-R^{20}$.

7. A compound according to claim 5, wherein $R^2$ represents a group selected from the group consisting of methyl, ethyl, n-propyl, isopropyl, n-butyl, sec-butyl, isobutyl, tert-butyl, n-pentyl, sec-pentyl, n-hexyl and n-heptyl, wherein the group can in each case optionally be substituted with 1, 2, 3, 4 or 5 substituents independently selected from the group consisting of F, Cl, Br, I, $-CN$, $-NO_2$, $-OH$, $-SH$ and $-NH_2$;

a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, indanyl and indenyl, wherein the group can in each case optionally be substituted with 1, 2, 3, 4 or 5 substituents independently selected from the group consisting of oxo (=O), thioxo (=S), F, Cl, Br, I, $-CN$, $-CF_3$, $-SF_5$, $-OH$, $-O-CH_3$, $-O-C_2H_5$, $-NH_2$, $-NO_2$, $-O-CF_3$, $-S-CF_3$, $-SH$, $-S-CH_3$, $-S-C_2H_5$, methyl, ethyl, n-propyl, isopropyl, n-butyl, sec-butyl, isobutyl, tert-butyl, $-O(=O)-OH$, $-O(=O)-O-CH_3$, $-O(=O)-O-C_2H_5$, $-O(=O)-O-C(CH_3)_3$, $-O-C(=O)-CH_3$, $-O-C(=O)-C_2H_5$, $-O-C(=O)-C(CH_3)_3$, $-N(CH_3)_2$, $-N(C_2H_5)_2$, $-NH-CH_3$, $-NH-C_2H_5$, $-NH-C(=O)-O-CH_3$, $-NH-C(=O)-O-C_2H_5$, $-NH-C(=O)-O-C(CH_3)_3$, $-C(=O)-H$, $-C(=O)-CH_3$, $-C(=O)-C_2H_5$, $-C(=O)-C(CH_3)_3$, $-C(=O)-NH_2$, $-C(=O)-NH-CH_3$, $-C(=O)-NH-C_2H_5$, $-C(=O)-N-(CH_3)_2$, $-C(=O)-N-(C_2H_5)_2$, $-S(=O)_2-CH_3$ and $-S(=O)_2-C_2H_5$;

a phenyl group corresponding to formula XX

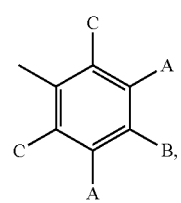

XX wherein the line represents the bond of this phenyl group to the spiro compound of formula I; and A, B and C each represent H or a substituent independently selected from the group consisting of F, Cl, Br, I, $-CN$, $-CF_3$, $-SF_5$, $-OH$, $-O-CH_3$, $-O-C_2H_5$, $-NH_2$, $-NO_2$, $-O-CF_3$, $-S-CF_3$, $-SH$, $-S-CH_3$, $-S-C_2H_5$, methyl, ethyl, n-propyl, isopropyl, n-butyl, sec-butyl, isobutyl, tert-butyl, cyclohexyl, cyclopentyl, $-C(=O)-OH$, $-C(=O)-O-CH_3$, $-C(=O)-O-C_2H_5$, $-C(=O)-O-C(CH_3)_3$, $-O-C(=O)-CH_3$, $-O-C(=O)-C_2H_5$, $-O-C(=O)-C(CH_3)_3$, $-N(CH_3)_2$, $-N(C_2H_5)_2$, $-NH-CH_3$, $-NH-C_2H_5$, $-NH-C(=O)-O-CH_3$, $-NH-C(=O)-O-C_2H_5$, $-NH-C(=O)-O-C(CH_3)_3$, $-C(=O)-H$, $-C(=O)-CH_3$, $-C(=O)-C_2H_5$, $-C(=O)-C(CH_3)_3$, $-C(=O)-NH_2$, $-C(=O)-NH-CH_3$, —C(=O)—NH—C$_2$H$_5$, —C(=O)—N—(CH$_3$)$_2$, —C(=O)—N—(C$_2$H$_5$)$_2$, —S(~0)$_2$—CH$_3$, —S(~0)$_2$—C$_2$H$_5$, —S(~0)$_2$ phenyl, —NH—S(~0)$_2$—CH$_3$, —NH—S(=O)$_2$—C$_2$H$_5$, —S(=O)$_2$—NH—CH$_3$, —S(=O)$_2$—NH—C$_2$H$_5$ and —NH—S(=O)$_2$ phenyl;

with the proviso that either of the two positions A and position B of formula XX are not both substituted with substituents which are respectively bound to the phenyl group via an identical atom selected from the group consisting of oxygen, sulfur and nitrogen;

a group selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, 2H-benzo[1,4]oxazin-3(4H)-onyl, (3,4)-dihydroquinolin-2(1H)-onyl, [3,4]-dihydro-2H-1,4-benzoxazinyl and benzothiazolyl, wherein the group can in each case optionally be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —O(=O)—O—CH$_3$, —O(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(~0)—N—(C$_2$H$_5$)$_2$, —S(~0)$_2$—CH$_3$, —S(~0)$_2$—C$_2$H$_5$, —S(~0)$_2$ phenyl, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$, cyclohexyl, cyclopentyl, pyridinyl, pyridazinyl, —(CH$_2$)-benzo[b]furanyl, —O-phenyl, —O-benzyl, phenyl and benzyl, wherein in each case the cyclic portion of the groups pyridinyl, cyclopentyl, cyclohexyl, pyridazinyl, —S(=O)$_2$ phenyl, —O-phenyl, —O-benzyl, phenyl, —(CH$_2$)—benzo[b]furanyl and benzyl can be substituted with 1, 2, 3, 4 or 5 substituents independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl; or —(CHR$^{17}$)—R$^{20}$, —(CHR$^{17}$)—(CHR$^{18}$)—R$^{20}$ or —(CHR$^{17}$)—(CHR$^{18}$)—(CHR$^{19}$)—R$^{20}$.

8. A compound according to claim 1, wherein R$^3$ represents a group selected from the group consisting of methyl, ethyl, n-propyl, isopropyl, n-butyl, sec-butyl, isobutyl, tert-butyl, n-pentyl, sec-pentyl, n-hexyl and n-heptyl, wherein the group can in each case optionally be substituted with 1, 2, 3, 4 or 5 substituents independently selected from the group consisting of F, Cl, Br, I, —CN, —NO$_2$, —OH, —SH and —NH$_2$.

9. A compound according to claim 1, wherein R$^9$ represents a group selected from the group consisting of methyl, ethyl, n-propyl, isopropyl, n-butyl, sec-butyl, isobutyl, tert-butyl, n-pentyl, n-hexyl, n-heptyl, vinyl, 1-propenyl, 2-propenyl, 1-butenyl, 2-butenyl, 3-butenyl, 2-methyl-1-propenyl, ethinyl, 1-propinyl, 2-propinyl, 1-butinyl, 2-butinyl and 3-butinyl, wherein the group can in each case optionally be substituted with 1, 2, 3, 4 or 5 substituents independently selected from the group consisting of F, Cl, Br, I, —CN, —NO$_2$, —OH, —SH and —NH$_2$; or a group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl and benzothiazolyl, wherein the group can in each case optionally be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, n-pentyl, n-hexyl, n-heptyl, n-octyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$ phenyl, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$, cyclohexyl, cyclopentyl, morpholinyl, piperidinyl, piperazinyl, pyrrolidinyl, pyridinyl, pyridazinyl, —(CH$_2$)— benzo[b]furanyl, —O-phenyl, —O-benzyl, phenyl and benzyl, wherein in each case the cyclic portion of the groups pyridinyl, cyclopentyl, cyclohexyl, pyridazinyl, —S(=O)$_2$ phenyl, —O-phenyl, —O-benzyl, phenyl, —(CH$_2$)-benzo[b]furanyl and benzyl can be substituted with 1, 2, 3, 4 or 5 substituents independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl.

10. A compound according to claim 1, wherein R$^{11}$ and R$^{12}$ each independently represent a group selected from the group consisting of methyl, ethyl, n-propyl, isopropyl, n-butyl, sec-butyl, isobutyl, tert-butyl, n-pentyl, sec-pentyl, n-hexyl and n-heptyl;

a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl; or a group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, 11. A compound according to claim 5, wherein $R^{17}$, $R^{18}$, and $R^{19}$ each independently represent hydrogen;

a group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl, 3-butenyl, ethinyl, 1-propinyl, 2-propinyl, 1-butinyl, 2-butinyl and 3-butinyl; or a phenyl group which can be substituted with 1, 2, 3, 4 or 5 substituents independently selected from the group consisting of F, Cl, Br, I, —CN, —CF$_3$, —O—CH$_3$, —O—C$_2$H$_5$, —NO$_2$, —O—CF$_3$, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —C(=O)—CH$_3$, —C(=O)—C$_2$H$_5$, —C(=O)—C(CH$_3$)$_3$, cyclohexyl, cyclopentyl, —O-phenyl, —O-benzyl and phenyl.

12. A compound according to claim 5, wherein $R^{20}$ represents a group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$);

a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, indanyl, indenyl, (1,4)-benzodioxanyl, (1,2,3,4)-tetrahydronaphthyl, (1,2,3,4)-tetrahydroquinolinyl and (1,2,3,4)-tetrahydroquinazolinyl, wherein the group can in each case optionally be substituted with 1, 2, 3, 4 or 5 substituents independently selected from the group consisting of oxo (=O), thioxo (=S), F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$ phenyl, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$, cyclohexyl, cyclopentyl, pyridinyl, pyridazinyl, —(CH$_2$)-benzo[b]furanyl, —O-phenyl, —O-benzyl, phenyl and benzyl, wherein in each case the cyclic portion of the groups pyridinyl, cyclopentyl, cyclohexyl, pyridazinyl, —S(=O)$_2$ phenyl, —O-phenyl, —O-benzyl, phenyl, —(CH$_2$)-benzo[b]furanyl and benzyl can be substituted with 1, 2, 3, 4 or 5 substituents independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl; or a group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl and benzothiazolyl, wherein the group can in each case optionally be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, n-pentyl, n-hexyl, n-heptyl, n-octyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)—C(CH$_3$)$_3$, —N(CH$_3$)$_2$, —N(C$_2$H$_5$)$_2$, —NH—CH$_3$, —NH—C$_2$H$_5$, —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—C(CH$_3$)$_3$, —C(=O)—NH$_2$, —C(=O)—NH—CH$_3$, —C(=O)—NH—C$_2$H$_5$, —C(=O)—N—(CH$_3$)$_2$, —C(=O)—N—(C$_2$H$_5$)$_2$, —S(=O)$_2$—CH$_3$, —S(=O)$_2$—C$_2$H$_5$, —S(=O)$_2$ phenyl, —NH—S(=O)$_2$—CH$_3$, —NH—S(=O)$_2$—C$_2$H$_5$, —S(=O)$_2$—NH—CH$_3$, —S(=O)$_2$—NH—C$_2$H$_5$, cyclohexyl, cyclopentyl, morpholinyl, piperidinyl, piperazinyl, pyrrolidinyl, pyridinyl, pyridazinyl, —(CH$_2$)— benzo[b]furanyl, —O-phenyl, —O-benzyl, phenyl and benzyl, wherein in each case the cyclic portion of the groups pyridinyl, cyclopentyl, cyclohexyl, morpholinyl, piperidinyl, piperazinyl, pyrrolidinyl, pyridazinyl, —S(=O)$_2$ phenyl, —O-phenyl, —O-benzyl, phenyl, —(CH$_2$)— benzo[b]furanyl and benzyl can be substituted with 1, 2, 3, 4 or 5 substituents independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CF$_3$, —S—CF$_3$, phenyl and —O-benzyl.

13. A compound according claim 1, wherein m is 0, 1 or 2.

14. A compound according to claim 5, wherein m is 0, 1, 2, 3 or 4;

n is 1;

$R^1$ represents a —C(=O)—$R^9$ group;

$R^2$ represents a group selected from the group consisting of methyl, ethyl, n-propyl, isopropyl, n-butyl, sec-butyl, isobutyl, tert-butyl, n-pentyl, sec-pentyl, n-hexyl and n-heptyl;

a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl and thiomorpholinyl;

a phenyl group which can be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, cyclopentyl, cyclohexyl, —S(=O)$_2$—CH$_3$, —S(=O)$_2$—C$_2$H$_5$, —NH—S(=O)$_2$—CH$_3$, —NH—S(=O)$_2$—C$_2$H$_5$, —NH—S(=O)$_2$ phenyl, —S(=O)$_2$—NH—CH$_3$ and —S(=O)$_2$—NH—C$_2$H$_5$;

with the proviso that either one of the two meta positions and the para position of said phenyl group are not both substituted with substituents which are respectively bound to the phenyl group via an identical atom selected from the group consisting of oxygen, sulfur and nitrogen;

a group selected from the group consisting of naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl, [1,2,3,4]-tetrahydronaphthyl, [1,2,3,4]-tetrahydroquinolinyl, [1,2,3,4]-tetrahydroisoquinolinyl, 2H-benzo[1,4]oxazin-3(4H)-onyl, (3,4)-dihydroquinolin-2(1H)-onyl, [1,2,3,4]-tetrahydroquinazolinyl, [3,4]-dihydro-2H-1,4-benzoxazinyl and benzothiazolyl, wherein the group can in each case optionally be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, —S(=O)$_2$—CH$_3$, —S(=O)$_2$—C$_2$H$_5$, —NH—S(=O)$_2$—CH$_3$, —NH—S(=O)$_2$—C$_2$H$_5$, —S(=O)$_2$—NH—CH$_3$ and —S(=O)$_2$—NH—C$_2$H$_5$; or —(CHR$^{17}$)—R$^{20}$, —(CHR$^{17}$)—(CHR$^{18}$)—R$^{20}$ or —(CHR$^{17}$)—(CHR$^{18}$)—(CHR$^{19}$)—R$^{20}$;

R$^3$ represents a group selected from the group consisting of methyl, ethyl, n-propyl, isopropyl, n-butyl, sec-butyl, isobutyl, tert-butyl, n-pentyl, sec-pentyl, n-hexyl and n-heptyl;

R$^4$ represents hydrogen;

R$^9$ represents a group selected from the group consisting of phenyl, naphthyl, (1,3)-benzodioxolyl, (1,4)-benzodioxanyl, thiophenyl, furanyl, pyrrolyl, pyrazolyl, pyranyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinoxalinyl, quinolinyl, isoquinolinyl, benzimidazolyl, benzoxazolyl, benzotriazolyl, benzisoxazolyl and benzothiazolyl, wherein the group can in each case optionally be substituted with 1, 2, 3, 4 or 5 substituents independently selected from the group consisting of F, Cl, Br, I, —CN, —CF$_3$, —O—CF$_3$, —S—CF$_3$, —SF$_5$, —OH, —O—CH$_3$, —O—C$_2$H$_5$, —NH—S(=O)$_2$—CH$_3$, morpholinyl, piperidinyl, pyrrolidinyl, piperazinyl, phenyl, methyl, ethyl, n-propyl, isopropyl, n-butyl, sec-butyl, isobutyl, tert-butyl, n-pentyl, n-hexyl, n-heptyl and n-octyl; R$^{17}$, R$^{18}$, and R$^{19}$ each independently represent hydrogen;

a group selected from the group consisting of methyl, ethyl, n-propyl, isopropyl, n-butyl, sec-butyl, isobutyl and tert-butyl; or a phenyl group which can be substituted with 1, 2, 3, 4 or 5 substituents independently selected from the group consisting of F, Cl, Br, I, —CN, —CF$_3$, —O—CH$_3$, —O—C$_2$H$_5$, —NO$_2$, —O—CF$_3$, methyl, ethyl, n-propyl, isopropyl, n-butyl, sec-butyl, isobutyl and tert-butyl; and R$^{20}$ represents an aryl group selected from the group consisting of phenyl and naphthyl, wherein said aryl group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, methyl, ethyl, n-propyl, isopropyl, n-butyl, sec-butyl, isobutyl, tert-butyl, n-pentyl, n-hexyl, n-heptyl and n-octyl.

15. A compound according to claim 5, wherein m is 0, 1 or 2;

n is 1;

R$^1$ represents a —C(=O)—R$^9$ group; R$^2$ represents a group selected from the group consisting of methyl, ethyl, n-propyl, isopropyl, n-butyl, sec-butyl, isobutyl, tert-butyl, n-pentyl, sec-pentyl, n-hexyl and n-heptyl;

a phenyl group corresponding to formula XX

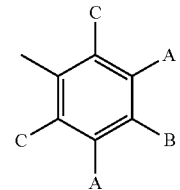

XX wherein the line represents the bond of this phenyl group to the spiro compound of formula I;

A and B each represent a substituent independently selected from the group consisting of H, F, Cl, Br, I, —CF$_3$, —SF$_5$, —OH, —O—CH$_3$, —O—C$_2$H$_5$, —O—CF$_3$, —S—CF$_3$, methyl, ethyl, n-propyl, isopropyl, n-butyl, sec-butyl, isobutyl, tert-butyl, cyclopentyl, cyclohexyl, —NH—S(=O)$_2$—CH$_3$ and —NH—S(=O)$_2$ phenyl;

with the proviso that either of the two positions A and position B of formula XX are not both substituted with substituents which are respectively bound to the phenyl group via an identical atom selected from the group consisting of oxygen, sulfur and nitrogen;

C represents H;

a group selected from the group consisting of naphthyl, quinolinyl, (1,4)-benzodioxanyl, (1,3)-benzodioxolyl, pyridinyl, thiazolyl and oxazolyl, wherein the group can in each case optionally be substituted with 1, 2, 3, 4 or 5 substituents independently selected from the group consisting of F, Cl, Br, I, —O—CH$_3$, —O—C$_2$H$_5$, methyl, ethyl, n-propyl, isopropyl, n-butyl, sec-butyl, isobutyl, tert-butyl, —S(=O)$_2$—CH$_3$, —S(=O)$_2$—C$_2$H$_5$, —NH—S(=O)$_2$—CH$_3$, —NH—S(=O)$_2$—C$_2$H$_5$, —S(=O)$_2$—NH—CH$_3$ and —S(=O)$_2$—NH—C$_2$H$_5$; or —(CHR$^{17}$)—R$^{20}$, —(CHR$^{17}$)—(CHR$^{18}$)—R$^{20}$ or —(CHR$^{17}$)—(CHR$^{18}$)—(CHR$^{19}$)—R$^{20}$;

R$^3$ represents a group selected from the group consisting of methyl, ethyl, n-propyl, isopropyl, n-butyl, sec-butyl, isobutyl, tert-butyl and n-pentyl;

R⁴ represents hydrogen;
R⁹ represents
a group selected from the group consisting of phenyl, pyridinyl and naphthyl, wherein the group can in each case optionally be substituted with 1, 2, 3, 4 or 5 substituents independently selected from the group consisting of F, Cl, Br, I, —CF₃, —O—CF₃, —S—CF₃, —OH, —O—CH₃, —O—C₂H₅, —NH—S(=O)₂—CH₃, morpholinyl, piperidinyl, pyrrolidinyl, piperazinyl, phenyl, methyl, ethyl, n-propyl, isopropyl, n-butyl, sec-butyl, isobutyl, tert-butyl, n-pentyl, n-hexyl, n-heptyl and n-octyl; R¹⁷, R¹⁸, and R¹⁹ each independently represent hydrogen;
a group selected from the group consisting of methyl, ethyl, n-propyl, isopropyl, n-butyl, sec-butyl, isobutyl and tert-butyl; or
a phenyl group; and
R²⁰ represents a phenyl group.

16. A compound according to claim 5, wherein
m is 0, 1 or 2;
n is 1;
R¹ represents a —C(=O)—R⁹ group; R² represents a tert-butyl group;
a group selected from the group consisting of phenyl, 2-methanesulfonamidephenyl, 2-ethanesulfonamidephenyl, 2-trifluoromethylphenyl, 2-trifluoromethylsulfanylphenyl, 2-ethylphenyl, 2-tert-butylphenyl, 2-ethylaminosulfonylphenyl, 2-methylaminosulfonylphenyl, 2-bromophenyl, 2-chlorophenyl, 2-fluorophenyl, 2-methylphenyl, 2-trifluoromethoxyphenyl, 2-methoxyphenyl, 2-ethoxyphenyl, 2-propylphenyl, 2-iodophenyl, 3-chlorophenyl, 3-methylphenyl, 3-tert-butylphenyl, 3-trifluoromethylsulfanylphenyl, 3-trifluoromethylphenyl, 3-methanesulfonamidephenyl, 3-ethanesulfonamidephenyl, 3-fluorophenyl, 3-propylphenyl, 3-isopropylphenyl, 3-bromophenyl, 3-methoxyphenyl, 3-ethylphenyl, 3-ethylaminosulfonylphenyl, 3-methylaminosulfonylphenyl, 3-ethoxyphenyl, 3-trifluoromethoxyphenyl, 3-iodophenyl, 4-methylaminosulfonylphenyl, 4-ethylaminosulfonylphenyl, 4-methanesulfonamidephenyl, 4-ethanesulfonamidephenyl, 4-bromophenyl, 4-methoxyphenyl, 4-chlorophenyl, 4-fluorophenyl, 4-tert-butylphenyl, 4-trifluoromethylsulfanylphenyl, 4-methylphenyl, 4-isopropylphenyl, 4-trifluoromethylphenyl, 4-propylphenyl, 4-iodophenyl, 4-trifluoromethoxyphenyl, 4-ethylphenyl, 4-ethoxyphenyl, 2-fluoro-3-trifluoromethylphenyl, (2,3)-difluorophenyl, (2,3)-dimethylphenyl, (2,3)-dichlorophenyl, 3-fluoro-2-trifluoromethylphenyl, (2,4)-dichlorophenyl, (2,4)-difluorophenyl, 4-fluoro-2-trifluoromethylphenyl, (2,4)-dimethoxyphenyl, 2-chloro-4-fluorophenyl, (2,4)-dibromophenyl, 2-fluoro-4-trifluoromethylphenyl, (2,5)-difluorophenyl, 2-fluoro-5-trifluoromethylphenyl, 5-fluoro-2-trifluoromethylphenyl, 5-chloro-2-trifluoromethylphenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-fluoro-6-trifluoromethylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl, (2,6)-dibromophenyl, (2,6)-dichlorophenyl, 3-chloro-2-fluorophenyl, (3,4)-dichlorophenyl, 4-fluoro-3-trifluoromethylphenyl, 3-fluoro-4-trifluoromethylphenyl, (3,4)-difluorophenyl, 4-chloro-3-trifluoromethyl, 4-bromo-3-methylphenyl, 4-bromo-5-methylphenyl, 3-chloro-4-fluorophenyl, (3,4)-dibromophenyl, 4-chloro-3-methylphenyl, 4-bromo-3-methylphenyl, 4-fluoro-3-methylphenyl, (3,5)-dimethoxyphenyl, (3,5)-bis-trifluoromethylphenyl, (3,5)-difluorophenyl, (3,5)-dichlorophenyl, 3-fluoro-5-trifluoromethylphenyl, 5-fluoro-3-trifluoromethylphenyl, (3,5)-dibromophenyl, 5-chloro-4-fluorophenyl, 5-bromo-4-methylphenyl, (2,3,4)-trifluorophenyl, (2,3,4)-trichlorophenyl, (2,3,6)-trifluorophenyl, 5-chloro-2-methoxyphenyl, (2,3)-difluoro-4-methylphenyl, (2,4,5)-trifluorophenyl, (2,4,5)-trichlorophenyl, (2,4)-dichloro-5-fluorophenyl, (2,4,6)-trichlorophenyl, (2,4,6)-trimethylphenyl, (2,4,6)-trifluorophenyl, (2,4,6)-trimethoxyphenyl, (2,3,4,5)-tetrafluorophenyl, 4-methoxy-2,3,6-trimethylphenyl, 4-methoxy-2,3,6-trimethylphenyl, 4-chloro-2,5-dimethylphenyl, 2-chloro-6-fluoro-3-methylphenyl, 6-chloro-2-fluoro-3-methyl, (2,3,4,5,6)-pentafluorophenyl, 3-fluoro-4-methylsulfonamidophenyl, 3-chloro-4-methylsulfonamidophenyl, 3-bromo-4-methylsulfonamidophenyl, 3-methoxy-4-methylsulfonamidophenyl, 3-hydroxy-4-methylsulfonamidophenyl, 3-trifluoromethyl-4-methylsulfonamidophenyl, 3-trifluoromethoxy-4-methylsulfonamidophenyl, 3-methyl-4-methylsulfonamidophenyl, 3-ethyl-4-methylsulfonamidophenyl, 3-isopropyl-4-methylsulfonamidophenyl, 3-propyl-4-methylsulfonamidophenyl, 3-tert-butyl-4-methylsulfonamidophenyl, 3-fluoro-4-phenylsulfonamidophenyl, 3-chloro-4-phenylsulfonamidophenyl, 3-bromo-4-phenylsulfonamidophenyl, 3-methoxy-4-phenylsulfonamidophenyl, 3-hydroxy-4-phenylsulfonamidophenyl, 3-trifluoromethyl-4-phenylsulfonamidophenyl, 3-trifluoromethoxy-4-phenylsulfonamidophenyl, 3-methyl-4-phenylsulfonamidophenyl, 3-ethyl-4-phenylsulfonamidophenyl, 3-isopropyl-4-phenylsulfonamidophenyl, 3-propyl-4-phenylsulfonamidophenyl, 3-tert-butyl-4-phenylsulfonamidophenyl, 4-fluoro-3-methylsulfonamidophenyl, 4-chloro-3-methylsulfonamidophenyl, 4-bromo-3-methylsulfonamidophenyl, 4-methoxy-3-methylsulfonamidophenyl, 4-hydroxy-3-methylsulfonamidophenyl, 4-trifluoromethyl-3-methylsulfonamidophenyl, 4-trifluoromethoxy-3-methylsulfonamidophenyl, 4-methyl-3-methylsulfonamidophenyl, 4-ethyl-3-methylsulfonamidophenyl, 4-isopropyl-3-methylsulfonamidophenyl, 4-propyl-3-methylsulfonamidophenyl, 4-tert-butyl-3-methylsulfonamidophenyl, 4-fluoro-3-phenylsulfonamidophenyl, 4-chloro-3-phenylsulfonamidophenyl, 4-bromo-3-phenylsulfonamidophenyl, 4-methoxy-3-phenylsulfonamidophenyl, 4-hydroxy-3-phenylsulfonamidophenyl, 4-trifluoromethyl-3-phenylsulfonamidophenyl, 4-trifluoromethoxy-3-phenylsulfonamidophenyl, 4-methyl-3-phenylsulfonamidophenyl, 4-ethyl-3-phenylsulfonamidophenyl, 4-isopropyl-3-phenylsulfonamidophenyl, 4-propyl-3-phenylsulfonamidophenyl, 4-tert-butyl-3-phenylsulfonamidophenyl, 2-cyclohexylphenyl, 3-cyclohexylphenyl and 4-cyclohexylphenyl;
a group selected from the group consisting of quinolinyl, (1,4)-benzodioxanyl, (1,3)-benzodioxolyl, naphthyl and thiazolyl;

a pyridinyl group, wherein said pyridinyl group optionally may be substituted with 1 or 2 substituents independently selected from the group consisting of F, Cl and Br; —(CHR$^{17}$)—R$^{20}$ or —(CHR$^{17}$)—(CHR$^{18}$)—R$^{20}$;

R$^3$ represents a methyl or ethyl group;

R$^4$ represents hydrogen; R$^9$ representsa group selected from the group consisting of phenyl, pyridinyl and naphthyl, wherein the group can in each case optionally be substituted with 1, 2, 3, 4 or 5 substituents independently selected from the group consisting of F, Cl, Br, I, —CF$_3$, —O—CF$_3$, —S—CF$_3$, —OH, —O—CH$_3$, —O—C$_2$H$_5$, —NH—S(=O)$_2$—CH$_3$, morpholinyl, piperidinyl, pyrrolidinyl, piperazinyl, phenyl, methyl, ethyl, n-propyl, isopropyl, n-butyl, sec-butyl, isobutyl, tert-butyl, n-pentyl, n-hexyl, n-heptyl and n-octyl;

R$^{17}$ and R$^{18}$ each independently represent hydrogen;

a group selected from the group consisting of methyl, ethyl, n-propyl, isopropyl, n-butyl, sec-butyl, isobutyl and tert-butyl; or a phenyl group; and R$^{20}$ represents a phenyl group.

17. A compound selected from the group consisting of:
[1] 3-(3-methoxyphenyl)-1-oxa-2,8-diazaspiro[4.5]dec-2-ene-8-carboxylic acid phenylamide
[2] 3-phenyl-1-oxa-2,8-diazaspiro[4.5]dec-2-ene-8-carboxylic acid phenylamide
[3] 3-(4-chlorophenyl)-1-oxa-2,8-diazaspiro[4.5]dec-2-ene-8-carboxylic acid phenylamide
[4] 3-(4-tert-butylphenyl)-1-oxa-2,8-diazaspiro[4.5]dec-2-ene-8-carboxylic acid phenylamide
[5] 3-p-tolyl-1-oxa-2,8-diazaspiro[4.5]dec-2-ene-8-carboxylic acid phenylamide
[6] 3-(4-trifluoromethylphenyl)-1-oxa-2,8-diazaspiro[4.5]dec-2-ene-8-carboxylic acid phenylamide
[7] 3-(3-methoxyphenyl)-1-oxa-2,8-diazaspiro[4.5]dec-2-ene-8-carboxylic acid-m-tolylamide
[8] 3-(3-methoxyphenyl)-1-oxa-2,8-diazaspiro[4.5]dec-2-ene-8-carboxylic acid-m-tolylamide
[9] 3-phenyl-1-oxa-2,8-diazaspiro[4.5]dec-2-ene-8-carboxylic acid-m-tolylamide
[10] 3-(4-chlorophenyl)-1-oxa-2,8-diazaspiro[4.5]dec-2-ene-8-carboxylic acid-m-tolylamide
[11] 3-(4-tert-butylphenyl)-1-oxa-2,8-diazaspiro[4.5]dec-2-ene-8-carboxylic acid-m-tolylamide
[12] 3-p-tolyl-1-oxa-2,8-diazaspiro[4.5]dec-2-ene-8-carboxylic acid-m-tolylamide
[13] 3-(4-trifluoromethylphenyl)-1-oxa-2,8-diazaspiro[4.5]dec-2-ene-8-carboxylic acid-m-tolylamide
[14] 3-(3-methoxyphenyl)-1-oxa-2,8-diazaspiro[4.5]dec-2-ene-8-carboxylic acid-(3-ethylphenyl)amide
[15] 3-(3-methoxyphenyl)-1-oxa-2,8-diazaspiro[4.5]dec-2-ene-8-carboxylic acid-(3-ethylphenyl)amide
[16] 3-phenyl-1-oxa-2,8-diazaspiro[4.5]dec-2-ene-8-carboxylic acid-(3-ethylphenyl)amide
[17] 3-(4-chlorophenyl)-1-oxa-2,8-diazaspiro[4.5]dec-2-ene-8-carboxylic acid-(3-ethylphenyl)amide
[18] 3-(4-tert-butylphenyl)-1-oxa-2,8-diazaspiro[4.5]dec-2-ene-8-carboxylic acid-(3-ethylphenyl)amide
[19] 3-p-tolyl-1-oxa-2,8-diazaspiro[4.5]dec-2-ene-8-carboxylic acid-(3-ethylphenyl)amide
[20] 3-(4-trifluoromethylphenyl)-1-oxa-2,8-diazaspiro[4.5]dec-2-ene-8-carboxylic acid-(3-ethylphenyl)amide
[21] 3-(3-methoxyphenyl)-1-oxa-2,8-diazaspiro[4.5]dec-2-ene-8-carboxylic acid-(2-propylphenyl)amide
[22] 3-phenyl-1-oxa-2,8-diazaspiro[4.5]dec-2-ene-8-carboxylic acid-(2-propylphenyl)amide
[23] 3-(4-chlorophenyl)-1-oxa-2,8-diazaspiro[4.5]dec-2-ene-8-carboxylic acid-(2-propylphenyl)amide
[24] 3-(4-tert-butylphenyl)-1-oxa-2,8-diazaspiro[4.5]dec-2-ene-8-carboxylic acid-(2-propylphenyl)amide
[25] 3-p-tolyl-1-oxa-2,8-diazaspiro[4.5]dec-2-ene-8-carboxylic acid-(2-propylphenyl)amide
[26] 3-(4-trifluoromethylphenyl)-1-oxa-2,8-diazaspiro[4.5]dec-2-ene-8-carboxylic acid-(2-propylphenyl)amide
[27] 3-(3-methoxyphenyl)-1-oxa-2,8-diazaspiro[4.5]dec-2-ene-8-carboxylic acid-(4-fluorophenyl)amide
[28] 3-phenyl-1-oxa-2,8-diazaspiro[4.5]dec-2-ene-8-carboxylic acid-(4-fluorophenyl)amide
[29] 3-(4-chlorophenyl)-1-oxa-2,8-diazaspiro[4.5]dec-2-ene-8-carboxylic acid-(4-fluorophenyl)amide
[30] 3-(4-tert-butylphenyl)-1-oxa-2,8-diazaspiro[4.5]dec-2-ene-8-carboxylic acid-(4-fluorophenyl)amide
[31] 3-p-tolyl-1-oxa-2,8-diazaspiro[4.5]dec-2-ene-8-carboxylic acid-(4-fluorophenyl)amide
[32] 3-(4-trifluoromethylphenyl)-1-oxa-2,8-diazaspiro[4.5]dec-2-ene-8-carboxylic acid-(4-fluorophenyl)amide
[33] 3-(3-methoxyphenyl)-1-oxa-2,8-diazaspiro[4.5]dec-2-ene-8-carboxylic acid-(3-chlorophenyl)amide
[34] 3-phenyl-1-oxa-2,8-diazaspiro[4.5]dec-2-ene-8-carboxylic acid-(3-chlorophenyl)amide
[35] 3-(4-chlorophenyl)-1-oxa-2,8-diazaspiro[4.5]dec-2-ene-8-carboxylic acid-(3-chlorophenyl)amide
[36] 3-(4-tert-butylphenyl)-1-oxa-2,8-diazaspiro[4.5]dec-2-ene-8-carboxylic acid-(3-chlorophenyl)amide
[37] 3-p-tolyl-1-oxa-2,8-diazaspiro[4.5]dec-2-ene-8-carboxylic acid-(3-chlorophenyl)amide
[38] 3-(4-trifluoromethylphenyl)-1-oxa-2,8-diazaspiro[4.5]dec-2-ene-8-carboxylic acid-(3-chlorophenyl)amide
[39] 3-(3-methoxyphenyl)-1-oxa-2,8-diazaspiro[4.5]dec-2-ene-8-carboxylic acid-(4-chlorophenyl)amide
[40] 3-phenyl-1-oxa-2,8-diazaspiro[4.5]dec-2-ene-8-carboxylic acid-(4-chlorophenyl)amide
[41] 3-(4-chlorophenyl)-1-oxa-2,8-diazaspiro[4.5]dec-2-ene-8-carboxylic acid-(4-chlorophenyl)amide
[42] 3-(4-tert-butylphenyl)-1-oxa-2,8-diazaspiro[4.5]dec-2-ene-8-carboxylic acid-(4-chlorophenyl)amide
[43] 3-p-tolyl-1-oxa-2,8-diazaspiro[4.5]dec-2-ene-8-carboxylic acid-(4-chlorophenyl)amide
[44] 3-phenyl-1-oxa-2,8-diazaspiro[4.5]dec-2-ene-8-carboxylic acid-(4-iodophenyl)amide
[45] 3-(4-tert-butylphenyl)-1-oxa-2,8-diazaspiro[4.5]dec-2-ene-8-carboxylic acid-(4-iodophenyl)amide
[46] 3-(4-trifluoromethylphenyl)-1-oxa-2,8-diazaspiro[4.5]dec-2-ene-8-carboxylic acid-(4-iodophenyl)amide
[47] 3-(3-methoxyphenyl)-1-oxa-2,8-diazaspiro[4.5]dec-2-ene-8-carboxylic acid-(4-methoxyphenyl)amide
[48] 3-phenyl-1-oxa-2,8-diazaspiro[4.5]dec-2-ene-8-carboxylic acid-(4-methoxyphenyl)amide
[49] 3-(4-chlorophenyl)-1-oxa-2,8-diazaspiro[4.5]dec-2-ene-8-carboxylic acid-(4-methoxyphenyl)amide
[50] 3-(4-tert-butylphenyl)-1-oxa-2,8-diazaspiro[4.5]dec-2-ene-8-carboxylic acid-(4-methoxyphenyl)amide
[51] 3-p-tolyl-1-oxa-2,8-diazaspiro[4.5]dec-2-ene-8-carboxylic acid-(4-methoxyphenyl)amide
[52] 3-(4-trifluoromethylphenyl)-1-oxa-2,8-diazaspiro[4.5]dec-2-ene-8-carboxylic acid-(4-methoxyphenyl)amide
[53] 3-(3-methoxyphenyl)-1-oxa-2,8-diazaspiro[4.5]dec-2-ene-8-carboxylic acid-(2-methylsulfanylphenyl)amide

[54] 3-phenyl-1-oxa-2,8-diazaspiro[4.5]dec-2-ene-8-carboxylic acid-(2-methylsulfanylphenyl)amide
[55] 3-(4-chlorophenyl)-1-oxa-2,8-diazaspiro[4.5]dec-2-ene-8-carboxylic acid-(2-methylsulfanylphenyl)amide
[56] 3-(4-tert-butylphenyl)-1-oxa-2,8-diazaspiro[4.5]dec-2-ene-8-carboxylic acid-(2-methylsulfanylphenyl)amide
[57] 3-p-tolyl-1-oxa-2,8-diazaspiro[4.5]dec-2-ene-8-carboxylic acid-(2-methylsulfanylphenyl)amide
[58] 3-(4-trifluoromethylphenyl)-1-oxa-2,8-diazaspiro[4.5]dec-2-ene-8-carboxylic acid-(2-methylsulfanylphenyl)amide
[59] 3-(3-methoxyphenyl)-1-oxa-2,8-diazaspiro[4.5]dec-2-ene-8-carboxylic acid-(3-methylsulfanylphenyl)amide
[60] 3-phenyl-1-oxa-2,8-diazaspiro[4.5]dec-2-ene-8-carboxylic acid-(3-methylsulfanylphenyl)amide
[61] 3-(4-chlorophenyl)-1-oxa-2,8-diazaspiro[4.5]dec-2-ene-8-carboxylic acid-(3-methylsulfanylphenyl)amide
[62] 3-(4-tert-butylphenyl)-1-oxa-2,8-diazaspiro[4.5]dec-2-ene-8-carboxylic acid-(3-methylsulfanylphenyl)amide
[63] 3-p-tolyl-1-oxa-2,8-diazaspiro[4.5]dec-2-ene-8-carboxylic acid-(3-methylsulfanylphenyl)amide
[64] 3-(4-trifluoromethylphenyl)-1-oxa-2,8-diazaspiro[4.5]dec-2-ene-8-carboxylic acid-(3-methylsulfanylphenyl)amide
[65] 3-(3-methoxyphenyl)-1-oxa-2,8-diazaspiro[4.5]dec-2-ene-8-carboxylic acid-(4-methylsulfanylphenyl)amide
[66] 3-phenyl-1-oxa-2,8-diazaspiro[4.5]dec-2-ene-8-carboxylic acid-(4-methylsulfanylphenyl)amide
[67] 3-(4-chlorophenyl)-1-oxa-2,8-diazaspiro[4.5]dec-2-ene-8-carboxylic acid-(4-methylsulfanylphenyl)amide
[68] 3-(4-tert-butylphenyl)-1-oxa-2,8-diazaspiro[4.5]dec-2-ene-8-carboxylic acid-(4-methylsulfanylphenyl)amide
[69] 3-p-tolyl-1-oxa-2,8-diazaspiro[4.5]dec-2-ene-8-carboxylic acid-(4-methylsulfanylphenyl)amide
[70] 3-(4-trifluoromethylphenyl)-1-oxa-2,8-diazaspiro[4.5]dec-2-ene-8-carboxylic acid-(4-methylsulfanylphenyl)amide
[71] 3-(3-methoxyphenyl)-1-oxa-2,8-diazaspiro[4.5]dec-2-ene-8-carboxylic acid-(2-isopropylphenyl)amide
[72] 3-phenyl-1-oxa-2,8-diazaspiro[4.5]dec-2-ene-8-carboxylic acid-(2-isopropylphenyl)amide
[73] 3-(4-chlorophenyl)-1-oxa-2,8-diazaspiro[4.5]dec-2-ene-8-carboxylic acid-(2-isopropylphenyl)amide
[74] 3-(4-tert-butylphenyl)-1-oxa-2,8-diazaspiro[4.5]dec-2-ene-8-carboxylic acid-(2-isopropylphenyl)amide
[75] 3-p-tolyl-1-oxa-2,8-diazaspiro[4.5]dec-2-ene-8-carboxylic acid-(2-isopropylphenyl)amide
[76] 3-(4-trifluoromethylphenyl)-1-oxa-2,8-diazaspiro[4.5]dec-2-ene-8-carboxylic acid-(2-isopropylphenyl)amide
[77] 3-(3-methoxyphenyl)-1-oxa-2,8-diazaspiro[4.5]dec-2-ene-8-carboxylic acid-(4-isopropylphenyl)amide
[78] 3-phenyl-1-oxa-2,8-diazaspiro[4.5]dec-2-ene-8-carboxylic acid-(4-isopropylphenyl)amide
[79] 3-(4-chlorophenyl)-1-oxa-2,8-diazaspiro[4.5]dec-2-ene-8-carboxylic acid-(4-isopropylphenyl)amide
[80] 3-(4-tert-butylphenyl)-1-oxa-2,8-diazaspiro[4.5]dec-2-ene-8-carboxylic acid-(4-isopropylphenyl)amide
[81] 3-p-tolyl-1-oxa-2,8-diazaspiro[4.5]dec-2-ene-8-carboxylic acid-(4-isopropylphenyl)amide
[82] 3-(4-trifluoromethylphenyl)-1-oxa-2,8-diazaspiro[4.5]dec-2-ene-8-carboxylic acid-(4-isopropylphenyl)amide
[83] 3-(3-methoxyphenyl)-1-oxa-2,8-diazaspiro[4.5]dec-2-ene-8-carboxylic acid-(2-trifluoromethylphenyl)amide
[84] 3-phenyl-1-oxa-2,8-diazaspiro[4.5]dec-2-ene-8-carboxylic acid-(2-trifluoromethylphenyl)amide
[85] 3-(4-chlorophenyl)-1-oxa-2,8-diazaspiro[4.5]dec-2-ene-8-carboxylic acid-(2-trifluoromethylphenyl)amide
[86] 3-(4-tert-butylphenyl)-1-oxa-2,8-diazaspiro[4.5]dec-2-ene-8-carboxylic acid-(2-trifluoromethylphenyl)amide
[87] 3-p-tolyl-1-oxa-2,8-diazaspiro[4.5]dec-2-ene-8-carboxylic acid-(2-trifluoromethylphenyl)amide
[88] 3-(4-trifluoromethylphenyl)-1-oxa-2,8-diazaspiro[4.5]dec-2-ene-8-carboxylic acid-(2-trifluoromethylphenyl)amide
[89] 3-(3-methoxyphenyl)-1-oxa-2,8-diazaspiro[4.5]dec-2-ene-8-carboxylic acid-(3-trifluoromethylphenyl)amide
[90] 3-phenyl-1-oxa-2,8-diazaspiro[4.5]dec-2-ene-8-carboxylic acid-(3-trifluoromethylphenyl)amide
[91] 3-(4-chlorophenyl)-1-oxa-2,8-diazaspiro[4.5]dec-2-ene-8-carboxylic acid-(3-trifluoromethylphenyl)amide
[92] 3-(4-tert-butylphenyl)-1-oxa-2,8-diazaspiro[4.5]dec-2-ene-8-carboxylic acid-(3-trifluoromethylphenyl)amide
[93] 3-p-tolyl-1-oxa-2,8-diazaspiro[4.5]dec-2-ene-8-carboxylic acid-(3-trifluoromethylphenyl)amide
[94] 3-(4-trifluoromethylphenyl)-1-oxa-2,8-diazaspiro[4.5]dec-2-ene-8-carboxylic acid-(3-trifluoromethylphenyl)amide
[95] 3-phenyl-1-oxa-2,8-diazaspiro[4.5]dec-2-ene-8-carboxylic acid biphenyl-4-amide
[96] 3-(4-tert-butylphenyl)-1-oxa-2,8-diazaspiro[4.5]dec-2-ene-8-carboxylic acid biphenyl-4-amide
[97] 3-p-tolyl-1-oxa-2,8-diazaspiro[4.5]dec-2-ene-8-carboxylic acid biphenyl-4-amide
[98] 3-(3-methoxyphenyl)-1-oxa-2,8-diazaspiro[4.5]dec-2-ene-8-carboxylic acid-(2-phenoxyphenyl)amide
[99] 3-phenyl-1-oxa-2,8-diazaspiro[4.5]dec-2-ene-8-carboxylic acid-(2-phenoxyphenyl)amide
[100] 3-(4-chlorophenyl)-1-oxa-2,8-diazaspiro[4.5]dec-2-ene-8-carboxylic acid-(2-phenoxyphenyl)amide
[101] 3-(4-tert-butylphenyl)-1-oxa-2,8-diazaspiro[4.5]dec-2-ene-8-carboxylic acid-(2-phenoxyphenyl)amide
[102] 3-p-tolyl-1-oxa-2,8-diazaspiro[4.5]dec-2-ene-8-carboxylic acid-(2-phenoxyphenyl)amide
[103] 3-(4-trifluoromethylphenyl)-1-oxa-2,8-diazaspiro[4.5]dec-2-ene-8-carboxylic acid-(2-phenoxyphenyl)amide
[104] 3-(3-methoxyphenyl)-1-oxa-2,8-diazaspiro[4.5]dec-2-ene-8-carboxylic acid-(4-benzyloxyphenyl)amide
[105] 3-phenyl-1-oxa-2,8-diazaspiro[4.5]dec-2-ene-8-carboxylic acid-(4-benzyloxyphenyl)amide
[106] 3-(4-chlorophenyl)-1-oxa-2,8-diazaspiro[4.5]dec-2-ene-8-carboxylic acid-(4-benzyloxyphenyl)amide
[ω] 3-(4-tert-butylphenyl)-1-oxa-2,8-diazaspiro[4.5]dec-2-ene-8-carboxylic acid-(4-benzyloxyphenyl)amide
[•] 3-p-tolyl-1-oxa-2,8-diazaspiro[4.5]dec-2-ene-8-carboxylic acid-(4-benzyloxyphenyl)amide
[109] 3-(4-trifluoromethylphenyl)-1-oxa-2,8-diazaspiro[4.5]dec-2-ene-8-carboxylic acid-(4-benzyloxyphenyl)amide

[110] 3-(3-methoxyphenyl)-1-oxa-2,8-diazaspiro[4.5]dec-2-ene-8-carboxylic acid cyclohexylamide
[111] 3-phenyl-1-oxa-2,8-diazaspiro[4.5]dec-2-ene-8-carboxylic acid cyclohexylamide
[112] 3-(4-chlorophenyl)-1-oxa-2,8-diazaspiro[4.5]dec-2-ene-8-carboxylic acid cyclohexylamide
[113] 3-(4-tert-butylphenyl)-1-oxa-2,8-diazaspiro[4.5]dec-2-ene-8-carboxylic acid cyclohexylamide
[114] 3-p-tolyl-1-oxa-2,8-diazaspiro[4.5]dec-2-ene-8-carboxylic acid cyclohexylamide
[115] 3-(4-trifluoromethylphenyl)-1-oxa-2,8-diazaspiro[4.5]dec-2-ene-8-carboxylic acid cyclohexylamide
[116] 3-(3-methoxyphenyl)-1-oxa-2,8-diazaspiro[4.5]dec-2-ene-8-carboxylic acid benzylamide
[117] 3-phenyl-1-oxa-2,8-diazaspiro[4.5]dec-2-ene-8-carboxylic acid benzylamide
[118] 3-(4-chlorophenyl)-1-oxa-2,8-diazaspiro[4.5]dec-2-ene-8-carboxylic acid benzylamide
[119] 3-(4-tert-butylphenyl)-1-oxa-2,8-diazaspiro[4.5]dec-2-ene-8-carboxylic acid benzylamide
[120] 3-p-tolyl-1-oxa-2,8-diazaspiro[4.5]dec-2-ene-8-carboxylic acid benzylamide
[121] 3-(4-trifluoromethylphenyl)-1-oxa-2,8-diazaspiro[4.5]dec-2-ene-8-carboxylic acid benzylamide
[122] 3-(3-methoxyphenyl)-1-oxa-2,8-diazaspiro[4.5]dec-2-ene-8-carboxylic acid phenethylamide
[123] 3-phenyl-1-oxa-2,8-diazaspiro[4.5]dec-2-ene-8-carboxylic acid phenethylamide
[124] 3-(4-chlorophenyl)-1-oxa-2,8-diazaspiro[4.5]dec-2-ene-8-carboxylic acid phenethylamide
[125] 3-(4-tert-butylphenyl)-1-oxa-2,8-diazaspiro[4.5]dec-2-ene-8-carboxylic acid phenethylamide
[126] 3-p-tolyl-1-oxa-2,8-diazaspiro[4.5]dec-2-ene-8-carboxylic acid phenethylamide
[127] 3-(4-trifluoromethylphenyl)-1-oxa-2,8-diazaspiro[4.5]dec-2-ene-8-carboxylic acid phenethylamide
[128] 3-(3-methoxyphenyl)-1-oxa-2,8-diazaspiro[4.5]dec-2-ene-8-carboxylic acid-4-methylbenzylamide
[129] 3-phenyl-1-oxa-2,8-diazaspiro[4.5]dec-2-ene-8-carboxylic acid-4-methylbenzylamide
[130] 3-(4-chlorophenyl)-1-oxa-2,8-diazaspiro[4.5]dec-2-ene-8-carboxylic acid-4-methylbenzylamide
[131] 3-(4-tert-butylphenyl)-1-oxa-2,8-diazaspiro[4.5]dec-2-ene-8-carboxylic acid-4-methylbenzylamide
[132] 3-p-tolyl-1-oxa-2,8-diazaspiro[4.5]dec-2-ene-8-carboxylic acid-4-methylbenzylamide
[133] 3-(4-trifluoromethylphenyl)-1-oxa-2,8-diazaspiro[4.5]dec-2-ene-8-carboxylic acid-4-methylbenzylamide
[134] 3-(3-methoxyphenyl)-1-oxa-2,8-diazaspiro[4.5]dec-2-ene-8-carboxylic acid-4-methoxybenzylamide
[135] 3-phenyl-1-oxa-2,8-diazaspiro[4.5]dec-2-ene-8-carboxylic acid-4-methoxybenzylamide
[136] 3-(4-chlorophenyl)-1-oxa-2,8-diazaspiro[4.5]dec-2-ene-8-carboxylic acid-4-methoxybenzylamide
[137] 3-(4-tert-butylphenyl)-1-oxa-2,8-diazaspiro[4.5]dec-2-ene-8-carboxylic acid-4-methoxybenzylamide
[138] 3-p-tolyl-1-oxa-2,8-diazaspiro[4.5]dec-2-ene-8-carboxylic acid-4-methoxybenzylamide
[139] 3-(4-trifluoromethylphenyl)-1-oxa-2,8-diazaspiro[4.5]dec-2-ene-8-carboxylic acid-4-methoxybenzylamide
[140] 3-(3-methoxyphenyl)-1-oxa-2,8-diazaspiro[4.5]dec-2-ene-8-carboxylic acid-(4-tert-butylphenyl)amide
[141] 3-phenyl-1-oxa-2,8-diazaspiro[4.5]dec-2-ene-8-carboxylic acid-(4-tert-butylphenyl)amide
[142] 3-(4-chlorophenyl)-1-oxa-2,8-diazaspiro[4.5]dec-2-ene-8-carboxylic acid-(4-tert-butylphenyl)amide
[143] 3-(4-tert-butylphenyl)-1-oxa-2,8-diazaspiro[4.5]dec-2-ene-8-carboxylic acid-(4-tert-butylphenyl)amide
[144] 3-p-tolyl-1-oxa-2,8-diazaspiro[4.5]dec-2-ene-8-carboxylic acid-(4-tert-butylphenyl)amide
[145] 3-(4-trifluoromethylphenyl)-1-oxa-2,8-diazaspiro[4.5]dec-2-ene-8-carboxylic acid-(4-tert-butylphenyl)amide
[146] 3-(3-methoxyphenyl)-1-oxa-2,8-diazaspiro[4.5]dec-2-ene-8-carboxylic acid p-tolylamide
[147] 3-phenyl-1-oxa-2,8-diazaspiro[4.5]dec-2-ene-8-carboxylic acid p-tolylamide
[148] 3-(4-chlorophenyl)-1-oxa-2,8-diazaspiro[4.5]dec-2-ene-8-carboxylic acid p-tolylamide
[149] 3-(4-tert-butylphenyl)-1-oxa-2,8-diazaspiro[4.5]dec-2-ene-8-carboxylic acid p-tolylamide
[150] 3-(3-methoxyphenyl)-1-oxa-2,8-diazaspiro[4.5]dec-2-ene-8-carboxylic acid o-tolylamide
[151] 3-phenyl-1-oxa-2,8-diazaspiro[4.5]dec-2-ene-8-carboxylic acid o-tolylamide
[152] 3-(4-chlorophenyl)-1-oxa-2,8-diazaspiro[4.5]dec-2-ene-8-carboxylic acid o-tolylamide
[153] 3-(4-tert-butylphenyl)-1-oxa-2,8-diazaspiro[4.5]dec-2-ene-8-carboxylic acid o-tolylamide
[154] 3-p-tolyl-1-oxa-2,8-diazaspiro[4.5]dec-2-ene-8-carboxylic acid o-tolylamide
[155] 3-(4-trifluoromethylphenyl)-1-oxa-2,8-diazaspiro[4.5]dec-2-ene-8-carboxylic acid o-tolylamide
[156] 3-(3-methoxyphenyl)-1-oxa-2,8-diazaspiro[4.5]dec-2-ene-8-carboxylic acid-(2-ethylphenyl)amide
[157] 3-phenyl-1-oxa-2,8-diazaspiro[4.5]dec-2-ene-8-carboxylic acid-(2-ethylphenyl)amide
[158] 3-(4-chlorophenyl)-1-oxa-2,8-diazaspiro[4.5]dec-2-ene-8-carboxylic acid-(2-ethylphenyl)amide
[159] 3-(4-tert-butylphenyl)-1-oxa-2,8-diazaspiro[4.5]dec-2-ene-8-carboxylic acid-(2-ethylphenyl)amide
[160] 3-p-tolyl-1-oxa-2,8-diazaspiro[4.5]dec-2-ene-8-carboxylic acid-(2-ethylphenyl)amide
[161] 3-(4-trifluoromethylphenyl)-1-oxa-2,8-diazaspiro[4.5]dec-2-ene-8-carboxylic acid-(2-ethylphenyl)amide
[162] 3-(3-methoxyphenyl)-1-oxa-2,8-diazaspiro[4.5]dec-2-ene-8-carboxylic acid-(4-ethylphenyl)amide
[163] 3-phenyl-1-oxa-2,8-diazaspiro[4.5]dec-2-ene-8-carboxylic acid-(4-ethylphenyl)amide
[164] 3-(4-chlorophenyl)-1-oxa-2,8-diazaspiro[4.5]dec-2-ene-8-carboxylic acid-(4-ethylphenyl)amide
[165] 3-(4-tert-butylphenyl)-1-oxa-2,8-diazaspiro[4.5]dec-2-ene-8-carboxylic acid-(4-ethylphenyl)amide
[166] 3-p-tolyl-1-oxa-2,8-diazaspiro[4.5]dec-2-ene-8-carboxylic acid-(4-ethylphenyl)amide
[167] 3-(4-trifluoromethylphenyl)-1-oxa-2,8-diazaspiro[4.5]dec-2-ene-8-carboxylic acid-(4-ethylphenyl)amide
[168] 3-(3-methoxyphenyl)-1-oxa-2,8-diazaspiro[4.5]dec-2-ene-8-carboxylic acid-(2-fluorophenyl)amide
[169] 3-phenyl-1-oxa-2,8-diazaspiro[4.5]dec-2-ene-8-carboxylic acid-(2-fluorophenyl)amide
[1710] 3-(4-chlorophenyl)-1-oxa-2,8-diazaspiro[4.5]dec-2-ene-8-carboxylic acid-(2-fluorophenyl)amide
[171] 3-(4-tert-butylphenyl)-1-oxa-2,8-diazaspiro[4.5]dec-2-ene-8-carboxylic acid-(2-fluorophenyl)amide
[172] 3-p-tolyl-1-oxa-2,8-diazaspiro[4.5]dec-2-ene-8-carboxylic acid-(2-fluorophenyl)amide

[173] 3-(4-trifluoromethylphenyl)-1-oxa-2,8-diazaspiro[4.5]dec-2-ene-8-carboxylic acid-(2-fluorophenyl)amide
[174] 3-(3-methoxyphenyl)-1-oxa-2,8-diazaspiro[4.5]dec-2-ene-8-carboxylic acid-(3-fluorophenyl)amide
[175] 3-phenyl-1-oxa-2,8-diazaspiro[4.5]dec-2-ene-8-carboxylic acid-(3-fluorophenyl)amide
[176] 3-(4-chlorophenyl)-1-oxa-2,8-diazaspiro[4.5]dec-2-ene-8-carboxylic acid-(3-fluorophenyl)amide
[177] 3-(4-tert-butylphenyl)-1-oxa-2,8-diazaspiro[4.5]dec-2-ene-8-carboxylic acid-(3-fluorophenyl)amide
[178] 3-p-tolyl-1-oxa-2,8-diazaspiro[4.5]dec-2-ene-8-carboxylic acid-(3-fluorophenyl)amide
[179] 3-(4-trifluoromethylphenyl)-1-oxa-2,8-diazaspiro[4.5]dec-2-ene-8-carboxylic acid-(3-fluorophenyl)amide
[180] 3-(3-methoxyphenyl)-1-oxa-2,8-diazaspiro[4.5]dec-2-ene-8-carboxylic acid-(2-chlorophenyl)amide
[181] 3-phenyl-1-oxa-2,8-diazaspiro[4.5]dec-2-ene-8-carboxylic acid-(2-chlorophenyl)amide
[182] 3-(4-chlorophenyl)-1-oxa-2,8-diazaspiro[4.5]dec-2-ene-8-carboxylic acid-(2-chlorophenyl)amide
[183] 3-(4-tert-butylphenyl)-1-oxa-2,8-diazaspiro[4.5]dec-2-ene-8-carboxylic acid-(2-chlorophenyl)amide
[184] 3-p-tolyl-1-oxa-2,8-diazaspiro[4.5]dec-2-ene-8-carboxylic acid-(2-chlorophenyl)amide
[185] 3-(4-trifluoromethylphenyl)-1-oxa-2,8-diazaspiro[4.5]dec-2-ene-8-carboxylic acid-(2-chlorophenyl)amide
[186] 3-(3-methoxyphenyl)-1-oxa-2,8-diazaspiro[4.5]dec-2-ene-8-carboxylic acid-(2-bromophenyl)amide
[187] 3-phenyl-1-oxa-2,8-diazaspiro[4.5]dec-2-ene-8-carboxylic acid-(2-bromophenyl)amide
[188] 3-(4-chlorophenyl)-1-oxa-2,8-diazaspiro[4.5]dec-2-ene-8-carboxylic acid-(2-bromophenyl)amide
[189] 3-(4-tert-butylphenyl)-1-oxa-2,8-diazaspiro[4.5]dec-2-ene-8-carboxylic acid-(2-bromophenyl)amide
[190] 3-p-tolyl-1-oxa-2,8-diazaspiro[4.5]dec-2-ene-8-carboxylic acid-(2-bromophenyl)amide
[191] 3-(4-trifluoromethylphenyl)-1-oxa-2,8-diazaspiro[4.5]dec-2-ene-8-carboxylic acid-(2-bromophenyl)amide
[192] 3-(3-methoxyphenyl)-1-oxa-2,8-diazaspiro[4.5]dec-2-ene-8-carboxylic acid-(3-bromophenyl)amide
[193] 3-phenyl-1-oxa-2,8-diazaspiro[4.5]dec-2-ene-8-carboxylic acid-(3-bromophenyl)amide
[194] 3-(4-tert-butylphenyl)-1-oxa-2,8-diazaspiro[4.5]dec-2-ene-8-carboxylic acid-(3-bromophenyl)amide
[195] 3-(4-trifluoromethylphenyl)-1-oxa-2,8-diazaspiro[4.5]dec-2-ene-8-carboxylic acid-(3-bromophenyl)amide
[196] 3-(3-methoxyphenyl)-1-oxa-2,8-diazaspiro[4.5]dec-2-ene-8-carboxylic acid-(4-bromophenyl)amide
[197] 3-phenyl-1-oxa-2,8-diazaspiro[4.5]dec-2-ene-8-carboxylic acid-(4-bromophenyl)amide
[198] 3-(3-methoxyphenyl)-1-oxa-2,8-diazaspiro[4.5]dec-2-ene-8-carboxylic acid-(2-methoxyphenyl)amide
[199] 3-phenyl-1-oxa-2,8-diazaspiro[4.5]dec-2-ene-8-carboxylic acid-(2-methoxyphenyl)amide
[200] 3-(4-chlorophenyl)-1-oxa-2,8-diazaspiro[4.5]dec-2-ene-8-carboxylic acid-(2-methoxyphenyl)amide
[201] 3-(4-tert-butylphenyl)-1-oxa-2,8-diazaspiro[4.5]dec-2-ene-8-carboxylic acid-(2-methoxyphenyl)amide
[202] 3-p-tolyl-1-oxa-2,8-diazaspiro[4.5]dec-2-ene-8-carboxylic acid-(2-methoxyphenyl)amide
[203] 3-(4-trifluoromethylphenyl)-1-oxa-2,8-diazaspiro[4.5]dec-2-ene-8-carboxylic acid-(2-methoxyphenyl)amide
[204] 3-(3-methoxyphenyl)-1-oxa-2,8-diazaspiro[4.5]dec-2-ene-8-carboxylic acid-(3-methoxyphenyl)amide
[205] 3-phenyl-1-oxa-2,8-diazaspiro[4.5]dec-2-ene-8-carboxylic acid-(3-methoxyphenyl)amide
[206] 3-(4-chlorophenyl)-1-oxa-2,8-diazaspiro[4.5]dec-2-ene-8-carboxylic acid-(3-methoxyphenyl)amide
[207] 3-(4-tert-butylphenyl)-1-oxa-2,8-diazaspiro[4.5]dec-2-ene-8-carboxylic acid-(3-methoxyphenyl)amide
[208] 3-p-tolyl-1-oxa-2,8-diazaspiro[4.5]dec-2-ene-8-carboxylic acid-(3-methoxyphenyl)amide
[209] 3-(4-trifluoromethylphenyl)-1-oxa-2,8-diazaspiro[4.5]dec-2-ene-8-carboxylic acid-(3-methoxyphenyl)amide
[210] 3-(3-methoxyphenyl)-1-oxa-2,8-diazaspiro[4.5]dec-2-ene-8-carboxylic acid-(4-trifluoromethylphenyl)amide
[211] 3-phenyl-1-oxa-2,8-diazaspiro[4.5]dec-2-ene-8-carboxylic acid-(4-trifluoromethylphenyl)amide
[212] 3-(4-chlorophenyl)-1-oxa-2,8-diazaspiro[4.5]dec-2-ene-8-carboxylic acid-(4-trifluoromethylphenyl)amide
[213] 3-(4-tert-butylphenyl)-1-oxa-2,8-diazaspiro[4.5]dec-2-ene-8-carboxylic acid-(4-trifluoromethylphenyl)amide
[214] 3-p-tolyl-1-oxa-2,8-diazaspiro[4.5]dec-2-ene-8-carboxylic acid-(4-trifluoromethylphenyl)amide
[215] 3-(4-trifluoromethylphenyl)-1-oxa-2,8-diazaspiro[4.5]dec-2-ene-8-carboxylic acid-(4-trifluoromethylphenyl)amide
[216] 3-(3-methoxyphenyl)-1-oxa-2,8-diazaspiro[4.5]dec-2-ene-8-carboxylic acid-(4-phenoxyphenyl)amide
[217] 3-(4-chlorophenyl)-1-oxa-2,8-diazaspiro[4.5]dec-2-ene-8-carboxylic acid-(4-phenoxyphenyl)amide
[218] 3-(4-tert-butylphenyl)-1-oxa-2,8-diazaspiro[4.5]dec-2-ene-8-carboxylic acid-(4-phenoxyphenyl)amide
[219] 3-p-tolyl-1-oxa-2,8-diazaspiro[4.5]dec-2-ene-8-carboxylic acid-(4-phenoxyphenyl)amide
[220] 3-(4-trifluoromethylphenyl)-1-oxa-2,8-diazaspiro[4.5]dec-2-ene-8-carboxylic acid-(4-phenoxyphenyl)amide
[221] 3-(3-methoxyphenyl)-1-oxa-2,8-diazaspiro[4.5]dec-2-ene-8-carboxylic acid-(2-chloro-5-trifluoromethylphenyl)amide
[222] 3-phenyl-1-oxa-2,8-diazaspiro[4.5]dec-2-ene-8-carboxylic acid-(2-chloro-5-trifluoromethylphenyl)amide
[223] 3-(4-chlorophenyl)-1-oxa-2,8-diazaspiro[4.5]dec-2-ene-8-carboxylic acid-(2-chloro-5-trifluoromethylphenyl)amide
[224] 3-(4-tert-butylphenyl)-1-oxa-2,8-diazaspiro[4.5]dec-2-ene-8-carboxylic acid-(2-chloro-5-trifluoromethylphenyl)amide
[225] 3-p-tolyl-1-oxa-2,8-diazaspiro[4.5]dec-2-ene-8-carboxylic acid-(2-chloro-5-trifluoromethylphenyl)amide
[226] 3-(4-trifluoromethylphenyl)-1-oxa-2,8-diazaspiro[4.5]dec-2-ene-8-carboxylic acid-(2-chloro-5-trifluoromethylphenyl)amide
[227] 3-(3-methoxyphenyl)-1-oxa-2,8-diazaspiro[4.5]dec-2-ene-8-carboxylic acid-(4-chloro-2-trifluoromethylphenyl)amide
[228] 3-phenyl-1-oxa-2,8-diazaspiro[4.5]dec-2-ene-8-carboxylic acid-(4-chloro-2-trifluoromethylphenyl)amide

[229] 3-(4-chlorophenyl)-1-oxa-2,8-diazaspiro[4.5]dec-2-ene-8-carboxylic acid-(4-chloro-2-trifluoromethylphenyl)amide
[230] 3-(4-tert-butylphenyl)-1-oxa-2,8-diazaspiro[4.5]dec-2-ene-8-carboxylic acid-(4-chloro-2-trifluoromethylphenyl)amide
[231] 3-p-tolyl-1-oxa-2,8-diazaspiro[4.5]dec-2-ene-8-carboxylic acid-(4-chloro-2-trifluoromethylphenyl)amide
[232] 3-(3-methoxyphenyl)-1-oxa-2,8-diazaspiro[4.5]dec-2-ene-8-carboxylic acid-(4-chloro-3-trifluoromethylphenyl)amide
[233] 3-phenyl-1-oxa-2,8-diazaspiro[4.5]dec-2-ene-8-carboxylic acid-(4-chloro-3-trifluoromethylphenyl)amide
[234] 3-(4-chlorophenyl)-1-oxa-2,8-diazaspiro[4.5]dec-2-ene-8-carboxylic acid-(4-chloro-3-trifluoromethylphenyl)amide
[235] 3-(4-tert-butylphenyl)-1-oxa-2,8-diazaspiro[4.5]dec-2-ene-8-carboxylic acid-(4-chloro-3-trifluoromethylphenyl)amide
[236] 3-p-tolyl-1-oxa-2,8-diazaspiro[4.5]dec-2-ene-8-carboxylic acid-(4-chloro-3-trifluoromethylphenyl)amide
[237] 3-(4-trifluoromethylphenyl)-1-oxa-2,8-diazaspiro[4.5]dec-2-ene-8-carboxylic acid-(4-chloro-3-trifluoromethylphenyl)amide
[238] 3-(3-methoxyphenyl)-1-oxa-2,8-diazaspiro[4.5]dec-2-ene-8-carboxylic acid-(2-tert-butyl-6-methylphenyl)amide
[239] 3-phenyl-1-oxa-2,8-diazaspiro[4.5]dec-2-ene-8-carboxylic acid-(2-tert-butyl-6-methylphenyl)amide
[240] 3-(4-chlorophenyl)-1-oxa-2,8-diazaspiro[4.5]dec-2-ene-8-carboxylic acid-(2-tert-butyl-6-methylphenyl)amide
[241] 3-(4-tert-butylphenyl)-1-oxa-2,8-diazaspiro[4.5]dec-2-ene-8-carboxylic acid-(2-tert-butyl-6-methylphenyl)amide
[242] 3-p-tolyl-1-oxa-2,8-diazaspiro[4.5]dec-2-ene-8-carboxylic acid-(2-tert-butyl-6-methylphenyl)amide
[243] 3-(4-trifluoromethylphenyl)-1-oxa-2,8-diazaspiro[4.5]dec-2-ene-8-carboxylic acid-(2-tert-butyl-6-methylphenyl)amide
[244] 3-(3-methoxyphenyl)-1-oxa-2,8-diazaspiro[4.5]dec-2-ene-8-carboxylic acid-(4-trifluoromethoxyphenyl)amide
[245] 3-phenyl-1-oxa-2,8-diazaspiro[4.5]dec-2-ene-8-carboxylic acid-(4-trifluoromethoxyphenyl)amide
[246] 3-(4-chlorophenyl)-1-oxa-2,8-diazaspiro[4.5]dec-2-ene-8-carboxylic acid-(4-trifluoromethoxyphenyl)amide
[247] 3-(4-tert-butylphenyl)-1-oxa-2,8-diazaspiro[4.5]dec-2-ene-8-carboxylic acid-(4-trifluoromethoxyphenyl)amide
[248] 3-p-tolyl-1-oxa-2,8-diazaspiro[4.5]dec-2-ene-8-carboxylic acid-(4-trifluoromethoxyphenyl)amide
[249] 3-(3-methoxyphenyl)-1-oxa-2,8-diazaspiro[4.5]dec-2-ene-8-thiocarboxylic acid cyclohexylamide
[250] 3-phenyl-1-oxa-2,8-diazaspiro[4.5]dec-2-ene-8-thiocarboxylic acid cyclohexylamide
[251] 3-(4-chlorophenyl)-1-oxa-2,8-diazaspiro[4.5]dec-2-ene-8-thiocarboxylic acid cyclohexylamide
[252] 3-(4-tert-butylphenyl)-1-oxa-2,8-diazaspiro[4.5]dec-2-ene-8-thiocarboxylic acid cyclohexylamide
[253] 3-p-tolyl-1-oxa-2,8-diazaspiro[4.5]dec-2-ene-8-thiocarboxylic acid cyclohexylamide
[254] 3-(4-trifluoromethylphenyl)-1-oxa-2,8-diazaspiro[4.5]dec-2-ene-8-thiocarboxylic acid cyclohexylamide
[255] 3-(3-methoxyphenyl)-1-oxa-2,8-diazaspiro[4.5]dec-2-ene-8-thiocarboxylic acid phenylamide
[256] 3-phenyl-1-oxa-2,8-diazaspiro[4.5]dec-2-ene-8-thiocarboxylic acid phenylamide
[257] 3-(4-chlorophenyl)-1-oxa-2,8-diazaspiro[4.5]dec-2-ene-8-thiocarboxylic acid phenylamide
[258] 3-(4-tert-butylphenyl)-1-oxa-2,8-diazaspiro[4.5]dec-2-ene-8-thiocarboxylic acid phenylamide
[259] 3-p-tolyl-1-oxa-2,8-diazaspiro[4.5]dec-2-ene-8-thiocarboxylic acid phenylamide
[260] 3-(4-trifluoromethylphenyl)-1-oxa-2,8-diazaspiro[4.5]dec-2-ene-8-thiocarboxylic acid phenylamide
[261] 3-(3-methoxyphenyl)-1-oxa-2,8-diazaspiro[4.5]dec-2-ene-8-thiocarboxylic acid-(3-trifluoromethylphenyl)amide
[262] 3-phenyl-1-oxa-2,8-diazaspiro[4.5]dec-2-ene-8-thiocarboxylic acid-(3-trifluoromethylphenyl)amide
[263] 3-(4-chlorophenyl)-1-oxa-2,8-diazaspiro[4.5]dec-2-ene-8-thiocarboxylic acid-(3-trifluoromethylphenyl)amide
[264] 3-(4-tert-butylphenyl)-1-oxa-2,8-diazaspiro[4.5]dec-2-ene-8-thiocarboxylic acid-(3-trifluoromethylphenyl)amide
[265] 3-p-tolyl-1-oxa-2,8-diazaspiro[4.5]dec-2-ene-8-thiocarboxylic acid-(3-trifluoromethylphenyl)amide
[266] 3-(4-trifluoromethylphenyl)-1-oxa-2,8-diazaspiro[4.5]dec-2-ene-8-thiocarboxylic acid-(3-trifluoromethylphenyl)amide
[267] 3-(3-methoxyphenyl)-1-oxa-2,8-diazaspiro[4.5]dec-2-ene-8-thiocarboxylic acid-(2-methoxyphenyl)amide
[268] 3-phenyl-1-oxa-2,8-diazaspiro[4.5]dec-2-ene-8-thiocarboxylic acid-(2-methoxyphenyl)amide
[269] 3-(4-chlorophenyl)-1-oxa-2,8-diazaspiro[4.5]dec-2-ene-8-thiocarboxylic acid-(2-methoxyphenyl)amide
[270] 3-(4-tert-butylphenyl)-1-oxa-2,8-diazaspiro[4.5]dec-2-ene-8-thiocarboxylic acid-(2-methoxyphenyl)amide
[271] 3-p-tolyl-1-oxa-2,8-diazaspiro[4.5]dec-2-ene-8-thiocarboxylic acid-(2-methoxyphenyl)amide
[272] 3-(4-trifluoromethylphenyl)-1-oxa-2,8-diazaspiro[4.5]dec-2-ene-8-thiocarboxylic acid-(2-methoxyphenyl)amide
[273] 3-(3-methoxyphenyl)-1-oxa-2,8-diazaspiro[4.5]dec-2-ene-8-thiocarboxylic acid-(3-methoxyphenyl)amide
[274] 3-phenyl-1-oxa-2,8-diazaspiro[4.5]dec-2-ene-8-thiocarboxylic acid-(3-methoxyphenyl)amide
[275] 3-(4-chlorophenyl)-1-oxa-2,8-diazaspiro[4.5]dec-2-ene-8-thiocarboxylic acid-(3-methoxyphenyl)amide
[276] 3-p-tolyl-1-oxa-2,8-diazaspiro[4.5]dec-2-ene-8-thiocarboxylic acid-(3-methoxyphenyl)amide
[277] 3-(4-trifluoromethylphenyl)-1-oxa-2,8-diazaspiro[4.5]dec-2-ene-8-thiocarboxylic acid-(3-methoxyphenyl)amide
[278] 3-(3-methoxyphenyl)-1-oxa-2,8-diazaspiro[4.5]dec-2-ene-8-thiocarboxylic acid-(4-tert-butylphenyl)amide
[279] 3-phenyl-1-oxa-2,8-diazaspiro[4.5]dec-2-ene-8-thiocarboxylic acid-(4-tert-butylphenyl)amide
[280] 3-(4-chlorophenyl)-1-oxa-2,8-diazaspiro[4.5]dec-2-ene-8-thiocarboxylic acid-(4-tert-butylphenyl)amide
[281] 3-(4-tert-butylphenyl)-1-oxa-2,8-diazaspiro[4.5]dec-2-ene-8-thiocarboxylic acid-(4-tert-butylphenyl)amide

[282] 3-p-tolyl-1-oxa-2,8-diazaspiro[4.5]dec-2-ene-8-thiocarboxylic acid-(4-tert-butylphenyl)amide
[283] 3-(4-trifluoromethylphenyl)-1-oxa-2,8-diazaspiro[4.5]dec-2-ene-8-thiocarboxylic acid-(4-tert-butylphenyl)amide
[284] 3-(3-methoxyphenyl)-1-oxa-2,8-diazaspiro[4.5]dec-2-ene-8-carboxylic acid-2-methylbenzylamide
[285] 3-phenyl-1-oxa-2,8-diazaspiro[4.5]dec-2-ene-8-carboxylic acid-2-methylbenzylamide
[286] 3-(4-chlorophenyl)-1-oxa-2,8-diazaspiro[4.5]dec-2-ene-8-carboxylic acid-2-methylbenzylamide
[287] 3-(4-tert-butylphenyl)-1-oxa-2,8-diazaspiro[4.5]dec-2-ene-8-carboxylic acid-2-methylbenzylamide
[288] 3-(4-chlorophenyl)-1-oxa-2,8-diazaspiro[4.5]dec-2-ene-8-thiocarboxylic acid cyclopentylamide
[289] 3-(4-tert-butylphenyl)-1-oxa-2,8-diazaspiro[4.5]dec-2-ene-8-thiocarboxylic acid cyclopentylamide
[290] 3-p-tolyl-1-oxa-2,8-diazaspiro[4.5]dec-2-ene-8-thiocarboxylic acid cyclopentylamide
[291] 3-(4-trifluoromethylphenyl)-1-oxa-2,8-diazaspiro[4.5]dec-2-ene-8-thiocarboxylic acid cyclopentylamide
[292] 3-phenyl-1-oxa-2,8-diazaspiro[4.5]dec-2-ene-8-thiocarboxylic acid cyclohexylmethylamide
[293] 3-(4-chlorophenyl)-1-oxa-2,8-diazaspiro[4.5]dec-2-ene-8-thiocarboxylic acid cyclohexylmethylamide
[294] 3-(4-tert-butylphenyl)-1-oxa-2,8-diazaspiro[4.5]dec-2-ene-8-thiocarboxylic acid cyclohexylmethylamide
[295] 3-p-tolyl-1-oxa-2,8-diazaspiro[4.5]dec-2-ene-8-thiocarboxylic acid cyclohexylmethylamide
[296] 3-(4-trifluoromethylphenyl)-1-oxa-2,8-diazaspiro[4.5]dec-2-ene-8-thiocarboxylic acid cyclohexylmethylamide
[297] 3-(3-methoxyphenyl)-1-oxa-2,8-diazaspiro[4.5]dec-2-ene-8-thiocarboxylic acid cyclooctylamide
[298] 3-phenyl-1-oxa-2,8-diazaspiro[4.5]dec-2-ene-8-thiocarboxylic acid cyclooctylamide
[299] 3-(4-chlorophenyl)-1-oxa-2,8-diazaspiro[4.5]dec-2-ene-8-thiocarboxylic acid cyclooctylamide
[300] 3-p-tolyl-1-oxa-2,8-diazaspiro[4.5]dec-2-ene-8-thiocarboxylic acid cyclooctylamide
[301] 3-(4-trifluoromethylphenyl)-1-oxa-2,8-diazaspiro[4.5]dec-2-ene-8-thiocarboxylic acid cyclooctylamide
[302] 3-(3-methoxyphenyl)-1-oxa-2,8-diazaspiro[4.5]dec-2-ene-8-thiocarboxylic acid-(2-morpholin-4-yl-ethyl)amide
[303] 3-tert-butyl-1-oxa-2,8-diazaspiro[4.5]dec-2-ene-8-carboxylic acid-(4-tert-butylphenyl)amide
[304] 3-phenyl-1-(3-phenyl-1-oxa-2,8-diazaspiro[4.5]dec-2-en-8-yl)propinone
[305] 1-(3-tert-butyl-1-oxa-2,8-diazaspiro[4.5]dec-2-en-8-yl)-3-phenylpropinone
[306] 3-phenyl-1-oxa-2,8-diazaspiro[4.5]dec-2-ene-8-carboxylic acid-(4-tert-butylphenyl)methylamide
[307] (4-tert-butylphenyl)-(3-phenyl-1-oxa-2,8-diazaspiro[4.5]dec-2-en-8-yl)methanone
[308] (4-hydroxy-3-methoxyphenyl)-(3-phenyl-1-oxa-2,8-diazaspiro[4.5]dec-2-en-8-yl)methanone
[309] (4-iodophenyl)-(3-phenyl-1-oxa-2,8-diazaspiro[4.5]dec-2-en-8-yl)methanone
[310] 3-tert-butyl-1-oxa-2,8-diazaspiro[4.5]dec-2-ene-8-carboxylic acid p-tolylamide
[311] 3-(4-trifluoromethoxyphenyl)-1-oxa-2,8-diazaspiro[4.5]dec-2-ene-8-carboxylic acid p-tolylamide
[312] 3-(3-methoxyphenyl)-1-oxa-2,8-diazaspiro[4.5]dec-2-ene-8-carboxylic acid-(4-tert-butylphenyl)amide
[313] 2-(4-tert-butylphenyl)-1-(3-phenyl-1-oxa-2,8-diazaspiro[4.5] dec-2-en-8-yl)ethanone
[314] 1-(3-phenyl-1-oxa-2,8-diazaspiro[4.5] dec-2-en-8-yl)-3-(4-trifluoromethylphenyl)propenone
[315] 3-(4-hydroxy-3-methoxyphenyl)-1-(3-phenyl-1-oxa-2,8-diazaspiro[4.5] dec-2-en-8-yl)propenone
[316] (4-tert-butylphenyl)-[3-(4-tert-butylphenyl)-1-oxa-2,8-diazaspiro[4.5] dec-2-en-8-yl]methanone
[317] 3-(4-tert-butylphenyl)-1-[3-(4-tert-butylphenyl)-1-oxa-2,8-diazaspiro[4.5] dec-2-en-8-yl]propenone
[318] 3-(4-tert-butylphenyl)-1-[3-(4-trifluoromethoxyphenyl)-1-oxa-2,8-diazaspiro[4.5] dec-2-en-8-yl]propenone
[319] 3-naphthalen-2-yl-1-oxa-2,8-diazaspiro[4.5] dec-2-ene-8-carboxylic acid-(4-ethylphenyl)amide
[320] 1-(3-phenyl-1-oxa-2,8-diazaspiro[4.5] dec-2-en-8-yl)-3,3-di-p-tolylpropenone
[321] 3-(4-tert-butylphenyl)-2-methyl-1-(3-phenyl-1-oxa-2,8-diazaspiro[4.5] dec-2-en-8-yl)propenone
[322] 3-phenyl-1-oxa-2,8-diazaspiro[4.5] dec-2-ene-8-carboxylic acid benzhydrylamide
[323] 3-(4-tert-butylphenyl)-1-(3-phenyl-1-oxa-2,8-diazaspiro[4.5] dec-2-en-8-yl)propenone
[324] 2-(4-tert-butylbenzylidene)-1-(3-phenyl-1-oxa-2,8-diazaspiro[4.5] dec-2-en-8-yl)-buten-1-one
[325] 3-(4-isopropylphenyl)-1-(3-phenyl-1-oxa-2,8-diazaspiro[4.5] dec-2-en-8-yl)propenone
[326] 3-(4-octylphenyl)-1-(3-phenyl-1-oxa-2,8-diazaspiro[4.5] dec-2-en-8-yl)propenone
[327] 3-(4-butylphenyl)-1-(3-phenyl-1-oxa-2,8-diazaspiro[4.5] dec-2-en-8-yl)propenone
[328] 3-(4-pentylphenyl)-1-(3-phenyl-1-oxa-2,8-diazaspiro[4.5] dec-2-en-8-yl)propenone
[329] 3-(3-chloropyridin-2-yl)-1-oxa-2,8-diazaspiro[4.5] dec-2-ene-8-carboxylic acid-(4-tert-butylphenyl)amide
[330] 3-phenyl-1-oxa-2,8-diazaspiro[4.5]dec-2-ene-8-thiocarboxylic acid-(4-pentafluorosulfanylphenyl)amide
[331] (3-(4-chloro-3-methoxyphenyl)-1-oxa-2,8-diazaspiro[4.5] dec-2-en-8-yl)(9H-xanthen-9-yl)methanone
[332] (9H-fluoren-9-yl)(3-(3-methoxyphenyl)-1-oxa-2,8-diazaspiro[4.5]dec-2-en-8-yl)methanone
[333] N-(4-tert-butylphenyl)-3-(3-chlorophenyl)-1-oxa-2,8-diazaspiro[4.5]dec-2-ene-8-carboxamide
[334] (E)-3-(4-cyclohexylphenyl)-1-(3-(3-methoxyphenyl)-1-oxa-2,8-diazaspiro[4.5]dec-2-en-8-yl)prop-2-en-1-one
[335] N-(4-tert-butylphenyl)-3-(4-cyclohexylphenyl)-1-oxa-2,8-diazaspiro[4.5]dec-2-ene-8-carboxamide
[336] (E)-3-(4-tert-butylphenyl)-3-phenyl-1-(3-phenyl-1-oxa-2,8-diazaspiro[4.5]dec-2-en-8-yl)prop-2-en-1-one
[337] (2E,4E)-3-(4-tert-butylphenyl)-5-phenyl-1-(3-phenyl-1-oxa-2,8-diazaspiro[4.5]dec-2-en-8-yl)penta-2,4-dien-1-one
[338] (Z)-3-(4-tert-butylphenyl)-1-(3-phenyl-1-oxa-2,8-diazaspiro[4.5]dec-2-en-8-yl)-3-(thiophen-3-yl)prop-2-en-1-one
[339] (E)-3-(4-tert-butylphenyl)-1-(3-(3-methoxyphenyl)-1-oxa-2,8-diazaspiro[4.5]dec-2-en-8-yl)-3-(4-(trifluoromethyl)phenyl)prop-2-en-1-one
[340] (E)-N-(5-(8-(3-(4-tert-butylphenyl)acryloyl)-1-oxa-2,8-diazaspiro[4.5]dec-2-ene-3-yl)-2-fluorophenyl)methanesulfonamide
[341] (E)-3-(4-pentafluorosulfanyl)-1-(3-(3-methoxyphenyl)-1-oxa-2,8-diazaspiro[4.5]dec-2-en-8-yl)prop-2-en-1-one

[342] (E)-1-(3-(3-methoxyphenyl)-1-oxa-2,8-diazaspiro[4.5]dec-2-en-8-yl)-3-(2-morpholino-6-(trifluoromethyl)pyridin-3-yl)prop-2-en-1-one
[343] N-(2-fluoro-4-(1-oxo-1-(3-phenyl-1-oxa-2,8-diazaspiro[4.5]dec-2-en-8-yl)propan-2-yl)phenyl)methanesulfonamide
[344] N-(2-fluoro-4-(1-(3-(3-methoxyphenyl)-1-oxa-2,8-diazaspiro[4.5]dec-2-en-8-yl)-1-oxopropan-2-yl)phenyl)methanesulfonamide
[344] (Z)-3-(4-tert-butylphenyl)-1-(3-(3-methoxyphenyl)-1-oxa-2,8-diazaspiro[4.5]dec-2-en-8-yl)-3-(thiophen-3-yl)prop-2-en-1-one
[345] (E)-3-(3-bromophenyl)-1-(3-phenyl-1-oxa-2,8-diazaspiro[4.5]dec-2-en-8-yl)prop-2-en-1-one
[346] (E)-3-(2-bromophenyl)-1-(3-phenyl-1-oxa-2,8-diazaspiro[4.5] dec-2-en-8-yl)prop-2-en-1-one
[347] 3-(3-fluorophenyl)-N-(4-(trifluoromethyl)phenyl)-1-oxa-2,8-diazaspiro[4.5] dec-2-ene-8-carboxamide
[348] N-(4-tert-butylphenyl)-3-(4-fluorophenyl)-1-oxa-2,8-diazaspiro[4.5]dec-2-ene-8-carboxamide
[349] 3-(4-tert-butylphenyl)-1-(3-phenyl-1-oxa-2,8-diazaspiro[4.5] dec-2-en-8-yl)propan-1-one
[351] N-(4-tert-butylphenyl)-3-(3-fluorophenyl)-1-oxa-2,8-diazaspiro[4.5]dec-2-ene-8-carboxamide
[352] N-(4-tert-butylphenyl)-3-(2-fluorophenyl)-1-oxa-2,8-diazaspiro[4.5]dec-2-ene-8-carboxamide
[353] (E)-3-(4-tert-butylphenyl)-1-(3-(3-fluorophenyl)-1-oxa-2,8-diazaspiro[4.5] dec-2-en-8-yl)prop-2-en-1-one
[354] (Z)-1-(3-(3-methoxyphenyl)-1-oxa-2,8-diazaspiro[4.5]dec-2-en-8-yl)-4,4-dimethyl-3-phenylpent-2-en-1-one
[355] (E)-1-(3-phenyl-1-oxa-2,8-diazaspiro[4.5]dec-2-en-8-yl)-3-(2-(piperidin-1-yl)-6-(trifluoromethyl)pyridin-3-yl)prop-2-en-1-one
[356] (E)-1-(3-(3-chlorophenyl)-1-oxa-2,8-diazaspiro[4.5]dec-2-en-8-yl)-3-(2-(piperidin-1-yl)-6-(trifluoromethyl)pyridin-3-yl)prop-2-en-1-one
[357] (2E,4E)-3-tert-butyl-1-(3-(3-methoxyphenyl)-1-oxa-2,8-diazaspiro[4.5] dec-8-en-8-yl)-5-phenylpenta-2,4-dien-1-one
[358] (2E,4E)-3-(4-tert-butylphenyl)-1-(3-(3-fluorophenyl)-1-oxa-2,8-diazaspiro[4.5] dec-2-en-8-yl)-5-phenylpenta-2,4-dien-1-one
[359] (Z)-3-(4-tert-butylphenyl)-3-(3,4-dichlorophenyl)-1-(3-(2-fluorophenyl)-1-oxa-2,8-diazaspiro[4.5] dec-2-en-8-yl)prop-2-en-1-one
[360] (Z)-3-(4-tert-butylphenyl)-3-(3,4-dichlorophenyl)-1-(3-(3-fluorophenyl)-1-oxa-2,8-diazaspiro[4.5] dec-2-en-8-yl)prop-2-en-1-one
[361] 1-(3-(3-methoxyphenyl)-1-oxa-2,8-diazaspiro[4.5]dec-2-en-8-yl)-3-(4-(trifluoromethyl)phenyl)prop-2-yn-1-one
[362] (E)-1-(3-(3-methoxyphenyl)-1-oxa-2,8-diazaspiro[4.5]dec-2-en-8-yl)-3-(6-(trifluoromethyl)pyridin-3-yl)prop-2-en-1-one
[363] 1-(3-phenyl-1-oxa-2,8-diazaspiro[4.5]dec-2-en-8-yl)-3-(4-(trifluoromethyl)phenyl)prop-2-yn-1-one
[364] N-(4-tert-butylphenyl)-3-(2-fluorophenyl)-6-methyl-1-oxa-2,8-diazaspiro[4.5]dec-2-ene-8-carboxamide
[365] (E)-1-(3-(3-fluorophenyl)-1-oxa-2,8-diazaspiro[4.5]dec-2-en-8-yl)-3-(2-(piperidin-1-yl)-6-(trifluoromethyl)pyridin-3-yl)prop-2-en-1-one
[366] N-(2-fluoro-4-(1-(3-(3-fluorophenyl)-1-oxa-2,8-diazaspiro[4.5]dec-2-en-8-yl)-1-oxopropan-2-yl)phenyl)methanesulfonamide
[367] (E)-1-(6-methyl-3-phenyl-1-oxa-2,8-diazaspiro[4.5]dec-2-en-8-yl)-3-(2-(piperidin-1-yl)-6-(trifluoromethyl)pyridin-3-yl)prop-2-en-1-one
[368] (E)-3-(2-bromo-4-tert-butylphenyl)-1-(3-phenyl-1-oxa-2,8-diazaspiro[4.5]dec-2-en-8-yl)prop-2-en-1-one
[369] N-(4-tert-butylphenyl)-6-methyl-3-phenyl-1-oxa-2,8-diazaspiro[4.5]dec-2-ene-8-carboxamide
[370] 2-(4-tert-butylphenyl)-1-(3-phenyl-1-oxa-2,8-diazaspiro[4.5]dec-2-en-8-yl)propan-1-one
[371] N-(4-tert-butylphenyl)-3-phenyl-1-oxa-2,7-diazaspiro[4.4]non-2-ene-7-carboxamide
[372] N-(4-tert-butylbenzyl)-3-phenyl-1-oxa-2,8-diazaspiro[4.5]dec-2-ene-8-carboxamide
[373] N-(4-tert-butylphenyl)-3-phenyl-1-oxa-2,8-diazaspiro[4.6]undec-2-ene-8-carboxamide
[374] N-(4-tert-butylbenzyl)-3-(3-methoxyphenyl)-1-oxa-2,8-diazaspiro[4.5]dec-2-ene-8-carboxamide
[375] N-(1-(4-tert-butylphenyl)ethyl)-3-(3-methoxyphenyl)-1-oxa-2,8-diazaspiro[4.5]dec-2-ene-8-carboxamide
[376] N-(4-tert-butylcyclohexyl)-3-phenyl-1-oxa-2,8-diazaspiro[4.5]dec-2-ene-8-carboxamide
[377] N-(4-tert-butylphenethyl)-3-phenyl-1-oxa-2,8-diazaspiro[4.5]dec-2-ene-8-carboxamide
[378] N-(4-tert-butylphenyl)-3-(4-chloro-3-methoxyphenyl)-1-oxa-2,8-diazaspiro[4.5]dec-2-ene-8-carboxamide
[379] 8-(5-tert-butyl-1H-benzo[d]imidazol-2-yl)-3-phenyl-1-oxa-2,8-diazaspiro[4.5]dec-2-ene
[380] 3-phenyl-8-(5-(trifluoromethyl)-1H-benzo[d]imidazol-2-yl)-1-oxa-2,8-diazaspiro[4.5]dec-2-ene
[381] (E)-N-(2-fluoro-4-(3-oxo-3-(3-phenyl-1-oxa-2,8-diazaspiro[4.5]dec-2-en-8-yl)prop-1-enyl)phenyl)methanesulfonamide
[382] (E)-N-(2-fluoro-4-(3-(3-(3-methoxyphenyl)-1-oxa-2,8-diazaspiro[4.5]dec-2-en-8-yl)-3-oxoprop-1-enyl)phenyl)methanesulfonamide
[383] 5-tert-butyl-2-(3-phenyl-1-oxa-2,8-diazaspiro[4.5]dec-2-en-8-yl)benzo[d]oxazole
[384] 5-tert-butyl-2-(3-(3-methoxyphenyl)-1-oxa-2,8-diazaspiro[4.5]dec-2-en-8-yl)benzo[d]oxazole
[385] 6-methyl-3-phenyl-N-(4-(trifluoromethyl)phenyl)-1-oxa-2,8-diazaspiro[4.5]dec-2-ene-8-carboxamide
[386] 3-benzyl-N-(4-tert-butylphenyl)-1-oxa-2,8-diazaspiro[4.5]dec-2-ene-8-carboxamide
[387] N-(4-tert-butylphenyl)-3-phenethyl-1-oxa-2,8-diazaspiro[4.5]dec-2-ene-8-carboxamide
[388] 3-(4-hydroxy-3-methoxyphenyl)-1-(3-phenyl-1-oxa-2,8-diazaspiro[4.5]decen-8-yl)propenone
[389] 3-(4-tert-butylphenyl)-1-(3-phenyl-1-oxa-2,8-diazaspiro[4.5]decen-8-yl)propenone
[390] 3-(3-chloropyridin-2-yl)-1-oxa-2,8-diazaspiro[4.5]dec-2-ene-8-carboxylic acid-(4-tert-butylphenyl)amide
[391] 3,3-di-p-tolyl-1-(3-p-tolyl-1-oxa-2,8-diazaspiro[4.5]dec-2-en-8-yl)propenone
[392] 3-(4-tert-butylphenyl)-1-[3-(4-chlorophenyl)-1-oxa-2,8-diazaspiro[4.5]dec-2-en-8-yl]propenone
[393] 3-(4-tert-butylphenyl)-2-ethyl-1-(3-p-tolyl-1-oxa-2,8-diazaspiro[4.5]dec-2-en-8-yl)propenone
[394] (4-tert-butylphenyl)-(3-p-tolyl-1-oxa-2,8-diazaspiro[4.5]dec-2-en-8-yl)methanone
[395] 3-(4-tert-butylphenyl)-1-(3-p-tolyl-1-oxa-2,8-diazaspiro[4.5]dec-2-en-8-yl)propenone
[396] 3-(4-tert-butylphenyl)-2-methyl-1-(3-p-tolyl-1-oxa-2,8-diazaspiro[4.5]dec-2-en-8-yl)propenone
[397] 2-(4-tert-butylphenyl)-1-[3-(3-methoxyphenyl)-1-oxa-2,8-diazaspiro[4.5] dec-2-en-8-yl]-but-2-en-1-one

[398] 3-(4-tert-butylphenyl)-1-[3-(3-methoxyphenyl)-1-oxa-2,8-diazaspiro[4.5] dec-2-en-8-yl]propinone
[399] 3-(4-tert-butylphenyl)-1-[3-(3-methoxyphenyl)-1-oxa-2,8-diazaspiro[4.5] dec-2-en-8-yl]propenone
[400] 1-[3-(3-methoxyphenyl)-1-oxa-2,8-diazaspiro[4.5] dec-2-en-8-yl]-2,2-diphenyl-propan-1-one
[401] 1-[3-(3-methoxyphenyl)-1-oxa-2,8-diazaspiro[4.5] dec-2-en-8-yl]-2,2-diphenylethanone
[402] 3-(3-methoxyphenyl)-1-oxa-2,8-diazaspiro[4.5] dec-2-ene-8-carboxylic acid-(2,3)-dihydrobenzo[1.4] dioxin-6-yl)amide
[403] 3-(6-tert-butylpyridin-3-yl)-1-[3-(3-methoxyphenyl)-1-oxa-2,8-diazaspiro[4.5]dec-2-en-8-yl]propenone
[404] 3-(6-tert-butylpyridin-3-yl)-1-[3-(4-chloro-3-methoxyphenyl)-1-oxa-2,8-diazaspiro[4.5] dec-2-en-8-yl]propenone
[405] 2,2-diphenyl-1-(3-phenyl-1-oxa-2,8-diazaspiro[4.5] dec-2-en-8-yl)-propan-1-one
[406] 3-(6-tert-butylpyridin-3-yl)-1-(3-phenyl-1-oxa-2,8-diazaspiro[4.5]dec-2-en-8-yl)propenone
[407] 3-(4-isopropylphenyl)-1-oxa-2,8-diazaspiro[4.5] dec-2-ene-8-carboxylic acid-(4-tert-butylphenyl)amide
[408] 3-(2,3-dihydrobenzo[1,4] dioxin-6-yl)-1-oxa-2,8-diazaspiro[4.5] dec-2-ene-8-carboxylic acid-(4-tert-butylphenyl)amide
[409] N-[2-fluoro-4-[3-(3-methoxyphenyl)-1-oxa-2,8-diazaspiro[4.5][dec-2-ene-8-carbonyl]phenyl]methanesulfonamide
[410] N-[2-fluoro-4-(3-phenyl-1-oxa-2,8-diazaspiro[4.5] [dec-2-ene-8-carbonyl]phenyl]methanesulfonamide
[411] 3-(4-cyclohexylphenyl)-1-(3-phenyl-1-oxa-2,8-diazaspiro[4.5] dec-2-en-8-yl)propenone
[412] 1-[3-(3-methoxyphenyl)-1-oxa-2,8-diazaspiro[4.5] dec-2-en-8-yl]-2,2,2-triphenylethanone
[413] [3-(3-methoxyphenyl)-1-oxa-2,8-diazaspiro[4.5] dec-2-en-8-yl]-(9H-xanthen-9-yl)methanone
[414] [3-(4-chloro-3-methoxyphenyl)-1-oxa-2,8-diazaspiro[4.5]dec-2-en-8-yl]-(9H-fluoren-9-yl)methanone
[415] [3-(4-chloro-3-methoxyphenyl)-1-oxa-2,8-diazaspiro[4.5]dec-2-en-8-yl]-(2-chloro-6-trifluoromethylpyridin-3-yl)methanone
[416] [3-(3-methoxyphenyl)-1-oxa-2,8-diazaspiro[4.5] dec-2-en-8-yl]-(2-morpholin-4-yl-6-trifluoromethylpyridin-3-yl)methanone
[417] 3-(4-tert-butylphenyl)-1-[3-(3-chlorophenyl)-1-oxa-2,8-diazaspiro[4.5]dec-2-en-8-yl]propenone
[418] 3-(4-tert-butylphenyl)-1-[3-(2,3-dihydrobenzo[1.4] dioxin-6-yl)-1-oxa-2,8-diazaspiro[4.5]dec-2-en-8-yl-propenone
[419] 3-(4-tert-butylphenyl)-1-[3-(4-cyclohexylphenyl)-1-oxa-2,8-diazaspiro[4.5]dec-2-en-8-yl]propenone
[420] N-[4-[3-(4-cyclohexylphenyl)-1-oxa-2,8-diazaspiro [4.5]dec-2-ene-8-carbonyl]-2-fluorophenyl]methanesulfonamide
[421] 2-hydroxy-2,2-diphenyl-1-(3-phenyl-1-oxa-2,8-diazaspiro[4.5]dec-2-8-yl]ethanone
[422] (3-phenyl-1-oxa-2,8-diazaspiro[4.5]dec-2-en-8-yl)-(9H-xanthen-9-yl)methanone
[426] 3-(4-tert-butylphenyl)-1-(3-quinolin-3-yl-1-oxa-2,8-diazaspiro[4.5]dec-2-en-8-yl)propenone
[424] 3-(2,3-dihydrobenzo[1.4]dioxin-6-yl)-1-oxa-2,8-diazaspiro[4.5]dec-2-ene-8-carboxylic acid-(4-trilfuoromethylphenyl)amide
[425] 3-(3-chlorophenyl)-1-oxa-2,8-diazaspiro[4.5]dec-2-ene-8-carboxylic acid-(4-trilfuormethylphenyl)amide
[426] (4-tert-butylphenyl)-[3-(3-methoxyphenyl)-1-oxa-2,8-diazaspiro[4.5]dec-2-en-8-yl]methanone
[427] 3-(4-cyclohexylphenyl)-1-oxa-2,8-diaza-sprio[4.5] dec-2-ene-8-carboxylic acid-(4-trifluoromethylphenyl) amide
[428] 3-(4-tert-butylphenyl)-3-(4-chlorophenyl)-1-[3-(3-chlorophenyl)-1-oxa-2,8-diazaspiro[4.5]dec-2-en-8-yl]propenone
[429] 3-(4-tert-butylphenyl)-1-[3-(3-chlorophenyl)-1-oxa-2,8-diazaspiro[4.5]dec-2-en-8-yl]-3-(3-methoxyphenyl)propenone
[430] 3-(4-tert-butylphenyl)-1-[3-(4-chloro-3-methoxyphenyl)-1-oxa-2,8-diazaspiro[4.5]dec-2-en-8-yl]-3-(4-trifluoromethylphenyl)propenone
[431] 3-(4-pentafluorosulfanylphenyl)-1-[3-(3-methoxyphenyl)-1-oxa-2,8-diazaspiro[4.5]dec-2-en-8-yl]propenone
[432] 3-(4-tert-butylphenyl)-1-[3-(4-chloro-3-methoxyphenyl)-1-oxa-2,8-diazaspiro[4.5]dec-2-en-8-yl]propenone
[433] 3-(4-tert-butylphenyl)-1-[3-(4-chloro-3-methoxyphenyl)-1-oxa-2,8-diazaspiro[4.5]dec-2-en-8-yl]propinone
[434] 3-(4-tert-butylphenyl)-1-[3-(3-methoxyphenyl)-1-oxa-2,8-diazaspiro[4.5]dec-2-en-8-yl]-3-(2-trifluoromethylphenyl)propenone
[435] 3-thiazol-2-yl-1-oxa-2,8-diazaspiro[4.5]dec-2-ene-8-carboxylic acid-(4-isopropylphenyl)amide
[436] 3-thiazol-2-yl-1-oxa-2,8-diazaspiro[4.5]dec-2-ene-8-carboxylic acid-(4-trifluoromethoxyphenyl)amide
[437] 3,3-bis-(4-tert-butylphenyl)-1-(3-phenyl-1-oxa-2,8-diazaspiro[4.5]dec-2-en-8-yl)propenone
[438] 3-thiazol-2-yl-1-oxa-2,8-diazaspiro[4.5]dec-2-ene-8-carboxylic acid-(4-tert-butylphenyl)amide;
and physiologically compatible salts thereof.

18. A compound according to claim 1, wherein in a FLIPR assay in a concentration of 10 μM said compound displays inhibition of the $Ca^{2+}$ ion inflow in dorsal root ganglia of rats of at least 30% compared to the maximum achievable inhibition of the $Ca^{2+}$ ion inflow with capsaicin in a concentration of 10 μM.

19. A method of prerparing a substituted spiro compound corresponding to formula I according to claim 1, wherein
a compound of general formula II,

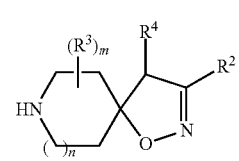

wherein $R^2$, $R^3$, $R^4$, m and n are as defined in claim 1, is reacted in a reaction medium, optionally in the presence of at least one base, with a compound of general formula $R^9$—C(=O)-LG, wherein $R^9$ is as defined in claim 1 and LG represents a leaving group, or in a reaction medium in the presence of at least one coupling reagent, optionally in the presence of at least one base, with a compound of general formula $R^9$—C(=O)—OH, wherein $R^9$ is as defined in claim 1, to form a compound of general formula I, wherein $R^2$ to $R^4$, m and n are as defined above and $R^1$ represents —C(=O)—$R^9$, and the compound of general formula I is optionally purified and/or isolated.

20. A pharmaceutical composition comprising a compound according to claim 1, and at least one physiologically compatible excipient.

21. A method of treating or inhibiting a disorder or disease state selected from pain in a subject in need thereof, said method comprising administering to said subject a pharmaceutically effective amount of a compound according to claim 1.

22. A method according to claim 21, wherein said disorder or disease state is pain selected from the group consisting of acute pain, chronic pain and neuropathic pain.

* * * * *